US011913013B2

(12) United States Patent
Sullivan et al.

(10) Patent No.: US 11,913,013 B2
(45) Date of Patent: Feb. 27, 2024

(54) CHIMPANZEE ADENOVIRAL VECTOR-BASED FILOVIRUS VACCINES

(71) Applicants: The Government of the United States of America as Represented by the Secretary of the Department of Health and Human Services, Rockville, MD (US); Sabin Vaccine Institute, Washington, DC (US)

(72) Inventors: Nancy J. Sullivan, Kensington, MD (US); Gary J. Nabel, Washington, DC (US); Clement Asiedu, Olney, MD (US); Cheng Cheng, Rockville, MD (US); Alfredo Nicosia, Rome (IT); Riccardo Cortese, Rome (IT); Virginia Ammendola, Naples (IT); Stefano Colloca, Rome (IT)

(73) Assignee: SABIN VACCINE INSTITUTE, Washington, DC (US)

( * ) Notice: Subject to any disclaimer, the term of this patent is extended or adjusted under 35 U.S.C. 154(b) by 112 days.

(21) Appl. No.: 17/389,421

(22) Filed: Jul. 30, 2021

(65) Prior Publication Data

US 2022/0064669 A1 Mar. 3, 2022

Related U.S. Application Data

(60) Continuation of application No. 16/751,470, filed on Jan. 24, 2020, now abandoned, which is a continuation of application No. 15/339,225, filed on Oct. 31, 2016, now Pat. No. 10,584,355, which is a division of application No. 13/641,655, filed as application No. PCT/US2011/032682 on Apr. 15, 2011, now Pat. No. 9,526,777.

(60) Provisional application No. 61/325,166, filed on Apr. 16, 2010.

(51) Int. Cl.

| | |
|---|---|
| ***C12N 15/86*** | (2006.01) |
| ***C12N 15/861*** | (2006.01) |
| ***C07K 14/08*** | (2006.01) |
| ***A61K 39/12*** | (2006.01) |
| ***C07K 14/005*** | (2006.01) |
| *A61K 39/00* | (2006.01) |
| *C12N 15/863* | (2006.01) |
| *C12N 7/00* | (2006.01) |

(52) U.S. Cl.

CPC .............. *C12N 15/86* (2013.01); *A61K 39/12* (2013.01); *C07K 14/005* (2013.01); *C07K 14/08* (2013.01); *C12N 15/861* (2013.01); *A61K 2039/5254* (2013.01); *A61K 2039/5256* (2013.01); *A61K 2039/545* (2013.01); *C12N 7/00* (2013.01); *C12N 15/8636* (2013.01); *C12N 2710/10341* (2013.01); *C12N 2710/10343* (2013.01); *C12N 2710/24111* (2013.01); *C12N 2710/24141* (2013.01); *C12N 2760/14111* (2013.01); *C12N 2760/14134* (2013.01)

(58) Field of Classification Search

CPC ...... A61K 39/12; C12N 15/86; C12N 15/861; C12N 2710/10341; C12N 2760/14134

See application file for complete search history.

(56) References Cited

U.S. PATENT DOCUMENTS

| | | | | |
|---|---|---|---|---|
| 8,101,739 | B2 * | 1/2012 | Sullivan | A61P 31/12 424/204.1 |
| 8,216,834 | B2 * | 7/2012 | Colloca | C07K 14/70503 435/456 |
| 9,718,863 | B2 * | 8/2017 | Colloca | C12N 7/00 |

OTHER PUBLICATIONS

Roy, S., et al., 2006, Generation of an adenoviral vaccine vector based on simian adenovirus 21, J. Gen. Virol. 87:2477-2485.*

* cited by examiner

*Primary Examiner* — Jeffrey S Parkin
(74) *Attorney, Agent, or Firm* — WCF IP

(57) ABSTRACT

This invention provides vaccines for inducing an immune response and protection against filovirus infection for use as a preventative vaccine in humans. In particular, the invention provides chimpanzee adenoviral vectors expressing filovirus proteins from different strains of Ebolavirus (EBOV) or Marburg virus (MARV).

5 Claims, 13 Drawing Sheets

Specification includes a Sequence Listing.

Figure 1A
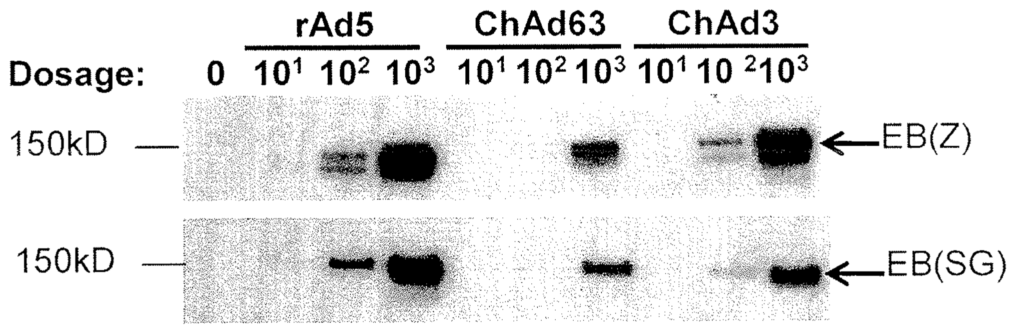
Figure 1B

Figure 6A
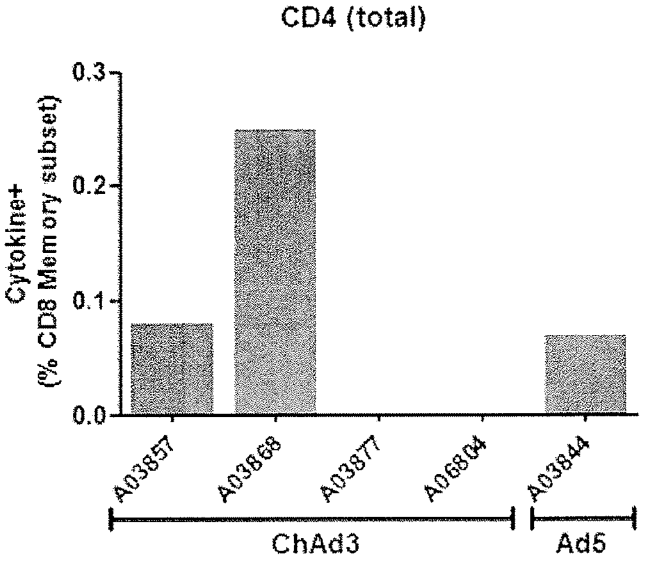
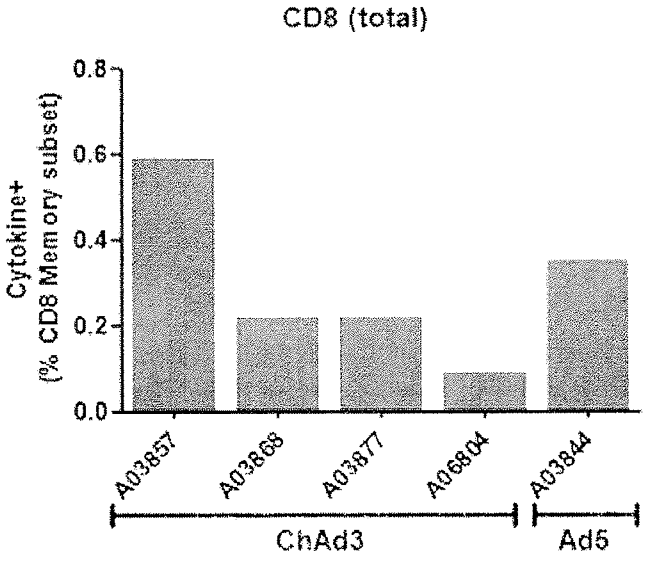
Figure 6B

Figure 7

| Vaccine | N | Survival |
|---|---|---|
| ChAd3-EBOV-GP | 4 | 100% |
| rAd5-EBOV-GP | 1 | 100%* |
| None | 1 | 0%** |

Figure 9A
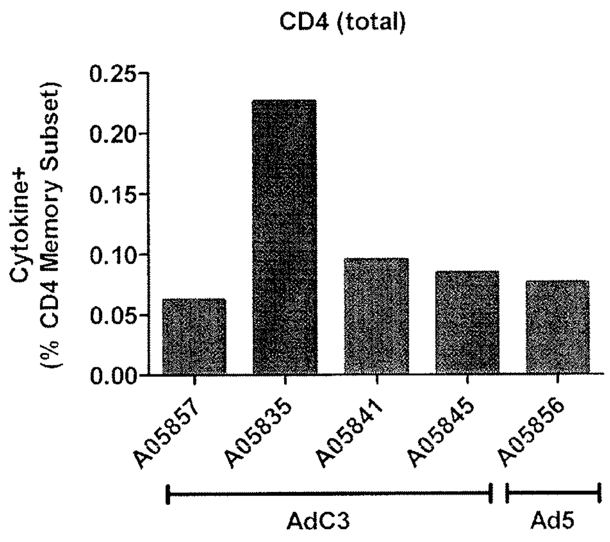
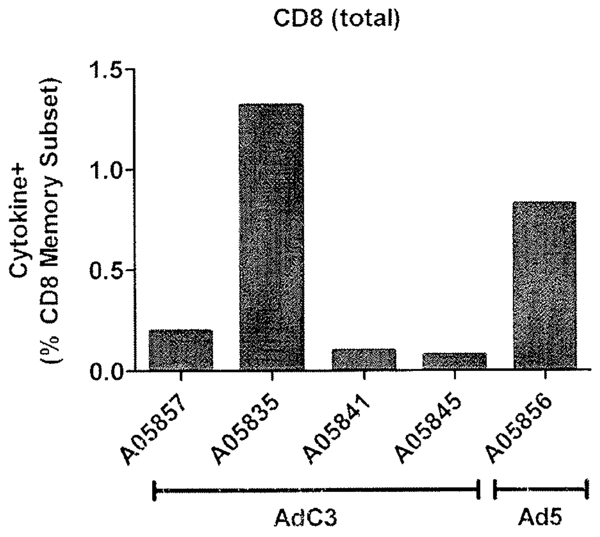
Figure 9B

Figure 10

| Vaccine | N | Survival |
|---|---|---|
| rChAd3-EBOV-GP | 4 | % |
| rAd5-EBOV-GP | 1 | 100%* |
| None | 1 | 0%** |

Red: Z (non-humanized)
Blue: Zh (humanized)

* p<0.05
** p<0.01
*** p<0.001

CHIMPANZEE ADENOVIRAL VECTOR-BASED FILOVIRUS VACCINES

CROSS-REFERENCES TO RELATED APPLICATIONS

This application is a Continuation Application of U.S. application Ser. No. 15/339,225 filed Oct. 31, 2016, which is a Divisional Application of U.S. application Ser. No. 13/641,655, filed Jan. 2, 2013, which is a U.S. National Phase Application of PCT/US2011/032682, filed Apr. 15, 2011 which claims the benefit of US Provisional Patent Application No. 61/325,166, filed Apr. 16, 2010 each of which are incorporated herein by reference in their entirety.

REFERENCE TO SEQUENCE LISTING

This application includes a Sequence Listing as a text file named "77867-591100US-854933_SEQLIST.txt" created Oct. 15, 2012, and containing 387,507 bytes. The material contained in this text file is incorporated by reference in its entirety for all purposes.

FIELD OF THE INVENTION

This invention relates generally to viral vaccines and, more particularly, to filovirus vaccines based on chimpanzee adenoviral vectors.

BACKGROUND OF THE INVENTION

The Ebola viruses, and the genetically-related Marburg virus, viruses of the Filoviridae family, are associated with outbreaks of highly lethal hemorrhagic fever in humans and primates in North America, Europe, and Africa (Peters, C. J. et al. in: *Fields Virology*, eds. Fields, B. N. et al. 1161-1176, Philadelphia, Lippincott-Raven, 1996; Peters, C. J. et al. 1994 *Semin Virol* 5:147-154). Ebola viruses are negative-stranded RNA viruses comprised of five subtypes, including those described in the Zaire, Sudan, Reston, Ivory Coast and Bundibugyo episodes (Sanchez, A. et al. 1996 *PNAS USA* 93:3602-3607). The Ebola virus, was first recognized during an outbreak in 1976 in the Ebola River valley of Zaire (currently the Democratic Republic of the Congo), Africa. Mortality rates vary between different species, spanning from approximately 35 to 90% for the most virulent ones, Zaire and Sudan. The development of effective vaccines and/or drugs is a high priority. The Ebola (EBOV) and Marburg (MARV) viruses have also been categorized as priority class A pathogens due to their virulence, ease of dissemination, lack of effective countermeasures to prevent or treat them, and their potential to cause public panic and social disruption.

Although several subtypes have been defined, the genetic organization of Ebola viruses is similar, each containing seven linearly arrayed genes. Among the viral proteins, the envelope glycoprotein exists in two alternative forms, a 50-70 kilodalton (kDa) secreted protein of unknown function encoded by the viral genome and a 130 kDa transmembrane glycoprotein generated by RNA editing that mediates viral entry (Peters, C. J. et al. in: *Fields Virology*, eds. Fields, B. N. et al. 1161-1176, Philadelphia, Lippincott-Raven, 1996; Sanchez, A. et al. 1996 *PNAS USA* 93:3602-3607). Other structural gene products include the nucleoprotein (NP), matrix proteins VP24 and VP40, presumed nonstructural proteins VP30 and VP35, and the viral polymerase (reviewed in Peters, C. J. et al. in: *Fields Virology*, eds.

Fields, B. N. et al. 1161-1176, Philadelphia, Lippincott-Raven, 1996). Although spontaneous variation of its RNA sequence does occur in nature, there appears to be less nucleotide polymorphism within Ebola subtypes than among other RNA viruses (Sanchez, A. et al. 1996 *PNAS USA* 93:3602-3607), suggesting that immunization may be useful in protecting against this disease. Previous attempts to elicit protective immune responses against Ebola virus using traditional active and passive immunization approaches have, however, not succeeded in primates (Peters, C. J. et al. in: *Fields Virology*, eds. Fields, B. N. et al. 1161-1176, Philadelphia, Lippincott-Raven, 1996: Clegg. J. C. S. et al. 1997 *New Generation Vaccines*, eds.: Levine, M. M. et al. 749-765, New York, NY. Marcel Dekker, Inc.; Jahrling, P. B. et al. 1996 *Arch Virol Suppl* 11:135-140).

Replication-defective adenovirus vectors (rAd) are powerful inducers of cellular immune responses and have therefore come to serve as useful vectors for gene-based vaccines, particularly for lentiviruses and filoviruses, as well as other nonviral pathogens (Shiver, et al., (2002) *Nature* 415(6869): 331-5; (Hill, et al., *Hum Vaccin* 6(1): 78-83.; Sullivan, et al., (2000) *Nature* 408(6812): 605-9; Sullivan et al., (2003) *Nature* 424(6949): 681-4; Sullivan, et al., (2006) PLoS Med 3(6): e177; Radosevic, et al., (2007); Santra, et al., (2009) *Vaccine* 27(42): 5837-45. Adenovirus-based vaccines have several advantages as human vaccines since they can be produced to high titers under GMP conditions and have proven to be safe and immunogenic in humans (Asmuth, et al., *J Infect Dis* 201(1): 132-41; Kibuuka, et al., *J Infect Dis* 201(4): 600-7: Koup, et al., *PLoS One* 5(2): e9015.; Catanzaro, et al., (2006). *J Infect Dis* 194(12): 1638-49; Harro, et al., (2009) *Clin Vaccine Immunol* 16(9): 1285-92). While most of the initial vaccine work was conducted using rAd5 due to its significant potency in eliciting broad antibody and CD8+ T cell responses, pre-existing immunity to rAd5 in humans may limit efficacy (Catanzaro, (2006); Cheng, et al., (2007) *PLoS Pathog* 3(2): e25.; McCoy, et al., (2007) *J Virol* 81(12): 6594-604.; Buchbinder, et al., (2008) *Lancet* 372 (9653): 1881-93). This property might restrict the use of rAd5 in clinical applications for many vaccines that are currently in development including Ebola virus (EBOV) and Marburg virus (MARV).

To circumvent the issue of pre-existing immunity to rAd5, several alternative vectors are currently under investigation. These include adenoviral vectors derived from rare human serotypes and vectors derived from other animals such as chimpanzees (Vogels, et al., (2003) *J Virol* 77(15): 8263-71; Abbink, et al., (2007) *J Virol* 81: 4654-63; Santra, (2009) *Vaccine* 27(42): 5837-45). Chimpanzee adenoviral vectors are also described in WO 2010/086189, WO 2005/071093 and WO 98/10087.

It would thus be desirable to provide a vaccine to elicit an immune response against a filovirus or disease caused by infection with filovirus using improved adenoviral vectors. It would further be desirable to provide methods of making and using said vaccine. The present invention addresses these and other needs.

BRIEF SUMMARY OF THE INVENTION

This invention provides vaccines for inducing an immune response and protection against filovirus infection for use as a preventative vaccine in humans. In particular, the invention provides chimpanzee adenoviral vectors (adenoviral vectors derived from chimpanzees) expressing filovirus proteins. For example, these vaccines include chimpanzee adenovirus serotypes ChAd3, ChAd63, PanAd3, PanAd1, PanAd2, or ChAd83 expressing filovirus envelope glycoprotein (GP), including different strains of Ebolavirus (EBOV) or Marburg (MARV). Exemplary Chimp Adenoviral Ebola and Marburg sequences are provided in SEQ ID NOs:1-9.

DEFINITIONS

An “adenovirus capsid protein” refers to a protein on the capsid of an adenovirus (e.g., chimpanzee adenovirus) that is involved in determining the serotype and/or tropism of a particular adenovirus. Adenoviral capsid proteins typically include the fiber, penton and/or hexon proteins. As used herein an “adenovirus capsid protein” may be, for example, a chimeric capsid protein that includes capsid protein sequences from two adenoviral iolates.

The terms “adjuvant” and “immune stimulant” are used interchangeably herein, and are defined as one or more substances that cause stimulation of the immune system. In this context, an adjuvant is used to enhance an immune response to the adenovirus vectors of the invention.

The term “corresponding to”, when applied to positions of amino acid residues in sequences, means corresponding positions in a plurality of sequences when the sequences are optimally aligned.

The terms “identical” or percent “identity,” in the context of two or more nucleic acids or polypeptide sequences, (e.g., adenovirus capsid proteins of the invention and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

An “isolated” nucleic acid molecule or adenovirus vector is a nucleic acid molecule (e.g., DNA or RNA) or virus, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

“Operably linked” indicates that two or more DNA segments are joined together such that they function in concert for their intended purposes. For example, coding sequences are operably linked to promoter in the correct reading frame such that transcription initiates in the promoter and proceeds through the coding segment(s) to the terminator.

A “polynucleotide” is a single- or double-stranded polymer of deoxyribonucleotide or ribonucleotide bases typically read from the 5' to the 3' end. Polynucleotides include RNA and DNA, and may be isolated from natural sources, synthesized in vitro, or prepared from a combination of natural and synthetic molecules. When the term is applied to double-stranded molecules it is used to denote overall length and will be understood to be equivalent to the term “base pairs”.

A “polypeptide” is a polymer of amino acid residues joined by peptide bonds, whether produced naturally or synthetically. Polypeptides of less than about 50 amino acid residues are commonly referred to as “oligopeptides”.

The term “promoter” is used herein for its art-recognized meaning to denote a portion of a gene containing DNA sequences that provide for the binding of RNA polymerase and initiation of transcription of an operably linked coding sequence. Promoter sequences are typically found in the 5' non-coding regions of genes.

A “protein” is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The phrase “substantially identical,” in the context of two nucleic acids or polypeptides of the invention (e.g., adenovirus capsid proteins or filovirus antigens), refers to two or more sequences or subsequences that have at least 60%, 65%, 70%, 75%, 80%, 85%, 90%, and 95% nucleotide or amino acid residue identity, when compared and aligned for maximum correspondence, as measured using one of the following sequence comparison algorithms or by visual inspection. In some embodiments, the substantial identity exists over a region of the sequences that is at least about 50 residues, at least about 100 residues, or at least about 150 residues in length. In one embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues: always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

A further indication that two nucleic acid sequences or polypeptides of the invention are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

BRIEF DESCRIPTION OF THE DRAWINGS

FIGS. 1A-1B Transgene expression by rAd5, ChAd63 and ChAd3 vectors. FIG. 1A is a schematic of the genomic features of rAd vector. FIG. 1B shows Ebola GP expression in HEK 293 cells. The cells were transduced with rAd5. ChAd63 or ChAd3 vectors at 0, or $10^1$ to $10^3$ vp/cell as indicated. The cell lysates were harvested at 20 hours post transduction and subjected to SDS-PAGE and Western blot analysis.

FIGS. 2A and 2B show % IFN-γ-producing CD4+ and CD8+ T cells, respectively. FIG. 2C shows detection of IgG by ELISA Serum IgG (sera were diluted at 1:1000). *$p<0.05$; ***$p<0.001$.

FIGS. 3A and 3B show % IFN-γ-producing CD4+ and CD8+ T cells, FIG. 3C shows Serum IgG (serum was diluted at 1:1000). *$p<0.05$; ***$p<0.001$.

FIGS. 4A and 4B show % IFN-γ-producing CD4+ and CD8+ T cells, respectively. FIG. 4C shows Serum IgG (sera were diluted at 1:1000). *$p<0.05$; **$p<0.01$.

FIGS. 6A-6B ChAd3 Ebola GP (Zaire) single immunization generates antigen-specific CD4+ and CD8+ T cell responses. Cynomolgus macaques were immunized with rAd5 or ChAd3 encoding EBOV-GP at a dose of $10^{11}$ vp intramuscularly. Blood cells were collected 4 weeks post immunization to detect cellular immune responses by intracellular cytokine staining after stimulation with EBOV-GP peptides. FIG. 6A shows % cytokine-producing CD4+ T cells, FIG. 6B shows % cytokine-producing CD8+ T cells.

FIG. 7. ChAd3 Ebola GP (Zaire) single immunization protects nonhuman primates against infectious challenge with a lethal dose of EBOV-Zaire. Cynomolgus macaques were immunized with rAd5 or ChAd3 encoding EBOV-GP at a dose of $10^{11}$ vp intramuscularly. Subjects were challenged with 1000 PFU of EBOV-Zaire by the intramuscular route at 5 weeks after vaccination. *Additional 10 historical controls performed with the same vaccine and infectious virus challenge stock have yielded the same survival result, **More than 50 historical controls with the same infectious challenge stock have yielded the same survival result.

FIGS. 9A-9B A single immunization with $10^{10}$ vp of rAdC3 Ebola (Zaire) elicits antigen-specific CD4+ and CD8+ T cell responses. Cynomolgus macaques were vaccinated with rAdC3 or rAd5 encoding EBOV-GP at a dose of $10^{10}$ vp intramuscularly. Blood cells were collected 4 weeks post immunization to detect cellular immune responses by intracellular cytokine staining after stimulation with EBOV-GP peptides. FIG. 9A shows % cytokine producing CD4+ T cells, FIG. 9B shows % cytokine producing CD8+ T cells.

FIG. 10. A single immunization with $10^{10}$ vp of rAdC3 Ebola (Zaire) protects nonhuman primates against infectious challenge with a lethal dose of EBOV-Zaire. Cynomolgus macaques were vaccinated with rAdC3 or rAd5 encoding EBOV-GP at a dose of $10^{10}$ vp intramuscularly. Subjects were challenged with 1000 PFU of EBOV-Zaire by the intramuscular route at 5 weeks post vaccination. *Additional 10 historical controls that received the same vaccine and infectious virus challenge stock have yielded the same survival result. **More than 50 historical controls injected with the same infectious challenge stock have yielded the same survival result.

FIG. 11A shows CD4 cellular immune responses in PBMC. FIG. 11B shows CD8 cellular immune responses in PMBC and FIG. 11C shows humoral responses (IgG) to EBOV-GP. Each were measured at three week post immunization by ICS and ELISA, respectively. Zh: humanized EBOV-GP; Z: non-humanized EBOV-GP; *: $p<0.05$; : $p<0.01$; *: $p<0.001$.

FIG. 12A shows CD4 cellular immune responses in PBMC and FIG. 12B shows CD8 cellular immune responses in PBMC. FIG. 12C shows humoral responses (IgG) to EBOV-GP. Each were measured at week 5 by ICS and ELISA, respectively. 5: rAd5; C3: rChAd3; C63: rChAd63; *: $p<0.05$; : $p<0.01$; *: $p<0.001$.

FIG. 13A shows CD4 cellular immune responses in PBMC and FIG. 13B shows CD8 cellular immune responses in PBMC. FIG. 13C shows humoral responses (IgG) to EBOV-GP. Each were measured at week 6 by ICS and ELISA, respectively. 5: rAd5; C3: rChAd3; C63: rChAd63; $p<0.05$; : $p<0.01$; *: $p<0.001$.

DETAILED DESCRIPTION

Figure 2A:
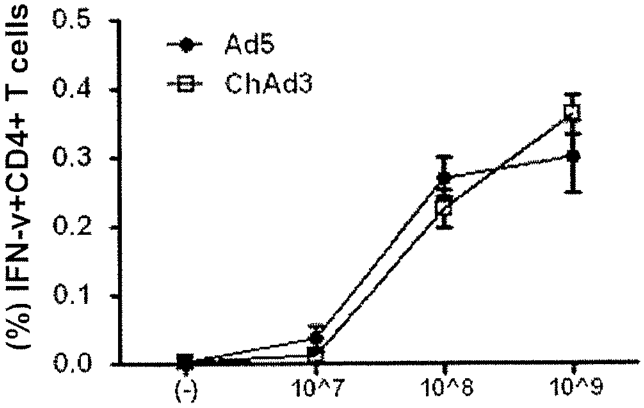
FIGS. 2A-2C ChAd3 Ebola GP (Zaire) single immunization generated comparable CD4+ T cell and IgG responses to rAd5. The mice were immunized with rAd5 Ebola (Zaire) or ChAd3 Ebola (Zaire) at $10^7$, $10^8$ and $10^9$ vp intramuscularly. The spleens and sera were harvested 3 weeks post immunization to detect cellular immune responses by ICS (intracellular cytokine staining) and IgG by ELISA.
Figure 2B:
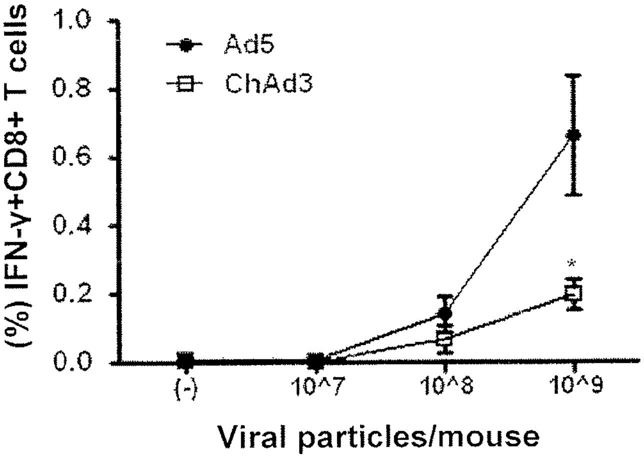
Figure 2C:
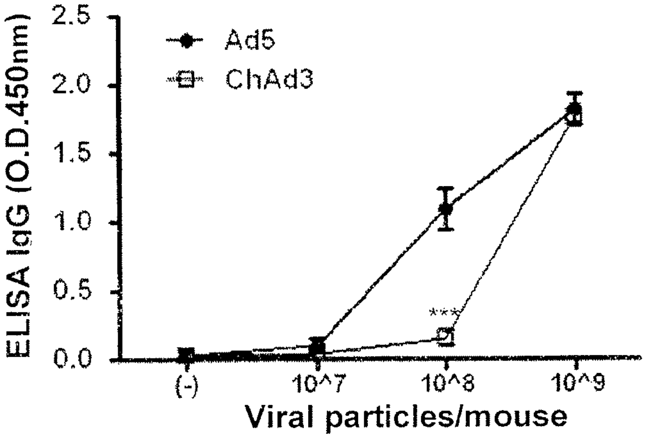
Figure 3A:
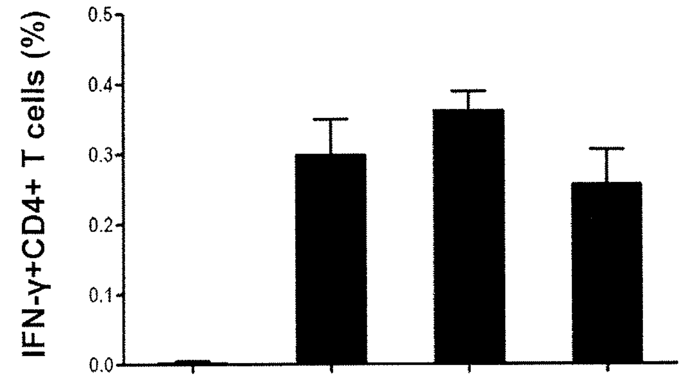
FIGS. 3A-3C ChAd3 Ebola (Zaire) single immunization generated stronger cellular and humoral responses than ChAd63. Mice were immunized with rAd5, ChAd3 or ChAd63 at $10^9$ vp intramuscularly. Spleens and serum were harvested 3 weeks post immunization to detect cellular immune responses by ICS and IgG response by ELISA.
Figure 3B:
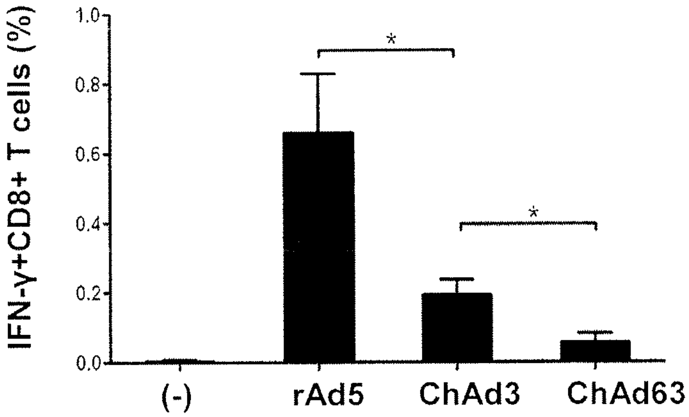
Figure 3C:
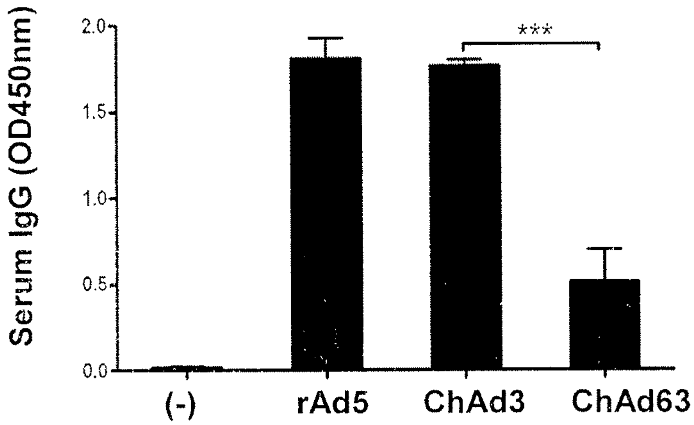
Figure 4A:
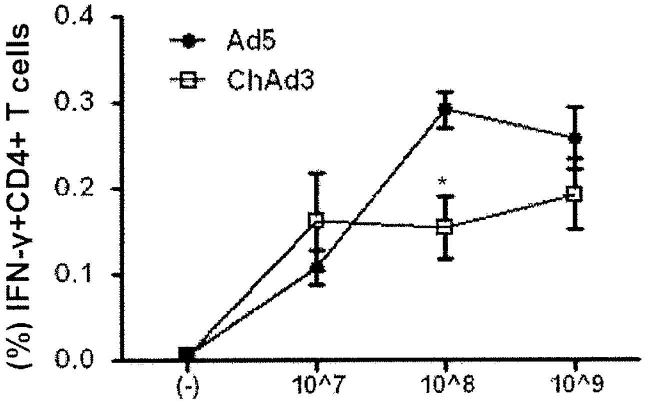
FIGS. 4A-4C ChAd3 Ebola (S/G) single immunization generated comparable cellular and humoral responses to rAd5. Mice were immunized with rAd5 Ebola (S/G) or ChAd3 Ebola (S/G) at 107, 108 and 109 vp intramuscularly. Spleens and sera were harvested 3 weeks post immunization to detect cellular immune responses by ICS and IgG by ELISA.
Figure 4B:
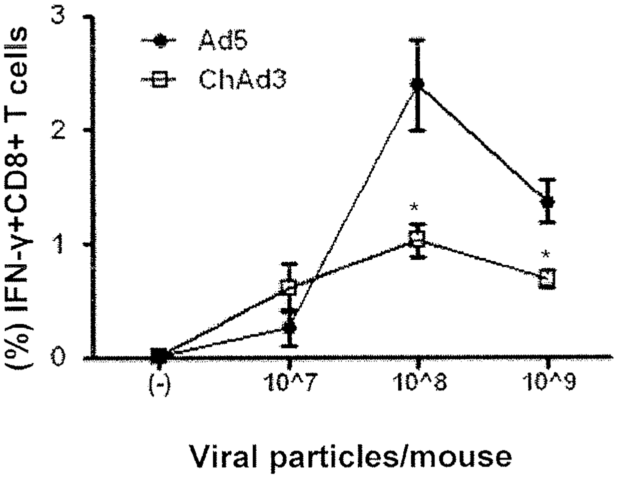
Figure 4C:
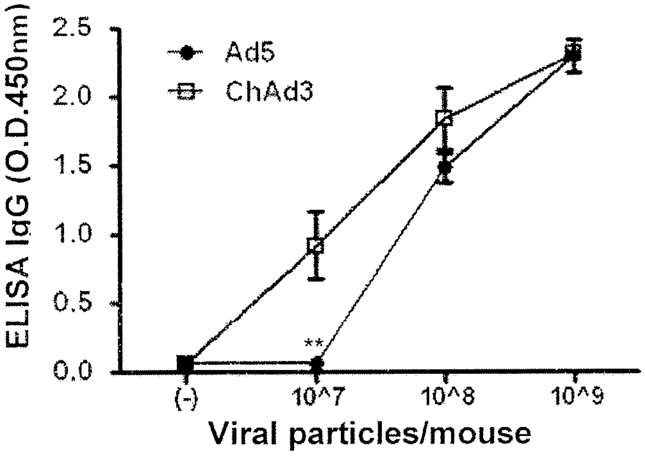
Figure 5:
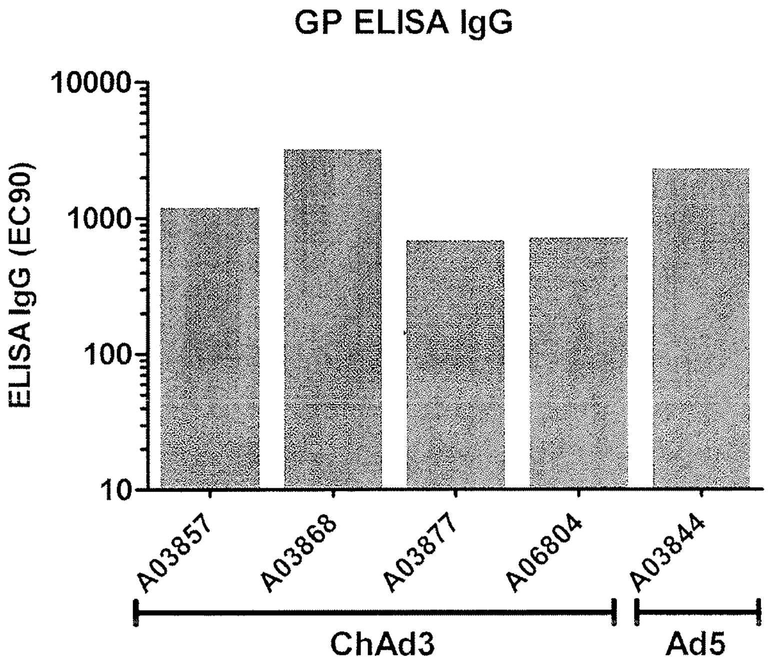
FIG. 5. ChAd3 Ebola (Zaire) single immunization generates antigen-specific antibody responses. Cynomolgus macaques were immunized with rAd5 or ChAd3 encoding EBOV-GP at a dose of 1011 vp intramuscularly. Serum was collected 4 weeks post immunization to detect IgG response by ELISA against EBOV GP.

The present invention also relates to chimpanzee adenovirus vectors which include the nucleic acid molecules of the present invention, host cells which are genetically engineered with the recombinant vectors, the production of filovirus polypeptides or fragments thereof by recombinant techniques and these chimpanzee adenovirus vectors for use in inducing an immune response.

The present invention also relates to pharmaceutical compositions (also referred to as immunogenic compositions) comprising the chimpanzee vectors described above, and a pharmaceutically acceptable diluent, carrier, or excipient carrier as well as to such compositions for use in inducing an immune response. Additionally the compositions may also contain an aqueous medium or a water containing suspension, often mixed with other constituents in order to increase the activity and/or the shelf life. These constituents may be salt. pH buffers, stabilizers (such as skimmed milk or casein hydrolysate), emulsifiers, and preservatives. An adjuvant may be included in the pharmaceutical composition to augment the immune response to the viral antigen expressed from the recombinant virus.

Filovirus Antigens

The nucleic acid molecules of the invention may encode structural gene products of any filovirus species. There are five species of Ebola viruses, Zaire (type species, also referred to herein as ZEBOV), Sudan (also referred to herein as SEBOV), Reston, Bundibugyo, and Ivory Coast. There is a single species of Marburg virus (also referred to herein as MARV).

The particular antigen expressed in the vectors of the invention is not a critical aspect of the present invention. The adenoviral vectors of the invention can be used to express proteins comprising an antigenic determinant of a wide variety of filovirus antigens. In a typical embodiment, the vectors of the invention include nucleic acid encoding the transmembrane form of the viral glycoprotein (GP). In other embodiments, the vectors of the invention may encode the secreted form of the viral glycoprotein (SGP), or the viral nucleoprotein (NP).

One of skill will recognize that the nucleic acid molecules encoding the filovirus antigenic protein may be modified, e.g., the nucleic acid molecules set forth herein may be mutated, as long as the modified expressed protein elicits an immune response against a pathogen or disease. Thus, as used herein, the term “filovirus antigenic protein” refers to a protein that comprises at least one antigenic determinant of a filovirus protein described above. The term encompasses filovirus antigens (i.e., gene products of a filovirus), as well as recombinant proteins that comprise one or more filovirus antigenic determinants.

In some embodiments, the protein may be mutated so that it is less toxic to cells (see e.g., WO2006/037038). The present invention also includes vaccines comprising a combination of nucleic acid molecules. For example, and without limitation, nucleic acid molecules encoding GP, SGP and NP of the Zaire, Sudan and Ivory Coast Ebola strains may be combined in any combination, in one vaccine composition.

Adenoviral Vectors

As noted above, exposure to certain adenoviruses has resulted in immune responses against certain adenoviral serotypes, which can affect efficacy of adenoviral vaccines. The present invention provides adenoviral vectors comprising capsid proteins from chimpanzee adenoviruses.

Thus, the vectors of the invention comprise a chimpanzee adenovirus capsid protein (e.g., a fiber, penton or hexon protein). One of skill will recognize that it is not necessary that an entire chimpanzee capsid protein be used in the vectors of the invention. Thus, chimeric capsid proteins that include at least a part of a chimpanzee capsid protein can be used in the vectors of the invention. The vectors of the invention may also comprise capsid proteins in which the fiber, penton, and hexon proteins are each derived from a different serotype, so long as at least one capsid protein is derived from a chimpanzee adenovirus. For example, the fiber protein can be derived from PanAd3, the penton from ChAd3, and the hexon from ChAd63. In other embodiments, the fiber, penton and hexon proteins can be those provided in SEQ ID NOS:1-9.

In certain embodiments the recombinant adenovirus vector of the invention is derived mainly or entirely from a chimpanzee adenovirus. Exemplary chimpanzee adenoviruses are known in the art and include, for example, ChAd3 and ChAd63 (described in WO 2005/071093), and PanAd3, PanAd1, PanAd2, and ChAd83 (described in WO 2010/086189). ChAd 3, ChAd63, and ChAd83 were isolated from the common chimpanzee (*Pan troglodytes*) and PanAd3, PanAd1, PanAd2 were isolated from the bonobo or pygmy chimpanzee (*Pan paniscus*).

In some embodiments, the adenovirus is replication deficient, e.g. because it contains a deletion in the E1 region of the genome. This allows propagation of such adenoviruses in well known complementing cell lines that express the E1 genes, such as for example 293 cells, PER.C6 cells, and the like. In certain embodiments, the adenovirus is a chimpanzee adenovirus, with a deletion in the E1 and E3 region into which an expression cassette encoding the antigen has been cloned. The construction of chimpanzee adenovirus comprising heterologous sequences encoding antigens is described in WO 2005/071093 and WO 2010/086189.

Typically, a vector of the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention may be in the form of RNA or in the form of DNA obtained by cloning or produced synthetically. The DNA may be double-stranded or single-stranded.

The adenovirus vectors of the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention may contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell. Suitable cell lines include, for example, PER.C6, 911, 293, and E1 A549.

As noted above, a wide variety of filovirus antigenic proteins can be expressed in the vectors of the invention. If required, the heterologous gene encoding the filovirus antigenic protein can be codon-optimized to ensure proper expression in the treated host (e.g., human). Thus, codon-optimized antigens are also referred to as humanized antigens. In some embodiments, the viral GP, SGP or NP protein is codon-optimized. For example, codon-optimized antigens include those of SEQ ID NOS: II, 12, and 14. Codon-optimization is a technology widely applied in the art. Typically, the heterologous gene is cloned into the E1 and/or the E3 region of the adenoviral genome.

The heterologous filovirus gene may be under the control of (i.e., operably linked to) an adenovirus-derived promoter (e.g., the Major Late Promoter) or may be under the control of a heterologous promoter. Examples of suitable heterologous promoters include the CMV promoter and the RSV promoter. In some embodiments, the promoter is located upstream of the heterologous gene of interest within an expression cassette.

As noted above, the adenovirus vectors of the invention can comprise a wide variety of filovirus antigens known to those of skill in the art.

Immunogenic Compositions

Purified or partially purified adenovirus vectors of the invention may be formulated as a vaccine (also referred to as an "immunogenic composition") according to methods well known in the art. Such compositions may include adjuvants to enhance immune responses. The optimal ratios of each component in the formulation may be determined by techniques well known to those skilled in the art.

The preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The compositions are suitable for single administrations or a series of administrations. When given as a series, inoculations subsequent to the initial (priming) administration are given to boost the immune response and are typically referred to as booster inoculations. The compositions of the invention can be used as a boosting composition primed by antigen using any of a variety of different priming compositions, or as the priming composition. Thus, one aspect of the present invention provides a method of priming and/or boosting an immune response to an antigen in an individual. For example, in some embodiments, a priming administration of one adenoviral vector of the invention is followed by a booster inoculation of the second adenoviral vector.

The timing of the administration of boosting compositions is well within the skill in the art. Boosting compositions are generally administered weeks or months after administration of the priming composition, for example, about 2-3 weeks or 4 weeks, or 8 weeks, or 16 weeks, or 20 weeks, or 24 weeks, or 28 weeks, or 32 weeks or one to two years. Methods of accelerated vaccination by administering a single dose of a recombinant adenovirus are described for example in U.S. Pat. No. 7,635,485.

The compositions of the invention may comprise other filovirus antigens or the priming or boosting inoculations may comprise other antigens. The other antigens used in combination with the adenovirus vectors of the invention are not critical to the invention and may be, for example, filovirus antigens, nucleic acids expressing them, virus like particles (VLPs), or prior art viral vectors. Such viral vectors include, for example, other adenoviral vectors, vaccinia virus vectors, avipox vectors such as fowlpox or canarypox, herpes virus vectors, vesicular stomatitis virus vectors, or alphavirus vectors. One of skill will recognize that the immunogenic compositions of the invention may comprise multiple antigens and vectors.

The antigens in the respective priming and boosting compositions (however many boosting compositions are employed) need not be identical, but should share antigenic determinants.

In some embodiments, heterologous prime-boost approaches can be used, for example, priming with Pan3-EBOV and boosting with ChAd3EBOV, priming with ChAd3EBOV and boosting with rLCMV (recombinant lymphocytic choriomeningitis virus), or priming with ChAd63EBOV and boosting with rLCMV. The rLCMV can be constructed as described in Flatz, L. et al., Nature Medicine, 16:339-345, 2010, except that the sequence encoding the antigenic protein is a sequence encoding a filovirus GP protein of the invention. In other embodiments, the boost can be rMVA (modified vaccinia virus Ankara) encoding an Ebola GP protein. Preparation and use of rMVA vectors is known and described for example in Ourmanov el al. *J. Virol.* 83:5388-5400, 2009 and Martinon el al. *Vaccine* 26:532-545, 2008. The vaccines of the invention can be used to generate protection against all human EBOV threats including Bundibugyo and Ivory Coast in a single vaccine. Finally, the vaccines against EBOV and MARV may also be mixed into a single inoculation in order to provide protection against both filoviruses simultaneously. In "prime and boost" immunization regimes, the immune response induced by administration of a priming composition is boosted by administration of a boosting composition. Effective boosting can be achieved using replication-defective adenovirus vectors, following priming with any of a variety of different types of priming compositions, as described for example in U.S. Pat. No. 7,094,598, which is incorporated herein by reference.

As noted above, the immunogenic compositions of the invention may comprise adjuvants. Adjuvants suitable for co-administration in accordance with the present invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-1, GcMAF, B-alethine, MPC-026, Adjuvax, CpG ODN, Betafectin, Alum, and MF59.

Other adjuvants that may be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-1, IL-2, IL-4, IL-6, IL-8, IL-10, and IL-12 or encoding nucleic acids therefore.

As noted above, the compositions of the invention may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, intramucosal (e.g., gut), intranasal, intramuscular, or intraperitoneal routes. Administration is typically intramuscular.

Intramuscular administration of the immunogenic compositions may be achieved by using a needle to inject a suspension of the adenovirus vector. An alternative is the use of a needless injection device to administer the composition (using, e.g., Biojector™) or a freeze-dried powder containing the vaccine.

For intravenous, cutaneous or subcutaneous injection, or injection at the site of affliction, the adenovirus vector will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, or Lactated Ringer's Injection. Preservatives, stabilizers, buffers, antioxidants and/or other additives may be included, as required. A slow-release formulation may also be employed.

Typically, administration will have a prophylactic aim to generate an immune response against a filovirus antigen before infection or development of symptoms. Diseases and disorders that may be treated or prevented in accordance with the present invention include those in which an immune response may play a protective or therapeutic role. In other embodiments, the adenovirus vectors can be administered for post-exposure prophylactics.

The immunogenic compositions containing the adenovirus vectors are administered to a subject, giving rise to an anti-filovirus immune response in the subject. An amount of a composition sufficient to induce a detectable immune response is defined to be an "immunologically effective dose." As shown below, the immunogenic compositions of the invention induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus vectors and optional formulation of such particles into compositions, the adenovirus vectors may be administered to an individual, particularly human or other primate. Administration may be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but may be for use in an experimental context, for instance in investigation of mechanisms of immune responses to the adenovirus vector.

In one exemplary regimen, the adenovirus vector is administered (e.g., intramuscularly) in the range of from about 100 μl to about 10 ml of saline solution containing concentrations of from about $10^4$ to $10^{12}$ virus particles/mi. Typically, the adenovirus vector is administered in an amount of about $10^9$ to about $10^{12}$ viral particles (vp) to a human subject during one administration. For example, the adenovirus vector can be administered in an amount of about $10^9$, $10^{10}$, $10^{11}$, or $10^{12}$ vp per administration. In some embodiments, the dose administered is from about $10^{11}$ to about $10^{12}$ vp. An initial vaccination can be followed by a boost as described above. The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

The present invention also provides kits for enhancing the immunity of a host to a pathogen. These kits may include any one ore more vaccines according to the present invention in combination with a composition for delivering the vaccine to a host and/or a device, such as a syringe, for delivering the vaccine to a host.

The vaccine according to the invention is administered as a pre-exposure (or post-exposure) single dose in a manner compatible with the dosage formulation, and in such amount as will be prophylactively effective. Immunity is defined as the induction of a significant level of protection after vaccination compared to an unvaccinated human or other host.

The vaccine of the present invention, i.e., the recombinant virus, may be administered to a host, such as a human subject, via any pharmaceutically acceptable routes of administration. The routes of administration include, but are not limited to, intramuscular, intratracheal, subcutaneous, intranasal, intradermal, rectal, oral and parental route of administration. Routes of administration may be combined, if desired, or adjusted depending upon the type of the pathogenic virus to be immunized against and the desired body site of protection.

Doses or effective amounts of the recombinant virus may depend on factors such as the condition, the selected viral antigen, the age, weight and health of the host, and may vary among hosts. The appropriate titer of the recombinant virus of the present invention to be administered to an individual is the titer that can modulate an immune response against the viral antigen and elicits antibodies against the pathogenic virus from which the antigen is derived. An effective titer can be determined using an assay for determining the activity of immunoeffector cells following administration of the vaccine to the individual or by monitoring the effectiveness of the therapy using well known in vivo diagnostic assays.

The chimp Ad vectors of the invention can be used as single inoculations to provide either immediate (e.g., 2-4 weeks) or long-term (e.g., one year) immune protection.

Nucleic Acid Molecules

As indicated herein, nucleic acid molecules of the present invention may be in the form of RNA or in the form of DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand. By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a modified or wild-type filovirus or adenovirus structural gene product; and DNA molecules which comprise a sequence substantially different from those described above but which, due to the degeneracy of the genetic code, still encode an ORF of a filovirus structural gene product. Of course, the genetic code is well known in the art.

The present invention is further directed to fragments of the nucleic acid molecules described herein. By a fragment of a nucleic acid molecule having the nucleotide sequence of an ORF encoding a wild-type filovirus or adenovirus structural gene product is intended fragments at least about 15 nt., at least about 20 nt., at least about 30 nt., or at least about 40 nt. in length. Of course, larger fragments 50, 100, 150, 200, 250, 300, 350, 400, 450, or 500 nt. in length are also intended according to the present invention as are fragments corresponding to most, if not all, of the nucleotide sequence of the ORF encoding a wild-type filovirus or adenovirus structural gene product. By a fragment at least 20 nt. in length, for example, is intended fragments which include 20 or more contiguous bases from the nucleotide sequence of the ORF of a wild-type filovirus or adenovirus structural gene product.

In another aspect, the invention provides a nucleic acid molecule comprising a polynucleotide which hybridizes under stringent hybridization conditions to a portion of the polynucleotide in a nucleic acid molecule of the invention described above. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt.), at least about 20 nt., at least about 30 nt., or about 30-70 nt. of the reference polynucleotide.

By a portion of a polynucleotide of "at least 20 nt. in length," for example, is intended 20 or more contiguous nucleotides from the nucleotide sequence of the reference polynucleotide. Of course, a polynucleotide which hybridizes only to a poly A sequence or a complementary stretch of T (or U) residues, would not be included in a polynucleotide of the invention used to hybridize to a portion of a nucleic acid of the invention, since such a polynucleotide would hybridize to any nucleic acid molecule containing a poly A stretch or the complement thereof (e.g., practically any double-stranded cDNA clone).

As indicated herein, nucleic acid molecules of the present invention which encode a filovirus structural gene product may include, but are not limited to those encoding the amino acid sequence of the full-length polypeptide, by itself, the coding sequence for the full-length polypeptide and additional sequences, such as those encoding a leader or secretory sequence, such as a pre-, or pro- or prepro-protein sequence, the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; and additional coding sequence which codes for additional amino acids, such as those which provide additional functionalities.

The present invention further relates to variants of the nucleic acid molecules of the present invention, which encode portions, analogs or derivatives of the filovirus or adenovirus structural gene product. Variants may occur naturally, such as a natural allelic variant. By an "allelic variant" is intended one of several alternate forms of a gene occupying a given locus on a genome of an organism. (Genes 1/. Lewin, B., ed., John Wiley & Sons. 1985 New York). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. In some embodiments, the variations are silent substitutions, additions and deletions, which do not alter the properties and activities of the filovirus or adenovirus structural gene product or portions thereof. In some embodiments the variants are conservative substitutions.

Further embodiments of the invention include nucleic acid molecules comprising a polynucleotide having a nucleotide sequence at least 95% identical, or at least 96%, 97%, 98% or 99% identical to a nucleotide sequence encoding a polypeptide having the amino acid sequence of a wild-type filovirus or adenovirus structural gene product or fragment thereof or a nucleotide sequence complementary thereto.

By a polynucleotide having a nucleotide sequence at least, for example, 95% "identical" to a reference nucleotide sequence encoding a filovirus or adenovirus structural gene product is intended that the nucleotide sequence of the polynucleotide is identical to the reference sequence except that the polynucleotide sequence may include up to five point mutations per each 100 nucleotides of the reference nucleotide sequence encoding the virus structural gene product. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to the reference nucleotide sequence can be determined conventionally using known computer programs such as the Bestfit program (Wisconsin Sequence Analysis Package, Version 8 for Unix, Genetics Computer Group, University Research Park, 575 Science Drive, Madison. Wis. 53711). Bestfit uses the local homology algorithm of Smith and Waterman, 1981 Advances in Applied Mathematics 2:482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence shown herein in the Sequence Listing will encode a polypeptide of the invention. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having the desired activity. This is because the skilled artisan is fully aware of amino acid substitutions that are either less likely or not likely to significantly affect protein function (e.g., replacing one aliphatic amino acid with a second aliphatic amino acid).

For example, guidance concerning how to make phenotypically silent amino acid substitutions is provided in Bowie, J. U. et al. 1990 *Science* 247:1306-1310, wherein the authors indicate that proteins are surprisingly tolerant of amino acid substitutions.

Polypeptides and Fragments

The invention further provides filovirus and adenovirus polypeptides having the amino acid sequence encoded by an open reading frame (ORF) of a wild-type or modified filovirus or adenovirus structural gene, or a peptide or polypeptide comprising a portion thereof.

It will be recognized in the art that some amino acid sequences of the filovirus polypeptides can be varied without significant effect on the structure or function of the protein. If such differences in sequence are contemplated, it should be remembered that there will be critical areas on the protein which determine activity.

Thus, the invention further includes variations of the filovirus or adenovirus polypeptides which show substantial antigenic or other relevant biological activity. Such mutants include deletions, insertions, inversions, repeats, and type substitutions. As indicated, guidance concerning which amino acid changes are likely to be phenotypically silent can be found in Bowie, J. U. et al. 1990 *Science* 247:1306-1310.

Thus, the fragment, derivative or analog of the polypeptide of the invention may be (i) one in which one or more of the amino acid residues are substituted with a conserved or non-conserved amino acid residue and such substituted amino acid residue may or may not be one encoded by the genetic code, or (ii) one in which one or more of the amino acid residues include a substituent group, or (iii) one in which additional amino acids are fused to the mature polypeptide. Such fragments, derivatives and analogs are deemed to be within the scope of those skilled in the art from the teachings herein.

Of course, the number of amino acid substitutions a skilled artisan would make depends on many factors, including those described above. Generally speaking, the number of amino acid substitutions for any given filovirus or adenovirus polypeptide will not be more than 50, 40, 30, 20, 10, 5 or 3.

Amino acids in the filovirus or adenovirus polypeptides of the present invention that are essential for the desired function can be identified by methods known in the art, such as site-directed mutagenesis or alanine-scanning mutagenesis (Cunningham & Wells 1989 *Science* 244:1081-1085). The latter procedure introduces single alanine mutations at every residue in the molecule. The resulting mutant molecules are then tested for biological activity such as changes in immunological character.

The polypeptides of the present invention are conveniently provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the filovirus or adenovirus polypeptide can be substantially purified by the one-step method described in Smith and Johnson 1988 Gene 67:31-40.

The polypeptides of the present invention include a polypeptide comprising a polypeptide having the amino acid sequence of a wild-type filovirus structural gene product or portion thereof or encoded by a nucleic acid sequence shown herein in the Sequence Listing; as well as polypeptides which are at least 95% identical, or at least 96%, 97%, 98%, or 99% identical to those described above.

By a polypeptide having an amino acid sequence at least, for example, 95% "identical" to a reference amino acid sequence of an filovirus or adenovirus polypeptide is intended that the amino acid sequence of the polypeptide is identical to the reference sequence except that the polypeptide sequence may include up to five amino acid alterations per each 100 amino acids of the reference amino acid of the filovirus or adenovirus polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98%, or 99% identical to a reference amino acid sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

EXAMPLES

The following examples are offered to illustrate, but not to limit the claimed invention.

Example 1

This example shows that humoral and cellular responses generated by ChAdC3 Ebola (S/G) and ChAdC3 Ebola (Zaire) were comparable to those generated by rAd 5Ebola (S/G) and rAd5 Ebola (Zaire) respectively.

Immunization of cynomologous macaques with ChAdC3 Ebola (Zaire) produced antigen-specific antibody and Cd4+ and Cd8+ T cell responses. Protection against infection with a lethal dose of EBOV-Zaire was also demonstrated, as 4 macaques survived the challenge after immunization with ChAdC3 Ebola (Zaire) (see FIGS. 1-7).

Example 2

This example shows that a single immunization with rChAdC3 Ebola (Zaire) elicited humoral and cellular immune responses comparable to those generated by rAd5 Ebola (Zaire).

Figure 8:
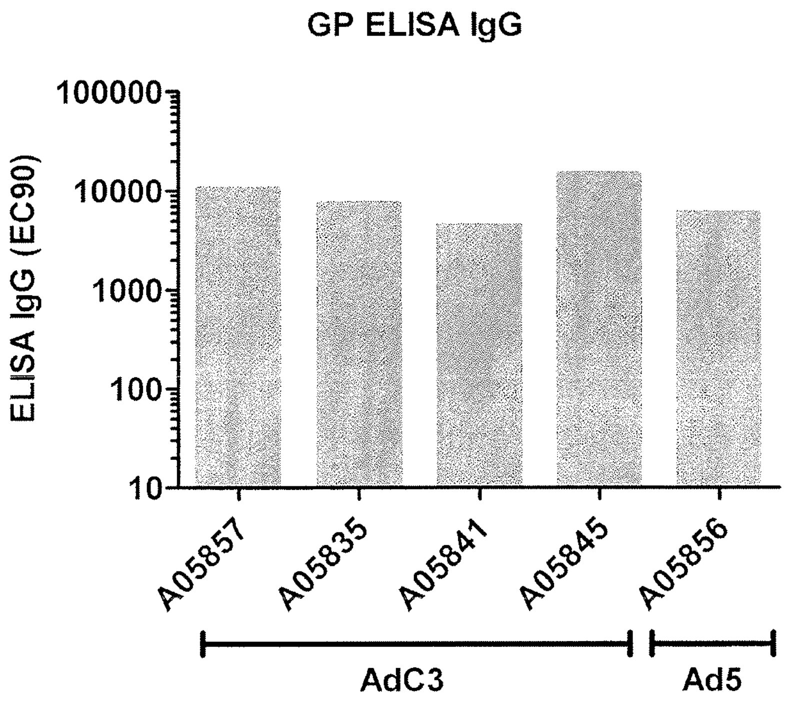
FIG. 8. A single immunization with $10^{10}$ vp of rAdC3 Ebola (Zaire) elicits antigen-specific Antibody responses. Cynomolgus macaques were vaccinated with rAdC3 or rAd5 encoding EBOV-GP at a dose of $10^{10}$ vp intramuscularly. Serum was collected at 4 weeks post Immunization to detect IgG responses against EBOV GP by ELISA.

Immunization of cynomologous macaques with rChAdC3 Ebola (Zaire) produced antigen-specific antibody and Cd4+ and Cd8+ T cell responses. Protection against infection with a lethal dose of EBOV-Zaire was also demonstrated, as 4 out of 4 macaques survived the challenge after immunization with rChAdC3 Ebola (Zaire) (see FIGS. 8-10).

Example 3

This example shows that a single immunization with adenoviral vectors encoding humanized Ebola glycoprotein (EBOV-GP) induced stronger cellular and humoral responses in mice than adenoviral vectors encoding non-humanized EBOV-GP.

Figure 11A:
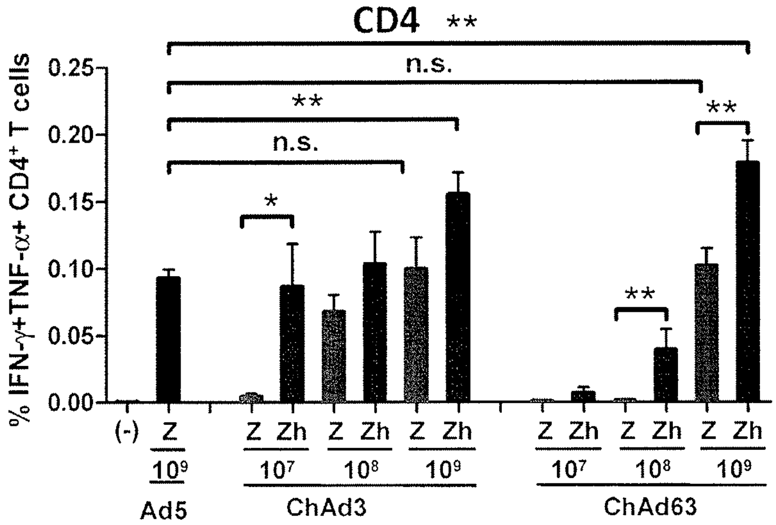
FIGS. 11A-11C rChAd vectors encoding humanized EBOV-GP or non-humanized EBOV-GP elicited potent immune responses in mice. Five 6-8 weeks female Balb/C mice in each group were immunized with rAd EBOV-GP at indicated $10^7$ or $10^8$ or $10^9$ viral particles through intramuscular injection.
Figure 11B:
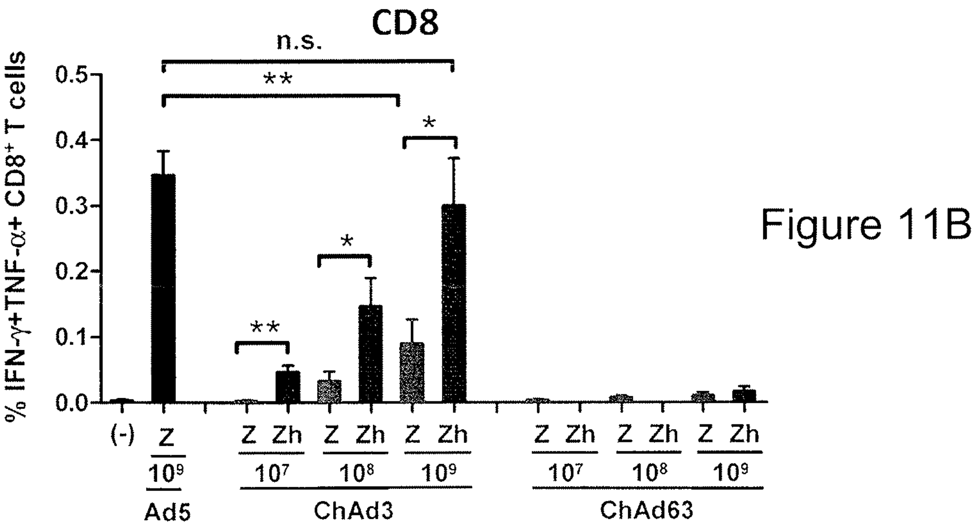
Figure 11C:
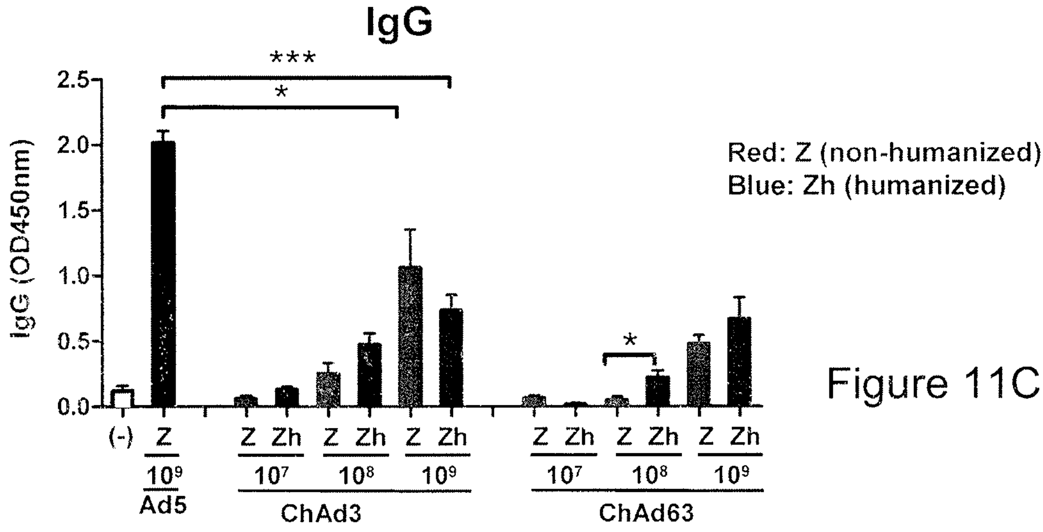

Groups of female Balb/C mice were immunized with rAd EBOV-GP (Z) at a dose of $10^7$, $10^8$, and $10^9$ viral particles via intramuscular injection. Cellular immune responses (Cd4+ and Cd8+ T cell responses) in PBMC and humoral responses (IgG) to EBOV-GP were measured at three weeks post immunization by ICS (intracellular cytokine staining) and ELISA, respectively. As shown in FIG. 11, immunization with adenoviral vectors rChAd3 and rChAd63 encoding EBOV-GP (Zh) codon optimized for expression in humans produced significantly higher percentages of CD4+ T cells that express cytokines IFN-γ and TNF-α than the same vectors encoding non-humanized (wild-type) EBOV-GP (Z) (SEQ ID NO:10), and these responses were significantly greater than the response due to rAd5 at $10^9$ viral particles.

Immunization with rChAd3 encoding humanized EBOV-GP produced significantly higher percentages of CD8+ T cells that express cytokines IFN-γ and TNF-α than the same vector encoding non-humanized EBOV-GP, and the percentage of cytokine positive cells was comparable, although not significantly different, to the percentage of cytokine positive CD8+ T cells produced by rAd5 at $10^9$ viral particles (see FIG. 11). There was no significant difference in the CD8+ response produced by rChAd63 encoding humanized and non-humanized EBOV-GP.

Immunization with rChAd63 encoding humanized EBOV-GP produced significantly higher IgG when compared to the same vector encoding non-humanized EBOV-GP at $10^8$ viral particles. There was no significant difference in the IgG response by rChAd3 encoding humanized and non-humanized EBOV-GP. Further, the IgG response by rChAd3 and rChAd63 encoding humanized and non-humanized EBOV-GP was significantly lower than response generated by Ad5 (see FIG. 11).

Example 4

This example shows that a prime/boost regimen using adenoviral vectors encoding EBOV-GP generated potent immune responses in mice.

Groups of female Balb/C mice were immunized with $10^8$ and $10^9$ rAd EBOV-GP (Z) viral particles via intramuscular injection at week 0 and boosted at week 3. Cellular and humoral immune responses were measured as described above at week 5.

Figure 12A:
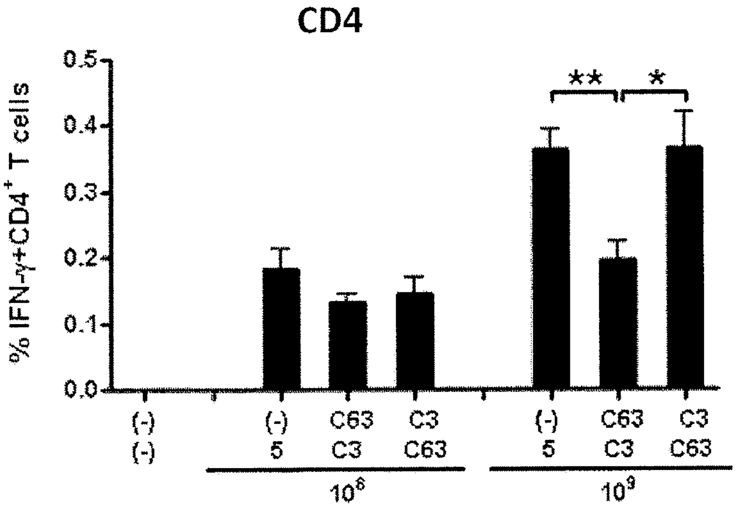
FIGS. 12A-12C rChAd prime and boost regimen generated potent immune responses in mice. Five 6-8 weeks female Balb/C mice in each group were immunized with rAd EBOV-GP at week 0 and boosted at week 3, at $10^8$ or $10^9$ viral particles as indicated through intramuscular injection.
Figure 12B:
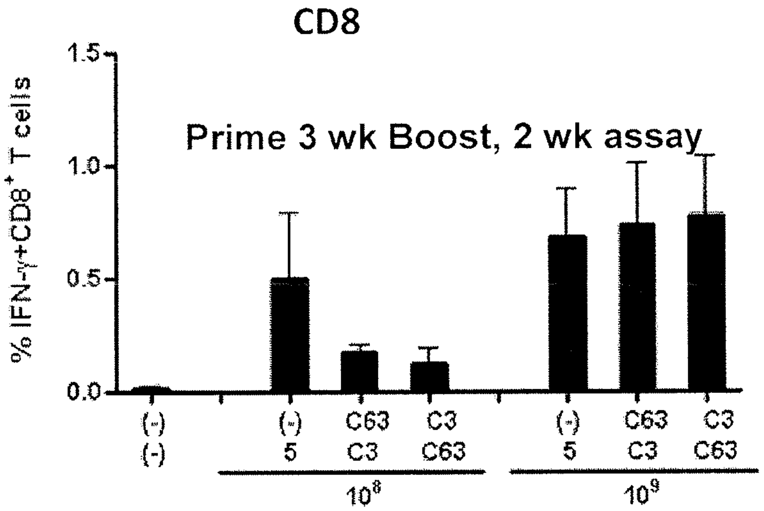
Figure 12C:
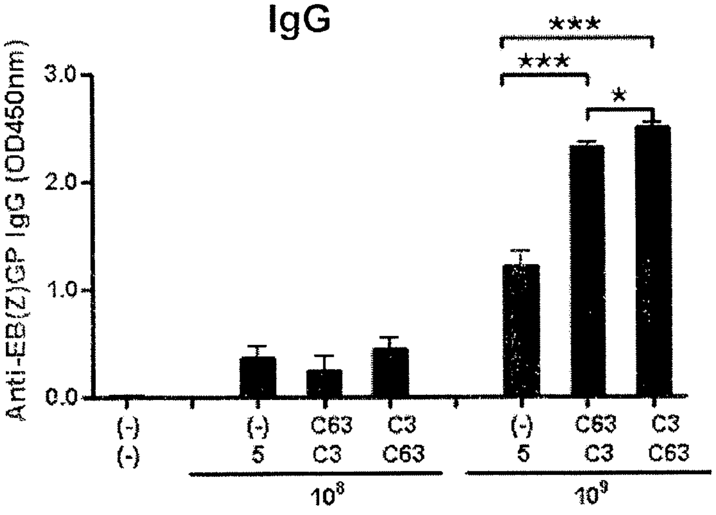

As shown in FIG. 12, prime with $10^9$ particles of rChAd3 and boost with $10^9$ particles of rChAd63 generated similar CD4+ and CD8+ responses as a single immunization at 3 weeks with rAd5. Likewise, prime with $10^9$ particles of rChAd63 and boost with $10^9$ particles of rChAd3 generated a similar CD8+ response as a single immunization at 3 weeks with rAd5, whereas this regimen produced a significantly lower CD4+ response.

Prime with $10^9$ particles of rChAd3 and boost with $10^9$ particles of rChAd63 generated a significantly higher IgG response than a single rAd5 immunization at 3 weeks.

Similarly, prime with $10^9$ particles of rChAd63 and boost with $10^9$ particles of rChAd3 generated a significantly higher IgG response than a single rAd5 immunization at 3 weeks.

Figure 13A:
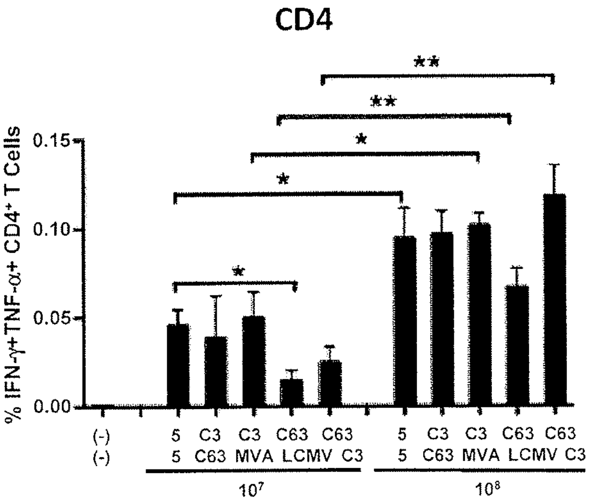
FIGS. 13A-13C rAd, rMVA and rLCMV vectors used in prime and boost regimen generated potent immune responses in mice. Five 6-8 weeks female Balb/C mice in each group were immunized with vectors encoding EBOV-GP at week 0 and boosted at week 4. rAd vectors were dosed at $10^7$ or $10^8$ viral particles as indicated, and MVA vectors at $10^5$ pfu, LCMV at $10^6$ pfu, through intramuscular injection
Figure 13B:
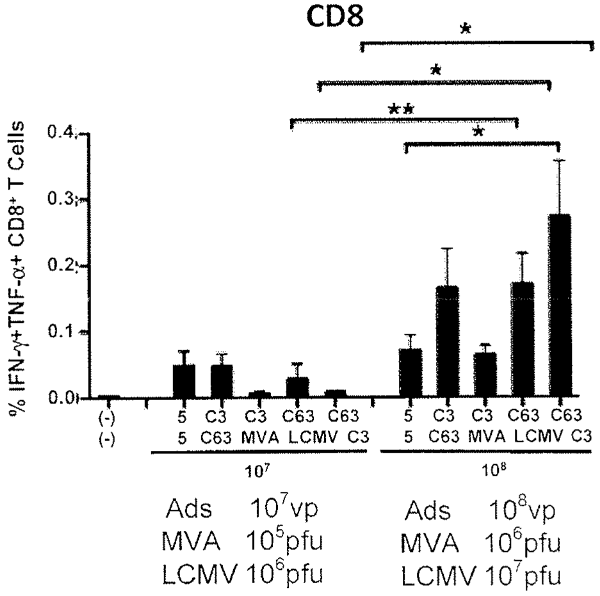
Figure 13C:
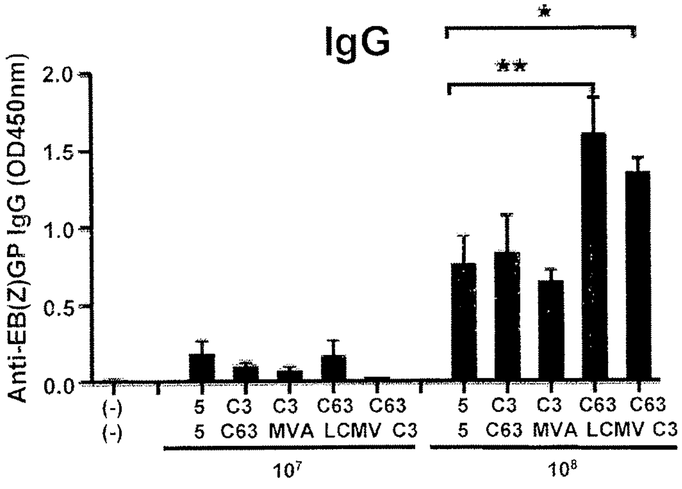

As shown in FIG. 13, prime with $10^8$ particles of rChAd63 and boost with $10^8$ particles of rChAd3 induced higher CD8+ and IgG responses than prime and boost with rAd5. The LCMV and MVA vectors were prepared as described above.

In summary, the above examples demonstrate that rChAd3 consistently generated comparable immune responses as rAd5 for single administration. Further, prime and boost with rChAd3/rChAd63, ChAd63/ChAd3, and ChAd3/LCMV are useful candidates for a combination regimen.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. An isolated nucleic acid molecule, wherein the isolated nucleic acid molecule comprises a sequence selected from the group consisting of SEQ ID NO:4, SEQ ID NO:5, SEQ ID NO:6, SEQ ID NO:7, SEQ ID NO:8, and SEQ ID NO:9.

2. The isolated nucleic acid molecule of claim 1, further comprising a promoter operably linked to said nucleic acid molecule.

3. The isolated nucleic acid molecule of claim 2, wherein the promoter is a CMV promoter.

4. A composition, comprising the isolated nucleic acid molecule of claim 1 and a pharmaceutically acceptable carrier.

5. The composition of claim 4, wherein the isolated nucleic acid molecule is contained in a viral particle.

* * * * *

SEQUENCE LISTING

```
<160> NUMBER OF SEQ ID NOS: 14

<210> SEQ ID NO 1
<211> LENGTH: 33104
<212> TYPE: DNA
<213> ORGANISM: Artificial Sequence
<220> FEATURE:
<223> OTHER INFORMATION: synthetic chimpanzee adenovirus serotype ChAd3
      with Ebola virus Zaire wild type transmembrane
      envelope glycoprotein (GP) insert (ChAd3 Ebola
      Zaire (PB/6001))
<220> FEATURE:
<221> NAME/KEY: CDS
<222> LOCATION: (2143)...(4444)
<223> OTHER INFORMATION: Ebola virus Zaire wild type transmembrane
      envelope glycoprotein (GP) insert in ChAd3 Ebola Zaire (PB/6001)
<220> FEATURE:
<221> NAME/KEY: CDS
<222> LOCATION: (15413)...(17194)
<223> OTHER INFORMATION: chimpanzee adenovirus serotype ChAd3 penton
<220> FEATURE:
<221> NAME/KEY: CDS
<222> LOCATION: (19086)...(21968)
<223> OTHER INFORMATION: chimpanzee adenovirus serotype ChAd3 hexon
<220> FEATURE:
<221> NAME/KEY: CDS
<222> LOCATION: (29962)...(31647)
<223> OTHER INFORMATION: chimpanzee adenovirus serotype ChAd3 fiber

<400> SEQUENCE: 1

catcatcaat aatatacctt attttggatt gaagccaata tgataatgag atgggcggcg     60

cggggcgggg cgcggggcgg gaggcgggtt tgggggcggg ccggcgggcg gggcggtgtg    120

gcggaagtgg actttgtaag tgtggcggat gtgacttgct agtgccgggc gcggtaaaag    180

tgacgttttc cgtgcgcgac aacgcccccg ggaagtgaca tttttcccgc ggtttttacc    240

ggatgttgta gtgaatttgg gcgtaaccaa gtaagatttg gccattttcg cgggaaaact    300

gaaacgggga agtgaaatct gattaatttt gcgttagtca taccgcgtaa tatttgtcta    360

gggccgaggg actttggccg attacgtgga ggactcgccc aggtgttttt tgaggtgaat    420

ttccgcgttc cgggtcaaag tctccgtttt attattatag gatatcccat tgcatacgtt    480

gtatccatat cataatatgt acatttatat tggctcatgt ccaacattac cgccatgttg    540

acattgatta ttgactagtt attaatagta atcaattacg gggtcattag ttcatagccc    600

atatatggag ttccgcgtta cataacttac ggtaaatggc ccgcctggct gaccgcccaa    660

cgacccccgc ccattgacgt caataatgac gtatgttccc atagtaacgc caatagggac    720

tttccattga cgtcaatggg tggagtattt acggtaaact gcccacttgg cagtacatca    780

agtgtatcat atgccaagta cgccccctat tgacgtcaat gacggtaaat ggcccgcctg    840

gcattatgcc cagtacatga ccttatggga ctttcctact tggcagtaca tctacgtatt    900

agtcatcgct attaccatgg tgatgcggtt ttggcagtac atcaatgggc gtggatagcg    960
```

-continued

```
gtttgactca cggggatttc caagtctcca ccccattgac gtcaatggga gtttgttttg   1020
gaaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg acgtaagtac   1320
cgcctataga ctctataggc acaccccttt ggctcttatg catgctatac tgtttttggc   1380
ttggggccta tacacccccg cttccttatg ctataggtga tggtatagct tagcctatag   1440
gtgtgggtta ttgaccatta ttgaccactc ccctattggt gacgatactt tccattacta   1500
atccataaca tggctctttg ccacaactat ctctattggc tatatgccaa tactctgtcc   1560
ttcagagact gacacggact ctgtattttt acaggatggg gtcccattta ttatttacaa   1620
attcacatat acaacaacgc cgtcccccgt gcccgcagtt tttattaaac atagcgtggg   1680
atctccacgc gaatctcggg tacgtgttcc ggacatgggc tcttctccgg tagcggcgga   1740
gcttccacat ccgagccctg gtcccatgcc tccagcggct catggtcgct cggcagctcc   1800
ttgctcctaa cagtggaggc cagacttagg cacagcacaa tgcccaccac caccagtgtg   1860
ccgcacaagg ccgtggcggt agggtatgtg tctgaaaatg agcgtggaga ttgggctcgc   1920
acggctgacg cagatggaag acttaaggca gcggcagaag aagatgcagg cagctgagtt   1980
gttgtattct gataagagtc agaggtaact cccgttgcgg tgctgttaac ggtggagggc   2040
agtgtagtct gagcagtact cgttgctgcc gcgcgcgcca ccagacataa tagctgacag   2100
actaacagac tgttcctttc catgggtctt ttctgcagtc accgtcgtcg acacgtgtga   2160
tcagatatcg cggccgctct agaccaggcc ctggatcgat ccaacaacac aatgggcgtt   2220
acaggaatat tgcagttacc tcgtgatcga ttcaagagga catcattctt tctttgggta   2280
attatccttt tccaaagaac attttccatc ccacttggag tcatccacaa tagcacatta   2340
caggttagtg atgtcgacaa actagtttgt cgtgacaaac tgtcatccac aaatcaattg   2400
agatcagttg gactgaatct cgaagggaat ggagtggcaa ctgacgtgcc atctgcaact   2460
aaaagatggg gcttcaggtc cggtgtccca ccaaaggtgg tcaattatga agctggtgaa   2520
tgggctgaaa actgctacaa tcttgaaatc aaaaaacctg acgggagtga gtgtctacca   2580
gcagcgccag acgggattcg gggcttcccc cggtgccggt atgtgcacaa agtatcagga   2640
acgggaccgt gtgccggaga ctttgccttc cataaagagg gtgctttctt cctgtatgat   2700
cgacttgctt ccacagttat ctaccgagga acgactttcg ctgaaggtgt cgttgcattt   2760
ctgatactgc cccaagctaa gaaggacttc ttcagctcac accccttgag agagccggtc   2820
aatgcaacgg aggacccgtc tagtggctac tattctacca caattagata tcaggctacc   2880
ggttttggaa ccaatgagac agagtacttg ttcgaggttg acaatttgac ctacgtccaa   2940
cttgaatcaa gattcacacc acagtttctg ctccagctga atgagacaat atatacaagt   3000
gggaaaagga gcaataccac gggaaaacta atttggaagg tcaaccccga aattgataca   3060
acaatcgggg agtgggcctt ctgggaaact aaaaaaaacc tcactagaaa aattcgcagt   3120
gaagagttgt ctttcacagt tgtatcaaac ggagccaaaa acatcagtgg tcagagtccg   3180
gcgcgaactt cttccgaccc agggaccaac acaacaactg aagaccacaa aatcatggct   3240
tcagaaaatt cctctgcaat ggttcaagtg cacagtcaag gaagggaagc tgcagtgtcg   3300
catctaacaa cccttgccac aatctccacg agtccccaat ccctcacaac caaaccaggt   3360
```

-continued

```
ccggacaaca gcacccataa tacacccgtg tataaacttg acatctctga ggcaactcaa   3420
gttgaacaac atcaccgcag aacagacaac gacagcacag cctccgacac tccctctgcc   3480
acgaccgcag ccggaccccc aaaagcagag aacaccaaca cgagcaagag cactgacttc   3540
ctggaccccg ccaccacaac aagtccccaa aaccacagcg agaccgctgg caacaacaac   3600
actcatcacc aagataccgg agaagagagt gccagcagcg ggaagctagg cttaattacc   3660
aatactattg ctggagtcgc aggactgatc acaggcggga gaagaactcg aagagaagca   3720
attgtcaatg ctcaacccaa atgcaaccct aatttacatt actggactac tcaggatgaa   3780
ggtgctgcaa tcggactggc ctggatacca tatttcgggc cagcagccga gggaatttac   3840
atagaggggc taatgcacaa tcaagatggt ttaatctgtg ggttgagaca gctggccaac   3900
gagacgactc aagctcttca actgttcctg agagccacaa ctgagctacg caccttttca   3960
atcctcaacc gtaaggcaat tgatttcttg ctgcagcgat ggggcggcac atgccacatt   4020
ctgggaccgg actgctgtat cgaaccacat gattggacca agaacataac agacaaaatt   4080
gatcagatta ttcatgattt tgttgataaa acccttccgg accagggga caatgacaat   4140
tggtggacag gatggagaca atggataccg gcaggtattg gagttacagg cgttgtaatt   4200
gcagttatcg ctttattctg tatatgcaaa tttgtctttt agtttttctt cagattgctt   4260
catggaaaag ctcagcctca aatcaatgaa accaggattt aattatatgg attacttgaa   4320
tctaagatta cttgacaaat gataatataa tacactggag ctttaaacat agccaatgtg   4380
attctaactc ctttaaactc acagttaatc ataaacaagg tttgaggtac cgagctcgaa   4440
ttgatctgct gtgccttcta gttgccagcc atctgttgtt tgcccctccc ccgtgccttc   4500
cttgaccctg gaaggtgcca ctcccactgt cctttcctaa taaaatgagg aaattgcatc   4560
gcattgtctg agtaggtgtc attctattct ggggggtggg gtggggcagg acagcaaggg   4620
ggaggattgg gaagacaata gcaggcatgc tggggatgcg gtgggcgata tcagcgatcg   4680
ctgaggtggg tgagtgggcg tggcctgggg tggtcatgaa aatatataag ttgggggtct   4740
tagggtctct ttatttgtgt tgcagagacc gccggagcca tgagcgggag cagcagcagc   4800
agcagtagca gcagcgcctt ggatggcagc atcgtgagcc cttatttgac gacgcggatg   4860
ccccactggg ccggggtgcg tcagaatgtg atgggctcca gcatcgacgg ccgacccgtc   4920
ctgcccgcaa attccgccac gctgacctat gcgaccgtcg cggggacgcc gttggacgcc   4980
accgccgccg ccgccgccac cgcagccgcc tcggccgtgc gcagcctggc cacggacttt   5040
gcattcctgg gaccactggc gacaggggct acttctcggg ccgctgctgc cgccgttcgc   5100
gatgacaagc tgaccgccct gctggcgcag ttggatgcgc ttactcggga actgggtgac   5160
ctttctcagc aggtcatggc cctgcgccag caggtctcct ccctgcaagc tggcgggaat   5220
gcttctccca caaatgccgt ttaagataaa taaaaccaga ctctgtttgg attaaagaaa   5280
agtagcaagt gcattgctct ctttatttca taattttccg cgcgcgatag gccctagacc   5340
agcgttctcg gtcgttgagg gtgcggtgta tcttctccag gacgtggtag aggtggctct   5400
ggacgttgag atacatgggc atgagcccgt cccgggggtg gaggtagcac cactgcagag   5460
cttcatgctc cggggtggtg ttgtagatga tccagtcgta gcaggagcgc tgggcatggt   5520
gcctaaaaat gtccttcagc agcaggccga tggccagggg gaggcccttg gtgtaagtgt   5580
ttacaaaacg gttaagttgg gaagggtgca ttcggggaga gatgatgtgc atcttggact   5640
gtatttttag attggcgatg tttccgccca gatcccttct gggattcatg ttgtgcagga   5700
```

-continued

```
ccaccagtac agtgtatccg gtgcacttgg ggaatttgtc atgcagctta gagggaaaag   5760
cgtggaagaa cttggagacg cccttgtggc ctcccagatt ttccatgcat tcgtccatga   5820
tgatggcaat gggcccgcgg gaggcagctt gggcaaagat atttctgggg tcgctgacgt   5880
cgtagttgtg ttccagggtg aggtcgtcat aggccatttt tacaaagcgc gggcggaggg   5940
tgcccgactg ggggatgatg gtcccctctg gccctggggc gtagttgccc tcgcagatct   6000
gcatttccca ggccttaatc tcggaggggg gaatcatatc cacctgcggg gcgatgaaga   6060
aaacggtttc cggagccggg gagattaact gggatgagag caggtttcta agcagctgtg   6120
attttccaca accggtgggc ccataaataa cacctataac cggttgcagc tggtagttta   6180
gagagctgca gctgccgtcg tcccggagga ggggggccac ctcgttgagc atgtccctga   6240
cgcgcatgtt ctccccgacc agatccgcca gaaggcgctc gccgcccagg gacagcagct   6300
cttgcaagga agcaaagttt ttcagcggct tgaggccgtc cgccgtgggc atgtttttca   6360
gggtctggct cagcagctcc aggcggtccc agagctcggt gacgtgctct acggcatctc   6420
tatccagcat atctcctcgt ttcgcgggtt ggggcgactt tcgctgtagg gcaccaagcg   6480
gtggtcgtcc agcggggcca aagtcatgtc cttccatggg cgcagggtcc tcgtcagggt   6540
ggtctgggtc acggtgaagg ggtgcgctcc gggctgagcg cttgccaagg tgcgcttgag   6600
gctggttctg ctggtgctga agcgctgccg gtcttcgccc tgcgcgtcgg ccaggtagca   6660
tttgaccatg gtgtcatagt ccagcccctc cgcggcgtgt cccttggcgc gcagcttgcc   6720
cttggaggtg gcgccgcacg aggggcagag caggctcttg agcgcgtaga gcttgggggc   6780
gaggaagacc gattcggggg agtaggcgtc cgcgccgcag accccgcaca cggtctcgca   6840
ctccaccagc caggtgagct cggggcgcgc cgggtcaaaa accaggtttc ccccatgctt   6900
tttgatgcgt ttcttacctc gggtctccat gaggtggtgt ccccgctcgg tgacgaagag   6960
gctgtccgtg tctccgtaga ccgacttgag ggtcttttc tccagggggg tccctcggtc   7020
ttcctcgtag aggaactcgg accactctga gacgaaggcc cgcgtccagg ccaggacgaa   7080
ggaggctatg tgggaggggt agcggtcgtt gtccactagg gggtccacct tctccaaggt   7140
gtgaagacac atgtcgcctt cctcggcgtc caggaaggtg attggcttgt aggtgtaggc   7200
cacgtgaccg gggttcctg acggggggt ataaaagggg gtgggggcgc gctcgtcgtc   7260
actctcttcc gcatcgctgt ctgcgagggc cagctgctgg ggtgagtatt ccctctcgaa   7320
ggcgggcatg acctccgcgc tgaggttgtc agtttccaaa aacgaggagg atttgatgtt   7380
cacctgtccc gaggtgatac ctttgagggt acccgcgtcc atctggtcag aaaacacgat   7440
ctttttattg tccagcttgg tggcgaacga cccgtagagg gcgttggaga gcagcttggc   7500
gatggagcgc agggtctggt tcttgtccct gtcggcgcgc tccttggccg cgatgttgag   7560
ctgcacgtac tcgcgcgcga cgcagcgcca ctcggggaag acggtggtgc gctcgtcggg   7620
caccaggcgc acgcgccagc cgcggttgtg cagggtgacc aggtccacgc tggtggcgac   7680
ctcgccgcgc aggcgctcgt tggtccagca gagacggccg cccttgcgcg agcagaaggg   7740
gggcaggggg tcgagctggg tctcgtccgg ggggtccgcg tccacggtga aaaccccggg   7800
gcgcaggcgc gcgtcgaagt agtctatctt gcaaccttgc atgtccagcg cctgctgcca   7860
gtcgcgggcg gcgagcgcgc gctcgtaggg gttgagcggc gggccccagg gcatggggtg   7920
ggtgagtgcg gaggcgtaca tgccgcagat gtcatagacg tagaggggct cccgcaggac   7980
cccgatgtag gtggggtagc agcggccgcc gcggatgctg gcgcgcacgt agtcatacag   8040
ctcgtgcgag gggcgagga ggtcggggcc caggttggtg cgggcggggc gctccgcgcg   8100
```

-continued

```
gaagacgatc tgcctgaaga tggcatgcga gttggaagag atggtggggc gctggaagac   8160
gttgaagctg gcgtcctgca ggccgacggc gtcgcgcacg aaggaggcgt aggagtcgcg   8220
cagcttgtgt accagctcgg cggtgacctg cacgtcgagc gcgcagtagt cgagggtctc   8280
gcggatgatg tcatatttag cctgcccctt ctttttccac agctcgcggt tgaggacaaa   8340
ctcttcgcgg tctttccagt actcttggat cgggaaaccg tccggttccg aacggtaaga   8400
gcctagcatg tagaactggt tgacggcctg gtaggcgcag cagcccttct ccacggggag   8460
ggcgtaggcc tgcgcggcct tgcggagcga ggtgtgggtc agggcgaagg tgtccctgac   8520
catgactttg aggtactggt gcttgaagtc ggagtcgtcg cagccgcccc gctcccagag   8580
cgagaagtcg gtgcgcttct tggagcgggg gttgggcaga gcgaaggtga catcgttgaa   8640
gaggattttg cccgcgcggg gcatgaagtt gcgggtgatg cggaagggcc ccggcacttc   8700
agagcggttg ttgatgacct gggcggcgag cacgatctcg tcgaagccgt tgatgttgtg   8760
gcccacgatg tagagttcca ggaagcgggg ccggcccttt acggtgggca gcttctttag   8820
ctcttcgtag gtgagctcct cgggcgaggc gaggccgtgc tcggccaggg cccagtccgc   8880
gaggtgcggg ttgtctctga ggaaggactc ccagaggtcg cgggccagga gggtctgcag   8940
gcggtccctg aaggtcctga actggcggcc cacggccatt ttttcggggg tgatgcagta   9000
gaaggtgagg gggtcttgct gccagcggtc ccagtcgagc tgcagggcga ggtcgcgcgc   9060
ggcggtgacc aggcgctcgt cgcccccgaa tttcatgacc agcatgaagg gcacgagctg   9120
ctttccgaag gcccccatcc aagtgtaggt ctctacatcg taggtgacaa agaggcgctc   9180
cgtgcgagga tgcgagccga tcgggaagaa ctggatctcc cgccaccagt tggaggagtg   9240
gctgttgatg tggtggaagt agaagtcccg tcgccgggcc gaacactcgt gctggctttt   9300
gtaaaagcga gcgcagtact ggcagcgctg cacgggctgt acctcctgca cgagatgcac   9360
ctttcgcccg cgcacgagga agccgagggg aaatctgagc cccccgcctg gctcgcggca   9420
tggctggtgc tcttctactt tggatgcgtg tccgtctccg tctggctcct cgaggggtgt   9480
tacggtggag cggaccacca cgccgcgcga gccgcaggtc cagatatcgg cgcgcggcgg   9540
tcggagtttg atgacgacat cgcgcagctg ggagctgtcc atggtctgga gctcccgcgg   9600
cggcggcagg tcagccggga gttcttgcag gttcacctcg cagagtcggg ccagggcgcg   9660
gggcaggtct aggtggtacc tgatctctag ggcgtgttgg gtggcggcgt cgatggcttg   9720
caggagcccg catccccggg gggcgacgac ggtgccccgc ggggtggtgg tggtggtggt   9780
ggtggtggtg gtggcggtgc agctcagaag cggtgccgcg ggcgggcccc cggaggtagg   9840
gggggctccg gtcccgccgg caggggcggc agcggcacgt cggcgtggag cgcgggcagg   9900
agttggtgct gtgcccggag gttgctggcg aaggcgacga cgcggcggtt gatctcctgg   9960
atctggcgcc tctgcgtgaa gacgacgggc ccggtgagct tgaacctgaa agagagttcg  10020
acagaatcaa tctcggtgtc attgaccgcg gcctggcgca ggatctcctg cacgtctccc  10080
gagttgtctt ggtaggcgat ctcggccatg aactgctcga tctcttcctc ctggaggtct  10140
ccgcgtccgg cgcgttccac ggtggccgcc aggtcgttgg agatgcgccc catgagctgc  10200
gagaaggcgt tgagtccgcc ctcgttccag actcggctgt agaccacgcc cccctggtca  10260
tcgcgggcgc gcatgaccac ctgcgcgagg ttgagctcca cgtgccgcgc gaagacggcg  10320
tagttgcgca gacgctggaa gaggtagttg agggtggtgg cggtgtgctc ggccacgaag  10380
aagttcatga cccagcggcg caacgtggat tcgttgatgt cccccaaggc ctccagccgt  10440
```

-continued

```
tccatggcct cgtagaagtc cacggcgaag ttgaaaaact gggagttgcg cgccgacacg  10500
gtcaactcct cctccagaag acggatgagc tcggcgacgg tgtcgcgcac ctcgcgctcg  10560
aaggctatgg ggatctcttc ctccgctagc atcaccacct cctcctcttc ctcctcttct  10620
ggcacttcca tgatggcttc ctcctcttcg gggggcggcg gcggcggcgg tgggggaggg  10680
ggcgctctgc gccggcggcg gcgcaccggg aggcggtcca cgaagcgcgc gatcatctcc  10740
ccgcggcggc ggcgcatggt ctcggtgacg gcgcggccgt tctcccgggg gcgcagttgg  10800
aagacgccgc cggacatctg gtgctggggc gggtggccgt gaggcagcga aacggcgctg  10860
acgatgcatc tcaacaattg ctgcgtaggt acgccgccga gggacctgag ggagtccata  10920
tccaccggat ccgaaaacct ttcgaggaag gcgtctaacc agtcgcagtc gcaaggtagg  10980
ctgagcaccg tggcgggcgg cggggggtgg ggggagtgtc tggcggaggt gctgctgatg  11040
atgtaattga agtaggcgga cttgacacgg cggatggtcg acaggagcac catgtccttg  11100
ggtccggcct gctggatgcg gaggcggtcg gctatgcccc aggcttcgtt ctggcatcgg  11160
cgcaggtcct tgtagtagtc ttgcatgagc ctttccaccg gcacctcttc tccttcctct  11220
tctgcttctt ccatgtctgc ttcggccctg gggcggcgcc gcgccccct gcccccatg  11280
cgcgtgaccc cgaacccct gagcggttgg agcagggcca ggtcggcgac gacgcgctcg  11340
gccaggatgg cctgctgcac ctgcgtgagg gtggtttgga agtcatccaa gtccacgaag  11400
cggtggtagg cgcccgtgtt gatggtgtag gtgcagttgg ccatgacgga ccagttgacg  11460
gtctggtggc ccggttgcga catctcggtg tacctgagtc gcgagtaggc gcgggagtcg  11520
aagacgtagt cgttgcaagt ccgcaccagg tactggtagc ccaccaggaa gtgcggcggc  11580
ggctggcggt agaggggcca gcgcagggtg gcgggggctc cgggggccag gtcttccagc  11640
atgaggcggt ggtaggcgta gatgtacctg gacatccagg tgatacccgc ggcggtggtg  11700
gaggcgcgcg ggaagtcgcg cacccggttc cagatgttgc gcaggggcag aaagtgctcc  11760
atggtaggcg tgctctgtcc agtcagacgc gcgcagtcgt tgatactcta gaccagggaa  11820
aacgaaagcc ggtcagcggg cactcttccg tggtctggtg aatagatcgc aagggtatca  11880
tggcggaggg cctcggttcg agccccgggt ccgggccgga cggtccgcca tgatccacgc  11940
ggttaccgcc cgcgtgtcga acccaggtgt gcgacgtcag acaacggtgg agtgttcctt  12000
ttggcgtttt tctggccggg cgccggcgtc gcgtaagaga ctaagccgcg aaagcgaaag  12060
cagtaagtgg ctcgctcccc gtagccggag ggatccttgc taagggttgc gttgcggcga  12120
accccggttc gaatcccgta ctcgggccgg ccggacccgc ggctaaggtg ttggattggc  12180
ctccccctcg tataaagacc ccgcttgcgg attgactccg gacacgggga cgagcccctt  12240
ttatttttgc tttccccaga tgcatccggt gctgcggcag atgcgccccc cgccccagca  12300
gcagcaacaa caccagcaag agcggcagca acagcagcgg gagtcatgca gggcccccctc  12360
acccaccctc ggcgggccgg ccacctcggc gtccgcggcc gtgtctggcg cctgcggcgg  12420
cggcgggggg ccggctgacg accccgagga gcccccgcgg cgcagggcca gacactacct  12480
ggacctggag gagggcgagg gcctggcgcg gctgggggcg ccgtctcccg agcgccaccc  12540
gcgggtgcag ctgaagcgcg actcgcgcga ggcgtacgtg cctcggcaga acctgttcag  12600
ggaccgcgcg ggcgaggagc ccgaggagat gcgggacagg aggttcagcg cagggcggga  12660
gctgcggcag gggctgaacc gcgagcggct gctgcgcgag gaggactttg agcccgacgc  12720
gcggacgggg atcagccccg cgcgcgcgca cgtggcggcc gccgacctgg tgacggcgta  12780
cgagcagacg gtgaaccagg agatcaactt ccaaaagagt ttcaacaacc acgtgcgcac  12840
```

-continued gctggtggcg cgcgaggagg tgaccatcgg gctgatgcac ctgtgggact ttgtaagcgc 12900
gctggtgcag aaccccaaca gcaagcctct gacggcgcag ctgttcctga tagtgcagca 12960
cagcagggac aacgaggcgt ttagggacgc gctgctgaac atcaccgagc ccgagggtcg 13020
gtggctgctg gacctgatta acatcctgca gagcatagtg gtgcaggagc gcagcctgag 13080
cctggccgac aaggtggcgg ccatcaacta ctcgatgctg agcctgggca agttttacgc 13140
gcgcaagatc taccagacgc cgtacgtgcc catagacaag gaggtgaaga tcgacggttt 13200
ttacatgcgc atggcgctga aggtgctcac cctgagcgac gacctgggcg tgtaccgcaa 13260
cgagcgcatc cacaaggccg tgagcgtgag ccggcggcgc gagctgagcg accgcgagct 13320
gatgcacagc ctgcagcggg cgctggcggg cgccggcagc ggcgacaggg aggcggagtc 13380
ctacttcgat gcgggggcgg acctgcgctg ggcgcccagc cggcgggccc tggaggccgc 13440
gggggtccgc gaggactatg acgaggacgg cgaggaggat gaggagtacg agctagagga 13500
gggcgagtac ctggactaaa ccgcgggtgg tgtttccggt agatgcaaga cccgaacgtg 13560
gtggacccgg cgctgcgggc ggctctgcag agccagccgt ccggccttaa ctcctcagac 13620
gactggcgac aggtcatgga ccgcatcatg tcgctgacgg cgcgtaaccc ggacgcgttc 13680
cggcagcagc cgcaggccaa caggctctcc gccatcctgg aggcggtggt gcctgcgcgc 13740
tcgaacccca cgcacgagaa ggtgctggcc atagtgaacg cgctggccga gaacagggcc 13800
atccgcccgg acgaggccgg gctggtgtac gacgcgctgc tgcagcgcgt ggcccgctac 13860
aacagcggca acgtgcagac caacctggac cggctggtgg gggacgtgcg cgaggcggtg 13920
gcgcagcgcg agcgcgcgga tcggcagggc aacctgggct ccatggtggc gctgaatgcc 13980
ttcctgagca cgcagccggc caacgtgccg cgggggcagg aagactacac caactttgtg 14040
agcgcgctgc ggctgatggt gaccgagacc ccccagagcg aggtgtacca gtcgggcccg 14100
gactacttct tccagaccag cagacagggc ctgcagacgg tgaacctgag ccaggctttc 14160
aagaacctgc gggggctgtg gggcgtgaag gcgcccaccg gcgaccgggc gacggtgtcc 14220
agcctgctga cgcccaactc gcgcctgctg ctgctgctga tcgcgccgtt cacggacagc 14280
ggcagcgtgt cccgggacac ctacctgggg cacctgctga ccctgtaccg cgaggccatc 14340
gggcaggcgc aggtggacga gcacaccttc caggagatca ccagcgtgag ccgcgcgctg 14400
gggcaggagg acacgagcag cctggaggcg actctgaact acctgctgac caaccggcgg 14460
cagaagattc cctcgctgca cagcctgacc tccgaggagg agcgcatctt gcgctacgtg 14520
cagcagagcg tgagcctgaa cctgatgcgc gacggggtga cgcccagcgt ggcgctggac 14580
atgaccgcgc gcaacatgga accgggcatg tacgccgcgc accggcctta catcaaccgc 14640
ctgatggact acctgcatcg cgcggcggcc gtgaaccccg agtactttac caacgccatc 14700
ctgaacccgc actggctccc gccgcccggg ttctacagcg gggcttcga ggtcccggag 14760
gccaacgatg gcttcctgtg ggacgacatg gacgacagcg tgttctcccc gcggccgcag 14820
gcgctggcgg aagcgtccct gctgcgtccc aagaaggagg aggaggaggc gagtcgccgc 14880
cgcggcagca gcggcgtggc ttctctgtcc gagctggggg cggcagccgc cgcgcgcccc 14940
gggtccctgg gcggcagccc ctttccgagc ctggtggggt ctctgcacag cgagcgcacc 15000
acccgccctc ggctgctggg cgaggacgag tacctgaata actccctgct gcagccggtg 15060
cgggagaaaa acctgccccc cgccttcccc aacaacggga tagagagcct ggtggacaag 15120
atgagcagat ggaagaccta tgcgcaggag cacagggacg cgcccgcgct ccggccgccc 15180

-continued acgcggcgcc agcgccacga ccggcagcgg gggctggtgt gggatgacga ggactccgcg 15240
gacgatagca gcgtgctgga cctgggaggg agcggcaacc cgttcgcgca cctgcgcccc 15300
cgcctgggga ggatgtttta aaaaaaaaaa aagcaagaag catgatgcaa aattaaataa 15360
aactcaccaa ggccatggcg accgagcgtt ggtttcttgt gttcccttca gtatgcggcg 15420
cgcggcgatg taccaggagg gacctcctcc ctcttacgag agcgtggtgg gcgcggcggc 15480
ggcggcgccc tcttctccct ttgcgtcgca gctgctggag ccgccgtacg tgcctccgcg 15540
ctacctgcgg cctacggggg ggagaaacag catccgttac tcggagctgg cgcccctgtt 15600
cgacaccacc cgggtgtacc tggtggacaa caagtcggcg gacgtggcct ccctgaacta 15660
ccagaacgac cacagcaatt ttttgaccac ggtcatccag aacaatgact acagcccgag 15720
cgaggccagc acccagacca tcaatctgga tgaccggtcg cactggggcg gcgacctgaa 15780
aaccatcctg cacaccaaca tgcccaacgt gaacgagttc atgttcacca ataagttcaa 15840
ggcgcgggtg atggtgtcgc gctcgcacac caaggaagac cgggtggagc tgaagtacga 15900
gtgggtggag ttcgagctgc cagagggcaa ctactccgag accatgacca ttgacctgat 15960
gaacaacgcg atcgtggagc actatctgaa agtgggcagg caaaacgggg tcctggagag 16020
cgacatcggg gtcaagttcg acaccaggaa cttccgcctg gggctggacc ccgtgaccgg 16080
gctggttatg cccggggtgt acaccaacga ggccttccat cccgacatca tcctgctgcc 16140
cggctgcggg gtggacttca cttacagccg cctgagcaac ctcctgggca tccgcaagcg 16200
gcagcccttc caggagggct tcaggatcac ctacgaggac ctggaggggg gcaacatccc 16260
cgcgctcctc gatgtggagg cctaccagga tagcttgaag gaaaatgagg cgggacagga 16320
ggataccacc cccgccgcct ccgccgccgc cgagcagggc gaggatgctg ctgacaccgc 16380
ggccgcggac ggggcagagg ccgaccccgc tatggtggtg gaggctcccg agcaggagga 16440
ggatatgaat gacagtgcgg tgcgcggaga caccttcgtc acccgggggg aggaaaagca 16500
agcggaggcc gaggccgcgg ccgaggaaaa gcaactggcg gcagcagcgg cggcggcggc 16560
gttggccgcg gcggaggctg agtctgaggg gaccaagccc gccaaggagc ccgtgattaa 16620
gcccctgacc gaagatagca agaagcgcag ttacaacctg ctcaaggaca gcaccaacac 16680
cgcgtaccgc agctggtacc tggcctacaa ctacggcgac ccgtcgacgg gggtgcgctc 16740
ctggaccctg ctgtgcacgc cggacgtgac ctgcggctcg gagcaggtgt actggtcgct 16800
gcccgacatg atgcaagacc ccgtgacctt ccgctccacg cggcaggtca gcaacttccc 16860
ggtggtgggc gccgagctgc tgcccgtgca ctccaagagc ttctacaacg accaggccgt 16920
ctactcccag ctcatccgcc agttcacctc tctgacccac gtgttcaatc gctttcctga 16980
gaaccagatt ctggcgcgcc cgcccgcccc caccatcacc accgtcagtg aaaacgttcc 17040
tgctctcaca gatcacggga cgctaccgct gcgcaacagc atcggaggag tccagcgagt 17100
gaccgttact gacgccagac gccgcacctg cccctacgtt tacaaggcct tgggcatagt 17160
ctcgccgcgc gtcctttcca gccgcacttt ttgagcaaca ccaccatcat gtccatcctg 17220
atctcaccca gcaataactc cggctgggga ctgctgcgcg cgcccagcaa gatgttcgga 17280
ggggcgagga agcgttccga gcagcacccc gtgcgcgtgc gcgggcactt ccgcgccccc 17340
tggggagcgc acaaacgcgg ccgcgcgggg cgcaccaccg tggacgacgc catcgactcg 17400
gtggtggagc aggcgcgcaa ctacaggccc gcggtctcta ccgtggacgc ggccatccag 17460
accgtggtgc ggggcgcgcg gcggtacgcc aagctgaaga gccgccggaa gcgcgtggcc 17520
cgccgccacc gccgccgacc cggggccgcc gccaaacgcg ccgccgcggc cctgcttcgc 17580

-continued

```
cgggccaagc gcacgggccg ccgcgccgcc atgagggccg cgcgccgctt ggccgccggc  17640
atcaccgccg ccaccatggc cccccgtacc cgaagacgcg cggccgccgc cgccgccgcc  17700
gccatcagtg acatggccag caggcgccgg ggcaacgtgt actgggtgcg cgactcggtg  17760
accggcacgc gcgtgcccgt gcgcttccgc ccccgcgga cttgagatga tgtgaaaaaa  17820
caacactgag tctcctgctg ttgtgtgtat cccagcggcg gcggcgcgcg cagcgtcatg  17880
tccaagcgca aaatcaaaga agagatgctc caggtcgtcg cgccggagat ctatgggccc  17940
ccgaagaagg aagagcagga ttcgaagccc cgcaagataa agcgggtcaa aaagaaaaag  18000
aaagatgatg acgatgccga tggggaggtg gagttcctgc gcgccacggc gcccaggcgc  18060
ccggtgcagt ggaagggccg gcgcgtaaag cgcgtcctgc gccccggcac cgcggtggtc  18120
ttcacgcccg gcgagcgctc cacccggact ttcaagcgcg tctatgacga ggtgtacggc  18180
gacgaagacc tgctggagca ggccaacgag cgcttcggag agtttgctta cgggaagcgt  18240
cagcgggcgc tggggaagga ggacctgctg gcgctgccgc tggaccaggg caaccccacc  18300
cccagtctga agcccgtgac cctgcagcag gtgctgccga gcagcgcacc ctccgaggcg  18360
aagcggggtc tgaagcgcga gggcggcgac ctggcgccca ccgtgcagct catggtgccc  18420
aagcggcaga ggctggagga tgtgctggag aaaatgaaag tagaccccgg tctgcagccg  18480
gacatcaggg tccgtcccat caagcaggtg gcgccgggcc tcggcgtgca gaccgtggac  18540
gtggtcatcc ccaccggcaa ctcccccgcc gccaccacca ctaccgctgc ctccacggac  18600
atggagacac agaccgatcc cgccgcagcc gcagccgccg ccgcagccgc gacctcctcg  18660
gcggaggtgc agacggaccc ctggctgccg ccggcgatgt cagctccccg cgcgcgccgc  18720
ggacgcagaa agtacggcgc cgccaacgcg ctcctgcccg agtacgcctt gcatccttcc  18780
atcgcgccca cccccggcta ccgaggctat acctaccgcc cgcgaagagc caagggttcc  18840
acccgccgtc cccgccgacg cgccgccgcc accacccgcc gccgccgccg cagacgccag  18900
cccgcactgg ctccagtctc cgtgaggaga gtggcgcgcg acggacacac cctggtgctg  18960
cccagggcgc gctaccaccc cagcatcgtt taaaagcctg ttgtggttct tgcagatatg  19020
gccctcactt gccgcctccg tttcccggtg ccgggatacc gaggaggaag atcgcgccgc  19080
aggaggggtc tggccggccg cggcctgagc ggaggcagcc gccgcgcgca ccggcggcga  19140
cgcgccacca gccgacgcat gcgcggcggg gtgctgcccc tgttaatccc cctgatcgcc  19200
gcggcgatcg gcgccgtgcc cgggatcgcc tccgtggcct tgcaagcgtc ccagaggcat  19260
tgacagactt gcaaacttgc aaatatggaa aaaaaaaaaa aaccccaata aaaagtctag  19320
actctcacgc tcgcttggtc ctgtgactat tttgtagaat ggaagacatc aactttgcgt  19380
cgctggcccc gcgtcacggc tcgcgcccgt tcctgggaca ctggaacgat atcggcacca  19440
gcaacatgag cggtggcgcc ttcagttggg gctctctgtg gagcggcatt aaaagtatcg  19500
ggtctgccgt taaaaattac ggctcccggg cctggaacag cagcacgggc cagatgttga  19560
gagacaagtt gaaagagcag aacttccagc agaaggtggt ggagggcctg gcctccggca  19620
tcaacggggt ggtggacctg gccaaccagg ccgtgcagaa taaaatcaac agcagactgg  19680
acccccggcc gccggtggag gaggtgccgc cggcgctgga gacggtgtcc cccgatgggc  19740
gtggcgagaa gcgcccgcgg cccgataggg aagagaccac tctggtcacg cagaccgatg  19800
agccgccccc gtatgaggag gccctaaagc aaggtctgcc caccacgcgg cccatcgcgc  19860
ccatggccac cggggtggtg ggccgccaca cccccgccac gctggacttg cctccgcccg  19920
```

-continued

```
ccgatgtgcc gcagcagcag aaggcggcac agccgggccc gcccgcgacc gcctcccgtt  19980
cctccgccgg tcctctgcgc cgcgcggcca gcggcccccg cgggggggtc gcgaggcacg  20040
gcaactggca gagcacgctg aacagcatcg tgggtctggg ggtgcggtcc gtgaagcgcc  20100
gccgatgcta ctgaatagct tagctaacgt gttgtatgtg tgtatgcgcc ctatgtcgcc  20160
gccagaggag ctgctgagtc gccgccgttc gcgcgcccac caccaccgcc actccgcccc  20220
tcaagatggc gaccccatcg atgatgccgc agtggtcgta catgcacatc tcgggccagg  20280
acgcctcgga gtacctgagc cccgggctgg tgcagttcgc ccgcgccacc gagagctact  20340
tcagcctgag taacaagttt aggaacccca cggtggcgcc cacgcacgat gtgaccaccg  20400
accggtctca gcgcctgacg ctgcggttca ttcccgtgga ccgcgaggac accgcgtact  20460
cgtacaaggc gcggttcacc ctggccgtgg gcgacaaccg cgtgctggac atggcctcca  20520
cctactttga catccgcggg gtgctggacc ggggtcccac tttcaagccc tactctggca  20580
ccgcctacaa ctccctggcc cccaagggcg ctcccaactc ctgcgagtgg gagcaagagg  20640
aaactcaggc agttgaagaa gcagcagaag aggaagaaga agatgctgac ggtcaagctg  20700
aggaagagca agcagctacc aaaaagactc atgtatatgc tcaggctccc ctttctggcg  20760
aaaaaattag taaagatggt ctgcaaatag gaacggacgc tacagctaca gaacaaaaac  20820
ctatttatgc agaccctaca ttccagcccg aaccccaaat cggggagtcc cagtggaatg  20880
aggcagatgc tacagtcgcc ggcggtagag tgctaaagaa atctactccc atgaaaccat  20940
gctatggttc ctatgcaaga cccacaaatg ctaatggagg tcagggtgta ctaacggcaa  21000
atgcccaggg acagctagaa tctcaggttg aaatgcaatt cttttcaact tctgaaaacg  21060
cccgtaacga ggctaacaac attcagccca aattggtgct gtatagtgag gatgtgcaca  21120
tggagacccc ggatacgcac ctttcttaca agcccgcaaa aagcgatgac aattcaaaaa  21180
tcatgctggg tcagcagtcc atgcccaaca gacctaatta catcggcttc agagacaact  21240
ttatcggcct catgtattac aatagcactg gcaacatggg agtgcttgca ggtcaggcct  21300
ctcagttgaa tgcagtggtg gacttgcaag acagaaacac agaactgtcc taccagctct  21360
tgcttgattc catgggtgac agaaccagat acttttccat gtggaatcag gcagtggaca  21420
gttatgaccc agatgttaga attattgaaa atcatggaac tgaagacgag ctccccaact  21480
attgtttccc tctgggtggc ataggggtaa ctgacactta ccaggctgtt aaaaccaaca  21540
atggcaataa cgggggccag gtgacttgga caaaagatga aacttttgca gatcgcaatg  21600
aaataggggt gggaaacaat ttcgctatgg agatcaacct cagtgccaac ctgtggagaa  21660
acttcctgta ctccaacgtg gcgctgtacc taccagacaa gcttaagtac aacccctcca  21720
atgtggacat ctctgacaac cccaacacct acgattacat gaacaagcga gtggtggccc  21780
cggggctggt ggactgctac atcaacctgg gcgcgcgctg gtcgctggac tacatggaca  21840
acgtcaaccc cttcaaccac caccgcaatg cgggcctgcg ctaccgctcc atgctcctgg  21900
gcaacgggcg ctacgtgccc ttccacatcc aggtgcccca gaagttcttt gccatcaaga  21960
acctcctcct cctgccgggc tcctacacct acgagtggaa cttcaggaag gatgtcaaca  22020
tggtcctcca gagctctctg ggtaacgatc tcagggtgga cggggccagc atcaagttcg  22080
agagcatctg cctctacgcc accttcttcc ccatggccca caacacggcc tccacgctcg  22140
aggccatgct caggaacgac accaacgacc agtccttcaa tgactacctt tccgccgcca  22200
acatgctcta ccccataccc gccaacgcca ccaacgtccc catctccatc cctcgcgca   22260
actgggcggc cttccgcggc tgggccttca cccgcctcaa gaccaaggag acccccctccc 22320
```

tgggctcggg attcgacccc tactacacct actcgggctc tattccctac ctggacggca 22380
ccttctacct caaccacact ttcaagaagg tctcggtcac cttcgactcc tcggtcagct 22440
ggccgggcaa cgaccgtctg ctcacccccca acgagttcga gatcaagcgc tcggtcgacg 22500
gggaaggcta caacgtggcc cagtgcaaca tgaccaagga ctggttcctg gtccagatgc 22560
tggccaacta caacatcggc taccagggct tctacatccc agagagctac aaggacagga 22620
tgtactcctt cttcaggaac ttccagccca tgagccggca ggtggtggac cagaccaagt 22680
acaaggacta ccaggaggtg ggcatcatcc accagcacaa caactcgggc ttcgtgggct 22740
acctcgcccc caccatgcgc gagggacagg cctaccccgc caacttcccc tacccgctca 22800
taggcaagac cgcggtcgac agcatcaccc agaaaaagtt cctctgcgac cgcaccctct 22860
ggcgcatccc cttctccagc aacttcatgt ccatgggtgc gctctcggac ctgggccaga 22920
acttgctcta cgccaactcc gcccacgccc tcgacatgac cttcgaggtc gaccccatgg 22980
acgagcccac ccttctctat gttctgttcg aagtctttga cgtggtccgg gtccaccagc 23040
cgcaccgcgg cgtcatcgag accgtgtacc tgcgtacgcc cttctcggcc ggcaacgcca 23100
ccacctaaag aagcaagccg cagtcatcgc cgcctgcatg ccgtcgggtt ccaccgagca 23160
agagctcagg gccatcgtca gagacctggg atgcgggccc tatttttttgg gcaccttcga 23220 caagcgcttc cctggctttg tctccccaca caagctggcc tgcgccatcg tcaacacggc 23280
cggccgcgag accgggggcg tgcactggct ggcctttgcc tggaacccgc gctccaaaac 23340
atgcttcctc tttgacccct tcggcttttc ggaccagcgg ctcaagcaaa tctacgagtt 23400
cgagtacgag ggcttgctgc gtcgcagcgc catcgcctcc tcgcccgacc gctgcgtcac 23460
cctcgaaaag tccacccaga ccgtgcaggg gcccgactcg gccgcctgcg gtctcttctg 23520
ctgcatgttt ctgcacgcct ttgtgcactg gcctcagagt cccatggacc gcaaccccac 23580
catgaacttg ctgacggggg tgcccaactc catgctccaa agcccccagg tcgagcccac 23640
cctgcgccgc aaccaggagc agctctacag cttcctggag cgccactcgc cctacttccg 23700
ccgccacagc gcacagatca ggagggccac ctccttctgc cacttgcaag agatgcaaga 23760
agggtaataa cgatgtacac actttttttct caataaatgg catttttttt ttatttatac 23820
aagctctctg gggtattcat ttcccaccac caccacccgc cgttgtcgcc atctggctct 23880
atttagaaat cgaaagggtt ctgccgggag tcgccgtgcg ccacgggcag ggacacgttg 23940
cgatactggt agcgggtgcc ccacttgaac tcgggcacca ccaggcgagg cagctcgggg 24000
aagttttcgc tccacaggct gcgggtcagc accagcgcgt tcatcaggtc gggcgccgag 24060
atcttgaagt cgcagttggg gccgccgccc tgcgcgcgcg agttgcggta caccgggttg 24120
cagcactgga acaccaacag cgccgggtgc ttcacgctgg ccagcacgct gcggtcggag 24180
atcagctcgg cgtccaggtc ctccgcgttg ctcagcgcga acggggtcat cttgggcact 24240
tgccgcccca ggaagggcgc gtgccccggt ttcgagttgc agtcgcagcg cagcgggatc 24300
agcaggtgcc cgtgcccgga ctcggcgttg gggtacagcg cgcgcatgaa ggcctgcatc 24360
tggcggaagg ccatctgggc cttggcgccc tccgagaaga acatgccgca ggacttgccc 24420
gagaactggt ttgcggggca gctggcgtcg tgcaggcagc agcgcgcgtc ggtgttggcg 24480
atctgcacca cgttgcgccc ccaccggttc ttcacgatct tggccttgga cgattgctcc 24540
ttcagcgcgc gctgcccgtt ctcgctggtc acatccatct cgatcacatg ttccttgttc 24600
accatgctgc tgccgtgcag acacttcagc tcgccctccg tctcggtgca gcggtgctgc 24660

-continued

```
cacagcgcgc agcccgtggg ctcgaaagac ttgtaggtca cctccgcgaa ggactgcagg  24720
taccccctgca aaaagcggcc catcatggtc acgaaggtct tgttgctgct gaaggtcagc  24780
tgcagcccgc ggtgctcctc gttcagccag gtcttgcaca cggccgccag cgcctccacc  24840
tggtcgggca gcatcttgaa gttcaccttc agctcattct ccacgtggta cttgtccatc  24900
agcgtgcgcg ccgcctccat gcccttctcc caggccgaca ccagcggcag gctcacgggg  24960
ttcttcacca tcaccgtggc cgccgcctcc gccgcgcttt cgctttccgc cccgctgttc  25020
tcttcctctt cctcctcttc ctcgccgccg cccactcgca gcccccgcac cacggggtcg  25080
tcttcctgca ggcgctgcac cttgcgcttg ccgttgcgcc cctgcttgat gcgcacgggc  25140
gggttgctga agcccaccat caccagcgcg gcctcttctt gctcgtcctc gctgtccaga  25200
atgacctccg gggagggggg gttggtcatc ctcagtaccg aggcacgctt ctttttcttc  25260
ctgggggcgt tcgccagctc cgcggctgcg gccgctgccg aggtcgaagg ccgagggctg  25320
ggcgtgcgcg gcaccagcgc gtcttgcgag ccgtcctcgt cctcctcgga ctcgagacgg  25380
aggcgggccc gcttcttcgg gggcgcgcgg ggcggcggag gcggcggcgg cgacggagac  25440
ggggacgaga catcgtccag ggtgggtgga cggcgggccg cgccgcgtcc gcgctcgggg  25500
gtggtttcgc gctggtcctc ttcccgactg gccatctccc actgctcctt ctcctatagg  25560
cagaaagaga tcatggagtc tctcatgcga gtcgagaagg aggaggacag cctaaccgcc  25620
ccctctgagc cctccaccac cgccgccacc accgccaatg ccgccgcgga cgacgcgccc  25680
accgagacca ccgccagtac caccctcccc agcgacgcac ccccgctcga gaatgaagtg  25740
ctgatcgagc aggacccggg ttttgtgagc ggagaggagg atgaggtgga tgagaaggag  25800
aaggaggagg tcgccgcctc agtgccaaaa gaggataaaa agcaagacca ggacgacgca  25860
gataaggatg agacagcagt cgggcggggg aacggaagcc atgatgctga tgacggctac  25920
ctagacgtgg gagacgacgt gctgcttaag cacctgcacc gccagtgcgt catcgtctgc  25980
gacgcgctgc aggagcgctg cgaagtgccc ctggacgtgg cggaggtcag ccgcgcctac  26040
gagcggcacc tcttcgcgcc gcacgtgccc cccaagcgcc gggagaacgg cacctgcgag  26100
cccaacccgc gtctcaactt ctacccggtc ttcgcggtac ccgaggtgct ggccacctac  26160
cacatcttct tccaaaactg caagatcccc ctctcctgcc gcgctaaccg cacccgcgcc  26220
gacaaaaccc tgaccctgcg gcagggcgcc cacatacctg atattgcctc tctggaggaa  26280
gtgcccaaga tcttcgaggg tctcggtcgc gacgagaaac gggcggcgaa cgctctgcac  26340
ggagacagcg aaaacgagag tcactcgggg gtgctggtgg agctcgaggg cgacaacgcg  26400
cgcctggccg tactcaagcg cagcatagag gtcacccact ttgcctaccc ggcgctcaac  26460
ctgccccccca aggtcatgag tgtggtcatg ggcgagctca tcatgcgccg cgctcagccc  26520
ctggccgcgg atgcaaactt gcaagagtcc tccgaggaag gcctgcccgc ggtcagcgac  26580
gagcagctag cgcgctggct ggagacccgc gaccccgcgc agctggagga gcggcgcaag  26640
ctcatgatgg ccgcggtgct ggtcaccgtg gagctcgagt gtctgcagcg cttcttcgcg  26700
gaccccgaga tgcagcgcaa gctcgaggag accctgcact acaccttccg ccagggctac  26760
gtgcgccagg cctgcaagat ctccaacgtg gagctctgca acctggtctc ctacctgggc  26820
atcctgcacg agaaccgcct cgggcagaac gtcctgcact ccaccctcaa aggggaggcg  26880
cgccgcgact acatccgcga ctgcgcctac ctcttcctct gctacacctg gcagacggcc  26940
atgggggtct ggcagcagtg cctggaggag cgcaacctca aggagctgga aaagctactc  27000
aagcgcaccc tcagggacct ctggacgggc ttcaacgagc gctcggtggc cgccgcgctg  27060
```

gcggacatca tcttccccga gcgcctgctc aagaccctgc agcagggcct gcccgacttc 27120
accagccaga gcatgctgca gaactttagg actttcatcc tggagcgctc gggcatcctg 27180
cctgccactt gctgcgcgct gcccagcgac ttcgtgccca tcaagtacag ggagtgcccg 27240
ccgccgctct ggggccactg ctacctcttc cagctggcca actacctcgc ctaccactcg 27300
gacctcatgg aagacgtgag cggcgagggc ctgctcgagt gccactgccg ctgcaacctc 27360
tgcacgcccc accgctctct agtctgcaac ccgcagctgc tcagcgagag tcagattatc 27420
ggtaccttcg agctgcaggg tccctcgcct gacgagaagt ccgcggctcc ggggctgaaa 27480
ctcactccgg ggctgtggac ttccgcctac ctacgcaaat ttgtacctga ggactaccac 27540
gcccacgaga tcaggttcta cgaagaccaa tcccgcccgc ccaaggcgga gctcaccgcc 27600
tgcgtcatca cccaggggca catcctgggc caattgcaag ccatcaacaa agcccgccga 27660
gagttcttgc tgaaaaaggg tcgggggtg tacctggacc cccagtccgg cgaggagcta 27720
aacccgctac ccccgccgcc gccccagcag cgggaccttg cttcccagga tggcacccag 27780
aaagaagcag cagccgccgc cgccgcagcc atacatgctt ctggaggaag aggaggagga 27840
ctgggacagt caggcagagg aggtttcgga cgaggagcag gaggagatga tggaagactg 27900
ggaggaggac agcagcctag acgaggaagc ttcagaggcc gaagaggtgg cagacgcaac 27960
accatcaccc tcggtcgcag cccccctcgcc ggggcccctg aaatcctccg aacccagcac 28020
cagcgctata acctccgctc ctccggcgcc ggcgccaccc gcccgcagac ccaaccgtag 28080
atgggacacc acaggaaccg ggtcggtaa gtccaagtgc ccgccgccgc caccgcagca 28140
gcagcagcag cgccagggct accgctcgtg gcgcgggcac aagaacgcca tagtcgcctg 28200
cttgcaagac tgcgggggca acatctcttt cgcccggcgc ttcctgctat tccaccacgg 28260
ggtcgccttt ccccgcaatg tcctgcatta ctaccgtcat ctctacagcc cctactgcag 28320
cggcgaccca gaggcggcag cggcagccac agcggcgacc accacctagg aagatatcct 28380
ccgcgggcaa gacagcggca gcagcggcca ggagacccgc ggcagcagcg gcgggagcgg 28440
tgggcgcact gcgcctctcg cccaacgaac ccctctcgac ccgggagctc agacacagga 28500
tcttccccac tttgtatgcc atcttccaac agagcagagg ccaggagcag gagctgaaaa 28560
taaaaaacag atctctgcgc tccctcaccc gcagctgtct gtatcacaaa agcgaagatc 28620
agcttcggcg cacgctggag gacgcggagg cactcttcag caaatactgc gcgctcactc 28680
ttaaagacta gctccgcgcc cttctcgaat ttaggcggga gaaaactacg tcatcgccgg 28740
ccgccgccca gcccgcccag ccgagatgag caaagagatt cccacgccat acatgtggag 28800
ctaccagccg cagatgggac tcgcggcggg agcggcccag gactactcca cccgcatgaa 28860
ctacatgagc gcgggacccc acatgatctc acaggtcaac gggatccgcg cccagcgaaa 28920
ccaaatactg ctggaacagg cggccatcac cgccacgccc cgccataatc tcaacccccg 28980
aaattggccc gccgccctcg tgtaccagga aaccccctcc gccaccaccg tactacttcc 29040
gcgtgacgcc caggccgaag tccagatgac taactcaggg gcgcagctcg cgggcggctt 29100
tcgtcacggg gcgcggccgc tccgaccagg tataagacac ctgatgatca gaggccgagg 29160
tatccagctc aacgacgagt cggtgagctc ttcgctcggt ctccgtccgg acggaacttt 29220
ccagctcgcc ggatccggcc gctcttcgtt cacgccccgc caggcgtacc tgactctgca 29280
gacctcgtcc tcggagcccc gctccggagg catcggaacc ctccagttcg tggaggagtt 29340
cgtgccctcg gtctacttca accccttctc gggacctccc ggacgctacc ccgaccagtt 29400

-continued cattccgaac tttgacgcgg tgaaggactc ggcggacggc tacgactgaa tgtcaggtgc 29460
cgaggcagag cagcttcgcc tgagacacct cgagcactgc cgccgccaca agtgcttcgc 29520
ccgcggttcc ggtgagttct gctactttca gctacccgag gagcataccg aggggccggc 29580
gcacggcgtc cgcctgacca cccagggcga ggttacctgt tccctcatcc gggagttcac 29640
cctccgtccc ctgctagtgg agcgggagcg gggtccctgt gtcctaacta tcgcctgcaa 29700
ctgccctaac cctggattac atcaagatct ttgctgtcat ctctgtgctg agtttaataa 29760
acgctgagat cagaatctac tgggaattcg atttagtccc ctttaactaa tcaaacactg 29820
gaatcaataa aaagaatcac ttacttaaaa tcagacagca ggtctctgtc cagtttattc 29880
agcagcacct ccttcccctc ctcccaactc tggtactcca aacgccttct ggcggcaaac 29940
ttcctccaca ccctgaaggg aatgtcagat tcttgctcct gtccctccgc acccactatc 30000
ttcatgttgt tgcagatgaa gcgcaccaaa acgtctgacg agagcttcaa ccccgtgtac 30060
ccctatgaca cggaaagcgg ccctccctcc gtccctttcc tcacccctcc cttcgtgtct 30120
cccgatggat tccaagaaag cccccccggg gtcctgtctc tgaacctggc cgagcccctg 30180
gtcacttccc acggcatgct cgccctgaaa atgggaagtg gcctctccct ggacgacgct 30240
ggcaacctca cctctcaaga tatcaccacc gctagccctc ccctcaaaaa aaccaagacc 30300
aacctcagcc tagaaacctc atcccccta actgtaagca cctcaggcgc cctcaccgta 30360
gcagccgccg ctcccctggc agtggccggc acctccctca ccatgcaatc agaggccccc 30420
ctgacagtac aggatgcaaa actcaccctg gccaccaaag gcccccctgac cgtgtctgaa 30480 ggcaaactgg ccttgcaaac atcggccccg ctgacggccg ctgacagcag caccctcacc 30540
gttagcgcca caccaccaat taatgtaagc agtggaagtt taggcttaga catggaagac 30600
cctatgtata ctcacgatgg aaaactggga ataagaattg gggtccact aagagtagta 30660 gacagcttgc acacactcac tgtagttacc ggaaatggac taactgtaga taacaatgcc 30720
ctccaaacta gagttacggg cgccctaggt tatgacacat caggaaatct acaattgaga 30780
gctgcaggag gtatgcgaat tgatgcaaat ggccaactta tccttaatgt ggcataccca 30840
tttgatgctc agaacaatct cagccttaga cttggtcagg gacccctgta tataaacaca 30900
gaccacaacc tggatttgaa ttgcaacaga ggtctaacca caactaccac caacaacaca 30960
aaaaaacttg agactaaaat tagctcaggc ttagactatg acaccaatgg tgctgtcatt 31020
attaaacttg gcactggtct aagcttcgac aacacaggcg ccctaactgt gggaaacact 31080
ggtgatgata aactgactct gtggacgacc ccagacccat ctccaaattg cagaattcac 31140
tcagacaaag actgcaagtt tactctagtc ctaactaagt gtggaagcca aatcctggcc 31200
tctgtcgccg ccctagcggt atcaggaaat ctggcttcga taacaggcac cgttgccagc 31260
gttaccatct ttctcagatt tgatcagaat ggagtgctta tggaaaactc ctcgctagac 31320
aggcagtact ggaacttcag aaatggcaac tcaactaacg ctgcccccta caccaatgca 31380
gttgggttca tgccaaacct cgcagcatac cccaaaacgc aaagccagac tgctaaaaac 31440
aacattgtaa gtcaggttta cttgaatgga gacaaatcca aacccatgac ccttaccatc 31500
accctcaatg gaactaatga atccagtgaa actagccagg tgagtcacta ctccatgtca 31560
tttacatggg cttgggaaag tgggcaatat gccactgaaa cctttgccac caactccttc 31620
accttttctt acattgctga acaataaaaa gcatgacact gatgttcatt tctgattctt 31680
attttattat tttcaaacac aacaaaatca ttcaagtcat tcttccatct tagcttaata 31740
gacacagtag cttaatagac ccagtagtgc aaagccccat tctagcttat aactagtgga 31800

-continued gaagtactcg cctacatggg ggtagagtca taatcgtgca tcaggatagg gcggtggtgc 31860
tgcagcagcg cgcgaataaa ctgctgccgc cgccgctccg tcctgcagga atacaacatg 31920
gcagtggtct cctcagcgat gattcgcacc gcccgcagca taaggcgcct tgtcctccgg 31980
gcacagcagc gcaccctgat ctcacttaaa tcagcacagt aactgcagca cagcaccaca 32040
atattgttca aaatcccaca gtgcaaggcg ctgtatccaa agctcatggc ggggaccaca 32100
gaacccacgt ggccatcata ccacaagcgc aggtagatta agtggcgacc cctcataaac 32160
acgctggaca taaacattac ctcttttggc atgttgtaat tcaccacctc ccggtaccat 32220
ataaacctct gattaaacat ggcgccatcc accaccatcc taaaccagct ggccaaaacc 32280
tgcccgccgg ctatacactg cagggaaccg ggactggaac aatgacagtg gagagcccag 32340
gactcgtaac catggatcat catgctcgtc atgatatcaa tgttggcaca acacaggcac 32400
acgtgcatac acttcctcag gattacaagc tcctcccgcg ttagaaccat atcccaggga 32460
acaacccatt cctgaatcag cgtaaatccc acactgcagg gaagacctcg cacgtaactc 32520
acgttgtgca ttgtcaaagt gttacattcg ggcagcagcg gatgatcctc cagtatggta 32580
gcgcgggttt ctgtctcaaa aggaggtaga cgatccctac tgtacggagt gcgccgagac 32640
aaccgagatc gtgttggtcg tagtgtcatg ccaaatggaa cgccggacgt agtcatattt 32700
cctgaagtct tagatctctc aacgcagcac cagcaccaac acttcgcagt gtaaaaggcc 32760
aagtgccgag agagtatata taggaataaa aagtgacgta aacgggcaaa gtccaaaaaa 32820
cgcccagaaa aaccgcacgc gaacctacgc cccgaaacga aagccaaaaa acactagaca 32880
ctcccttccg gcgtcaactt ccgctttccc acgctacgtc acttgcccca gtcaaacaaa 32940
ctacatatcc cgaacttcca agtcgccacg cccaaaacac cgcctacacc tccccgcccg 33000
ccggcccgcc cccaaacccg cctcccgccc cgcgccccgc cccgcgccgc ccatctcatt 33060
atcatattgg cttcaatcca aaataaggta tattattgat gatg 33104

<210> SEQ ID NO 2
<211> LENGTH: 32337
<212> TYPE: DNA
<213> ORGANISM: Artificial Sequence
<220> FEATURE:
<223> OTHER INFORMATION: synthetic chimpanzee adenovirus serotype ChAd3 with Ebola virus Sudan/Gulu codon optimized transmembrane envelope glycoprotein (GP) insert (ChAd3 GP Ebola S/G (PB/6611))
<220> FEATURE:
<221> NAME/KEY: CDS
<222> LOCATION: (1634)...(3664)
<223> OTHER INFORMATION: Ebola virus Sudan/Gulu codon optimized transmembrane envelope glycoprotein (GP) insert in ChAd3 GP Ebola S/G (PB/6611)
<220> FEATURE:
<221> NAME/KEY: CDS
<222> LOCATION: (14646)...(16427)
<223> OTHER INFORMATION: chimpanzee adenovirus serotype ChAd3 penton
<220> FEATURE:
<221> NAME/KEY: CDS
<222> LOCATION: (19459)...(22338)
<223> OTHER INFORMATION: chimpanzee adenovirus serotype ChAd3 hexon
<220> FEATURE:
<221> NAME/KEY: CDS
<222> LOCATION: (29195)...(30881)
<223> OTHER INFORMATION: chimpanzee adenovirus serotype ChAd3 fiber

<400> SEQUENCE: 2
catcatcaat aatatacctt attttggatt gaagccaata tgataatgag atgggcggcg 60
cggggcgggg cgcggggcgg gaggcgggtt tgggggcggg ccggcgggcg gggcggtgtg 120

-continued

```
gcggaagtgg actttgtaag tgtggcggat gtgacttgct agtgccgggc gcggtaaaag    180
tgacgttttc cgtgcgcgac aacgcccccg ggaagtgaca tttttcccgc ggtttttacc    240
ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctccgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gaaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccatcggctc gcatctctcc ttcacgcgcc cgccgcccta cctgaggccg ccatccacgc   1320
cggttgagtc gcgttctgcc gcctcccgcc tgtggtgcct cctgaactgc gtccgccgtc   1380
taggtaagtt taaagctcag gtcgagaccg ggcctttgtc cggcgctccc ttggagccta   1440
cctagactca gccggctctc cacgctttgc ctgaccctgc ttgctcaact ctagttaacg   1500
gtggagggca gtgtagtctg agcagtactc gttgctgccg cgcgcgccac cagacataat   1560
agctgacaga ctaacagact gttcctttcc atgggtcttt tctgcagtca ccgtcgtcga   1620
cgatatcgcc gccatggagg gcctgagcct gctgcagctg cccagggaca agttcaggaa   1680
gagcagcttc ttcgtgtggg tgatcatcct gttccagaag gccttcagca tgcccctggg   1740
cgtggtgacc aacagcaccc tggaggtgac cgagatcgac cagctggtgt gcaaggacca   1800
cctggccagc accgaccagc tgaagagcgt gggcctgaac ctggagggca gcggcgtgag   1860
caccgacatc cccagcgcca ccaagaggtg gggcttcagg agcggcgtgc ctcccaaggt   1920
ggtgagctac gaggccggcg agtgggccga gaactgctac aacctggaga tcaagaagcc   1980
cgacggcagc gagtgcctgc ctcctcctcc tgacggcgtg aggggcttcc ccaggtgcag   2040
gtacgtgcac aaggcccagg gcaccggccc ctgccccggc gactacgcct tccacaagga   2100
cggcgccttc ttcctgtacg acaggctggc cagcaccgtg atctacaggg gcgtgaactt   2160
cgccgagggc gtgatcgcct tcctgatcct ggccaagccc aaggagacct tcctgcagag   2220
ccctcccatc agggaggccg tgaactacac cgagaacacc agcagctact acgccaccag   2280
ctatctagag tacgagatcg agaacttcgg cgcccagcac agcaccaccc tgttcaagat   2340
cgacaacaac accttcgtga ggctggacag gccccacacc cctcagttcc tgttccagct   2400
gaacgacacc atccacctgc accagcagct gagcaacacc accggcaggc tgatctggac   2460
```

-continued

```
cctggacgcc aacatcaacg ccgacatcgg cgagtgggcc ttctgggaga acaagaagaa   2520
cctgagcgag cagctgaggg gcgaggagct gagcttcgag gccctgagcc tgaacgagac   2580
cgaggacgac gacgccgcca gcagcaggat caccaagggc aggatcagcg acagggccac   2640
caggaagtac agcgacctgg tgcccaagaa cagccccggc atggtgcccc tgcacatccc   2700
cgagggcgag accaccctgc ccagccagaa cagcaccgag ggcaggaggg tgggcgtgaa   2760
cacccaggag accatcaccg agaccgccgc caccatcatc ggcaccaacg gcaaccacat   2820
gcagatcagc accatcggca tcaggcccag cagcagccag atccccagca gcagccccac   2880
caccgcccct agccccgagg cccagacccc caccacccac accagcggac ccagcgtgat   2940
ggccaccgag gagcccacca cccctcccgg cagcagcccc ggacccacca ccgaggcccc   3000
taccctgacc accccctgaga acatcaccac cgccgtgaag accgtgctgc cccaggagag   3060
caccagcaac ggcctgatca ccagcaccgt gaccggcatc ctgggcagcc tgggcctgag   3120
gaagaggagc aggaggcaga ccaacaccaa ggccaccggc aagtgcaacc ccaacctgca   3180
ctactggacc gcccaggagc agcacaacgc cgccggcatc gcctggattc cctacttcgg   3240
ccccggcgcc gagggcatct acaccgaggg cctgatgcac aaccagaacg ccctggtgtg   3300
cggcctgagg cagctggcca acgagaccac ccaggccctg cagctgttcc tgagggccac   3360
caccgagctg aggacctaca ccatcctgaa caggaaggcc atcgacttcc tgctgaggag   3420
gtggggcggc acctgcagga ttctgggccc cgactgctgc atcgagcccc acgactggac   3480
caagaacatc accgacaaga tcaaccagat catccacgac ttcatcgaca accctctgcc   3540
caaccaggac aacgacgaca actggtggac cggctggcgg cagtggatac ctgccggcat   3600
cggcatcacc ggcatcatca tcgccatcat cgctctgctg tgcgtgtgca agctgctgtg   3660
ctgagaattc agatctgctg tgccttctag ttgccagcca tctgttgttt gcccctcccc   3720
cgtgccttcc ttgaccctgg aaggtgccac tcccactgtc ctttcctaat aaaatgagga   3780
aattgcatcg cattgtctga gtaggtgtca ttctattctg gggggtgggg tggggcagga   3840
cagcaagggg gaggattggg aagacaatag caggcatgct ggggatgcgg tgggctctag   3900
atatcagcga tcgctgaggt gggtgagtgg gcgtggcctg gggtggtcat gaaaatatat   3960
aagttggggg tcttagggtc tctttatttg tgttgcagag accgccggag ccatgagcgg   4020
gagcagcagc agcagcagta gcagcagcgc cttggatggc agcatcgtga gcccttattt   4080
gacgacgcgg atgccccact gggccggggt gcgtcagaat gtgatgggct ccagcatcga   4140
cggccgaccc gtcctgcccg caaattccgc cacgctgacc tatgcgaccg tcgcggggac   4200
gccgttggac gccaccgccg ccgccgccgc caccgcagcc gcctcggccg tgcgcagcct   4260
ggccacggac tttgcattcc tggaccact ggcgacaggg gctacttctc gggccgctgc   4320
tgccgccgtt cgcgatgaca agctgaccgc cctgctggcg cagttggatg cgcttactcg   4380
ggaactgggt gacctttctc agcaggtcat ggccctgcgc cagcaggtct cctccctgca   4440
agctggcggg aatgcttctc ccacaaatgc cgtttaagat aaataaaacc agactctgtt   4500
tggattaaag aaaagtagca agtgcattgc tctctttatt tcataatttt ccgcgcgcga   4560
taggccctag accagcgttc tcggtcgttg agggtgcggt gtatcttctc caggacgtgg   4620
tagaggtggc tctggacgtt gagatacatg ggcatgagcc cgtcccgggg gtggaggtag   4680
caccactgca gagcttcatg ctccggggtg gtgttgtaga tgatccagtc gtagcaggag   4740
cgctgggcat ggtgcctaaa aatgtccttc agcagcaggc cgatggccag gggaggccc   4800
ttggtgtaag tgtttacaaa acggttaagt tgggaagggt gcattcgggg agagatgatg   4860
```

-continued

```
tgcatcttgg actgtatttt tagattggcg atgtttccgc ccagatccct tctgggattc   4920
atgttgtgca ggaccaccag tacagtgtat ccggtgcact tggggaattt gtcatgcagc   4980
ttagagggaa aagcgtggaa gaacttggag acgcccttgt ggcctcccag attttccatg   5040
cattcgtcca tgatgatggc aatgggcccg cgggaggcag cttgggcaaa gatatttctg   5100
gggtcgctga cgtcgtagtt gtgttccagg gtgaggtcgt cataggccat ttttacaaag   5160
cgcgggcgga gggtgcccga ctgggggatg atggtcccct ctggccctgg ggcgtagttg   5220
ccctcgcaga tctgcatttc ccaggcctta atctcggagg ggggaatcat atccacctgc   5280
ggggcgatga agaaaacggt ttccggagcc ggggagatta actgggatga gagcaggttt   5340
ctaagcagct gtgattttcc acaaccggtg ggcccataaa taacacctat aaccggttgc   5400
agctggtagt ttagagagct gcagctgccg tcgtcccgga ggaggggggc cacctcgttg   5460
agcatgtccc tgacgcgcat gttctccccg accagatccg ccagaaggcg ctcgccgccc   5520
agggacagca gctcttgcaa ggaagcaaag tttttcagcg gcttgaggcc gtccgccgtg   5580
ggcatgtttt tcagggtctg gctcagcagc tccaggcggt cccagagctc ggtgacgtgc   5640
tctacggcat ctctatccag catatctcct cgtttcgcgg gttggggcga ctttcgctgt   5700
agggcaccaa gcggtggtcg tccagcgggg ccaaagtcat gtccttccat gggcgcaggg   5760
tcctcgtcag ggtggtctgg gtcacggtga aggggtgcgc tccgggctga gcgcttgcca   5820
aggtgcgctt gaggctggtt ctgctggtgc tgaagcgctg ccggtcttcg ccctgcgcgt   5880
cggccaggta gcatttgacc atggtgtcat agtccagccc ctccgcggcg tgtcccttgg   5940
cgcgcagctt gcccttggag gtggcgccgc acgaggggca gagcaggctc ttgagcgcgt   6000
agagcttggg ggcgaggaag accgattcgg gggagtaggc gtccgcgccg cagaccccgc   6060
acacggtctc gcactccacc agccaggtga gctcggggcg cgccgggtca aaaaccaggt   6120
ttcccccatg ctttttgatg cgtttcttac ctcgggtctc catgaggtgg tgtccccgct   6180
cggtgacgaa gaggctgtcc gtgtctccgt agaccgactt gaggggtctt ttctccaggg   6240
gggtccctcg gtcttcctcg tagaggaact cggaccactc tgagacgaag gcccgcgtcc   6300
aggccaggac gaaggaggct atgtgggagg ggtagcggtc gttgtccact agggggtcca   6360
ccttctccaa ggtgtgaaga cacatgtcgc cttcctcggc gtccaggaag gtgattggct   6420
tgtaggtgta ggccacgtga ccgggggttc ctgacggggg ggtataaaag ggggtggggg   6480
cgcgctcgtc gtcactctct tccgcatcgc tgtctgcgag ggccagctgc tggggtgagt   6540
attccctctc gaaggcgggc atgacctccg cgctgaggtt gtcagtttcc aaaaacgagg   6600
aggatttgat gttcacctgt cccgaggtga tacctttgag ggtacccgcg tccatctggt   6660
cagaaaacac gatcttttta ttgtccagct tggtggcgaa cgacccgtag agggcgttgg   6720
agagcagctt ggcgatggag cgcagggtct ggttcttgtc cctgtcggcg cgctccttgg   6780
ccgcgatgtt gagctgcacg tactcgcgcg cgacgcagcg ccactcgggg aagacggtgg   6840
tgcgctcgtc gggcaccagg cgcacgcgcc agccgcggtt gtgcagggtg accaggtcca   6900
cgctggtggc gacctcgccg cgcaggcgct cgttggtcca gcagagacgg ccgcccttgc   6960
gcgagcagaa ggggggcagg gggtcgagct gggtctcgtc cggggggtcc gcgtccacgg   7020
tgaaaacccc ggggcgcagg cgcgcgtcga agtagtctat cttgcaacct tgcatgtcca   7080
gcgcctgctg ccagtcgcgg gcggcgagcg cgcgctcgta ggggttgagc ggcgggcccc   7140
agggcatggg gtgggtgagt gcggaggcgt acatgccgca gatgtcatag acgtagaggg   7200
```

-continued

```
gctcccgcag gaccccgatg taggtggggt agcagcggcc gccgcggatg ctggcgcgca   7260
cgtagtcata cagctcgtgc gagggggcga ggaggtcggg gcccaggttg gtgcgggcgg   7320
ggcgctccgc gcggaagacg atctgcctga agatggcatg cgagttggaa gagatggtgg   7380
ggcgctggaa gacgttgaag ctggcgtcct gcaggccgac ggcgtcgcgc acgaaggagg   7440
cgtaggagtc gcgcagcttg tgtaccagct cggcggtgac ctgcacgtcg agcgcgcagt   7500
agtcgagggt ctcgcggatg atgtcatatt tagcctgccc cttctttttc cacagctcgc   7560
ggttgaggac aaactcttcg cggtctttcc agtactcttg gatcgggaaa ccgtccggtt   7620
ccgaacggta agagcctagc atgtagaact ggttgacggc ctggtaggcg cagcagccct   7680
tctccacggg gagggcgtag gcctgcgcgg ccttgcggag cgaggtgtgg gtcagggcga   7740
aggtgtccct gaccatgact ttgaggtact ggtgcttgaa gtcggagtcg tcgcagccgc   7800
cccgctccca gagcgagaag tcggtgcgct tcttggagcg gggggttgggc agagcgaagg   7860
tgacatcgtt gaagaggatt ttgcccgcgc ggggcatgaa gttgcgggtg atgcggaagg   7920
gccccggcac ttcagagcgg ttgttgatga cctgggcggc gagcacgatc tcgtcgaagc   7980
cgttgatgtt gtggcccacg atgtagagtt ccaggaagcg gggccggccc tttacggtgg   8040
gcagcttctt tagctcttcg taggtgagct cctcgggcga ggcgaggccg tgctcggcca   8100
gggcccagtc cgcgaggtgc gggttgtctc tgaggaagga ctcccagagg tcgcgggcca   8160
ggagggtctg caggcggtcc ctgaaggtcc tgaactggcg gcccacggcc atttttcgg    8220
gggtgatgca gtagaaggtg agggggtctt gctgccagcg gtcccagtcg agctgcaggg   8280
cgaggtcgcg cgcggcggtg accaggcgct cgtcgccccc gaatttcatg accagcatga   8340
agggcacgag ctgctttccg aaggccccca tccaagtgta ggtctctaca tcgtaggtga   8400
caaagaggcg ctccgtgcga ggatgcgagc cgatcgggaa gaactggatc tcccgccacc   8460
agttggagga gtggctgttg atgtggtgga agtagaagtc ccgtcgccgg gccgaacact   8520
cgtgctggct tttgtaaaag cgagcgcagt actggcagcg ctgcacgggc tgtacctcct   8580
gcacgagatg cacctttcgc ccgcgcacga ggaagccgag gggaaatctg agccccccgc   8640
ctggctcgcg gcatggctgg tgctcttcta ctttggatgc gtgtccgtct ccgtctggct   8700
cctcgagggg tgttacggtg gagcggacca ccacgccgcg cgagccgcag gtccagatat   8760
cggcgcgcgg cggtcggagt ttgatgacga catcgcgcag ctgggagctg tccatggtct   8820
ggagctcccg cggcggcggc aggtcagccg ggagttcttg caggttcacc tcgcagagtc   8880
gggccagggc gcggggcagg tctaggtggt acctgatctc taggggcgtg ttggtggcgg   8940
cgtcgatggc ttgcaggagc ccgcatcccc ggggggcgac gacggtgccc cgcggggtgg   9000
tggtggtggt ggtggtggtg gtggtggcgg tgcagctcag aagcggtgcc gcgggcgggc   9060
ccccggaggt aggggggggct ccggtcccgc cggcaggggc ggcagcggca cgtcggcgtg   9120
gagcgcgggc aggagttggt gctgtgcccg gaggttgctg gcgaaggcga cgacgcggcg   9180
gttgatctcc tggatctggc gcctctgcgt gaagacgacg ggcccggtga gcttgaacct   9240
gaaagagagt tcgacagaat caatctcggt gtcattgacc gcggcctggc gcaggatctc   9300
ctgcacgtct cccgagttgt cttggtaggc gatctcggcc atgaactgct cgatctcttc   9360
ctcctggagg tctccgcgtc cggcgcgttc cacggtggcc gccaggtcgt tggagatgcg   9420
ccccatgagc tgcgagaagg cgttgagtcc gccctcgttc cagactcggc tgtagaccac   9480
gcccccctgg tcatcgcggg cgcgcatgac cacctgcgcg aggttgagct ccacgtgccg   9540
cgcgaagacg gcgtagttgc gcagacgctg gaagaggtag ttgagggtgg tggcggtgtg   9600
```

```
ctcggccacg aagaagttca tgacccagcg gcgcaacgtg gattcgttga tgtcccccaa    9660
ggcctccagc cgttccatgg cctcgtagaa gtccacggcg aagttgaaaa actgggagtt    9720
gcgcgccgac acggtcaact cctcctccag aagacggatg agctcggcga cggtgtcgcg    9780
cacctcgcgc tcgaaggcta tggggatctc ttcctccgct agcatcacca cctcctcctc    9840
ttcctcctct tctggcactt ccatgatggc ttcctcctct tcgggggcg gcggcggcgg     9900
cggtggggga gggggcgctc tgcgccggcg gcggcgcacc gggaggcggt ccacgaagcg    9960
cgcgatcatc tccccgcggc ggcggcgcat ggtctcggtg acggcgcggc cgttctcccg   10020
ggggcgcagt tggaagacgc cgccggacat ctggtgctgg ggcgggtggc cgtgaggcag   10080
cgaaacggcg ctgacgatgc atctcaacaa ttgctgcgta ggtacgccgc cgagggacct   10140
gagggagtcc atatccaccg gatccgaaaa cctttcgagg aaggcgtcta accagtcgca   10200
gtcgcaaggt aggctgagca ccgtggcggg cggcgggggg tggggggagt gtctggcgga   10260
ggtgctgctg atgatgtaat tgaagtaggc ggacttgaca cggcggatgg tcgacaggag   10320
caccatgtcc ttgggtccgg cctgctggat gcggaggcgg tcggctatgc cccaggcttc   10380
gttctggcat cggcgcaggt ccttgtagta gtcttgcatg agcctttcca ccggcacctc   10440
ttctccttcc tcttctgctt cttccatgtc tgcttcggcc ctggggcggc gccgcgcccc   10500
cctgcccccc atgcgcgtga ccccgaaccc cctgagcggt tggagcaggg ccaggtcggc   10560
gacgacgcgc tcggccagga tggcctgctg cacctgcgtg agggtggttt ggaagtcatc   10620
caagtccacg aagcggtggt aggcgcccgt gttgatggtg taggtgcagt tggccatgac   10680
ggaccagttg acggtctggt ggcccggttg cgacatctcg gtgtacctga gtcgcgagta   10740
ggcgcgggag tcgaagacgt agtcgttgca agtccgcacc aggtactggt agcccaccag   10800
gaagtgcggc ggcggctggc ggtagagggg ccagcgcagg gtggcggggg ctccgggggc   10860
caggtcttcc agcatgaggc ggtggtaggc gtagatgtac ctggacatcc aggtgatacc   10920
cgcggcggtg gtggaggcgc gcgggaagtc gcgcacccgg ttccagatgt tgcgcagggg   10980
cagaaagtgc tccatggtag gcgtgctctg tccagtcaga cgcgcgcagt cgttgatact   11040
ctagaccagg gaaaacgaaa gccggtcagc gggcactctt ccgtggtctg gtgaatagat   11100
cgcaagggta tcatggcgga gggcctcggt tcgagccccg ggtccgggcc ggacggtccg   11160
ccatgatcca cgcggttacc gcccgcgtgt cgaacccagg tgtgcgacgt cagacaacgg   11220
tggagtgttc cttttggcgt tttctggcc gggcgccggc gtcgcgtaag agactaagcc    11280
gcgaaagcga aagcagtaag tggctcgctc cccgtagccg gagggatcct tgctaagggt   11340
tgcgttgcgg cgaaccccgg ttcgaatccc gtactcgggc cggccggacc cgcggctaag   11400
gtgttggatt ggcctccccc tcgtataaag accccgcttg cggattgact ccggacacgg   11460
ggacgagccc cttttatttt tgctttcccc agatgcatcc ggtgctgcgg cagatgcgcc   11520
ccccgcccca gcagcagcaa caacaccagc aagagcggca gcaacagcag cgggagtcat   11580
gcagggcccc ctcacccacc ctcggcgggc cggccacctc ggcgtccgcg gccgtgtctg   11640
gcgcctgcgg cggcggcggg gggccggctg acgaccccga ggagcccccg cggcgcaggg   11700
ccagacacta cctggacctg gaggagggcg agggcctggc gcggctgggg gcgccgtctc   11760
ccgagcgcca cccgcgggtg cagctgaagc gcgactcgcg cgaggcgtac gtgcctcggc   11820
agaacctgtt cagggaccgc gcgggcgagg agcccgagga gatgcgggac aggaggttca   11880
gcgcagggcg ggagctgcgg caggggctga accgcgagcg gctgctgcgc gaggaggact   11940
```

-continued ttgagcccga cgcgcggacg gggatcagcc ccgcgcgcgc gcacgtggcg gccgccgacc 12000
tggtgacggc gtacgagcag acggtgaacc aggagatcaa cttccaaaag agtttcaaca 12060
accacgtgcg cacgctggtg gcgcgcgagg aggtgaccat cgggctgatg cacctgtggg 12120
actttgtaag cgcgctggtg cagaacccca acagcaagcc tctgacggcg cagctgttcc 12180
tgatagtgca gcacagcagg gacaacgagg cgtttaggga cgcgctgctg aacatcaccg 12240
agcccgaggg tcggtggctg ctggacctga ttaacatcct gcagagcata gtggtgcagg 12300
agcgcagcct gagcctggcc gacaaggtgg cggccatcaa ctactcgatg ctgagcctgg 12360
gcaagtttta cgcgcgcaag atctaccaga cgccgtacgt gcccatagac aaggaggtga 12420
agatcgacgg tttttacatg cgcatggcgc tgaaggtgct caccctgagc gacgacctgg 12480
gcgtgtaccg caacgagcgc atccacaagg ccgtgagcgt gagccggcgg cgcgagctga 12540
gcgaccgcga gctgatgcac agcctgcagc gggcgctggc gggcgccggc agcggcgaca 12600
gggaggcgga gtcctacttc gatgcggggg cggacctgcg ctgggcgccc agccggcggg 12660
ccctggaggc cgcgggggtc cgcgaggact atgacgagga cggcgaggag gatgaggagt 12720
acgagctaga ggagggcgag tacctggact aaaccgcggg tggtgtttcc ggtagatgca 12780
agacccgaac gtggtggacc cggcgctgcg ggcggctctg cagagccagc cgtccggcct 12840
taactcctca gacgactggc gacaggtcat ggaccgcatc atgtcgctga cggcgcgtaa 12900
cccggacgcg ttccggcagc agccgcaggc caacaggctc tccgccatcc tggaggcggt 12960
ggtgcctgcg cgctcgaacc ccacgcacga gaaggtgctg gccatagtga acgcgctggc 13020
cgagaacagg gccatccgcc cggacgaggc cgggctggtg tacgacgcgc tgctgcagcg 13080
cgtggcccgc tacaacagcg gcaacgtgca gaccaacctg gaccggctgg tgggggacgt 13140
gcgcgaggcg gtggcgcagc gcgagcgcgc ggatcggcag ggcaacctgg gctccatggt 13200
ggcgctgaat gccttcctga gcacgcagcc ggccaacgtg ccgcgggggc aggaagacta 13260
caccaacttt gtgagcgcgc tgcggctgat ggtgaccgag acccccccaga gcgaggtgta 13320
ccagtcgggc ccggactact tcttccagac cagcagacag ggcctgcaga cggtgaacct 13380
gagccaggct ttcaagaacc tgcgggggct gtggggcgtg aaggcgccca ccggcgaccg 13440
ggcgacggtg tccagcctgc tgacgcccaa ctcgcgcctg ctgctgctgc tgatcgcgcc 13500
gttcacggac agcggcagcg tgtcccggga cacctacctg ggcacctgc tgaccctgta 13560
ccgcgaggcc atcgggcagg cgcaggtgga cgagcacacc ttccaggaga tcaccagcgt 13620
gagccgcgcg ctggggcagg aggacacgag cagcctggag gcgactctga actacctgct 13680
gaccaaccgg cggcagaaga ttccctcgct gcacagcctg acctccgagg aggagcgcat 13740
cttgcgctac gtgcagcaga gcgtgagcct gaacctgatg cgcgacgggg tgacgcccag 13800
cgtggcgctg gacatgaccg cgcgcaacat ggaaccgggc atgtacgccg cgcaccggcc 13860
ttacatcaac cgcctgatgg actacctgca tcgcgcggcg gccgtgaacc ccgagtactt 13920
taccaacgcc atcctgaacc cgcactggct cccgccgccc gggttctaca gcgggggctt 13980
cgaggtcccg gaggccaacg atggcttcct gtgggacgac atggacgaca gcgtgttctc 14040
cccgcggccg caggcgctgg cggaagcgtc cctgctgcgt cccaagaagg aggaggagga 14100
ggcgagtcgc cgccgcggca gcagcggcgt ggcttctctg tccgagctgg gggcggcagc 14160
cgccgcgcgc cccgggtccc tgggcggcag cccctttccg agcctggtgg ggtctctgca 14220
cagcgagcgc accacccgcc ctcggctgct gggcgaggac gagtacctga ataactccct 14280
gctgcagccg gtgcgggaga aaaacctgcc ccccgccttc cccaacaacg ggatagagag 14340

-continued

```
cctggtggac aagatgagca gatggaagac ctatgcgcag gagcacaggg acgcgcccgc  14400

gctccggccg cccacgcggc gccagcgcca cgaccggcag cgggggctgg tgtgggatga  14460

cgaggactcc gcggacgata gcagcgtgct ggacctggga gggagcggca acccgttcgc  14520

gcacctgcgc ccccgcctgg ggaggatgtt ttaaaaaaaa aaaaagcaag aagcatgatg  14580

caaaattaaa taaaactcac caaggccatg gcgaccgagc gttggtttct tgtgttccct  14640

tcagtatgcg gcgcgcggcg atgtaccagg agggacctcc tccctcttac gagagcgtgg  14700

tgggcgcggc ggcggcggcg ccctcttctc cctttgcgtc gcagctgctg gagccgccgt  14760

acgtgcctcc gcgctacctg cggcctacgg gggggagaaa cagcatccgt tactcggagc  14820

tggcgcccct gttcgacacc acccgggtgt acctggtgga caacaagtcg gcggacgtgg  14880

cctccctgaa ctaccagaac gaccacagca attttttgac cacggtcatc cagaacaatg  14940

actacagccc gagcgaggcc agcacccaga ccatcaatct ggatgaccgg tcgcactggg  15000

gcggcgacct gaaaaccatc ctgcacacca acatgcccaa cgtgaacgag ttcatgttca  15060

ccaataagtt caaggcgcgg gtgatggtgt cgcgctcgca caccaaggaa gaccgggtgg  15120

agctgaagta cgagtgggtg gagttcgagc tgccagaggg caactactcc gagaccatga  15180

ccattgacct gatgaacaac gcgatcgtgg agcactatct gaaagtgggc aggcaaaacg  15240

gggtcctgga gagcgacatc ggggtcaagt tcgacaccag gaacttccgc ctggggctgg  15300

accccgtgac cgggctggtt atgcccgggg tgtacaccaa cgaggccttc catcccgaca  15360

tcatcctgct gcccggctgc ggggtggact tcacttacag ccgcctgagc aacctcctgg  15420

gcatccgcaa gcggcagccc ttccaggagg gcttcaggat cacctacgag gacctggagg  15480

ggggcaacat ccccgcgctc ctcgatgtgg aggcctacca ggatagcttg aaggaaaatg  15540

aggcgggaca ggaggatacc acccccgccg cctccgccgc cgccgagcag ggcgaggatg  15600

ctgctgacac cgcggccgcg gacggggcag aggccgaccc cgctatggtg gtggaggctc  15660

ccgagcagga ggaggatatg aatgacagtg cggtgcgcgg agacaccttc gtcacccggg  15720

gggaggaaaa gcaagcggag gccgaggccg cggccgagga aaagcaactg gcggcagcag  15780

cggcggcggc ggcgttggcc gcggcggagg ctgagtctga ggggaccaag cccgccaagg  15840

agcccgtgat taagcccctg accgaagata gcaagaagcg cagttacaac ctgctcaagg  15900

acagcaccaa caccgcgtac cgcagctggt acctggccta caactacggc gacccgtcga  15960

cgggggtgcg ctcctggacc ctgctgtgca cgccggacgt gacctgcggc tcggagcagg  16020

tgtactggtc gctgcccgac atgatgcaag accccgtgac cttccgctcc acgcggcagg  16080

tcagcaactt cccggtggtg ggcgccgagc tgctgcccgt gcactccaag agcttctaca  16140

acgaccaggc cgtctactcc cagctcatcc gccagttcac ctctctgacc cacgtgttca  16200

atcgctttcc tgagaaccag attctggcgc gcccgcccgc ccccaccatc accaccgtca  16260

gtgaaaacgt tcctgctctc acagatcacg ggacgctacc gctgcgcaac agcatcggag  16320

gagtccagcg agtgaccgtt actgacgcca gacgccgcac ctgcccctac gtttacaagg  16380

ccttgggcat agtctcgccg cgcgtccttt ccagccgcac tttttgagca acaccaccat  16440

catgtccatc ctgatctcac ccagcaataa ctccggctgg ggactgctgc gcgcgcccag  16500

caagatgttc ggaggggcga ggaagcgttc cgagcagcac cccgtgcgcg tgcgcgggca  16560

cttccgcgcc ccctggggag cgcacaaacg cggccgcgcg gggcgcacca ccgtggacga  16620

cgccatcgac tcggtggtgg agcaggcgcg caactacagg cccgcggtct ctaccgtgga  16680
```

-continued

```
cgcggccatc cagaccgtgg tgcggggcgc gcggcggtac gccaagctga agagccgccg  16740
gaagcgcgtg gcccgccgcc accgccgccg acccggggcc gccgccaaac gcgccgccgc  16800
ggccctgctt cgccgggcca agcgcacggg ccgccgcgcc gccatgaggg ccgcgcgccg  16860
cttggccgcc ggcatcaccg ccgccaccat ggcccccgt acccgaagac gcgcggccgc  16920
cgccgccgcc gccgccatca gtgacatggc cagcaggcgc cggggcaacg tgtactgggt  16980
gcgcgactcg gtgaccggca cgcgcgtgcc cgtgcgcttc cgcccccgc ggacttgaga  17040
tgatgtgaaa aaacaacact gagtctcctg ctgttgtgtg tatcccagcg gcggcggcgc  17100
gcgcagcgtc atgtccaagc gcaaaatcaa agaagagatg ctccaggtcg tcgcgccgga  17160
gatctatggg cccccgaaga aggaagagca ggattcgaag ccccgcaaga taaagcgggt  17220
caaaaagaaa aagaaagatg atgacgatgc cgatggggag gtggagttcc tgcgcgccac  17280
ggcgcccagg cgcccggtgc agtggaaggg ccggcgcgta aagcgcgtcc tgcgccccgg  17340
caccgcggtg gtcttcacgc ccggcgagcg ctccacccgg actttcaagc gcgtctatga  17400
cgaggtgtac ggcgacgaag acctgctgga gcaggccaac gagcgcttcg gagagtttgc  17460
ttacgggaag cgtcagcggg cgctggggaa ggaggacctg ctggcgctgc cgctggacca  17520
gggcaacccc acccccagtc tgaagcccgt gaccctgcag caggtgctgc cgagcagcgc  17580
accctccgag gcgaagcggg gtctgaagcg cgagggcggc gacctggcgc ccaccgtgca  17640
gctcatggtg cccaagcggc agaggctgga ggatgtgctg gagaaaatga aagtagaccc  17700
cggtctgcag ccggacatca gggtccgtcc catcaagcag gtggcgccgg gcctcggcgt  17760
gcagaccgtg gacgtggtca tccccaccgg caactccccc gccgccacca ccactaccgc  17820
tgcctccacg gacatggaga cacagaccga tcccgccgca gccgcagccg ccgccgcagc  17880
cgcgacctcc tcggcggagg tgcagacgga cccctggctg ccgccggcga tgtcagctcc  17940
ccgcgcgcgc cgcggacgca gaaagtacgg cgccgccaac gcgctcctgc ccgagtacgc  18000
cttgcatcct tccatcgcgc ccacccccgg ctaccgaggc tatacctacc gcccgcgaag  18060
agccaagggt tccacccgcc gtccccgccg acgcgccgcc gccaccaccc gccgccgccg  18120
ccgcagacgc cagcccgcac tggctccagt ctccgtgagg agagtggcgc gcgacggaca  18180
caccctggtg ctgcccaggg cgcgctacca ccccagcatc gtttaaaagc ctgttgtggt  18240
tcttgcagat atggccctca cttgccgcct ccgtttcccg gtgccgggat accgaggagg  18300
aagatcgcgc cgcaggaggg gtctggccgg ccgcggcctg agcggaggca gccgccgcgc  18360
gcaccggcgg cgacgcgcca ccagccgacg catgcgcggc ggggtgctgc ccctgttaat  18420
cccccctgatc gccgcggcga tcggcgccgt gcccgggatc gcctccgtgg ccttgcaagc  18480
gtcccagagg cattgacaga cttgcaaact tgcaaatatg gaaaaaaaaa aaaaaacccca  18540
ataaaaagtc tagactctca cgctcgcttg gtcctgtgac tattttgtag aatggaagac  18600
atcaactttg cgtcgctggc cccgcgtcac ggctcgcgcc cgttcctggg acactggaac  18660
gatatcggca ccagcaacat gagcggtggc gccttcagtt ggggctctct gtggagcggc  18720
attaaaagta tcgggtctgc cgttaaaaat tacggctccc gggcctggaa cagcagcacg  18780
ggccagatgt tgagagacaa gttgaaagag cagaacttcc agcagaaggt ggtggagggc  18840
ctggcctccg gcatcaacgg ggtggtggac ctggccaacc aggccgtgca gaataaaatc  18900
aacagcagac tggacccccg gccgccggtg gaggaggtgc cgccggcgct ggagacggtg  18960
tcccccgatg ggcgtggcga gaagcgcccg cggcccgata gggaagagac cactctggtc  19020
acgcagaccg atgagccgcc cccgtatgag gaggccctaa agcaaggtct gcccaccacg  19080
```

cggcccatcg cgcccatggc caccggggtg gtgggccgcc acaccccgc cacgctggac 19140
ttgcctccgc ccgccgatgt gccgcagcag cagaaggcgg cacagccggg cccgcccgcg 19200
accgcctccc gttcctccgc cggtcctctg cgccgcgcgg ccagcggccc ccgcgggggg 19260
gtcgcgaggc acggcaactg gcagagcacg ctgaacagca tcgtgggtct gggggtgcgg 19320
tccgtgaagc gccgccgatg ctactgaata gcttagctaa cgtgttgtat gtgtgtatgc 19380
gccctatgtc gccgccagag gagctgctga gtcgccgccg ttcgcgcgcc caccaccacc 19440
gccactccgc ccctcaagat ggcgacccca tcgatgatgc cgcagtggtc gtacatgcac 19500
atctcgggcc aggacgcctc ggagtacctg agccccgggc tggtgcagtt cgcccgcgcc 19560
accgagagct acttcagcct gagtaacaag tttaggaacc ccacggtggc gcccacgcac 19620
gatgtgacca ccgaccggtc tcagcgcctg acgctgcggt tcattcccgt ggaccgcgag 19680
gacaccgcgt actcgtacaa ggcgcggttc accctggccg tgggcgacaa ccgcgtgctg 19740
gacatggcct ccacctactt tgacatccgc ggggtgctgg accggggtcc cactttcaag 19800
ccctactctg gcaccgccta caactccctg gcccccaagg gcgctcccaa ctcctgcgag 19860
tgggagcaag aggaaactca ggcagttgaa gaagcagcag aagaggaaga agaagatgct 19920
gacggtcaag ctgaggaaga gcaagcagct accaaaaaga ctcatgtata tgctcaggct 19980
ccccttctg gcgaaaaaat tagtaaagat ggtctgcaaa taggaacgga cgctacagct 20040
acagaacaaa aacctattta tgcagaccct acattccagc ccgaacccca aatcggggag 20100
tcccagtgga atgaggcaga tgctacagtc gccggcggta gagtgctaaa gaaatctact 20160
cccatgaaac catgctatgg ttcctatgca agacccacaa atgctaatgg aggtcagggt 20220
gtactaacgg caaatgccca gggacagcta gaatctcagg ttgaaatgca attcttttca 20280
acttctgaaa acgcccgtaa cgaggctaac aacattcagc ccaaattggt gctgtatagt 20340
gaggatgtgc acatggagac cccggatacg cacctttctt acaagcccgc aaaaagcgat 20400
gacaattcaa aaatcatgct gggtcagcag tccatgccca acagacctaa ttacatcggc 20460
ttcagagaca actttatcgg cctcatgtat tacaatagca ctggcaacat gggagtgctt 20520
gcaggtcagg cctctcagtt gaatgcagtg gtggacttgc aagacagaaa cacagaactg 20580
tcctaccagc tcttgcttga ttccatgggt gacagaacca gatacttttc catgtggaat 20640
caggcagtgg acagttatga cccagatgtt agaattattg aaaatcatgg aactgaagac 20700
gagctcccca actattgttt ccctctgggt ggcatagggg taactgacac ttaccaggct 20760
gttaaaacca acaatggcaa taacgggggc caggtgactt ggacaaaaga tgaaactttt 20820
gcagatcgca atgaaatagg ggtgggaaac aatttcgcta tggagatcaa cctcagtgcc 20880
aacctgtgga gaaacttcct gtactccaac gtggcgctgt acctaccaga caagcttaag 20940
tacaacccct ccaatgtgga catctctgac aaccccaaca cctacgatta catgaacaag 21000
cgagtggtgg ccccggggct ggtggactgc tacatcaacc tgggcgcgcg ctggtcgctg 21060
gactacatgg acaacgtcaa ccccttcaac caccaccgca atgcgggcct gcgctaccgc 21120
tccatgctcc tgggcaacgg gcgctacgtg cccttccaca tccaggtgcc ccagaagttc 21180
tttgccatca agaacctcct cctcctgccg ggctcctaca cctacgagtg gaacttcagg 21240
aaggatgtca acatggtcct ccagagctct ctgggtaacg atctcagggt ggacggggcc 21300
agcatcaagt tcgagagcat ctgcctctac gccaccttct tccccatggc ccacaacacg 21360
gcctccacgc tcgaggccat gctcaggaac gacaccaacg accagtcctt caatgactac 21420
ctttccgccg ccaacatgct ctaccccata cccgccaacg ccaccaacgt ccccatctcc 21480
atcccctcgc gcaactgggc ggccttccgc ggctgggcct tcacccgcct caagaccaag 21540 gagacccccct ccctgggctc gggattcgac ccctactaca cctactcggg ctctattccc 21600
tacctggacg gcaccttcta cctcaaccac actttcaaga aggtctcggt caccttcgac 21660
tcctcggtca gctggccggg caacgaccgt ctgctcaccc ccaacgagtt cgagatcaag 21720
cgctcggtcg acggggaagg ctacaacgtg gcccagtgca acatgaccaa ggactggttc 21780
ctggtccaga tgctggccaa ctacaacatc ggctaccagg gcttctacat cccagagagc 21840
tacaaggaca ggatgtactc cttcttcagg aacttccagc ccatgagccg gcaggtggtg 21900
gaccagacca agtacaagga ctaccaggag gtgggcatca tccaccagca caacaactcg 21960
ggcttcgtgg gctacctcgc ccccaccatg cgcgagggac aggcctaccc cgccaacttc 22020
ccctacccgc tcataggcaa gaccgcggtc gacagcatca cccagaaaaa gttcctctgc 22080
gaccgcaccc tctggcgcat ccccttctcc agcaacttca tgtccatggg tgcgctctcg 22140
gacctgggcc agaacttgct ctacgccaac tccgcccacg ccctcgacat gaccttcgag 22200
gtcgacccca tggacgagcc cacccttctc tatgttctgt tcgaagtctt tgacgtggtc 22260
cgggtccacc agccgcaccg cggcgtcatc gagaccgtgt acctgcgtac gcccttctcg 22320
gccggcaacg ccaccaccta aagaagcaag ccgcagtcat cgccgcctgc atgccgtcgg 22380
gttccaccga gcaagagctc agggccatcg tcagagacct gggatgcggg ccctattttt 22440
tgggcacctt cgacaagcgc ttccctggct ttgtctcccc acacaagctg gcctgcgcca 22500
tcgtcaacac ggccggccgc gagaccgggg gcgtgcactg gctggccttt gcctggaacc 22560
cgcgctccaa aacatgcttc ctctttgacc ccttcggctt ttcggaccag cggctcaagc 22620
aaatctacga gttcgagtac gagggcttgc tgcgtcgcag cgccatcgcc tcctcgcccg 22680
accgctgcgt caccctcgaa aagtccaccc agaccgtgca ggggcccgac tcggccgcct 22740
gcggtctctt ctgctgcatg tttctgcacg cctttgtgca ctggcctcag agtcccatgg 22800
accgcaaccc caccatgaac ttgctgacgg gggtgcccaa ctccatgctc caaagccccc 22860
aggtcgagcc caccctgcgc cgcaaccagg agcagctcta cagcttcctg gagcgccact 22920
cgccctactt ccgccgccac agcgcacaga tcaggagggc cacctccttc tgccacttgc 22980
aagagatgca agaagggtaa taacgatgta cacacttttt tctcaataaa tggcattttt 23040
tttttattta tacaagctct ctggggtatt catttcccac caccaccacc cgccgttgtc 23100
gccatctggc tctatttaga aatcgaaagg gttctgccgg gagtcgccgt gcgccacggg 23160
cagggacacg ttgcgatact ggtagcgggt gccccacttg aactcgggca ccaccaggcg 23220
aggcagctcg gggaagtttt cgctccacag gctgcgggtc agcaccagcg cgttcatcag 23280
gtcgggcgcc gagatcttga agtcgcagtt ggggccgccg ccctgcgcgc gcgagttgcg 23340
gtacaccggg ttgcagcact ggaacaccaa cagcgccggg tgcttcacgc tggccagcac 23400
gctgcggtcg gagatcagct cggcgtccag gtcctccgcg ttgctcagcg cgaacggggt 23460
catcttgggc acttgccgcc ccaggaaggg cgcgtgcccc ggtttcgagt tgcagtcgca 23520
gcgcagcggg atcagcaggt gcccgtgccc ggactcggcg ttggggtaca gcgcgcgcat 23580
gaaggcctgc atctggcgga aggccatctg ggccttggcg ccctccgaga agaacatgcc 23640
gcaggacttg cccgagaact ggtttgcggg gcagctggcg tcgtgcaggc agcagcgcgc 23700
gtcggtgttg gcgatctgca ccacgttgcg cccccaccgg ttcttcacga tcttggcctt 23760
ggacgattgc tccttcagcg cgcgctgccc gttctcgctg gtcacatcca tctcgatcac 23820

-continued atgttccttg ttcaccatgc tgctgccgtg cagacacttc agctcgccct ccgtctcggt 23880
gcagcggtgc tgccacagcg cgcagcccgt gggctcgaaa gacttgtagg tcacctccgc 23940
gaaggactgc aggtacccct gcaaaaagcg gcccatcatg gtcacgaagg tcttgttgct 24000
gctgaaggtc agctgcagcc cgcggtgctc ctcgttcagc caggtcttgc acacggccgc 24060
cagcgcctcc acctggtcgg gcagcatctt gaagttcacc ttcagctcat tctccacgtg 24120
gtacttgtcc atcagcgtgc gcgccgcctc catgcccttc tcccaggccg acaccagcgg 24180
caggctcacg gggttcttca ccatcaccgt ggccgccgcc tccgccgcgc tttcgctttc 24240
cgccccgctg ttctcttcct cttcctcctc ttcctcgccg ccgcccactc gcagcccccg 24300
caccacgggg tcgtcttcct gcaggcgctg caccttgcgc ttgccgttgc gcccctgctt 24360
gatgcgcacg ggcgggttgc tgaagcccac catcaccagc gcggcctctt cttgctcgtc 24420
ctcgctgtcc agaatgacct ccggggaggg ggggttggtc atcctcagta ccgaggcacg 24480
cttctttttc ttcctggggg cgttcgccag ctccgcggct gcggccgctg ccgaggtcga 24540
aggccgaggg ctgggcgtgc gcggcaccag cgcgtcttgc gagccgtcct cgtcctcctc 24600
ggactcgaga cggaggcggg cccgcttctt cgggggcgcg cggggcggcg gaggcggcgg 24660
cggcgacgga gacggggacg agacatcgtc cagggtgggt ggacggcggg ccgcgccgcg 24720
tccgcgctcg gggggtggttt cgcgctggtc ctcttcccga ctggccatct cccactgctc 24780
cttctcctat aggcagaaag agatcatgga gtctctcatg cgagtcgaga aggaggagga 24840
cagcctaacc gccccctctg agccctccac caccgccgcc accaccgcca atgccgccgc 24900
ggacgacgcg cccaccgaga ccaccgccag taccaccctc cccagcgacg cacccccgct 24960
cgagaatgaa gtgctgatcg agcaggaccc gggttttgtg agcggagagg aggatgaggt 25020
ggatgagaag gagaaggagg aggtcgccgc ctcagtgcca aaagaggata aaaagcaaga 25080
ccaggacgac gcagataagg atgagacagc agtcgggcgg gggaacggaa gccatgatgc 25140
tgatgacggc tacctagacg tgggagacga cgtgctgctt aagcacctgc accgccagtg 25200
cgtcatcgtc tgcgacgcgc tgcaggagcg ctgcgaagtg cccctggacg tggcggaggt 25260
cagccgcgcc tacgagcggc acctcttcgc gccgcacgtg ccccccaagc gccgggagaa 25320
cggcacctgc gagcccaacc cgcgtctcaa cttctacccg gtcttcgcgg tacccgaggt 25380
gctggccacc taccacatct tcttccaaaa ctgcaagatc ccccctctcct gccgcgctaa 25440
ccgcacccgc gccgacaaaa ccctgaccct gcggcagggc gcccacatac ctgatattgc 25500
ctctctggag gaagtgccca agatcttcga gggtctcggt cgcgacgaga aacgggcggc 25560
gaacgctctg cacggagaca gcgaaaacga gagtcactcg gggtgctgg tggagctcga 25620
gggcgacaac gcgcgcctgg ccgtactcaa gcgcagcata gaggtcaccc actttgccta 25680
cccggcgctc aacctgcccc ccaaggtcat gagtgtggtc atgggcgagc tcatcatgcg 25740
ccgcgctcag cccctggccg cggatgcaaa cttgcaagag tcctccgagg aaggcctgcc 25800
cgcggtcagc gacgagcagc tagcgcgctg gctggagacc cgcgaccccg cgcagctgga 25860
ggagcggcgc aagctcatga tggccgcggt gctggtcacc gtggagctcg agtgtctgca 25920
gcgcttcttc gcggaccccg agatgcagcg caagctcgag gagaccctgc actacacctt 25980
ccgccagggc tacgtgcgcc aggcctgcaa gatctccaac gtggagctct gcaacctggt 26040
ctcctacctg ggcatcctgc acgagaaccg cctcgggcag aacgtcctgc actccaccct 26100
caaaggggag gcgcgccgcg actacatccg cgactgcgcc tacctcttcc tctgctacac 26160

-continued ctggcagacg gccatggggg tctggcagca gtgcctggag gagcgcaacc tcaaggagct 26220
ggaaaagcta ctcaagcgca ccctcaggga cctctggacg ggcttcaacg agcgctcggt 26280
ggccgccgcg ctggcggaca tcatcttccc cgagcgcctg ctcaagaccc tgcagcaggg 26340
cctgcccgac ttcaccagcc agagcatgct gcagaacttt aggactttca tcctggagcg 26400
ctcgggcatc ctgcctgcca cttgctgcgc gctgcccagc gacttcgtgc ccatcaagta 26460
cagggagtgc ccgccgccgc tctggggcca ctgctacctc ttccagctgg ccaactacct 26520
cgcctaccac tcggacctca tggaagacgt gagcggcgag ggcctgctcg agtgccactg 26580
ccgctgcaac ctctgcacgc cccaccgctc tctagtctgc aacccgcagc tgctcagcga 26640
gagtcagatt atcggtacct tcgagctgca gggtccctcg cctgacgaga agtccgcggc 26700
tccggggctg aaactcactc cggggctgtg gacttccgcc tacctacgca aatttgtacc 26760
tgaggactac cacgcccacg agatcaggtt ctacgaagac caatcccgcc cgcccaaggc 26820
ggagctcacc gcctgcgtca tcacccaggg gcacatcctg ggccaattgc aagccatcaa 26880
caaagcccgc cgagagttct tgctgaaaaa gggtcggggg gtgtacctgg acccccagtc 26940
cggcgaggag ctaaacccgc taccccccgcc gccgccccag cagcgggacc ttgcttccca 27000
ggatggcacc cagaaagaag cagcagccgc cgccgccgca gccatacatg cttctggagg 27060
aagaggagga ggactgggac agtcaggcag aggaggtttc ggacgaggag caggaggaga 27120
tgatggaaga ctgggaggag gacagcagcc tagacgagga agcttcagag gccgaagagg 27180
tggcagacgc aacaccatca ccctcggtcg cagcccccctc gccggggccc ctgaaatcct 27240
ccgaacccag caccagcgct ataacctccg ctcctccggc gccggcgcca cccgcccgca 27300
gacccaaccg tagatgggac accacaggaa ccggggtcgg taagtccaag tgcccgccgc 27360
cgccaccgca gcagcagcag cagcgccagg gctaccgctc gtggcgcggg cacaagaacg 27420
ccatagtcgc ctgcttgcaa gactgcgggg gcaacatctc tttcgcccgg cgcttcctgc 27480
tattccacca cggggtcgcc tttccccgca atgtcctgca ttactaccgt catctctaca 27540
gcccctactg cagcggcgac ccagaggcgg cagcggcagc cacagcggcg accaccacct 27600
aggaagatat cctccgcggg caagacagcg gcagcagcgg ccaggagacc cgcggcagca 27660
gcggcgggag cggtgggcgc actgcgcctc tcgcccaacg aacccctctc gacccgggag 27720
ctcagacaca ggatcttccc cactttgtat gccatcttcc aacagagcag aggccaggag 27780
caggagctga aaataaaaaa cagatctctg cgctccctca cccgcagctg tctgtatcac 27840
aaaagcgaag atcagcttcg gcgcacgctg gaggacgcgg aggcactctt cagcaaatac 27900
tgcgcgctca ctcttaaaga ctagctccgc gcccttctcg aatttaggcg ggagaaaact 27960
acgtcatcgc cggccgccgc ccagcccgcc cagccgagat gagcaaagag attcccacgc 28020
catacatgtg gagctaccag ccgcagatgg gactcgcggc gggagcggcc caggactact 28080
ccacccgcat gaactacatg agcgcgggac cccacatgat ctcacaggtc aacgggatcc 28140
gcgcccagcg aaaccaaata ctgctggaac aggcggccat caccgccacg ccccgccata 28200
atctcaaccc ccgaaattgg cccgccgccc tcgtgtacca ggaaaccccc tccgccacca 28260
ccgtactact tccgcgtgac gcccaggccg aagtccagat gactaactca ggggcgcagc 28320
tcgcgggcgg ctttcgtcac ggggcgcggc cgctccgacc aggtataaga cacctgatga 28380
tcagaggccg aggtatccag ctcaacgacg agtcggtgag ctcttcgctc ggtctccgtc 28440
cggacggaac tttccagctc gccggatccg gccgctcttc gttcacgccc cgccaggcgt 28500
acctgactct gcagacctcg tcctcggagc cccgctccgg aggcatcgga accctccagt 28560

-continued

```
tcgtggagga gttcgtgccc tcggtctact tcaacccctt ctcgggacct cccggacgct  28620
accccgacca gttcattccg aactttgacg cggtgaagga ctcggcggac ggctacgact  28680
gaatgtcagg tgccgaggca gagcagcttc gcctgagaca cctcgagcac tgccgccgcc  28740
acaagtgctt cgcccgcggt tccggtgagt tctgctactt tcagctaccc gaggagcata  28800
ccgaggggcc ggcgcacggc gtccgcctga ccacccaggg cgaggttacc tgttccctca  28860
tccgggagtt caccctccgt cccctgctag tggagcggga gcggggtccc tgtgtcctaa  28920
ctatcgcctg caactgccct aaccctggat tacatcaaga tctttgctgt catctctgtg  28980
ctgagtttaa taaacgctga gatcagaatc tactgggaat tcgatttagt cccctttaac  29040
taatcaaaca ctggaatcaa taaaaagaat cacttactta aaatcagaca gcaggtctct  29100
gtccagttta ttcagcagca cctccttccc ctcctcccaa ctctggtact ccaaacgcct  29160
tctggcggca aacttcctcc acaccctgaa gggaatgtca gattcttgct cctgtccctc  29220
cgcacccact atcttcatgt tgttgcagat gaagcgcacc aaaacgtctg acgagagctt  29280
caaccccgtg tacccctatg acacggaaag cggccctccc tccgtccctt tcctcacccc  29340
tcccttcgtg tctcccgatg gattccaaga aagccccccc ggggtcctgt ctctgaacct  29400
ggccgagccc ctggtcactt cccacggcat gctcgccctg aaaatgggaa gtggcctctc  29460
cctggacgac gctggcaacc tcacctctca agatatcacc accgctagcc ctcccctcaa  29520
aaaaaccaag accaacctca gcctagaaac ctcatccccc ctaactgtaa gcacctcagg  29580
cgccctcacc gtagcagccg ccgctcccct ggcagtggcc ggcacctccc tcaccatgca  29640
atcagaggcc cccctgacag tacaggatgc aaaactcacc ctggccacca aaggccccct  29700
gaccgtgtct gaaggcaaac tggccttgca aacatcggcc ccgctgacgg ccgctgacag  29760
cagcaccctc accgttagcg ccacaccacc aattaatgta agcagtggaa gtttaggctt  29820
agacatggaa gaccctatgt atactcacga tggaaaactg ggaataagaa ttgggggtcc  29880
actaagagta gtagacagct tgcacacact cactgtagtt accggaaatg gactaactgt  29940
agataacaat gccctccaaa ctagagttac gggcgcccta ggttatgaca catcaggaaa  30000
tctacaattg agagctgcag gaggtatgcg aattgatgca aatggccaac ttatccttaa  30060
tgtggcatac ccatttgatg ctcagaacaa tctcagcctt agacttggtc agggacccct  30120
gtatataaac acagaccaca acctggattt gaattgcaac agaggtctaa cccacaactac 30180
caccaacaac acaaaaaaac ttgagactaa aattagctca ggcttagact atgacaccaa  30240
tggtgctgtc attattaaac ttggcactgg tctaagcttc gacaacacag gcgccctaac  30300
tgtgggaaac actggtgatg ataaactgac tctgtggacg accccagacc catctccaaa  30360
ttgcagaatt cactcagaca aagactgcaa gtttactcta gtcctaacta agtgtggaag  30420
ccaaatcctg gcctctgtcg ccgccctagc ggtatcagga aatctggctt cgataacagg  30480
caccgttgcc agcgttacca tctttctcag atttgatcag aatggagtgc ttatggaaaa  30540
ctcctcgcta gacaggcagt actggaactt cagaaatggc aactcaacta acgctgcccc  30600
ctacaccaat gcagttgggt tcatgccaaa cctcgcagca taccccaaaa cgcaaagcca  30660
gactgctaaa aacaacattg taagtcaggt ttacttgaat ggagacaaat ccaaacccat  30720
gacccttacc atcaccctca atggaactaa tgaatccagt gaaactagcc aggtgagtca  30780
ctactccatg tcatttacat gggcttggga aagtgggcaa tatgccactg aaacctttgc  30840
caccaactcc ttcacctttt cttacattgc tgaacaataa aaagcatgac actgatgttc  30900
```

```
atttctgatt cttattttat tattttcaaa cacaacaaaa tcattcaagt cattcttcca  30960

tcttagctta atagacacag tagcttaata gacccagtag tgcaaagccc cattctagct  31020

tataactagt ggagaagtac tcgcctacat gggggtagag tcataatcgt gcatcaggat  31080

agggcggtgg tgctgcagca gcgcgcgaat aaactgctgc cgccgccgct ccgtcctgca  31140

ggaatacaac atggcagtgg tctcctcagc gatgattcgc accgcccgca gcataaggcg  31200

ccttgtcctc cgggcacagc agcgcaccct gatctcactt aaatcagcac agtaactgca  31260

gcacagcacc acaatattgt tcaaaatccc acagtgcaag gcgctgtatc caaagctcat  31320

ggcggggacc acagaaccca cgtggccatc ataccacaag cgcaggtaga ttaagtggcg  31380

acccctcata aacacgctgg acataaacat tacctctttt ggcatgttgt aattcaccac  31440

ctcccggtac catataaacc tctgattaaa catggcgcca tccaccacca tcctaaacca  31500

gctggccaaa acctgcccgc cggctataca ctgcagggaa ccgggactgg aacaatgaca  31560

gtggagagcc caggactcgt aaccatggat catcatgctc gtcatgatat caatgttggc  31620

acaacacagg cacacgtgca tacacttcct caggattaca agctcctccc gcgttagaac  31680

catatcccag ggaacaaccc attcctgaat cagcgtaaat cccacactgc agggaagacc  31740

tcgcacgtaa ctcacgttgt gcattgtcaa agtgttacat tcgggcagca gcggatgatc  31800

ctccagtatg gtagcgcggg tttctgtctc aaaaggaggt agacgatccc tactgtacgg  31860

agtgcgccga gacaaccgag atcgtgttgg tcgtagtgtc atgccaaatg gaacgccgga  31920

cgtagtcata tttcctgaag tcttagatct ctcaacgcag caccagcacc aacacttcgc  31980

agtgtaaaag gccaagtgcc gagagagtat atataggaat aaaaagtgac gtaaacgggc  32040

aaagtccaaa aaacgcccag aaaaaccgca cgcgaaccta cgccccgaaa cgaaagccaa  32100

aaaacactag acactccctt ccggcgtcaa cttccgcttt cccacgctac gtcacttgcc  32160

ccagtcaaac aaactacata tcccgaactt ccaagtcgcc acgcccaaaa caccgcctac  32220

acctccccgc ccgccggccc gcccccaaac ccgcctcccg ccccgcgccc cgccccgcgc  32280

cgcccatctc attatcatat tggcttcaat ccaaaataag gtatattatt gatgatg     32337
```

```
<210> SEQ ID NO 3
<211> LENGTH: 32381
<212> TYPE: DNA
<213> ORGANISM: Artificial Sequence
<220> FEATURE:
<223> OTHER INFORMATION: synthetic chimpanzee adenovirus serotype ChAd3
      with Marburg virus Angola codon optimized
      transmembrane envelope glycoprotein (GP) insert
      (ChAd3 Marburg (PB/6712))
<220> FEATURE:
<221> NAME/KEY: CDS
<222> LOCATION: (1666)...(3708)
<223> OTHER INFORMATION: Marburg virus Angola codon optimized
      transmembrane envelope glycoprotein (GP) insert in ChAd3 Marburg
      (PB/6712)
<220> FEATURE:
<221> NAME/KEY: CDS
<222> LOCATION: (14690)...(16470)
<223> OTHER INFORMATION: chimpanzee adenovirus serotype ChAd3 penton
<220> FEATURE:
<221> NAME/KEY: CDS
<222> LOCATION: (19503)...(22382)
<223> OTHER INFORMATION: chimpanzee adenovirus serotype ChAd3 hexon
<220> FEATURE:
<221> NAME/KEY: CDS
<222> LOCATION: (29239)...(30924)
<223> OTHER INFORMATION: chimpanzee adenovirus serotype ChAd3 fiber

<400> SEQUENCE: 3
```

-continued catcatcaat aatatacctt attttggatt gaagccaata tgataatgag atgggcggcg 60
cggggcgggg cgcggggcgg gaggcgggtt tgggggcggg ccggcgggcg gggcggtgtg 120
gcggaagtgg actttgtaag tgtggcggat gtgacttgct agtgccgggc gcggtaaaag 180
tgacgttttc cgtgcgcgac aacgcccccg ggaagtgaca tttttcccgc ggtttttacc 240
ggatgttgta gtgaatttgg gcgtaaccaa gtaagatttg gccattttcg cgggaaaact 300
gaaacgggga agtgaaatct gattaatttt gcgttagtca taccgcgtaa tatttgtcta 360
gggccgaggg actttggccg attacgtgga ggactcgccc aggtgttttt tgaggtgaat 420
ttccgcgttc cgggtcaaag tctccgtttt attattatag gatatcccat tgcatacgtt 480
gtatccatat cataatatgt acatttatat tggctcatgt ccaacattac cgccatgttg 540
acattgatta ttgactagtt attaatagta atcaattacg gggtcattag ttcatagccc 600
atatatggag ttccgcgtta cataacttac ggtaaatggc ccgcctggct gaccgcccaa 660
cgacccccgc ccattgacgt caataatgac gtatgttccc atagtaacgc caatagggac 720
tttccattga cgtcaatggg tggagtattt acggtaaact gcccacttgg cagtacatca 780
agtgtatcat atgccaagta cgccccctat tgacgtcaat gacggtaaat ggcccgcctg 840
gcattatgcc cagtacatga ccttatggga ctttcctact tggcagtaca tctacgtatt 900
agtcatcgct attaccatgg tgatgcggtt ttggcagtac atcaatgggc gtggatagcg 960
gtttgactca cggggatttc caagtctcca ccccattgac gtcaatggga gtttgttttg 1020
gaaccaaaat caacgggact ttccaaaatg tcgtaacaac tccgccccat tgacgcaaat 1080
gggcggtagg cgtgtacggt gggaggtcta tataagcaga gctctcccta tcagtgatag 1140
agatctccct atcagtgata gagatcgtcg acgagctcgt ttagtgaacc gtcagatcgc 1200
ctggagacgc catccacgct gttttgacct ccatagaaga caccgggacc gatccagcct 1260
ccatcggctc gcatctctcc ttcacgcgcc cgccgcccta cctgaggccg ccatccacgc 1320
cggttgagtc gcgttctgcc gcctcccgcc tgtggtgcct cctgaactgc gtccgccgtc 1380
taggtaagtt taaagctcag gtcgagaccg ggcctttgtc cggcgctccc ttggagccta 1440
cctagactca gccggctctc cacgctttgc ctgaccctgc ttgctcaact ctagttaacg 1500
gtggagggca gtgtagtctg agcagtactc gttgctgccg cgcgcgccac cagacataat 1560
agctgacaga ctaacagact gttcctttcc atgggtcttt tctgcagtca ccgtcgtcga 1620
cacgtgtgat cagatatcgc ggccgctcta gagatatcgg ccgccatgaa gaccacctgc 1680
ctgctgatca gcctgatcct gatccagggc gtgaagaccc tgcccatcct ggagatcgcc 1740
agcaacatcc agccccagaa cgtggacagc gtgtgcagcg gcaccctgca gaagaccgag 1800
gacgtgcacc tgatgggctt caccctgagc ggccagaagg tggccgacag ccctctggag 1860
gccagcaaga ggtgggcctt cagggccggc gtgcccccca agaacgtgga gtacaccgag 1920
ggcgaggagg ccaagacctg ctacaacatc agcgtgaccg accccagcgg caagagcctg 1980
ctgctggacc ctcccaccaa catcagggac taccctaagt gcaagaccat ccaccacatc 2040
cagggccaga accctcacgc ccagggcatc gccctgcacc tgtggggcgc cttcttcctg 2100
tacgacagga tcgccagcac caccatgtac agaggaaaag tgttcacaga gggaaacatc 2160
gctgctatga tcgtgaacaa gaccgtgcat aagatgatct tcagcagaca gggacaggga 2220
tatagacata tgaacctgac atccacaaac aagtactgga caagcagcaa cggaacacag 2280
acaaacgata caggatgttt tggaacactg caggaataca actccaccaa gaaccagaca 2340
tgtgccccta gcaagaagcc tctgcctctg cctacagctc atcctgaagt gaagctgaca 2400

-continued

```
tccacaagca cagatgccac aaagctgaac acaacagatc ctaatagcga cgacgaggat   2460
ctgacaacaa gcggatccgg atccggagaa caggaacctt atacaacaag cgacgctgct   2520
acaaaacagg gactgtcctc cacaatgcct cctacaccta gccctcagcc tagcacacct   2580
cagcagggag gcaacaacac aaaccattcc cagggagtgg tgacagaacc tggaaagaca   2640
aacacaacag cccagcctag catgcctcct cataacacaa caacaatcag cacaaacaac   2700
acctccaagc acaatctgag cacacctagc gtgcctattc agaatgccac caactacaac   2760
acacagtcca cagcccctga aaacgaacag acctccgccc cttccaaaac aaccctgctg   2820
cctacagaaa accctacaac agccaagagc acaaacagca caaagagccc tacaacaaca   2880
gtgcctaaca caacaaacaa gtatagcaca agccctagcc ctacacctaa ttccacagct   2940
cagcatctgg tgtattttag aagaaagaga aacatcctgt ggagagaagg agatatgttc   3000
ccttttctgg atggactgat caacgctcct atcgattttg atcctgtgcc taacacaaag   3060
acaatctttg atgaaagcag cagcagcgga gcctccgccg aagaagatca gcatgcctcc   3120
cctaacatca gcctgacact gagctatttt cctaaggtga acgaaaacac agcccattcc   3180
ggagaaaacg aaaacgattg tgatgccgaa ctgagaatct ggagcgtgca ggaagatgat   3240
ctggccgccg gactgagctg gatccctttt tttgggcccg gaattgaagg actgtacacc   3300
gccggcctga tcaagaacca gaacaacctg gtgtgcaggc tgaggaggct ggccaaccag   3360
accgccaaga gcctggagct gctgctgagg gtgaccaccg aggagaggac cttcagcctg   3420
atcaacaggc acgccatcga cttcctgctg gctaggtggg gcggcacctg caaggtgctg   3480
ggccccgact gctgcatcgg catcgaggac ctgagcagga acatcagcga gcagatcgac   3540
cagatcaaga aggacgagca gaaggagggc accggctggg gcctgggcgg caagtggtgg   3600
accagcgact ggggagtgct gacaaacctg ggaatcctgc tgctgctgag cattgccgtg   3660
ctcattgctc tgtcctgtat ctgtagaatc tttaccaagt acatcggatg atagatccag   3720
atctgctgtg ccttctagtt gccagccatc tgttgtttgc ccctcccccg tgccttcctt   3780
gaccctggaa ggtgccactc ccactgtcct ttcctaataa aatgaggaaa ttgcatcgca   3840
ttgtctgagt aggtgtcatt ctattctggg gggtggggtg gggcaggaca gcaaggggga   3900
ggattgggaa gacaatagca ggcatgctgg ggatgcggtg ggcgatatca gcgatcgctg   3960
aggtgggtga gtgggcgtgg cctggggtgg tcatgaaaat atataagttg ggggtcttag   4020
ggtctcttta tttgtgttgc agagaccgcc ggagccatga gcgggagcag cagcagcagc   4080
agtagcagca gcgccttgga tggcagcatc gtgagccctt atttgacgac gcggatgccc   4140
cactgggccg gggtgcgtca gaatgtgatg ggctccagca tcgacggccg acccgtcctg   4200
cccgcaaatt ccgccacgct gacctatgcg accgtcgcgg ggacgccgtt ggacgccacc   4260
gccgccgccg ccgccaccgc agccgcctcg gccgtgcgca gcctggccac ggactttgca   4320
ttcctgggac cactggcgac aggggctact tctcgggccg ctgctgccgc cgttcgcgat   4380
gacaagctga ccgccctgct ggcgcagttg gatgcgctta ctcgggaact gggtgacctt   4440
tctcagcagg tcatggccct gcgccagcag gtctcctccc tgcaagctgg cgggaatgct   4500
tctcccacaa atgccgttta agataaataa aaccagactc tgtttggatt aaagaaaagt   4560
agcaagtgca ttgctctctt tatttcataa ttttccgcgc gcgataggcc ctagaccagc   4620
gttctcggtc gttgagggtg cggtgtatct tctccaggac gtggtagagg tggctctgga   4680
cgttgagata catgggcatg agcccgtccc gggggtggag gtagcaccac tgcagagctt   4740
```

-continued

```
catgctccgg ggtggtgttg tagatgatcc agtcgtagca ggagcgctgg gcatggtgcc   4800
taaaaatgtc cttcagcagc aggccgatgg ccagggggag gcccttggtg taagtgttta   4860
caaaacggtt aagttgggaa gggtgcattc ggggagagat gatgtgcatc ttggactgta   4920
tttttagatt ggcgatgttt ccgcccagat cccttctggg attcatgttg tgcaggacca   4980
ccagtacagt gtatccggtg cacttgggga atttgtcatg cagcttagag ggaaaagcgt   5040
ggaagaactt ggagacgccc ttgtggcctc ccagattttc catgcattcg tccatgatga   5100
tggcaatggg cccgcgggag gcagcttggg caaagatatt tctggggtcg ctgacgtcgt   5160
agttgtgttc cagggtgagg tcgtcatagg ccatttttac aaagcgcggg cggagggtgc   5220
ccgactgggg gatgatggtc ccctctggcc ctggggcgta gttgccctcg cagatctgca   5280
tttcccaggc cttaatctcg gaggggggaa tcatatccac ctgcggggcg atgaagaaaa   5340
cggtttccgg agccggggag attaactggg atgagagcag gtttctaagc agctgtgatt   5400
ttccacaacc ggtgggccca taaataacac ctataaccgg ttgcagctgg tagtttagag   5460
agctgcagct gccgtcgtcc cggaggaggg gggccacctc gttgagcatg tccctgacgc   5520
gcatgttctc cccgaccaga tccgccagaa ggcgctcgcc gcccagggac agcagctctt   5580
gcaaggaagc aaagtttttc agcggcttga ggccgtccgc cgtgggcatg tttttcaggg   5640
tctggctcag cagctccagg cggtcccaga gctcggtgac gtgctctacg gcatctctat   5700
ccagcatatc tcctcgtttc gcgggttggg gcgactttcg ctgtagggca ccaagcggtg   5760
gtcgtccagc ggggccaaag tcatgtcctt ccatgggcgc agggtcctcg tcagggtggt   5820
ctgggtcacg gtgaaggggt gcgctccggg ctgagcgctt gccaaggtgc gcttgaggct   5880
ggttctgctg gtgctgaagc gctgccggtc ttcgccctgc gcgtcggcca ggtagcattt   5940
gaccatggtg tcatagtcca gcccctccgc ggcgtgtccc ttggcgcgca gcttgccctt   6000
ggaggtggcg ccgcacgagg ggcagagcag gctcttgagc gcgtagagct tgggggcgag   6060
gaagaccgat tcgggggagt aggcgtccgc gccgcagacc ccgcacacgg tctcgcactc   6120
caccagccag gtgagctcgg ggcgcgccgg gtcaaaaacc aggtttcccc catgcttttt   6180
gatgcgtttc ttacctcggg tctccatgag gtggtgtccc cgctcggtga cgaagaggct   6240
gtccgtgtct ccgtagaccg acttgagggg tcttttctcc aggggggtcc ctcggtcttc   6300
ctcgtagagg aactcggacc actctgagac gaaggcccgc gtccaggcca ggacgaagga   6360
ggctatgtgg gaggggtagc ggtcgttgtc cactaggggg tccaccttct ccaaggtgtg   6420
aagacacatg tcgccttcct cggcgtccag gaaggtgatt ggcttgtagg tgtaggccac   6480
gtgaccgggg gttcctgacg ggggggtata aaagggggtg ggggcgcgct cgtcgtcact   6540
ctcttccgca tcgctgtctg cgagggccag ctgctggggt gagtattccc tctcgaaggc   6600
gggcatgacc tccgcgctga ggttgtcagt ttccaaaaac gaggaggatt tgatgttcac   6660
ctgtcccgag gtgatacctt tgagggtacc cgcgtccatc tggtcagaaa acacgatctt   6720
tttattgtcc agcttggtgg cgaacgaccc gtagagggcg ttggagagca gcttggcgat   6780
ggagcgcagg gtctggttct tgtccctgtc ggcgcgctcc ttggccgcga tgttgagctg   6840
cacgtactcg cgcgcgacgc agcgccactc ggggaagacg gtggtgcgct cgtcgggcac   6900
caggcgcacg cgccagccgc ggttgtgcag ggtgaccagg tccacgctgg tggcgacctc   6960
gccgcgcagg cgctcgttgg tccagcagag acggccgccc ttgcgcgagc agaagggggg   7020
cagggggtcg agctgggtct cgtccggggg gtccgcgtcc acggtgaaaa ccccggggcg   7080
caggcgcgcg tcgaagtagt ctatcttgca accttgcatg tccagcgcct gctgccagtc   7140
```

-continued gcgggcggcg agcgcgcgct cgtaggggtt gagcggcggg ccccagggca tggggtgggt 7200
gagtgcggag gcgtacatgc cgcagatgtc atagacgtag aggggctccc gcaggacccc 7260
gatgtaggtg ggtagcagc ggccgccgcg gatgctggcg cgcacgtagt catacagctc 7320
gtgcgagggg gcgaggaggt cggggcccag gttggtgcgg gcggggcgct ccgcgcggaa 7380
gacgatctgc ctgaagatgg catgcgagtt ggaagagatg gtggggcgct ggaagacgtt 7440
gaagctggcg tcctgcaggc cgacggcgtc gcgcacgaag gaggcgtagg agtcgcgcag 7500
cttgtgtacc agctcggcgg tgacctgcac gtcgagcgcg cagtagtcga gggtctcgcg 7560
gatgatgtca tatttagcct gccccttctt tttccacagc tcgcggttga ggacaaactc 7620
ttcgcggtct ttccagtact cttggatcgg gaaaccgtcc ggttccgaac ggtaagagcc 7680
tagcatgtag aactggttga cggcctggta ggcgcagcag cccttctcca cggggagggc 7740
gtaggcctgc gcggccttgc ggagcgaggt gtgggtcagg gcgaaggtgt ccctgaccat 7800
gactttgagg tactggtgct tgaagtcgga gtcgtcgcag ccgccccgct cccagagcga 7860
gaagtcggtg cgcttcttgg agcgggggtt gggcagagcg aaggtgacat cgttgaagag 7920
gattttgccc gcgcggggca tgaagttgcg ggtgatgcgg aagggccccg gcacttcaga 7980
gcggttgttg atgacctggg cggcgagcac gatctcgtcg aagccgttga tgttgtggcc 8040
cacgatgtag agttccagga agcggggccg gccctttacg gtgggcagct tctttagctc 8100
ttcgtaggtg agctcctcgg gcgaggcgag gccgtgctcg gccagggccc agtccgcgag 8160
gtgcgggttg tctctgagga aggactccca gaggtcgcgg gccaggaggg tctgcaggcg 8220
gtccctgaag gtcctgaact ggcggcccac ggccattttt tcgggggtga tgcagtagaa 8280
ggtgaggggg tcttgctgcc agcggtccca gtcgagctgc agggcgaggt cgcgcgcggc 8340
ggtgaccagg cgctcgtcgc ccccgaattt catgaccagc atgaagggca cgagctgctt 8400
tccgaaggcc cccatccaag tgtaggtctc tacatcgtag gtgacaaaga ggcgctccgt 8460
gcgaggatgc gagccgatcg ggaagaactg gatctcccgc caccagttgg aggagtggct 8520
gttgatgtgg tggaagtaga agtcccgtcg ccgggccgaa cactcgtgct ggcttttgta 8580
aaagcgagcg cagtactggc agcgctgcac gggctgtacc tcctgcacga gatgcacctt 8640
tcgcccgcgc acgaggaagc cgaggggaaa tctgagcccc ccgcctggct cgcggcatgg 8700
ctggtgctct tctactttgg atgcgtgtcc gtctccgtct ggctcctcga ggggtgttac 8760
ggtggagcgg accaccacgc cgcgcgagcc gcaggtccag atatcggcgc gcggcggtcg 8820
gagtttgatg acgacatcgc gcagctggga gctgtccatg gtctggagct cccgcggcgg 8880
cggcaggtca gccgggagtt cttgcaggtt cacctcgcag agtcgggcca gggcgcgggg 8940
caggtctagg tggtacctga tctctagggg cgtgttggtg gcggcgtcga tggcttgcag 9000
gagcccgcat ccccgggggg cgacgacggt gccccgcggg gtggtggtgg tggtggtggt 9060
ggtggtggtg gcggtgcagc tcagaagcgg tgccgcgggc gggcccccgg aggtaggggg 9120
ggctccggtc ccgccggcag gggcggcagc ggcacgtcgg cgtggagcgc gggcaggagt 9180
tggtgctgtg cccggaggtt gctggcgaag gcgacgacgc ggcggttgat ctcctggatc 9240
tggcgcctct gcgtgaagac gacgggcccg gtgagcttga acctgaaaga gagttcgaca 9300
gaatcaatct cggtgtcatt gaccgcggcc tggcgcagga tctcctgcac gtctcccgag 9360
ttgtcttggt aggcgatctc ggccatgaac tgctcgatct cttcctcctg gaggtctccg 9420
cgtccggcgc gttccacggt ggccgccagg tcgttggaga tgcgccccat gagctgcgag 9480

-continued aaggcgttga gtccgccctc gttccagact cggctgtaga ccacgccccc ctggtcatcg 9540
cgggcgcgca tgaccacctg cgcgaggttg agctccacgt gccgcgcgaa gacggcgtag 9600
ttgcgcagac gctggaagag gtagttgagg gtggtggcgg tgtgctcggc cacgaagaag 9660
ttcatgaccc agcggcgcaa cgtggattcg ttgatgtccc ccaaggcctc cagccgttcc 9720
atggcctcgt agaagtccac ggcgaagttg aaaaactggg agttgcgcgc cgacacggtc 9780
aactcctcct ccagaagacg gatgagctcg gcgacggtgt cgcgcacctc gcgctcgaag 9840
gctatgggga tctcttcctc cgctagcatc accacctcct cctcttcctc ctcttctggc 9900
acttccatga tggcttcctc ctcttcgggg ggcggcggcg gcggcggtgg gggagggggc 9960
gctctgcgcc ggcggcggcg caccgggagg cggtccacga agcgcgcgat catctccccg 10020
cggcggcggc gcatggtctc ggtgacggcg cggccgttct cccgggggcg cagttggaag 10080
acgccgccgg acatctggtg ctggggcggg tggccgtgag gcagcgaaac ggcgctgacg 10140
atgcatctca acaattgctg cgtaggtacg ccgccgaggg acctgaggga gtccatatcc 10200
accggatccg aaaacctttc gaggaaggcg tctaaccagt cgcagtcgca aggtaggctg 10260
agcaccgtgg cgggcggcgg ggggtggggg gagtgtctgg cggaggtgct gctgatgatg 10320
taattgaagt aggcggactt gacacggcgg atggtcgaca ggagcaccat gtccttgggt 10380
ccggcctgct ggatgcggag gcggtcggct atgccccagg cttcgttctg gcatcggcgc 10440
aggtccttgt agtagtcttg catgagcctt tccaccggca cctcttctcc ttcctcttct 10500
gcttcttcca tgtctgcttc ggccctgggg cggcgccgcg cccccctgcc ccccatgcgc 10560
gtgaccccga accccctgag cggttggagc agggccaggt cggcgacgac gcgctcggcc 10620
aggatggcct gctgcacctg cgtgagggtg gtttggaagt catccaagtc cacgaagcgg 10680
tggtaggcgc ccgtgttgat ggtgtaggtg cagttggcca tgacggacca gttgacggtc 10740
tggtggcccg gttgcgacat ctcggtgtac ctgagtcgcg agtaggcgcg ggagtcgaag 10800
acgtagtcgt tgcaagtccg caccaggtac tggtagccca ccaggaagtg cggcggcggc 10860
tggcggtaga ggggccagcg cagggtggcg ggggctccgg gggccaggtc ttccagcatg 10920
aggcggtggt aggcgtagat gtacctggac atccaggtga tacccgcggc ggtggtggag 10980
gcgcgcggga agtcgcgcac ccggttccag atgttgcgca ggggcagaaa gtgctccatg 11040
gtaggcgtgc tctgtccagt cagacgcgcg cagtcgttga tactctagac cagggaaaac 11100
gaaagccggt cagcgggcac tcttccgtgg tctggtgaat agatcgcaag ggtatcatgg 11160
cggagggcct cggttcgagc cccgggtccg ggccggacgg tccgccatga tccacgcggt 11220
taccgcccgc gtgtcgaacc caggtgtgcg acgtcagaca acggtggagt gttccttttg 11280
gcgtttttct ggccgggcgc cggcgtcgcg taagagacta agccgcgaaa gcgaaagcag 11340
taagtggctc gctccccgta gccggaggga tccttgctaa gggttgcgtt gcggcgaacc 11400
ccggttcgaa tcccgtactc gggccggccg gacccgcggc taaggtgttg gattggcctc 11460
cccctcgtat aaagaccccg cttgcggatt gactccggac acggggacga gcccctttta 11520
tttttgcttt ccccagatgc atccggtgct gcggcagatg cgcccccgc cccagcagca 11580 gcaacaacac cagcaagagc ggcagcaaca gcagcgggag tcatgcaggg ccccctcacc 11640
caccctcggc gggccggcca cctcggcgtc cgcggccgtg tctggcgcct gcggcggcgg 11700
cggggggccg gctgacgacc ccgaggagcc cccgcggcgc agggccagac actacctgga 11760
cctggaggag ggcgagggcc tggcgcggct gggggcgccg tctcccgagc gccacccgcg 11820
ggtgcagctg aagcgcgact cgcgcgaggc gtacgtgcct cggcagaacc tgttcaggga 11880

-continued ccgcgcgggc gaggagcccg aggagatgcg ggacaggagg ttcagcgcag ggcgggagct 11940
gcggcagggg ctgaaccgcg agcggctgct gcgcgaggag gactttgagc ccgacgcgcg 12000
gacggggatc agccccgcgc gcgcgcacgt ggcggccgcc gacctggtga cggcgtacga 12060
gcagacggtg aaccaggaga tcaacttcca aaagagtttc aacaaccacg tgcgcacgct 12120
ggtggcgcgc gaggaggtga ccatcgggct gatgcacctg tgggactttg taagcgcgct 12180
ggtgcagaac cccaacagca agcctctgac ggcgcagctg ttcctgatag tgcagcacag 12240
cagggacaac gaggcgttta gggacgcgct gctgaacatc accgagcccg agggtcggtg 12300
gctgctggac ctgattaaca tcctgcagag catagtggtg caggagcgca gcctgagcct 12360
ggccgacaag gtggcggcca tcaactactc gatgctgagc ctgggcaagt tttacgcgcg 12420
caagatctac cagacgccgt acgtgcccat agacaaggag gtgaagatcg acggttttta 12480
catgcgcatg gcgctgaagg tgctcaccct gagcgacgac ctgggcgtgt accgcaacga 12540
gcgcatccac aaggccgtga gcgtgagccg gcggcgcgag ctgagcgacc gcgagctgat 12600
gcacagcctg cagcgggcgc tggcgggcgc cggcagcggc gacagggagg cggagtccta 12660
cttcgatgcg gggcggacc tgcgctgggc gcccagccgg cgggccctgg aggccgcggg 12720
ggtccgcgag gactatgacg aggacggcga ggaggatgag gagtacgagc tagaggaggg 12780
cgagtacctg gactaaaccg cgggtggtgt ttccggtaga tgcaagaccc gaacgtggtg 12840
gacccggcgc tgcgggcggc tctgcagagc cagccgtccg gccttaactc ctcagacgac 12900
tggcgacagg tcatggaccg catcatgtcg ctgacggcgc gtaacccgga cgcgttccgg 12960
cagcagccgc aggccaacag gctctccgcc atcctggagg cggtggtgcc tgcgcgctcg 13020
aaccccacgc acgagaaggt gctggccata gtgaacgcgc tggccgagaa cagggccatc 13080
cgcccggacg aggccgggct ggtgtacgac gcgctgctgc agcgcgtggc ccgctacaac 13140
agcggcaacg tgcagaccaa cctggaccgg ctggtggggg acgtgcgcga ggcggtggcg 13200
cagcgcgagc gcgcggatcg gcagggcaac ctgggctcca tggtggcgct gaatgccttc 13260
ctgagcacgc agccggccaa cgtgccgcgg gggcaggaag actacaccaa ctttgtgagc 13320
gcgctgcggc tgatggtgac cgagaccccc cagagcgagg tgtaccagtc gggcccggac 13380
tacttcttcc agaccagcag acagggcctg cagacggtga acctgagcca ggctttcaag 13440
aacctgcggg ggctgtgggg cgtgaaggcg cccaccggcg accgggcgac ggtgtccagc 13500
ctgctgacgc ccaactcgcg cctgctgctg ctgctgatcg cgccgttcac ggacagcggc 13560
agcgtgtccc gggacaccta cctggggcac ctgctgaccc tgtaccgcga ggccatcggg 13620
caggcgcagg tggacgagca caccttccag gagatcacca gcgtgagccg cgcgctgggg 13680
caggaggaca cgagcagcct ggaggcgact ctgaactacc tgctgaccaa ccggcggcag 13740
aagattccct cgctgcacag cctgacctcc gaggaggagc gcatcttgcg ctacgtgcag 13800
cagagcgtga gcctgaacct gatgcgcgac ggggtgacgc ccagcgtggc gctggacatg 13860
accgcgcgca acatggaacc gggcatgtac gccgcgcacc ggccttacat caaccgcctg 13920
atggactacc tgcatcgcgc ggcggccgtg aaccccgagt actttaccaa cgccatcctg 13980
aacccgcact ggctcccgcc gcccgggttc tacagcgggg gcttcgaggt cccggaggcc 14040
aacgatggct tcctgtggga cgacatggac gacagcgtgt tctccccgcg gccgcaggcg 14100
ctggcggaag cgtccctgct gcgtcccaag aaggaggagg aggaggcgag tcgccgccgc 14160
ggcagcagcg gcgtggcttc tctgtccgag ctgggggcgg cagccgccgc gcgccccggg 14220
tccctgggcg gcagcccctt tccgagcctg gtggggtctc tgcacagcga gcgcaccacc 14280
cgccctcggc tgctgggcga ggacgagtac ctgaataact ccctgctgca gccggtgcgg 14340
gagaaaaacc tgccccccgc cttccccaac aacgggatag agagcctggt ggacaagatg 14400
agcagatgga agacctatgc gcaggagcac agggacgcgc ccgcgctccg gccgcccacg 14460
cggcgccagc gccacgaccg gcagcggggg ctggtgtggg atgacgagga ctccgcggac 14520
gatagcagcg tgctggacct gggagggagc ggcaacccgt tcgcgcacct gcgcccccgc 14580
ctggggagga tgttttaaaa aaaaaaaaag caagaagcat gatgcaaaat taaataaaac 14640
tcaccaaggc catggcgacc gagcgttggt ttcttgtgtt cccttcagta tgcggcgcgc 14700
ggcgatgtac caggagggac ctcctccctc ttacgagagc gtggtgggcg cggcggcggc 14760
ggcgccctct tctccctttg cgtcgcagct gctggagccg ccgtacgtgc ctccgcgcta 14820
cctgcggcct acggggggga gaaacagcat ccgttactcg gagctggcgc ccctgttcga 14880
caccacccgg gtgtacctgg tggacaacaa gtcggcggac gtggcctccc tgaactacca 14940
gaacgaccac agcaattttt tgaccacggt catccagaac aatgactaca gcccgagcga 15000
ggccagcacc cagaccatca atctggatga ccggtcgcac tggggcggcg acctgaaaac 15060
catcctgcac accaacatgc ccaacgtgaa cgagttcatg ttcaccaata agttcaaggc 15120
gcgggtgatg gtgtcgcgct cgcacaccaa ggaagaccgg gtggagctga agtacgagtg 15180
ggtggagttc gagctgccag agggcaacta ctccgagacc atgaccattg acctgatgaa 15240
caacgcgatc gtggagcact atctgaaagt gggcaggcaa aacggggtcc tggagagcga 15300
catcggggtc aagttcgaca ccaggaactt ccgcctgggg ctggaccccg tgaccgggct 15360
ggttatgccc ggggtgtaca ccaacgaggc cttccatccc gacatcatcc tgctgcccgg 15420
ctgcggggtg gacttcactt acagccgcct gagcaacctc ctgggcatcc gcaagcggca 15480
gcccttccag gagggcttca ggatcaccta cgaggacctg gaggggggca acatccccgc 15540
gctcctcgat gtggaggcct accaggatag cttgaaggaa aatgaggcgg gacaggagga 15600
taccaccccc gccgcctccg ccgccgccga gcagggcgag gatgctgctg acaccgcggc 15660
cgcggacggg gcagaggccg accccgctat ggtggtggag gctcccgagc aggaggagga 15720
tatgaatgac agtgcggtgc gcggagacac cttcgtcacc cggggggagg aaaagcaagc 15780
ggaggccgag gccgcggccg aggaaaagca actggcggca gcagcggcgg cggcggcgtt 15840
ggccgcggcg gaggctgagt ctgaggggac caagcccgcc aaggagcccg tgattaagcc 15900
cctgaccgaa gatagcaaga agcgcagtta caacctgctc aaggacagca ccaacaccgc 15960
gtaccgcagc tggtacctgg cctacaacta cggcgacccg tcgacggggg tgcgctcctg 16020
gaccctgctg tgcacgccgg acgtgacctg cggctcggag caggtgtact ggtcgctgcc 16080
cgacatgatg caagaccccg tgaccttccg ctccacgcgg caggtcagca acttcccggt 16140
ggtgggcgcc gagctgctgc ccgtgcactc caagagcttc tacaacgacc aggccgtcta 16200
ctcccagctc atccgccagt tcacctctct gacccacgtg ttcaatcgct ttcctgagaa 16260
ccagattctg gcgcgcccgc ccgcccccac catcaccacc gtcagtgaaa acgttcctgc 16320
tctcacagat cacgggacgc taccgctgcg caacagcatc ggaggagtcc agcgagtgac 16380
cgttactgac gccagacgcc gcacctgccc ctacgtttac aaggccttgg gcatagtctc 16440
gccgcgcgtc ctttccagcc gcactttttg agcaacacca ccatcatgtc catcctgatc 16500
tcacccagca ataactccgg ctggggactg ctgcgcgcgc ccagcaagat gttcggaggg 16560
gcgaggaagc gttccgagca gcaccccgtg cgcgtgcgcg ggcacttccg cgcccccctgg 16620 ggagcgcaca aacgcggccg cgcggggcgc accaccgtgg acgacgccat cgactcggtg 16680
gtggagcagg cgcgcaacta caggcccgcg gtctctaccg tggacgcggc catccagacc 16740
gtggtgcggg gcgcgcggcg gtacgccaag ctgaagagcc gccggaagcg cgtggcccgc 16800
cgccaccgcc gccgacccgg ggccgccgcc aaacgcgccg ccgcggccct gcttcgccgg 16860
gccaagcgca cgggccgccg cgccgccatg agggccgcgc gccgcttggc cgccggcatc 16920
accgccgcca ccatggcccc ccgtacccga agacgcgcgg ccgccgccgc cgccgccgcc 16980
atcagtgaca tggccagcag gcgcccgggc aacgtgtact gggtgcgcga ctcggtgacc 17040
ggcacgcgcg tgcccgtgcg cttccgcccc ccgcggactt gagatgatgt gaaaaaacaa 17100
cactgagtct cctgctgttg tgtgtatccc agcggcggcg gcgcgcgcag cgtcatgtcc 17160
aagcgcaaaa tcaaagaaga gatgctccag gtcgtcgcgc cggagatcta tgggcccccg 17220
aagaaggaag agcaggattc gaagccccgc aagataaagc gggtcaaaaa gaaaaagaaa 17280
gatgatgacg atgccgatgg ggaggtggag ttcctgcgcg ccacggcgcc caggcgcccg 17340
gtgcagtgga agggccggcg cgtaaagcgc gtcctgcgcc ccggcaccgc ggtggtcttc 17400
acgcccggcg agcgctccac ccggactttc aagcgcgtct atgacgaggt gtacggcgac 17460
gaagacctgc tggagcaggc caacgagcgc ttcggagagt ttgcttacgg gaagcgtcag 17520
cgggcgctgg ggaaggagga cctgctggcg ctgccgctgg accagggcaa ccccaccccc 17580
agtctgaagc ccgtgaccct gcagcaggtg ctgccgagca gcgcaccctc cgaggcgaag 17640
cggggtctga agcgcgaggg cggcgacctg gcgcccaccg tgcagctcat ggtgcccaag 17700
cggcagaggc tggaggatgt gctggagaaa atgaaagtag accccggtct gcagccggac 17760
atcagggtcc gtcccatcaa gcaggtggcg ccgggcctcg gcgtgcagac cgtggacgtg 17820
gtcatcccca ccggcaactc cccgccgcc accaccacta ccgctgcctc cacggacatg 17880
gagacacaga ccgatcccgc cgcagccgca gccgccgccg cagccgcgac ctcctcggcg 17940
gaggtgcaga cggacccctg gctgccgccg gcgatgtcag ctccccgcgc gcgccgcgga 18000
cgcagaaagt acggcgccgc caacgcgctc ctgcccgagt acgccttgca tccttccatc 18060
gcgcccaccc ccggctaccg aggctatacc taccgcccgc gaagagccaa gggttccacc 18120
cgccgtcccc gccgacgcgc cgccgccacc acccgccgcc gccgccgcag acgccagccc 18180
gcactggctc cagtctccgt gaggagagtg gcgcgcgacg gacacaccct ggtgctgccc 18240
agggcgcgct accaccccag catcgtttaa aagcctgttg tggttcttgc agatatggcc 18300
ctcacttgcc gcctccgttt cccggtgccg ggataccgag gaggaagatc gcgccgcagg 18360
aggggtctgg ccggccgcgg cctgagcgga ggcagccgcc gcgcgcaccg gcggcgacgc 18420
gccaccagcc gacgcatgcg cggcggggtg ctgcccctgt taatccccct gatcgccgcg 18480
gcgatcggcg ccgtgcccgg gatcgcctcc gtggccttgc aagcgtccca gaggcattga 18540
cagacttgca aacttgcaaa tatggaaaaa aaaaaaaaac cccaataaaa agtctagact 18600
ctcacgctcg cttggtcctg tgactatttt gtagaatgga agacatcaac tttgcgtcgc 18660
tggccccgcg tcacggctcg cgcccgttcc tgggacactg gaacgatatc ggcaccagca 18720
acatgagcgg tggcgccttc agttggggct ctctgtggag cggcattaaa agtatcgggt 18780
ctgccgttaa aaattacggc tcccgggcct ggaacagcag cacgggccag atgttgagag 18840
acaagttgaa agagcagaac ttccagcaga aggtggtgga gggcctggcc tccggcatca 18900
acggggtggt ggacctggcc aaccaggccg tgcagaataa aatcaacagc agactggacc 18960

-continued cccggccgcc ggtggaggag gtgccgccgg cgctggagac ggtgtccccc gatgggcgtg 19020
gcgagaagcg cccgcggccc gatagggaag agaccactct ggtcacgcag accgatgagc 19080
cgcccccgta tgaggaggcc ctaaagcaag gtctgcccac cacgcggccc atcgcgccca 19140
tggccaccgg ggtggtgggc cgccacaccc ccgccacgct ggacttgcct ccgcccgccg 19200
atgtgccgca gcagcagaag gcggcacagc cgggcccgcc cgcgaccgcc tcccgttcct 19260
ccgccggtcc tctgcgccgc gcggccagcg gcccccgcgg gggggtcgcg aggcacggca 19320
actggcagag cacgctgaac agcatcgtgg gtctgggggt gcggtccgtg aagcgccgcc 19380
gatgctactg aatagcttag ctaacgtgtt gtatgtgtgt atgcgcccta tgtcgccgcc 19440
agaggagctg ctgagtcgcc gccgttcgcg cgcccaccac caccgccact ccgcccctca 19500
agatggcgac cccatcgatg atgccgcagt ggtcgtacat gcacatctcg ggccaggacg 19560
cctcggagta cctgagcccc gggctggtgc agttcgcccg cgccaccgag agctacttca 19620
gcctgagtaa caagtttagg aaccccacgg tggcgcccac gcacgatgtg accaccgacc 19680
ggtctcagcg cctgacgctg cggttcattc ccgtggaccg cgaggacacc gcgtactcgt 19740
acaaggcgcg gttcaccctg gccgtgggcg acaaccgcgt gctggacatg gcctccacct 19800
actttgacat ccgcggggtg ctggaccggg gtcccacttt caagccctac tctggcaccg 19860
cctacaactc cctggccccc aagggcgctc ccaactcctg cgagtgggag caagaggaaa 19920
ctcaggcagt tgaagaagca gcagaagagg aagaagaaga tgctgacggt caagctgagg 19980
aagagcaagc agctaccaaa aagactcatg tatatgctca ggctcccctt tctggcgaaa 20040
aaattagtaa agatggtctg caaataggaa cggacgctac agctacagaa caaaaaccta 20100
tttatgcaga ccctacattc cagcccgaac cccaaatcgg ggagtcccag tggaatgagg 20160
cagatgctac agtcgccggc ggtagagtgc taaagaaatc tactcccatg aaaccatgct 20220
atggttccta tgcaagaccc acaaatgcta atggaggtca gggtgtacta acggcaaatg 20280
cccagggaca gctagaatct caggttgaaa tgcaattctt ttcaacttct gaaaacgccc 20340
gtaacgaggc taacaacatt cagcccaaat tggtgctgta tagtgaggat gtgcacatgg 20400
agaccccgga tacgcacctt tcttacaagc ccgcaaaaag cgatgacaat tcaaaaatca 20460
tgctgggtca gcagtccatg cccaacagac ctaattacat cggcttcaga gacaacttta 20520
tcggcctcat gtattacaat agcactggca acatgggagt gcttgcaggt caggcctctc 20580
agttgaatgc agtggtggac ttgcaagaca gaaacacaga actgtcctac cagctcttgc 20640
ttgattccat gggtgacaga accagatact tttccatgtg gaatcaggca gtggacagtt 20700
atgacccaga tgttagaatt attgaaaatc atggaactga agacgagctc cccaactatt 20760
gtttccctct gggtggcata ggggtaactg acacttacca ggctgttaaa accaacaatg 20820
gcaataacgg gggccaggtg acttggacaa aagatgaaac ttttgcagat cgcaatgaaa 20880
taggggtggg aaacaatttc gctatggaga tcaacctcag tgccaacctg tggagaaact 20940
tcctgtactc caacgtggcg ctgtacctac cagacaagct taagtacaac ccctccaatg 21000
tggacatctc tgacaacccc aacacctacg attacatgaa caagcgagtg gtggccccgg 21060
ggctggtgga ctgctacatc aacctgggcg cgcgctggtc gctggactac atggacaacg 21120
tcaacccctt caaccaccac cgcaatgcgg gcctgcgcta ccgctccatg ctcctgggca 21180
acgggcgcta cgtgcccttc cacatccagg tgccccagaa gttctttgcc atcaagaacc 21240
tcctcctcct gccgggctcc tacacctacg agtggaactt caggaaggat gtcaacatgg 21300
tcctccagag ctctctgggt aacgatctca gggtggacgg ggccagcatc aagttcgaga 21360
gcatctgcct ctacgccacc ttcttcccca tggcccacaa cacggcctcc acgctcgagg 21420
ccatgctcag gaacgacacc aacgaccagt ccttcaatga ctacctttcc gccgccaaca 21480
tgctctaccc catacccgcc aacgccacca acgtccccat ctccatcccc tcgcgcaact 21540
gggcggcctt ccgcggctgg gccttcaccc gcctcaagac caaggagacc ccctccctgg 21600
gctcgggatt cgacccctac tacacctact cgggctctat tccctacctg gacggcacct 21660
tctacctcaa ccacactttc aagaaggtct cggtcacctt cgactcctcg gtcagctggc 21720
cgggcaacga ccgtctgctc acccccaacg agttcgagat caagcgctcg gtcgacgggg 21780
aaggctacaa cgtggcccag tgcaacatga ccaaggactg gttcctggtc cagatgctgg 21840
ccaactacaa catcggctac cagggcttct acatcccaga gagctacaag gacaggatgt 21900
actccttctt caggaacttc cagcccatga gccggcaggt ggtggaccag accaagtaca 21960
aggactacca ggaggtgggc atcatccacc agcacaacaa ctcgggcttc gtgggctacc 22020
tcgcccccac catgcgcgag ggacaggcct accccgccaa cttcccctac ccgctcatag 22080
gcaagaccgc ggtcgacagc atcacccaga aaaagttcct ctgcgaccgc accctctggc 22140
gcatcccctt ctccagcaac ttcatgtcca tgggtgcgct ctcggacctg ggccagaact 22200
tgctctacgc caactccgcc cacgccctcg acatgacctt cgaggtcgac cccatggacg 22260
agcccaccct tctctatgtt ctgttcgaag tctttgacgt ggtccgggtc caccagccgc 22320
accgcggcgt catcgagacc gtgtacctgc gtacgccctt ctcggccggc aacgccacca 22380
cctaaagaag caagccgcag tcatcgccgc ctgcatgccg tcgggttcca ccgagcaaga 22440
gctcagggcc atcgtcagag acctgggatg cgggccctat tttttgggca ccttcgacaa 22500
gcgcttccct ggctttgtct ccccacacaa gctggcctgc gccatcgtca acacggccgg 22560
ccgcgagacc gggggcgtgc actggctggc ctttgcctgg aacccgcgct ccaaaacatg 22620
cttcctcttt gacccctttcg gcttttcgga ccagcggctc aagcaaatct acgagttcga 22680
gtacgagggc ttgctgcgtc gcagcgccat cgcctcctcg cccgaccgct gcgtcaccct 22740
cgaaaagtcc acccagaccg tgcaggggcc cgactcggcc gcctgcggtc tcttctgctg 22800
catgtttctg cacgcctttg tgcactggcc tcagagtccc atggaccgca accccaccat 22860
gaacttgctg acgggggtgc ccaactccat gctccaaagc cccccaggtcg agcccaccct 22920
gcgccgcaac caggagcagc tctacagctt cctggagcgc cactcgccct acttccgccg 22980
ccacagcgca cagatcagga gggccacctc cttctgccac ttgcaagaga tgcaagaagg 23040
gtaataacga tgtacacact tttttctcaa taaatggcat ttttttttta tttatacaag 23100
ctctctgggg tattcatttc ccaccaccac cacccgccgt tgtcgccatc tggctctatt 23160
tagaaatcga aagggttctg ccgggagtcg ccgtgcgcca cgggcaggga cacgttgcga 23220
tactggtagc gggtgcccca cttgaactcg ggcaccacca ggcgaggcag ctcggggaag 23280
ttttcgctcc acaggctgcg ggtcagcacc agcgcgttca tcaggtcggg cgccgagatc 23340
ttgaagtcgc agttggggcc gccgccctgc gcgcgcgagt tgcggtacac cgggttgcag 23400
cactggaaca ccaacagcgc cgggtgcttc acgctggcca gcacgctgcg gtcggagatc 23460
agctcggcgt ccaggtcctc cgcgttgctc agcgcgaacg gggtcatctt gggcacttgc 23520
cgccccagga agggcgcgtg ccccggtttc gagttgcagt cgcagcgcag cgggatcagc 23580
aggtgcccgt gcccggactc ggcgttgggg tacagcgcgc gcatgaaggc ctgcatctgg 23640
cggaaggcca tctgggcctt ggcgccctcc gagaagaaca tgccgcagga cttgcccgag 23700

-continued

```
aactggtttg cggggcagct ggcgtcgtgc aggcagcagc gcgcgtcggt gttggcgatc  23760
tgcaccacgt tgcgccccca ccggttcttc acgatcttgg ccttggacga ttgctccttc  23820
agcgcgcgct gcccgttctc gctggtcaca tccatctcga tcacatgttc cttgttcacc  23880
atgctgctgc cgtgcagaca cttcagctcg ccctccgtct cggtgcagcg gtgctgccac  23940
agcgcgcagc ccgtgggctc gaaagacttg taggtcacct ccgcgaagga ctgcaggtac  24000
ccctgcaaaa agcggcccat catggtcacg aaggtcttgt tgctgctgaa ggtcagctgc  24060
agcccgcggt gctcctcgtt cagccaggtc ttgcacacgg ccgccagcgc ctccacctgg  24120
tcgggcagca tcttgaagtt caccttcagc tcattctcca cgtggtactt gtccatcagc  24180
gtgcgcgccg cctccatgcc cttctcccag gccgacacca gcggcaggct cacggggttc  24240
ttcaccatca ccgtggccgc cgcctccgcc gcgctttcgc tttccgcccc gctgttctct  24300
tcctcttcct cctcttcctc gccgccgccc actcgcagcc cccgcaccac ggggtcgtct  24360
tcctgcaggc gctgcacctt gcgcttgccg ttgcgcccct gcttgatgcg cacgggcggg  24420
ttgctgaagc ccaccatcac cagcgcggcc tcttcttgct cgtcctcgct gtccagaatg  24480
acctccgggg aggggggtt ggtcatcctc agtaccgagg cacgcttctt tttcttcctg  24540
ggggcgttcg ccagctccgc ggctgcggcc gctgccgagg tcgaaggccg agggctgggc  24600
gtgcgcggca ccagcgcgtc ttgcgagccg tcctcgtcct cctcggactc gagacggagg  24660
cgggcccgct tcttcggggg cgcgcggggc ggcggaggcg gcggcggcga cggagacggg  24720
gacgagacat cgtccagggt gggtggacgg cgggccgcgc cgcgtccgcg ctcgggggtg  24780
gtttcgcgct ggtcctcttc ccgactggcc atctcccact gctccttctc ctataggcag  24840
aaagagatca tggagtctct catgcgagtc gagaaggagg aggacagcct aaccgccccc  24900
tctgagccct ccaccaccgc cgccaccacc gccaatgccg ccgcggacga cgcgcccacc  24960
gagaccaccg ccagtaccac cctccccagc gacgcacccc cgctcgagaa tgaagtgctg  25020
atcgagcagg acccgggttt tgtgagcgga gaggaggatg aggtggatga gaaggagaag  25080
gaggaggtcg ccgcctcagt gccaaaagag gataaaaagc aagaccagga cgacgcagat  25140
aaggatgaga cagcagtcgg gcgggggaac ggaagccatg atgctgatga cggctaccta  25200
gacgtgggag acgacgtgct gcttaagcac ctgcaccgcc agtgcgtcat cgtctgcgac  25260
gcgctgcagg agcgctgcga agtgcccctg gacgtggcgg aggtcagccg cgcctacgag  25320
cggcacctct tcgcgccgca cgtgcccccc aagcgccggg agaacggcac ctgcgagccc  25380
aacccgcgtc tcaacttcta cccggtcttc gcggtacccg aggtgctggc cacctaccac  25440
atcttcttcc aaaactgcaa gatccccctc tcctgccgcg ctaaccgcac ccgcgccgac  25500
aaaaccctga ccctgcggca gggcgcccac atacctgata ttgcctctct ggaggaagtg  25560
cccaagatct tcgagggtct cggtcgcgac gagaaacggg cggcgaacgc tctgcacgga  25620
gacagcgaaa acgagagtca ctcgggggtg ctggtggagc tcgagggcga caacgcgcgc  25680
ctggccgtac tcaagcgcag catagaggtc acccactttg cctacccggc gctcaacctg  25740
ccccccaagg tcatgagtgt ggtcatgggc gagctcatca tgcgccgcgc tcagcccctg  25800
gccgcggatg caaacttgca agagtcctcc gaggaaggcc tgcccgcggt cagcgacgag  25860
cagctagcgc gctggctgga gacccgcgac cccgcgcagc tggaggagcg gcgcaagctc  25920
atgatggccg cggtgctggt caccgtggag ctcgagtgtc tgcagcgctt cttcgcggac  25980
cccgagatgc agcgcaagct cgaggagacc ctgcactaca ccttccgcca gggctacgtg  26040
cgccaggcct gcaagatctc caacgtggag ctctgcaacc tggtctccta cctgggcatc  26100
```

ctgcacgaga accgcctcgg gcagaacgtc ctgcactcca ccctcaaagg ggaggcgcgc 26160
cgcgactaca tccgcgactg cgcctacctc ttcctctgct acacctggca gacggccatg 26220
ggggtctggc agcagtgcct ggaggagcgc aacctcaagg agctggaaaa gctactcaag 26280
cgcaccctca gggacctctg gacgggcttc aacgagcgct cggtggccgc cgcgctggcg 26340
gacatcatct tccccgagcg cctgctcaag accctgcagc agggcctgcc cgacttcacc 26400
agccagagca tgctgcagaa ctttaggact ttcatcctgg agcgctcggg catcctgcct 26460
gccacttgct gcgcgctgcc cagcgacttc gtgcccatca agtacaggga gtgcccgccg 26520
ccgctctggg gccactgcta cctcttccag ctggccaact acctcgccta ccactcggac 26580
ctcatggaag acgtgagcgg cgagggcctg ctcgagtgcc actgccgctg caacctctgc 26640
acgccccacc gctctctagt ctgcaacccg cagctgctca gcgagagtca gattatcggt 26700
accttcgagc tgcagggtcc ctcgcctgac gagaagtccg cggctccggg gctgaaactc 26760
actccggggc tgtggacttc cgcctaccta cgcaaatttg tacctgagga ctaccacgcc 26820
cacgagatca ggttctacga agaccaatcc cgcccgccca aggcggagct caccgcctgc 26880
gtcatcaccc aggggcacat cctgggccaa ttgcaagcca tcaacaaagc ccgccgagag 26940
ttcttgctga aaaagggtcg gggggtgtac ctggaccccc agtccggcga ggagctaaac 27000
ccgctacccc cgccgccgcc ccagcagcgg gaccttgctt cccaggatgg cacccagaaa 27060
gaagcagcag ccgccgccgc cgcagccata catgcttctg gaggaagagg aggaggactg 27120
ggacagtcag gcagaggagg tttcggacga ggagcaggag gagatgatgg aagactggga 27180
ggaggacagc agcctagacg aggaagcttc agaggccgaa gaggtggcag acgcaacacc 27240
atcaccctcg gtcgcagccc cctcgccggg gcccctgaaa tcctccgaac ccagcaccag 27300
cgctataacc tccgctcctc cggcgccggc gccacccgcc cgcagaccca accgtagatg 27360
ggacaccaca ggaaccgggg tcggtaagtc caagtgcccg ccgccgccac cgcagcagca 27420
gcagcagcgc cagggctacc gctcgtggcg cgggcacaag aacgccatag tcgcctgctt 27480
gcaagactgc gggggcaaca tctctttcgc ccggcgcttc ctgctattcc accacggggt 27540
cgcctttccc cgcaatgtcc tgcattacta ccgtcatctc tacagcccct actgcagcgg 27600
cgacccagag gcggcagcgg cagccacagc ggcgaccacc acctaggaag atatcctccg 27660
cgggcaagac agcggcagca gcggccagga gacccgcggc agcagcggcg ggagcggtgg 27720
gcgcactgcg cctctcgccc aacgaacccc tctcgacccg ggagctcaga cacaggatct 27780
tccccacttt gtatgccatc ttccaacaga gcagaggcca ggagcaggag ctgaaaataa 27840
aaaacagatc tctgcgctcc ctcacccgca gctgtctgta tcacaaaagc gaagatcagc 27900
ttcggcgcac gctggaggac gcggaggcac tcttcagcaa atactgcgcg ctcactctta 27960
aagactagct ccgcgccctt ctcgaattta ggcgggagaa aactacgtca tcgccggccg 28020
ccgcccagcc cgcccagccg agatgagcaa agagattccc acgccataca tgtggagcta 28080
ccagccgcag atgggactcg cggcgggagc ggcccaggac tactccaccc gcatgaacta 28140
catgagcgcg ggaccccaca tgatctcaca ggtcaacggg atccgcgccc agcgaaacca 28200
aatactgctg gaacaggcgg ccatcaccgc cacgccccgc cataatctca acccccgaaa 28260
ttggcccgcc gccctcgtgt accaggaaac cccctccgcc accaccgtac tacttccgcg 28320
tgacgcccag gccgaagtcc agatgactaa ctcaggggcg cagctcgcgg gcggctttcg 28380
tcacggggcg cggccgctcc gaccaggtat aagacacctg atgatcagag gccgaggtat 28440
ccagctcaac gacgagtcgg tgagctcttc gctcggtctc cgtccggacg gaactttcca 28500
gctcgccgga tccggccgct cttcgttcac gccccgccag gcgtacctga ctctgcagac 28560
ctcgtcctcg gagccccgct ccggaggcat cggaaccctc cagttcgtgg aggagttcgt 28620
gccctcggtc tacttcaacc ccttctcggg acctcccgga cgctaccccg accagttcat 28680
tccgaacttt gacgcggtga aggactcggc ggacggctac gactgaatgt caggtgccga 28740
ggcagagcag cttcgcctga gacacctcga gcactgccgc cgccacaagt gcttcgcccg 28800
cggttccggt gagttctgct actttcagct acccgaggag cataccgagg ggccggcgca 28860
cggcgtccgc ctgaccaccc agggcgaggt tacctgttcc ctcatccggg agttcaccct 28920
ccgtcccctg ctagtggagc gggagcgggg tccctgtgtc ctaactatcg cctgcaactg 28980
ccctaaccct ggattacatc aagatctttg ctgtcatctc tgtgctgagt ttaataaacg 29040
ctgagatcag aatctactgg gaattcgatt tagtcccctt taactaatca aacactggaa 29100
tcaataaaaa gaatcactta cttaaaatca gacagcaggt ctctgtccag tttattcagc 29160
agcacctcct tcccctcctc ccaactctgg tactccaaac gccttctggc ggcaaacttc 29220
ctccacaccc tgaagggaat gtcagattct tgctcctgtc cctccgcacc cactatcttc 29280
atgttgttgc agatgaagcg caccaaaacg tctgacgaga gcttcaaccc cgtgtacccc 29340
tatgacacgg aaagcggccc tccctccgtc cctttcctca cccctccctt cgtgtctccc 29400
gatggattcc aagaaagccc ccccggggtc ctgtctctga acctggccga gcccctggtc 29460
acttcccacg gcatgctcgc cctgaaaatg ggaagtggcc tctccctgga cgacgctggc 29520
aacctcacct ctcaagatat caccaccgct agccctcccc tcaaaaaaac caagaccaac 29580
ctcagcctag aaacctcatc cccccctaact gtaagcacct caggcgccct caccgtagca 29640
gccgccgctc ccctggcagt ggccggcacc tccctcacca tgcaatcaga ggcccccctg 29700
acagtacagg atgcaaaact caccctggcc accaaaggcc ccctgaccgt gtctgaaggc 29760
aaactggcct tgcaaacatc ggccccgctg acggccgctg acagcagcac cctcaccgtt 29820
agcgccacac caccaattaa tgtaagcagt ggaagtttag gcttagacat ggaagaccct 29880
atgtatactc acgatggaaa actgggaata agaattgggg gtccactaag agtagtagac 29940
agcttgcaca cactcactgt agttaccgga aatggactaa ctgtagataa caatgccctc 30000
caaactagag ttacgggcgc cctaggttat gacacatcag gaaatctaca attgagagct 30060
gcaggaggta tgcgaattga tgcaaatggc caacttatcc ttaatgtggc atacccattt 30120
gatgctcaga acaatctcag ccttagactt ggtcagggac ccctgtatat aaacacagac 30180
cacaacctgg atttgaattg caacagaggt ctaaccacaa ctaccaccaa caacacaaaa 30240
aaacttgaga ctaaaattag ctcaggctta gactatgaca ccaatggtgc tgtcattatt 30300
aaacttggca ctggtctaag cttcgacaac acaggcgccc taactgtggg aaacactggt 30360
gatgataaac tgactctgtg gacgacccca gacccatctc caaattgcag aattcactca 30420
gacaaagact gcaagtttac tctagtccta actaagtgtg gaagccaaat cctggcctct 30480
gtcgccgccc tagcggtatc aggaaatctg gcttcgataa caggcaccgt tgccagcgtt 30540
accatctttc tcagatttga tcagaatgga gtgcttatgg aaaactcctc gctagacagg 30600
cagtactgga acttcagaaa tggcaactca actaacgctg cccccctacac caatgcagtt 30660
gggttcatgc caaacctcgc agcataccccc aaaacgcaaa gccagactgc taaaaacaac 30720
attgtaagtc aggtttactt gaatggagac aaatccaaac ccatgaccct taccatcacc 30780
ctcaatggaa ctaatgaatc cagtgaaact agccaggtga gtcactactc catgtcattt 30840

```
acatgggctt gggaaagtgg gcaatatgcc actgaaacct ttgccaccaa ctccttcacc  30900

ttttcttaca ttgctgaaca ataaaaagca tgacactgat gttcatttct gattcttatt  30960

ttattatttt caaacacaac aaaatcattc aagtcattct tccatcttag cttaatagac  31020

acagtagctt aatagaccca gtagtgcaaa gccccattct agcttataac tagtggagaa  31080

gtactcgcct acatgggggt agagtcataa tcgtgcatca ggatagggcg gtggtgctgc  31140

agcagcgcgc gaataaactg ctgccgccgc cgctccgtcc tgcaggaata caacatggca  31200

gtggtctcct cagcgatgat tcgcaccgcc cgcagcataa ggcgccttgt cctccgggca  31260

cagcagcgca ccctgatctc acttaaatca gcacagtaac tgcagcacag caccacaata  31320

ttgttcaaaa tcccacagtg caaggcgctg tatccaaagc tcatggcggg gaccacagaa  31380

cccacgtggc catcatacca caagcgcagg tagattaagt ggcgacccct cataaacacg  31440

ctggacataa acattacctc ttttggcatg ttgtaattca ccacctcccg gtaccatata  31500

aacctctgat taaacatggc gccatccacc accatcctaa accagctggc caaaacctgc  31560

ccgccggcta tacactgcag ggaaccggga ctggaacaat gacagtggag agcccaggac  31620

tcgtaaccat ggatcatcat gctcgtcatg atatcaatgt tggcacaaca caggcacacg  31680

tgcatacact tcctcaggat tacaagctcc tcccgcgtta gaaccatatc ccagggaaca  31740

acccattcct gaatcagcgt aaatcccaca ctgcagggaa gacctcgcac gtaactcacg  31800

ttgtgcattg tcaaagtgtt acattcgggc agcagcggat gatcctccag tatggtagcg  31860

cgggtttctg tctcaaaagg aggtagacga tccctactgt acggagtgcg ccgagacaac  31920

cgagatcgtg ttggtcgtag tgtcatgcca aatggaacgc cggacgtagt catatttcct  31980

gaagtcttag atctctcaac gcagcaccag caccaacact tcgcagtgta aaaggccaag  32040

tgccgagaga gtatatatag gaataaaaag tgacgtaaac gggcaaagtc caaaaaacgc  32100

ccagaaaaac cgcacgcgaa cctacgcccc gaaacgaaag ccaaaaaaca ctagacactc  32160

ccttccggcg tcaacttccg ctttcccacg ctacgtcact tgccccagtc aaacaaacta  32220

catatcccga acttccaagt cgccacgccc aaaacaccgc ctacacctcc ccgcccgccg  32280

gcccgccccc aaacccgcct cccgccccgc gccccgcccc gcgccgccca tctcattatc  32340

atattggctt caatccaaaa taaggtatat tattgatgat g                     32381
```

<210> SEQ ID NO 4
<211> LENGTH: 31881
<212> TYPE: DNA
<213> ORGANISM: Artificial Sequence
<220> FEATURE:
<223> OTHER INFORMATION: synthetic chimpanzee adenovirus serotype ChAd63 with Ebola virus Zaire wild type transmembrane envelope glycoprotein (GP) insert (ChAd63 Ebola Zaire (PB/6001))
<220> FEATURE:
<221> NAME/KEY: CDS
<222> LOCATION: (2139)...(4440)
<223> OTHER INFORMATION: Ebola virus Zaire wild type transmembrane envelope glycoprotein (GP) insert in ChAd63 Ebola Zaire (PB/6001)
<220> FEATURE:
<221> NAME/KEY: CDS
<222> LOCATION: (15152)...(16771)
<223> OTHER INFORMATION: chimpanzee adenovirus serotype ChAd63 penton
<220> FEATURE:
<221> NAME/KEY: CDS
<222> LOCATION: (19538)...(22414)
<223> OTHER INFORMATION: chimpanzee adenovirus serotype ChAd63 hexon
<220> FEATURE:
<221> NAME/KEY: CDS
<222> LOCATION: (28942)...(30219)
<223> OTHER INFORMATION: chimpanzee adenovirus serotype ChAd63 fiber

<400> SEQUENCE: 4
catcatcaat aatatacctc aaacttttgg tgcgcgttaa tatgcaaatg aggtgtttga 60
atttggggat gcggggcgct gattggctga gagacgggcg accgttaggg gcggggcggg 120
tgacgttttg atgacgtggc cgtgaggcgg agccggtttg caagttctcg tgggaaaagt 180
gacgtcaaac gaggtgtggt ttgaacacgg aaatactcaa ttttcccgcg ctctctgaca 240
ggaaatgagg tgtttctggg cggatgcaag tgaaaacggg ccattttcgc gcgaaaactg 300
aatgaggaag tgaaaatctg agtaattccg cgtttatggc agggaggagt atttgccgag 360
ggccgagtag actttgaccg attacgtggg ggtttcgatt accgtatttt tcacctaaat 420
ttccgcgtac ggtgtcaaag tccggtgttt ttacggatat ctccattgca tacgttgtat 480
ccatatcata atatgtacat ttatattggc tcatgtccaa cattaccgcc atgttgacat 540
tgattattga ctagttatta atagtaatca attacggggt cattagttca tagcccatat 600
atggagttcc gcgttacata acttacggta aatggcccgc ctggctgacc gcccaacgac 660
ccccgcccat tgacgtcaat aatgacgtat gttcccatag taacgccaat agggactttc 720
cattgacgtc aatgggtgga gtatttacgg taaactgccc acttggcagt acatcaagtg 780
tatcatatgc caagtacgcc ccctattgac gtcaatgacg gtaaatggcc cgcctggcat 840
tatgcccagt acatgacctt atgggacttt cctacttggc agtacatcta cgtattagtc 900
atcgctatta ccatggtgat gcggttttgg cagtacatca atgggcgtgg atagcggttt 960
gactcacggg gatttccaag tctccacccc attgacgtca atgggagttt gttttggaac 1020
caaaatcaac gggactttcc aaaatgtcgt aacaactccg ccccattgac gcaaatgggc 1080
ggtaggcgtg tacggtggga ggtctatata agcagagctc tccctatcag tgatagagat 1140
ctccctatca gtgatagaga tcgtcgacga gctcgtttag tgaaccgtca gatcgcctgg 1200
agacgccatc cacgctgttt tgacctccat agaagacacc gggaccgatc cagcctccgc 1260
ggccgggaac ggtgcattgg aacgcggatt ccccgtgcca agagtgacgt aagtaccgcc 1320
tatagactct ataggcacac ccctttggct cttatgcatg ctatactgtt tttggcttgg 1380
ggcctataca cccccgcttc cttatgctat aggtgatggt atagcttagc ctataggtgt 1440
gggttattga ccattattga ccactcccct attggtgacg atactttcca ttactaatcc 1500
ataacatggc tctttgccac aactatctct attggctata tgccaatact ctgtccttca 1560
gagactgaca cggactctgt atttttacag gatggggtcc catttattat ttacaaattc 1620
acatatacaa caacgccgtc ccccgtgccc gcagttttta ttaaacatag cgtgggatct 1680
ccacgcgaat ctcgggtacg tgttccggac atgggctctt ctccggtagc ggcggagctt 1740
ccacatccga gccctggtcc catgcctcca gcggctcatg gtcgctcggc agctccttgc 1800
tcctaacagt ggaggccaga cttaggcaca gcacaatgcc caccaccacc agtgtgccgc 1860
acaaggccgt ggcggtaggg tatgtgtctg aaaatgagcg tggagattgg gctcgcacgg 1920
ctgacgcaga tggaagactt aaggcagcgg cagaagaaga tgcaggcagc tgagttgttg 1980
tattctgata agagtcagag gtaactcccg ttgcggtgct gttaacggtg gagggcagtg 2040
tagtctgagc agtactcgtt gctgccgcgc gcgccaccag acataatagc tgacagacta 2100
acagactgtt cctttccatg ggtcttttct gcagtcaccg tcgtcgacac gtgtgatcag 2160
atatcgcggc cgctctagac caggccctgg atcgatccaa caacacaatg ggcgttacag 2220

-continued

```
gaatattgca gttacctcgt gatcgattca agaggacatc attctttctt tgggtaatta   2280
tccttttcca aagaacattt tccatcccac ttggagtcat ccacaatagc acattacagg   2340
ttagtgatgt cgacaaacta gtttgtcgtg acaaactgtc atccacaaat caattgagat   2400
cagttggact gaatctcgaa gggaatggag tggcaactga cgtgccatct gcaactaaaa   2460
gatggggctt caggtccggt gtcccaccaa aggtggtcaa ttatgaagct ggtgaatggg   2520
ctgaaaactg ctacaatctt gaaatcaaaa aacctgacgg gagtgagtgt ctaccagcag   2580
cgccagacgg gattcggggc ttccccggt gccggtatgt gcacaaagta tcaggaacgg   2640
gaccgtgtgc cggagacttt gccttccata aagagggtgc tttcttcctg tatgatcgac   2700
ttgcttccac agttatctac cgaggaacga ctttcgctga aggtgtcgtt gcatttctga   2760
tactgcccca agctaagaag gacttcttca gctcacaccc cttgagagag ccggtcaatg   2820
caacggagga cccgtctagt ggctactatt ctaccacaat tagatatcag gctaccggtt   2880
ttggaaccaa tgagacagag tacttgttcg aggttgacaa tttgacctac gtccaacttg   2940
aatcaagatt cacaccacag tttctgctcc agctgaatga gacaatatat acaagtggga   3000
aaaggagcaa taccacggga aaactaattt ggaaggtcaa ccccgaaatt gatacaacaa   3060
tcggggagtg ggccttctgg gaaactaaaa aaaacctcac tagaaaaatt cgcagtgaag   3120
agttgtcttt cacagttgta tcaaacggag ccaaaaacat cagtggtcag agtccggcgc   3180
gaacttcttc cgacccaggg accaacacaa caactgaaga ccacaaaatc atggcttcag   3240
aaaattcctc tgcaatggtt caagtgcaca gtcaaggaag ggaagctgca gtgtcgcatc   3300
taacaaccct tgccacaatc tccacgagtc cccaatccct cacaaccaaa ccaggtccgg   3360
acaacagcac ccataataca cccgtgtata aacttgacat ctctgaggca actcaagttg   3420
aacaacatca ccgcagaaca gacaacgaca gcacagcctc cgacactccc tctgccacga   3480
ccgcagccgg acccccaaaa gcagagaaca ccaacacgag caagagcact gacttcctgg   3540
accccgccac cacaacaagt ccccaaaacc acagcgagac cgctggcaac aacaacactc   3600
atcaccaaga taccggagaa gagagtgcca gcagcgggaa gctaggctta attaccaata   3660
ctattgctgg agtcgcagga ctgatcacag gcgggagaag aactcgaaga gaagcaattg   3720
tcaatgctca acccaaatgc aaccctaatt tacattactg gactactcag gatgaaggtg   3780
ctgcaatcgg actggcctgg ataccatatt tcgggccagc agccgaggga atttacatag   3840
aggggctaat gcacaatcaa gatggtttaa tctgtgggtt gagacagctg gccaacgaga   3900
cgactcaagc tcttcaactg ttcctgagag ccacaactga gctacgcacc ttttcaatcc   3960
tcaaccgtaa ggcaattgat ttcttgctgc agcgatgggg cggcacatgc cacattctgg   4020
gaccggactg ctgtatcgaa ccacatgatt ggaccaagaa cataacagac aaaattgatc   4080
agattattca tgattttgtt gataaaaccc ttccggacca gggggacaat gacaattggt   4140
ggacaggatg gagacaatgg ataccggcag gtattggagt tacaggcgtt gtaattgcag   4200
ttatcgcttt attctgtata tgcaaatttg tcttttagtt tttcttcaga ttgcttcatg   4260
gaaaagctca gcctcaaatc aatgaaacca ggatttaatt atatggatta cttgaatcta   4320
agattacttg acaaatgata atataataca ctggagcttt aaacatagcc aatgtgattc   4380
taactccttt aaactcacag ttaatcataa acaaggtttg aggtaccgag ctcgaattga   4440
tctgctgtgc cttctagttg ccagccatct gttgtttgcc cctcccccgt gccttccttg   4500
accctggaag gtgccactcc cactgtcctt tcctaataaa atgaggaaat tgcatcgcat   4560
tgtctgagta ggtgtcattc tattctgggg ggtggggtgg ggcaggacag caagggggag   4620
```

gattgggaag acaatagcag gcatgctggg gatgcggtgg gctctagata tcagcgatcg 4680
cgtgagtagt gtttgggggt gggtgggagc ctgcatgatg ggcagaatga ctaaaatctg 4740
tgtttttctg tgtgttgcag cagcatgagc ggaagcgcct cctttgaggg aggggtattc 4800
agcccttatc tgacggggcg tctcccctcc tgggcgggag tgcgtcagaa tgtgatggga 4860
tccacggtgg acggccggcc cgtgcagccc gcgaactctt caaccctgac ctacgcgacc 4920
ctgagctcct cgtccgtgga cgcagctgcc gccgcagctg ctgcttccgc cgccagcgcc 4980
gtgcgcggaa tggccctggg cgccggctac tacagctctc tggtggccaa ctcgagttcc 5040
accaataatc ccgccagcct gaacgaggag aagctgttgc tgctgatggc ccagctcgag 5100
gccctgaccc agcgcctggg cgagctgacc cagcaggtgg ctcagctgca ggcggagacg 5160
cgggccgcgg ttgccacggt gaaaaccaaa taaaaaatga atcaataaat aaacggagac 5220
ggttgttgat tttaacacag agtcttgaat ctttatttga tttttcgcgc gcggtaggcc 5280
ctggaccacc ggtctcgatc attgagcacc cggtggatct tttccaggac ccggtagagg 5340
tgggcttgga tgttgaggta catgggcatg agcccgtccc gggggtggag gtagctccat 5400
tgcagggcct cgtgctcggg ggtggtgttg taaatcaccc agtcatagca ggggcgcagg 5460
gcgtggtgct gcacgatgtc tttgaggagg agactgatgg ccacgggcag ccccttggtg 5520
taggtgttga cgaacctatt gagctgggag ggatgcatgc ggggggagat gagatgcatc 5580
ttggcctgga tcttgagatt ggcgatgttc ccgcccagat cccgccgggg gttcatgttg 5640
tgcaggacca ccagcacggt gtatccggtg cacttgggga atttgtcatg caacttggaa 5700
gggaaggcgt gaaagaattt ggagacgccc ttgtgaccgc ccaggttttc catgcactca 5760
tccatgatga tggcgatggg cccgtgggcg gcggcctggg caaagacgtt tcgggggtcg 5820
gacacatcgt agttgtggtc ctgggtgagc tcgtcatagg ccattttaat gaatttgggg 5880
cggagggtac ccgactgggg gacaaaggtg ccctcgatcc cgggggcgta gttcccctcg 5940
cagatctgca tctcccaggc cttgagctcg gagggggga tcatgtccac ctgcggggcg 6000
atgaaaaaaa cggtttccgg ggcgggggag atgagctgcg ccgaaagcag gttccggagc 6060
agctgggact tgccgcagcc ggtggggccg tagatgaccc cgatgaccgg ctgcaggtgg 6120
tagttgaggg agagacagct gccgtcctcg cggaggaggg gggccacctc gttcatcatc 6180
tcgcgcacat gcatgttctc gcgcacgagt tccgccagga ggcgctcgcc ccccagcgag 6240
aggagctctt gcagcgaggc gaagtttttc agcggcttga gcccgtcggc catgggcatt 6300
ttggagaggg tctgttgcaa gagttccaga cggtcccaga gctcggtgat gtgctctagg 6360
gcatctcgat ccagcagacc tcctcgtttc gcgggttggg gcgactgcgg gagtagggca 6420
ccaggcgatg ggcgtccagc gaggccaggg tccggtcctt ccagggtcgc agggtccgcg 6480
tcagcgtggt ctccgtcacg gtgaaggggt gcgcgccggg ctgggcgctt gcgagggtgc 6540
gcttcaggct catccggctg gtcgagaacc gctcccggtc ggcgccctgc gcgtcggcca 6600
ggtagcaatt gagcatgagt tcgtagttga gcgcctcggc cgcgtggccc ttggcgcgga 6660
gcttaccttt ggaagtgtgt ccgcagacgg gacagaggag ggacttgagg gcgtagagct 6720
tgggggcgag gaagacggac tcgggggcgt aggcgtccgc gccgcagctg gcgcagacgg 6780
tctcgcactc cacgagccag gtgaggtcgg ggcggtcggg gtcaaaaacg aggtttcctc 6840
cgtgcttttt gatgcgtttc ttacctctgg tctccatgag ctcgtgtccc cgctgggtga 6900
caaagaggct gtccgtgtcc ccgtagaccg actttatggg ccggtcctcg agcggggtgc 6960

-continued

```
cgcggtcctc gtcgtagagg aaccccgccc actccgagac gaaggcccgg gtccaggcca   7020
gcacgaagga ggccacgtgg gaggggtagc ggtcgttgtc caccagcggg tccaccttct   7080
ccagggtatg caagcacatg tccccctcgt ccacatccag gaaggtgatt ggcttgtaag   7140
tgtaggccac gtgaccgggg gtcccggccg ggggggtata aaagggggcg ggcccctgct   7200
cgtcctcact gtcttccgga tcgctgtcca ggagcgccag ctgttggggt aggtattccc   7260
tctcgaaggc gggcatgacc tcggcactca ggttgtcagt ttctagaaac gaggaggatt   7320
tgatattgac ggtgccgttg gagacgcctt tcatgagccc ctcgtccatc tggtcagaaa   7380
agacgatctt tttgttgtcg agcttggtgg cgaaggagcc gtagagggcg ttggagagca   7440
gcttggcgat ggagcgcatg gtctggttct tttccttgtc ggcgcgctcc ttggcggcga   7500
tgttgagctg cacgtactcg cgcgccacgc acttccattc ggggaagacg gtggtgagct   7560
cgtcgggcac gattctgacc cgccagccgc ggttgtgcag ggtgatgagg tccacgctgg   7620
tggccacctc gccgcgcagg ggctcgttgg tccagcagag gcgcccgccc ttgcgcgagc   7680
agaagggggg cagcgggtcc agcatgagct cgtcgggggg gtcggcgtcc acggtgaaga   7740
tgccgggcag gagctcgggg tcgaagtagc tgatgcaggt gcccagatcg tccagacttg   7800
cttgccagtc gcgcacggcc agcgcgcgct cgtaggggct gaggggcgtg ccccagggca   7860
tggggtgcgt gagcgcggag gcgtacatgc cgcagatgtc gtagacgtag aggggctcct   7920
ggaggacgcc gatgtaggtg gggtagcagc gcccccccgcg gatgctggcg cgcacgtagt   7980
cgtacagctc gtgcgagggc gcgaggagcc ccgtgccgag attggagcgc tgcggctttt   8040
cggcgcggta gacgatctgg cggaagatgg cgtgggagtt ggaggagatg gtgggcctct   8100
ggaagatgtt gaagtgggca tggggcagtc cgaccgagtc cctgatgaag tgggcgtagg   8160
agtcctgcag cttggcgacg agctcggcgg tgacgaggac gtccagggcg cagtagtcga   8220
gggtctcttg gatgatgtcg tacttgagct ggcccttctg cttccacagc tcgcggttga   8280
gaaggaactc ttcgcggtcc ttccagtact cttcgagggg gaacccgtcc tgatcggcac   8340
ggtaagagcc caccatgtag aactggttga cggccttgta ggcgcagcag cccttctcca   8400
cggggagggc gtaagcttgc gcggccttgc gcagggaggt gtgggtgagg gcgaaggtgt   8460
cgcgcaccat gactttgagg aactggtgct tgaagtcgag gtcgtcgcag ccgccctgct   8520
cccagagctg gaagtccgtg cgcttcttgt aggcggggtt gggcaaagcg aaagtaacat   8580
cgttgaagag gatcttgccc gcgcggggca tgaagttgcg agtgatgcgg aaaggctggg   8640
gcacctcggc ccggttgttg atgacctggg cggcgaggac gatctcgtcg aagccgttga   8700
tgttgtgccc gacgatgtag agttccacga atcgcgggcg gcccttgacg tggggcagct   8760
tcttgagctc gtcgtaggtg agctcggcgg ggtcgctgag cccgtgctgc tcgagggccc   8820
agtcggcgac gtgggggttg gcgctgagga aggaagtcca gagatccacg gccagggcgg   8880
tctgcaagcg gtcccggtac tgacggaact gctggcccac ggccattttt tcgggggtga   8940
cgcagtagaa ggtgcggggg tcgccgtgcc agcggtccca cttgagctgg agggcgaggt   9000
cgtgggcgag ctcgacgagc ggcgggtccc cggagagttt catgaccagc atgaagggga   9060
cgagctgctt gccgaaggac cccatccagg tgtaggtttc cacatcgtag gtgaggaaga   9120
gcctttcggt gcgaggatgc gagccgatgg ggaagaactg gatctcctgc caccagttgg   9180
aggaatggct gttgatgtga tggaagtaga aatgccgacg gcgcgccgag cactcgtgct   9240
tgtgtttata caagcgtccg cagtgctcgc aacgctgcac gggatgcacg tgctgcacga   9300
gctgtacctg ggttcctttg acgaggaatt tcagtgggca gtggagcgct ggcggctgca   9360
```

-continued tctggtgctg tactacgtcc tggccatcgg cgtggccatc gtctgcctcg atggtggtca 9420
tgctgacgag cccgcgcggg aggcaggtcc agacctcggc tcggacgggt cggagagcga 9480
ggacgagggc gcgcaggccg gagctgtcca gggtcctgag acgctgcgga gtcaggtcag 9540
tgggcagcgg cggcgcgcgg ttgacttgca ggagcttttc cagggcgcgc gggaggtcca 9600
gatggtactt gatctccacg gcgccgttgg tggcgacgtc cacggcttgc agggtcccgt 9660
gcccctgggg cgccaccacc gtgccccgtt tcttcttggg cggcggcggc tccatgctta 9720
gaagcggcgg cgaggacgcg cgccgggcgg caggggcggc tcggggcccg gaggcagggg 9780
cggcaggggc acgtcggcgc cgcgcgcggg caggttctgg tactgcgccc ggagaagact 9840
ggcgtgagcg acgacgcgac ggttgacgtc ctggatctga cgcctctggg tgaaggccac 9900
gggacccgtg agtttgaacc tgaaagagag ttcgacagaa tcaatctcgg tatcgttgac 9960
ggcggcctgc cgcaggatct cttgcacgtc gcccgagttg tcctggtagg cgatctcggt 10020
catgaactgc tcgatctcct cctcctgaag gtctccgcgg ccggcgcgct cgacggtggc 10080
cgcgaggtcg ttggagatgc ggcccatgag ctgcgagaag gcgttcatgc cggcctcgtt 10140
ccagacgcgg ctgtagacca cggctccgtc ggggtcgcgc gcgcgcatga ccacctgggc 10200
gaggttgagc tcgacgtggc gcgtgaagac cgcgtagttg cagaggcgct ggtagaggta 10260
gttgagcgtg gtggcgatgt gctcggtgac gaagaagtac atgatccagc ggcggagcgg 10320
catctcgctg acgtcgccca gggcttccaa gcgctccatg gcctcgtaga agtccacggc 10380
gaagttgaaa aactgggagt tgcgcgccga gacggtcaac tcctcctcca gaagacggat 10440
gagctcggcg atggtggcgc gcacctcgcg ctcgaaggcc ccgggggggct cctcttccat 10500 ttcctcctct tcctcctcca ctaacatctc ttctacttcc tcctcaggag gcggcggcgg 10560
gggaggggcc ctgcgtcgcc ggcggcgcac gggcagacgg tcgatgaagc gctcgatggt 10620
ctccccgcgc cggcgacgca tggtctcggt gacggcgcgc ccgtcctcgc ggggccgcag 10680
cgtgaagacg ccgccgcgca tctccaggtg gccgccgggg gggtctccgt tgggcaggga 10740
gagggcgctg acgatgcatc ttatcaattg acccgtaggg actccgcgca aggacctgag 10800
cgtctcgaga tccacgggat ccgaaaaccg ctgaacgaag gcttcgagcc agtcgcagtc 10860
gcaaggtagg ctgagcccgg tttcttgttc ttcgggtatt tggtcgggag gcgggcgggc 10920
gatgctgctg gtgatgaagt tgaagtaggc ggtcctgaga cggcggatgg tggcgaggag 10980
caccaggtcc ttgggcccgg cttgctggat gcgcagacgg tcggccatgc cccaggcgtg 11040
gtcctgacac ctggcgaggt ccttgtagta gtcctgcatg agccgctcca cgggcacctc 11100
ctcctcgccc gcgcggccgt gcatgcgcgt gagcccgaac ccgcgctgcg gctggacgag 11160
cgccaggtcg gcgacgacgc gctcggcgag gatggcctgc tggatctggg tgagggtggt 11220
ctggaagtcg tcgaagtcga cgaagcggtg gtaggctccg gtgttgatgg tgtaggagca 11280
gttggccatg acggaccagt tgacggtctg gtggccgggg cgcacgagct cgtggtactt 11340
gaggcgcgag taggcgcgcg tgtcgaagat gtagtcgttg caggtgcgca cgaggtactg 11400
gtatccgacg aggaagtgcg gcggcggctg gcggtagagc ggccatcgct cggtggcggg 11460
ggcgccgggc gcgaggtcct cgagcatgag gcggtggtag ccgtagatgt acctggacat 11520
ccaggtgatg ccggcggcgg tggtggaggc gcgcgggaac tcgcggacgc ggttccagat 11580
gttgcgcagc ggcaggaagt agttcatggt ggccgcggtc tggcccgtga ggcgcgcgca 11640
gtcgtggatg ctctagacat acgggcaaaa acgaaagcgg tcagcggctc gactccgtgg 11700

-continued cctggaggct aagcgaacgg gttgggctgc gcgtgtaccc cggttcgaat ctcgaatcag 11760
gctggagccg cagctaacgt ggtactggca ctcccgtctc gacccaagcc tgctaacgaa 11820
acctccagga tacggaggcg ggtcgttttt tggccttggt cgctggtcat gaaaaactag 11880
taagcgcgga aagcggccgc ccgcgatggc tcgctgccgt agtctggaga aagaatcgcc 11940
agggttgcgt tgcggtgtgc cccggttcga gcctcagcgc tcggcgccgg ccggattccg 12000
cggctaacgt gggcgtggct gccccgtcgt ttccaagacc ccttagccag ccgacttctc 12060
cagttacgga gcgagcccct cttttttttct tgtgtttttg ccagatgcat cccgtactgc 12120
ggcagatgcg cccccaccct ccaccacaac cgcccctacc gcagcagcag caacagccgg 12180
cgcttctgcc cccgccccag cagcagcagc cagccactac cgcggcggcc gccgtgagcg 12240
gagccggcgt tcagtatgac ctggccttgg aagagggcga ggggctggcg cggctggggg 12300
cgtcgtcgcc ggagcggcac ccgcgcgtgc agatgaaaag ggacgctcgc gaggcctacg 12360
tgcccaagca gaacctgttc agagacagga gcggcgagga gcccgaggag atgcgcgcct 12420
cccgcttcca cgcggggcgg gagctgcggc gcggcctgga ccgaaagcgg gtgctgaggg 12480
acgaggattt cgaggcggac gagctgacgg ggatcagccc cgcgcgcgcg cacgtggccg 12540
cggccaacct ggtcacggcg tacgagcaga ccgtgaagga ggagagcaac ttccaaaaat 12600
ccttcaacaa ccacgtgcgc acgctgatcg cgcgcgagga ggtgaccctg ggcctgatgc 12660
acctgtggga cctgctggag gccatcgtgc agaaccccac gagcaagccg ctgacggcgc 12720
agctgtttct ggtggtgcag cacagtcggg acaacgagac gttcagggag gcgctgctga 12780
atatcaccga gcccgagggc cgctggctcc tggacctggt gaacattctg cagagcatcg 12840
tggtgcagga gcgcgggctg ccgctgtccg agaagctggc ggccatcaac ttctcggtgc 12900
tgagcctggg caagtactac gctaggaaga tctacaagac cccgtacgtg cccatagaca 12960
aggaggtgaa gatcgatggg ttttacatgc gcatgaccct gaaagtgctg accctgagcg 13020
acgatctggg ggtgtaccgc aacgacagga tgcaccgcgc ggtgagcgcc agccgccggc 13080
gcgagctgag cgaccaggag ctgatgcaca gcctgcagcg ggccctgacc ggggccggga 13140
ccgaggggga gagctacttt gacatgggcg cggacctgcg ctggcagccc agccgccggg 13200
ccttggaagc tgccggcggc gtgccctacg tggaggaggt ggacgatgag gaggaggagg 13260
gcgagtacct ggaagactga tggcgcgacc gtatttttgc tagatgcagc aacagccacc 13320
gccgccgcct cctgatcccg cgatgcgggc ggcgctgcag agccagccgt ccggcattaa 13380
ctcctcggac gattggaccc aggccatgca acgcatcatg gcgctgacga cccgcaatcc 13440
cgaagccttt agacagcagc ctcaggccaa ccggctctcg gccatcctgg aggccgtggt 13500
gccctcgcgc tcgaacccca cgcacgagaa ggtgctggcc atcgtgaacg cgctggtgga 13560
gaacaaggcc atccgcggcg acgaggccgg gctggtgtac aacgcgctgc tggagcgcgt 13620
ggcccgctac aacagcacca acgtgcagac gaacctggac cgcatggtga ccgacgtgcg 13680
cgaggcggtg tcgcagcgcg agcggttcca ccgcgagtcg aacctgggct ccatggtggc 13740
gctgaacgcc ttcctgagca cgcagcccgc caacgtgccc cggggccagg aggactacac 13800
caacttcatc agcgcgctgc ggctgatggt ggccgaggtg ccccagagcg aggtgtacca 13860
gtcggggccg gactacttct tccagaccag tcgccagggc ttgcagaccg tgaacctgag 13920
ccaggctttc aagaacttgc agggactgtg gggcgtgcag gccccggtcg gggaccgcgc 13980
gacggtgtcg agcctgctga cgccgaactc gcgcctgctg ctgctgctgg tggcgccctt 14040
cacggacagc ggcagcgtga gccgcgactc gtacctgggc tacctgctta acctgtaccg 14100

-continued cgaggccatc gggcaggcgc acgtggacga gcagacctac caggagatca cccacgtgag 14160
ccgcgcgctg ggccaggagg acccgggcaa cctggaggcc accctgaact tcctgctgac 14220
caaccggtcg cagaagatcc cgccccagta cgcgctgagc accgaggagg agcgcatcct 14280
gcgctacgtg cagcagagcg tggggctgtt cttgatgcag gagggggcca cgcccagcgc 14340
cgcgctcgac atgaccgcgc gcaacatgga gcccagcatg tacgcccgca accgcccgtt 14400
catcaataag ctgatggact acttgcatcg ggcggccgcc atgaactcgg actactttac 14460
caacgccatc ttgaacccgc actggctccc gccgcccggg ttctacacgg gcgagtacga 14520
catgcccgac cccaacgacg ggttcctgtg ggacgacgtg gacagcagcg tgttctcgcc 14580
gcggcccacc accaccaccg tgtggaagaa agagggcggg gaccggcggc cgtcctcggc 14640
gctgtccggt cgcgcgggtg ctgccgcggc ggtgcccgag gctgccagcc ccttcccgag 14700
cctgcccttt tcgctgaaca gcgtgcgcag cagcgagctg ggtcggctga cgcggccgcg 14760
cctgctgggc gaggaggagt acctgaacga ctccttgttg aagcccgagc gcgagaagaa 14820
cttccccaat aacgggatag agagcctggt ggacaagatg agccgctgga agacgtacgc 14880
gcacgagcac agggacgagc cccgagctag cagcgcaggc acccgtagac gccagcggca 14940
cgacaggcag cggggactgg tgtgggacga tgaggattcc gccgacgaca gcagcgtgtt 15000
ggacttgggt gggagtggtg gtggtaaccc gttcgctcac ctgcgccccc gtatcgggcg 15060
cctgatgtaa gaatctgaaa aaataaaaga cggtactcac caaggccatg gcgaccagcg 15120
tgcgttcttc tctgttgttt gtagtagtat gatgaggcgc gtgtacccgg agggtcctcc 15180
tccctcgtac gagagcgtga tgcagcaggc ggtggcggcg gcgatgcagc ccccgctgga 15240
ggcgccttac gtgcccccgc ggtacctggc gcctacggag gggcggaaca gcattcgtta 15300
ctcggagctg gcacccttgt acgataccac ccggttgtac ctggtggaca acaagtcggc 15360
ggacatcgcc tcgctgaact accagaacga ccacagcaac ttcctgacca ccgtggtgca 15420
gaacaacgat ttcaccccca cggaggccag cacccagacc atcaactttg acgagcgctc 15480
gcggtggggc ggccagctga aaaccatcat gcacaccaac atgcccaacg tgaacgagtt 15540
catgtacagc aacaagttca aggcgcgggt gatggtctcg cgcaagaccc ccaacggggt 15600
cacggtaggg gatgattatg atggtagtca ggacgagctg acctacgagt gggtggagtt 15660
tgagctgccc gagggcaact tctcggtgac catgaccatc gatctgatga acaacgccat 15720
catcgacaac tacttggcgg tggggcggca gaacggggtg ctggagagcg acatcggcgt 15780
gaagttcgac acgcgcaact tccggctggg ctgggacccc gtgaccgagc tggtgatgcc 15840
gggcgtgtac accaacgagg ccttccaccc cgacatcgtc ctgctgcccg gctgcggcgt 15900
ggacttcacc gagagccgcc tcagcaacct gctgggcatc cgcaagcggc agcccttcca 15960
ggagggcttc cagatcctgt acgaggacct ggagggggggc aacatccccg cgctcttgga 16020
tgtcgaagcc tatgaagaaa gtaaggaaaa agcagaggct gaggcaacta cagccgtggc 16080
taccgccgcg actgtggcag atgccactgt caccaggggc gatacattcg ccacccaggc 16140
ggaggaagca gccgccctag cggcgaccga tgatagtgaa agtaagatag tcatcaagcc 16200
ggtggagaag gacagcaaga acaggagcta caacgttcta ccggatggaa agaacaccgc 16260
ctaccgcagc tggtacctgg cctacaacta cggcgacccc gagaagggcg tgcgctcctg 16320
gacgctgctc accacctcgg acgtcacctg cggcgtggag caagtctact ggtcgctgcc 16380
cgacatgatg caagacccgg tcaccttccg ctccacgcga caagttagca actacccggt 16440

-continued ggtgggcgcc gagctcctgc ccgtctactc caagagcttc ttcaacgagc aggccgtcta 16500
ctcgcagcag ctgcgtgcct tcacctcgct cacgcacgtc ttcaaccgct tccccgagaa 16560
ccagatcctc gtccgcccgc ccgcgcccac cattaccacc gtcagtgaaa acgttcctgc 16620
tctcacagat cacgggaccc tgccgctgcg cagcagtatc cggggagtcc agcgcgtgac 16680
cgtcactgac gccagacgcc gcacctgccc ctacgtctac aaggccctgg gcgtagtcgc 16740
gccgcgcgtc ctctcgagcc gcaccttcta aaaaatgtcc attctcatct cgcccagtaa 16800
taacaccggt tggggcctgc gcgcgcccag caagatgtac ggaggcgctc gccaacgctc 16860
cacgcaacac cccgtgcgcg tgcgcgggca cttccgcgct ccctggggcg ccctcaaggg 16920
ccgcgtgcgc tcgcgcacca ccgtcgacga cgtgatcgac caggtggtgg ccgacgcgcg 16980
caactacacg cccgccgccg cgcccgcctc caccgtggac gccgtcatcg acagcgtggt 17040
ggccgacgcg cgccggtacg cccgcgccaa gagccggcgg cggcgcatcg cccggcggca 17100
ccggagcacc cccgccatgc gcgcggcgcg agccttgctg cgcagggcca ggcgcacggg 17160
acgcagggcc atgctcaggg cggccagacg cgcggcctcc ggcagcagca gcgccggcag 17220
gacccgcaga cgcgcggcca cggcggcggc ggcggccatc gccagcatgt cccgcccgcg 17280
gcgcggcaac gtgtactggg tgcgcgacgc cgccaccggt gtgcgcgtgc ccgtgcgcac 17340
ccgccccccct cgcacttgaa gatgctgact tcgcgatgtt gatgtgtccc agcggcgagg 17400
aggatgtcca agcgcaaata caaggaagag atgctccagg tcatcgcgcc tgagatctac 17460
ggccccgcgg cggcggtgaa ggaggaaaga aagccccgca aactgaagcg ggtcaaaaag 17520
gacaaaaagg aggaggaaga tgacggactg gtggagtttg tgcgcgagtt cgcccccccgg 17580
cggcgcgtgc agtggcgcgg gcggaaagtg aaaccggtgc tgcggcccgg caccacggtg 17640
gtcttcacgc ccggcgagcg ttccggctcc gcctccaagc gctcctacga cgaggtgtac 17700
ggggacgagg acatcctcga gcaggcggtc gagcgtctgg gcgagtttgc ttacggcaag 17760
cgcagccgcc ccgcgccctt gaaagaggag gcggtgtcca tcccgctgga ccacggcaac 17820
cccacgccga gcctgaagcc ggtgaccctg cagcaggtgc tgccgagcgc ggcgccgcgc 17880
cggggcttca agcgcgaggg cggcgaggat ctgtacccga ccatgcagct gatggtgccc 17940
aagcgccaga agctggagga cgtgctggag cacatgaagg tggaccccga ggtgcagccc 18000
gaggtcaagg tgcggcccat caagcaggtg gccccgggcc tgggcgtgca gaccgtggac 18060
atcaagatcc ccacggagcc catggaaacg cagaccgagc ccgtgaagcc cagcaccagc 18120
accatggagg tgcagacgga tccctggatg ccagcggctt ccaccaccac cactcgccga 18180
agacgcaagt acggcgcggc cagcctgctg atgcccaact acgcgctgca tccttccatc 18240
atccccacgc cgggctaccg cggcacgcgc ttctaccgcg gctacaccag cagccgccgc 18300
cgcaagacca ccacccgccg ccgtcgtcgc agccgccgca gcagcaccgc gacttccgcc 18360
ttggtgcgga gagtgtatcg cagcgggcgc gagcctctga ccctgccgcg cgcgcgctac 18420
cacccgagca tcgccattta actaccgcct cctacttgca gatatggccc tcacatgccg 18480
cctccgcgtc cccattacgg gctaccgagg aagaaagccg cgccgtagaa ggctgacggg 18540
gaacgggctg cgtcgccatc accaccggcg gcggcgcgcc atcagcaagc ggttgggggg 18600
aggcttcctg cccgcgctga tccccatcat cgccgcggcg atcggggcga tccccggcat 18660
agcttccgtg gcggtgcagg cctctcagcg ccactgagac acaaaaaagc atggatttgt 18720
aataaaaaaa tggactgacg ctcctggtcc tgtgatgtgt gtttttagat ggaagacatc 18780
aatttttcgt ccctggcacc gcgacacggc acgcggccgt ttatgggcac ctggagcgac 18840

-continued atcggcaaca gccaactgaa cgggggcgcc ttcaattgga gcagtctctg gagcgggctt 18900
aagaatttcg ggtccacgct caaaacctat ggcaacaagg cgtggaacag cagcacaggg 18960
caggcgctga gggaaaagct gaaagagcag aacttccagc agaaggtggt cgatggcctg 19020
gcctcgggca tcaacggggt ggtggacctg gccaaccagg ccgtgcagaa acagatcaac 19080
agccgcctgg acgcggtccc gcccgcgggg tccgtggaga tgccccaggt ggaggaggag 19140
ctgcctcccc tggacaagcg cggcgacaag cgaccgcgtc ccgacgcgga ggagacgctg 19200
ctgacgcaca cggacgagcc gcccccgtac gaggaggcgg tgaaactggg tctgcccacc 19260
acgcggcccg tggcgcctct ggccaccggg gtgctgaaac ccagcagcag cagccagccc 19320
gcgaccctgg acttgcctcc gcctgcttcc cgcccctcca cagtggctaa gcccctgccg 19380
ccggtggccg tcgcgtcgcg cgcccccga ggccgccccc aggcgaactg gcagagcact 19440
ctgaacagca tcgtgggtct gggagtgcag agtgtgaagc gccgccgctg ctattaaaag 19500
acactgtagc gcttaacttg cttgtctgtg tgtgtatatg tatgtccgcc gaccagaagg 19560
aggaagaggc gcgtcgccga gttgcaagat ggccacccca tcgatgctgc cccagtgggc 19620
gtacatgcac atcgccggac aggacgcttc ggagtacctg agtccgggtc tggtgcagtt 19680
cgcccgcgcc acagacacct acttcagtct ggggaacaag tttaggaacc ccacggtggc 19740
gcccacgcac gatgtgacca ccgaccgcag ccagcggctg acgctgcgct tcgtgcccgt 19800
ggaccgcgag gacaacacct actcgtacaa agtgcgctac acgctggccg tgggcgacaa 19860
ccgcgtgctg gacatggcca gcacctactt tgacatccgc ggcgtgctgg atcggggccc 19920
cagcttcaaa ccctactccg gcaccgccta caacagccta gctcccaagg gagcgcccaa 19980
cacctcacag tggaaggatt ccgacagcaa aatgcatact tttggagttg ctgccatgcc 20040
cggtgttgtt ggtaaaaaaa tagaagccga tggtctgcct attggaatag attcatcctc 20100
tggaactgac accataattt atgctgataa aactttccaa ccagagccac aggttggaag 20160
tgacagttgg gtcgacacca atggtgcaga ggaaaaatat ggaggtagag ctcttaagga 20220
cactacaaac atgaagccct gctacggttc ttttgccagg cctaccaaca aagaaggtgg 20280
acaggctaac ataaaagatt ctgaaactgc cagcactact cctaactatg atatagattt 20340
ggcattcttt gacagcaaaa atattgcagc taactacgat ccagatattg taatgtacac 20400
agaaaatgtt gagttgcaaa ctccagatac tcatattgtg tttaagccag gaacttcaga 20460
tgaaagttca gaagccaatt tgggccagca ggccatgccc aacagaccca actacatcgg 20520
gttcagagac aactttatcg ggctcatgta ctacaacagc actggcaata tgggtgtact 20580
ggctggtcag gcctcccagc taaatgctgt ggtggacttg caggacagaa acaccgaact 20640
gtcctaccag ctcttgcttg actctctggg tgacagaacc aggtatttca gtatgtggaa 20700
tcaggcggtg gacagctatg accccgatgt gcgcattatt gaaaatcacg gtgtggagga 20760
tgaactcccc aattattgct tccctttgaa tggtgtaggc tttacagata cttaccaggg 20820
tgttaaagtt aagacagata cagccgctac tggtaccaat ggaacgcagt gggacaaaga 20880
tgataccaca gtcagcactg ccaatgagat ccactcaggc aatcctttcg ccatggagat 20940
caacatccag gccaacctgt ggcggaactt cctctacgcg aacgtggcgc tgtacctgcc 21000
cgactcctac aagtacacgc cggccaacat cacgctgccg accaacacca acacctacga 21060
ttacatgaac ggccgcgtgg tggcgccctc gctggtggac gcctacatca acatcggggc 21120
gcgctggtcg ctggacccca tggacaacgt caacccettc aaccaccacc gcaacgcggg 21180

-continued

```
cctgcgctac cgctccatgc tcctgggcaa cgggcgctac gtgcccttcc acatccaggt  21240
gccccaaaag tttttcgcca tcaagagcct cctgctcctg cccgggtcct acacctacga  21300
gtggaacttc cgcaaggacg tcaacatgat cctgcagagc tccctcggca acgacctgcg  21360
cacggacggg gcctccatcg ccttcaccag catcaacctc tacgccacct tcttccccat  21420
ggcgcacaac accgcctcca cgctcgaggc catgctgcgc aacgacacca acgaccagtc  21480
cttcaacgac tacctctcgg cggccaacat gctctacccc atcccggcca acgccaccaa  21540
cgtgcccatc tccatcccct cgcgcaactg ggccgccttc cgcggatggt ccttcacgcg  21600
cctcaagacc cgcgagacgc cctcgctcgg ctccgggttc gacccctact tcgtctactc  21660
gggctccatc ccctacctcg acggcacctt ctacctcaac cacaccttca agaaggtctc  21720
catcaccttc gactcctccg tcagctggcc cggcaacgac cgcctcctga cgcccaacga  21780
gttcgaaatc aagcgcaccg tcgacggaga gggatacaac gtggcccagt gcaacatgac  21840
caaggactgg ttcctggtcc agatgctggc ccactacaac atcggctacc agggcttcta  21900
cgtgcccgag ggctacaagg accgcatgta ctccttcttc cgcaacttcc agcccatgag  21960
ccgccaggtc gtggacgagg tcaactacaa ggactaccag gccgtcaccc tggcctacca  22020
gcacaacaac tcgggcttcg tcggctacct cgcgcccacc atgcgccagg gccagcccta  22080
ccccgccaac taccctacc cgctcatcgg caagagcgcc gtcgccagcg tcacccagaa  22140
aaagttcctc tgcgaccggg tcatgtggcg catccccttc tccagcaact tcatgtccat  22200
gggcgcgctc accgacctcg gccagaacat gctctacgcc aactccgccc acgcgctaga  22260
catgaatttc gaagtcgacc ccatggatga gtccaccctt ctctatgttg tcttcgaagt  22320
cttcgacgtc gtccgagtgc accagcccca ccgcggcgtc atcgaggccg tctacctgcg  22380
cacgcccttc tcggccggca acgccaccac ctaaagcccc gctcttgctt cttgcaagat  22440
gacggcctgt ggctccggcg agcaggagct cagggccatc ctccgcgacc tgggctgcgg  22500
gccctgcttc ctgggcacct tcgacaagcg cttcccggga ttcatggccc cgcacaagct  22560
ggcctgcgcc atcgtcaaca cggccggccg cgagaccggg ggcgagcact ggctggcctt  22620
cgcctggaac ccgcgctccc acacctgcta cctcttcgac cccttcgggt tctcggacga  22680
gcgcctcaag cagatctacc agttcgagta cgagggcctg ctgcgccgca gcgccctggc  22740
caccgaggac cgctgcatca ccctggaaaa gtccacccag accgtgcagg gtccgcgctc  22800
ggccgcctgc gggctcttct gctgcatgtt cctgcacgcc ttcgtgcact ggcccgaccg  22860
ccccatggac aagaacccca ccatgaactt gctgacgggg gtgcccaacg gcatgctcca  22920
gtcgccccag gtggaaccca ccctgcgccg caaccaggag gcgctctacc gcttcctcaa  22980
cgcccactcc gcctactttc gctcccaccg cgcgcgcatc gagaaggcca ccgccttcga  23040
ccgcatgaat caagacatgt aaactgtgtg tatgtgaatg ctttattcat cataataaac  23100
agcacatgtt tatgccacct tctctgaggc tctgacttta tttagaaatc gaaggggttc  23160
tgccggctct cggcgtgccc cgcgggcagg gatacgttgc ggaactggta cttgggcagc  23220
cacttgaact cggggatcag cagcttcggc acggggaggt cggggaacga gtcgctccac  23280
agcttgcgcg tgagttgcag ggcgcccagc aggtcgggcg cggagatctt gaaatcgcag  23340
ttgggacccg cgttctgcgc gcgagagttg cggtacacgg ggttgcagca ctggaacacc  23400
atcagggccg ggtgcttcac gctcgccagc accgtcgcgt cggtgatgcc ctccacgtcc  23460
agatcctcgg cgttggccat cccgaagggg gtcatcttgc aggtctgccg ccccatgctg  23520
ggcacgcagc cgggcttgtg gttgcaatcg cagtgcaggg ggatcagcat catctgagcc  23580
```

tgctcggagc tcatgcccgg gtacatggcc ttcatgaaag cctccagctg gcggaaggcc 23640
tgctgcgcct tgccgccctc ggtgaagaag accccacagg acttgctaga gaactggttg 23700
gtggcgcagc ccgcgtcgtg cacgcagcag cgcgcgtcgt tgttggccag ctgcaccacg 23760
ctgcgccccc agcggttctg ggtgatcttg gcccggtcgg ggttctcctt cagcgcgcgc 23820
tgcccgttct cgctcgccac atccatctcg atcgtgtgct ccttctggat catcacggtc 23880
ccgtgcaggc accgcagctt gccctcggcc tcggtgcacc cgtgcagcca cagcgcgcag 23940
ccggtgcact cccagttctt gtgggcgatc tgggagtgcg agtgcacgaa gccctgcagg 24000
aagcggccca tcatcgtggt cagggtcttg ttgctggtga aggtcagcgg gatgccgcgg 24060
tgctcctcgt tcacatacag gtggcagatg cggcggtaca cctcgccctg ctcgggcatc 24120
agctggaagg cggacttcag gtcgctctcc acgcggtacc gctccatcag cagcgtcatc 24180
acttccatgc ccttctccca ggccgaaacg atcggcaggc tcaggggggtt cttcaccgtc 24240 atcttagtcg ccgccgccga agtcaggggg tcgttctcgt ccagggtctc aaacactcgc 24300
ttgccgtcct tctcggtgat gcgcacgggg ggaaagctga agcccacggc cgccagctcc 24360
tcctcggcct gcctttcgtc ctcgctgtcc tggctgatgt cttgcaaagg cacatgcttg 24420
gtcttgcggg gtttcttttt gggcggcaga ggcggcggcg gagacgtgct gggcgagcgc 24480
gagttctcgc tcaccacgac tatttcttct tcttggccgt cgtccgagac cacgcggcgg 24540
taggcatgcc tcttctgggg cagaggcgga ggcgacgggc tctcgcggtt cggcgggcgg 24600
ctggcagagc cccttccgcg ttcgggggtg cgctcctggc ggcgctgctc tgactgactt 24660
cctccgcggc cggccattgt gttctcctag ggagcaacaa gcatggagac tcagccatcg 24720
tcgccaacat cgccatctgc cccgccgcc gacgagaacc agcagcagca gaatgaaagc 24780
ttaaccgccc cgccgcccag ccccacctcc gacgccgccg cggccccaga catgcaagag 24840
atggaggaat ccatcgagat tgacctgggc tacgtgacgc ccgcggagca cgaggaggag 24900
ctggcagcgc gcttttcagc cccggaagag aaccaccaag agcagccaga gcaggaagca 24960
gagagcgagc agcagcaggc tgggctcgag catggcgact acctgagcgg ggcagaggac 25020
gtgctcatca agcatctggc ccgccaaagc atcatcgtca aggacgcgct gctcgaccgc 25080
gccgaggtgc ccctcagcgt ggcggagctc agccgcgcct acgagcgcaa cctcttctcg 25140
ccgcgcgtgc cccccaagcg ccagcccaac ggcacctgcg agcccaaccc gcgcctcaac 25200
ttctacccgg tcttcgcggt gcccgaggcc ctggccacct accacctctt tttcaagaac 25260
caaaggatcc ccgtctcctg ccgcgccaac cgcacccgcg ccgacgccct gctcaacctg 25320
ggtcccggcg cccgcctacc tgatatcacc tccttggaag aggttcccaa gatcttcgag 25380
ggtctgggca gcgacgagac tcgggccgcg aacgctctgc aaggaagcgg agaggagcat 25440
gagcaccaca gcgccctggt ggagttggaa ggcgacaacg cgcgcctggc ggtgctcaag 25500
cgcacggtcg agctgaccca cttcgcctac ccggcgctca acctgccccc caaggtcatg 25560
agcgccgtca tggaccaggt gctcatcaag cgcgcctcgc ccctctcaga ggaggagatg 25620
caggaccccg agagctcgga cgagggcaag cccgtggtca gcgacgagca gctggcgcgc 25680
tggctgggag cgagcagcac cccccagagc ctggaagagc ggcgcaagct catgatggcc 25740
gtggtcctgg tgaccgtgga gctggagtgt ctgcgccgct tcttcgccga cgcggagacc 25800
ctgcgcaagg tcgaggagaa cctgcactac ctcttcaggc acgggttcgt gcgccaggcc 25860
tgcaagatct ccaacgtgga gctgaccaac ctggtctcct acatgggcat cctgcacgag 25920

-continued aaccgcctgg ggcagaacgt gctgcacacc accctgcgcg gggaggcccg ccgcgactac 25980
atccgcgact gcgtctacct gtacctctgc cacacctggc agacgggcat gggcgtgtgg 26040
cagcagtgcc tggaggagca gaacctgaaa gagctctgca agctcctgca gaagaacctc 26100
aaggccctgt ggaccgggtt cgacgagcgc accaccgcct cggacctggc cgacctcatc 26160
ttccccgagc gcctgcggct gacgctgcgc aacgggctgc ccgactttat gagccaaagc 26220
atgttgcaaa actttcgctc tttcatcctc gaacgctccg ggatcctgcc cgccacctgc 26280
tccgcactgc cctcggactt cgtgccgctg accttccgcg agtgcccccc gccgctctgg 26340
agccactgct acttgctgcg cctggccaac tacctggcct accactcgga cgtgatcgag 26400
gacgtcagca gcgagggtct gctcgagtgc cactgccgct gcaacctctg cacgccgcac 26460
cgctccttgg cctgcaaccc ccagctgctg agcgagaccc agatcatcgg caccttcgag 26520
ttgcaaggcc ccggcgaggg caagggggt ctcaaactca ccccggggct gtggacctcg 26580
gcctacttgc gcaagttcgt gcccgaggac taccatccct tcgagatcag gttctacgag 26640
gaccaatccc agccgcccaa ggccgagctg tcggcctgcg tcatcaccca gggggccatc 26700
ctggcccaat tgcaagccat ccagaaatcc cgccaagaat ttctgctgaa aaagggccac 26760
ggggtctact tggaccccca gaccggagag gagctcaacc ccagcttccc ccaggatgcc 26820
ccgaggaagc agcaagaagc tgaaagtgga gctgccgctg ccgccggagg atttggagga 26880
agactgggag agcagtcagg cagaggagat ggaagactgg gacagcactc aggcagagga 26940
ggacagcctg caagacagtc tggaggagga agacgaggtg gaggaggagg cagaggaaga 27000
agcagccgcc gccagaccgt cgtcctcggc ggaggagaaa gcaagcagca cggataccat 27060
ctccgctccg ggtcggggtc gcggcggccg ggcccacagt agatgggacg agaccgggcg 27120
cttcccgaac cccaccaccc agaccggtaa gaaggagcgg cagggataca agtcctggcg 27180
ggggcacaaa aacgccatcg tctcctgctt gcaagcctgc gggggcaaca tctccttcac 27240
ccggcgctac ctgctcttcc accgcggggt gaacttcccc cgcaacatct tgcattacta 27300
ccgtcacctc cacagcccct actactgttt ccaagaagag gcagaaaccc agcagcagca 27360
gcagaaaacc agcggcagca gcagcagcta gaaaatccac agcggcggca ggtggactga 27420
ggatcgcggc gaacgagccg gcgcagaccc gggagctgag gaaccggatc tttcccaccc 27480
tctatgccat cttccagcag agtcgggggc aggagcagga actgaaagtc aagaaccgtt 27540
ctctgcgctc gctcacccgc agttgtctgt atcacaagag cgaagaccaa cttcagcgca 27600
ctctcgagga cgccgaggct ctcttcaaca agtactgcgc gctcactctt aaagagtagc 27660
ccgcgcccgc ccacacacgg aaaaaggcgg gaattacgtc accacctgcg cccttcgccc 27720
gaccatcatc atgagcaaag agattcccac gccttacatg tggagctacc agccccagat 27780
gggcctggcc gccggcgccg cccaggacta ctccacccgc atgaactggc tcagtgccgg 27840
gcccgcgatg atctcacggg tgaatgacat ccgcgcccac cgaaaccaga tactcctaga 27900
acagtcagcg atcaccgcca cgccccgcca tcaccttaat ccgcgtaatt ggcccgccgc 27960
cctggtgtac caggaaattc cccagcccac gaccgtacta cttccgcgag acgcccaggc 28020
cgaagtccag ctgactaact caggtgtcca gctggccggc ggcgccgccc tgtgtcgtca 28080
ccgccccgct cagggtataa agcggctggt gatccgaggc agaggcacac agctcaacga 28140
cgaggtggtg agctcttcgc tgggtctgcg acctgacgga gtcttccaac tcgccggatc 28200
ggggagatct tccttcacgc ctcgtcaggc cgtcctgact ttggagagtt cgtcctcgca 28260
gccccgctcg ggcggcatcg gcactctcca gttcgtggag gagttcactc cctcggtcta 28320

-continued

```
cttcaacccc ttctccggct cccccggcca ctacccggac gagttcatcc cgaacttcga  28380
cgccatcagc gagtcggtgg acggctacga ttgaatgtcc catggtggcg cggctgacct  28440
agctcggctt cgacacctgg accactgtta attaatcgcc tctcctacga gctcctgcag  28500
cagcgccaga agttcacctg cctggtcgga gtcaacccca tcgtcatcac ccagcagtcg  28560
ggcgatacca aggggtgcat ccactgctcc tgcgactccc ccgactgcgt ccacactctg  28620
atcaagaccc tctgcggcct ccgcgacctc ctccccatga actaatcacc cccttatcca  28680
gtgaaataaa gatcatattg atgatgattt tacagaaata aagatacaat catattgatg  28740
atttgagttt aataaaaaat aaagaatcac ttacttgaaa tctgatacca ggtctctgtc  28800
catgttttct gccaacacca cttcactccc ctcttcccag ctctggtact gcaggccccg  28860
gcgggctgca aacttcctcc acacgctgaa ggggatgtca aattcctcct gtccctcaat  28920
cttcatttta tcttctatca gatgtccaaa aagcgcgtcc gggtggatga tgacttcgac  28980
cccgtctacc cctacgatgc agacaacgca ccgaccgtgc ccttcatcaa cccccccttc  29040
gtctcttcag atggattcca agagaagccc ctgggggtgc tgtccctgcg actggccgac  29100
cccgtcacca ccaagaacgg ggaaatcacc ctcaagctgg gagagggggt ggacctcgac  29160
tcctcgggaa aactcatctc caacacggcc accaaggccg ccgcccctct cagtttttcc  29220
aacaacacca tttcccttaa catggatcac cccttttaca ctaaagatgg aaaattatcc  29280
ttacaagttt ctccaccatt aaatatactg agaacaagca ttctaaacac actagcttta  29340
ggttttggat caggtttagg actccgtggc tctgccttgg cagtacagtt agtctctcca  29400
cttacatttg atactgatgg aaacataaag cttaccttag acagaggttt gcatgttaca  29460
acaggagatg caattgaaag caacataagc tgggctaaag gtttaaaatt tgaagatgga  29520
gccatagcaa ccaacattgg aaatgggtta gagtttggaa gcagtagtac agaaacaggt  29580
gttgatgatg cttacccaat ccaagttaaa cttggatctg gccttagctt tgacagtaca  29640
ggagccataa tggctggtaa caaagaagac gataaactca ctttgtggac aacacctgat  29700
ccatcgccaa actgtcaaat actcgcagaa aatgatgcaa aactaacact ttgcttgact  29760
aaatgtggta gtcaaatact ggccactgtg tcagtcttag ttgtaggaag tggaaaccta  29820
aaccccatta ctggcaccgt aagcagtgct caggtgtttc tacgttttga tgcaaacggt  29880
gttcttttaa cagaacattc tacactaaaa aaatactggg ggtataggca gggagatagc  29940
atagatggca ctccatatac caatgctgta ggattcatgc ccaatttaaa agcttatcca  30000
aagtcacaaa gttctactac taaaaataat atagtagggc aagtatacat gaatggagat  30060
gtttcaaaac ctatgcttct cactataacc ctcaatggta ctgatgacag caacagtaca  30120
tattcaatgt cattttcata cacctggact aatggaagct atgttggagc aacatttggg  30180
gctaactctt ataccttctc atacatcgcc caagaatgaa cactgtatcc caccctgcat  30240
gccaaccctt cccaccccac tctgtggaaa aaactctgaa acacaaaata aaataaagtt  30300
caagtgtttt attgattcaa cagttttaca ggattcgagc agttattttt cctccaccct  30360
cccaggacat ggaatacacc accctctccc cccgcacagc cttgaacatc tgaatgccat  30420
tggtgatgga catgcttttg gtctccacgt tccacacagt ttcagagcga gccagtctcg  30480
ggtcggtcag ggagatgaaa ccctccgggc acaattggga gaagtactcg cctacatggg  30540
ggtagagtca taatcgtgca tcaggatagg gcggtggtgc tgcagcagcg cgcgaataaa  30600
ctgctgccgc cgccgctccg tcctgcagga atacaacatg gcagtggtct cctcagcgat  30660
```

gattcgcacc gcccgcagca taaggcgcct tgtcctccgg gcacagcagc gcaccctgat 30720
ctcacttaaa tcagcacagt aactgcagca cagcaccaca atattgttca aaatcccaca 30780
gtgcaaggcg ctgtatccaa agctcatggc ggggaccaca gaacccacgt ggccatcata 30840
ccacaagcgc aggtagatta agtggcgacc cctcataaac acgctggaca taaacattac 30900
ctcttttggc atgttgtaat tcaccacctc ccggtaccat ataaacctct gattaaacat 30960
ggcgccatcc accaccatcc taaaccagct ggccaaaacc tgcccgccgg ctatacactg 31020
cagggaaccg ggactggaac aatgacagtg gagagcccag gactcgtaac catggatcat 31080
catgctcgtc atgatatcaa tgttggcaca acacaggcac acgtgcatac acttcctcag 31140
gattacaagc tcctcccgcg ttagaaccat atcccaggga acaacccatt cctgaatcag 31200
cgtaaatccc acactgcagg gaagacctcg cacgtaactc acgttgtgca ttgtcaaagt 31260
gttacattcg ggcagcagcg gatgatcctc cagtatggta gcgcgggttt ctgtctcaaa 31320
aggaggtaga cgatccctac tgtacggagt gcgccgagac aaccgagatc gtgttggtcg 31380
tagtgtcatg ccaaatggaa cgccggacgt agtcatattt cctgaagtct tggcgcgcca 31440
aagtctagaa gcggtccata gcttaccgag cggcagcagc agcggcacac aacaggcgca 31500
agagtcagag aaaagactga gctctaacct gtccgcccgc tctctgctca atatatagcc 31560
cagatctaca ctgacgtaaa ggccaaagtc taaaaatacc cgccaaatag tcacacacgc 31620
ccagcacacg cccagaaacc ggtgacacac tcaaaaaaat acgcgcactt cctcaaacgc 31680
ccaaactgcc gtcatttccg ggttcccacg ctacgtcatc aaaacacgac tttcaaattc 31740
cgtcgaccgt taaaaacgtc acccgccccg cccctaacgg tcgcccgtct ctcagccaat 31800
cagcgccccg catccccaaa ttcaaacacc tcatttgcat attaacgcgc accaaaagtt 31860
tgaggtatat tattgatgat g 31881

<210> SEQ ID NO 5
<211> LENGTH: 31110
<212> TYPE: DNA
<213> ORGANISM: Artificial Sequence
<220> FEATURE:
<223> OTHER INFORMATION: synthetic chimpanzee adenovirus serotype ChAd63
with Ebola virus Sudan/Gulu codon optimized
transmembrane envelope glycoprotein (GP) insert
(ChAd63 GP Ebola S/G (PB/6611))
<220> FEATURE:
<221> NAME/KEY: CDS
<222> LOCATION: (1630)...(3660)
<223> OTHER INFORMATION: Ebola virus Sudan/Gulu codon optimized
transmembrane envelope glycoprotein (GP) insert in ChAd63 GP Ebola
S/G (PB/6611)
<220> FEATURE:
<221> NAME/KEY: CDS
<222> LOCATION: (14372)...(16000)
<223> OTHER INFORMATION: chimpanzee adenovirus serotype ChAd63 penton
<220> FEATURE:
<221> NAME/KEY: CDS
<222> LOCATION: (18767)...(21643)
<223> OTHER INFORMATION: chimpanzee adenovirus serotype ChAd63 hexon
<220> FEATURE:
<221> NAME/KEY: CDS
<222> LOCATION: (28171)...(29448)
<223> OTHER INFORMATION: chimpanzee adenovirus serotype ChAd63 fiber

<400> SEQUENCE: 5
catcatcaat aatatacctc aaacttttgg tgcgcgttaa tatgcaaatg aggtgtttga 60
atttggggat gcggggcgct gattggctga gagacgggcg accgttaggg gcggggcggg 120
tgacgttttg atgacgtggc cgtgaggcgg agccggtttg caagttctcg tgggaaaagt 180

```
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaattccg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacggatat ctccattgca tacgttgtat    480
ccatatcata atatgtacat ttatattggc tcatgtccaa cattaccgcc atgttgacat    540
tgattattga ctagttatta atagtaatca attacggggt cattagttca tagcccatat    600
atggagttcc gcgttacata acttacggta aatggcccgc ctggctgacc gcccaacgac    660
ccccgcccat tgacgtcaat aatgacgtat gttcccatag taacgccaat agggactttc    720
cattgacgtc aatgggtgga gtatttacgg taaactgccc acttggcagt acatcaagtg    780
tatcatatgc caagtacgcc ccctattgac gtcaatgacg gtaaatggcc cgcctggcat    840
tatgcccagt acatgacctt atgggacttt cctacttggc agtacatcta cgtattagtc    900
atcgctatta ccatggtgat gcggttttgg cagtacatca atgggcgtgg atagcggttt    960
gactcacggg gatttccaag tctccacccc attgacgtca atgggagttt gttttggaac   1020
caaaatcaac gggactttcc aaaatgtcgt aacaactccg ccccattgac gcaaatgggc   1080
ggtaggcgtg tacggtggga ggtctatata agcagagctc tccctatcag tgatagagat   1140
ctccctatca gtgatagaga tcgtcgacga gctcgtttag tgaaccgtca gatcgcctgg   1200
agacgccatc cacgctgttt tgacctccat agaagacacc gggaccgatc cagcctccat   1260
cggctcgcat ctctccttca cgcgcccgcc gccctacctg aggccgccat ccacgccggt   1320
tgagtcgcgt tctgccgcct cccgcctgtg gtgcctcctg aactgcgtcc gccgtctagg   1380
taagtttaaa gctcaggtcg agaccgggcc tttgtccggc gctcccttgg agcctaccta   1440
gactcagccg gctctccacg ctttgcctga ccctgcttgc tcaactctag ttaacggtgg   1500
agggcagtgt agtctgagca gtactcgttg ctgccgcgcg cgccaccaga cataatagct   1560
gacagactaa cagactgttc ctttccatgg gtcttttctg cagtcaccgt cgtcgacgat   1620
atcgccgcca tggagggcct gagcctgctg cagctgccca gggacaagtt caggaagagc   1680
agcttcttcg tgtgggtgat catcctgttc cagaaggcct tcagcatgcc cctgggcgtg   1740
gtgaccaaca gcaccctgga ggtgaccgag atcgaccagc tggtgtgcaa ggaccacctg   1800
gccagcaccg accagctgaa gagcgtgggc ctgaacctgg agggcagcgg cgtgagcacc   1860
gacatcccca gcgccaccaa gaggtggggc ttcaggagcg gcgtgcctcc caaggtggtg   1920
agctacgagg ccggcgagtg ggccgagaac tgctacaacc tggagatcaa gaagcccgac   1980
ggcagcgagt gcctgcctcc tcctcctgac ggcgtgaggg gcttccccag gtgcaggtac   2040
gtgcacaagg cccagggcac cggcccctgc cccggcgact acgccttcca caaggacggc   2100
gccttcttcc tgtacgacag gctggccagc accgtgatct acaggggcgt gaacttcgcc   2160
gagggcgtga tcgccttcct gatcctggcc aagcccaagg agaccttcct gcagagccct   2220
cccatcaggg aggccgtgaa ctacaccgag aacaccagca gctactacgc caccagctat   2280
ctagagtacg agatcgagaa cttcggcgcc cagcacagca ccaccctgtt caagatcgac   2340
aacaacacct tcgtgaggct ggacaggccc cacacccctc agttcctgtt ccagctgaac   2400
gacaccatcc acctgcacca gcagctgagc aacaccaccg gcaggctgat ctggaccctg   2460
gacgccaaca tcaacgccga catcggcgag tgggccttct gggagaacaa gaagaacctg   2520
agcgagcagc tgaggggcga ggagctgagc ttcgaggccc tgagcctgaa cgagaccgag   2580
```

-continued

```
gacgacgacg ccgccagcag caggatcacc aagggcagga tcagcgacag ggccaccagg   2640
aagtacagcg acctggtgcc caagaacagc cccggcatgg tgcccctgca catccccgag   2700
ggcgagacca ccctgcccag ccagaacagc accgagggca ggagggtggg cgtgaacacc   2760
caggagacca tcaccgagac cgccgccacc atcatcggca ccaacggcaa ccacatgcag   2820
atcagcacca tcggcatcag gcccagcagc agccagatcc ccagcagcag ccccaccacc   2880
gcccctagcc ccgaggccca gacccccacc acccacacca gcggacccag cgtgatggcc   2940
accgaggagc ccaccacccc tcccggcagc agccccggac ccaccaccga ggcccctacc   3000
ctgaccaccc ctgagaacat caccaccgcc gtgaagaccg tgctgcccca ggagagcacc   3060
agcaacggcc tgatcaccag caccgtgacc ggcatcctgg gcagcctggg cctgaggaag   3120
aggagcagga ggcagaccaa caccaaggcc accggcaagt gcaaccccaa cctgcactac   3180
tggaccgccc aggagcagca caacgccgcc ggcatcgcct ggattcccta cttcggcccc   3240
ggcgccgagg gcatctacac cgagggcctg atgcacaacc agaacgccct ggtgtgcggc   3300
ctgaggcagc tggccaacga gaccacccag gccctgcagc tgttcctgag ggccaccacc   3360
gagctgagga cctacaccat cctgaacagg aaggccatcg acttcctgct gaggaggtgg   3420
ggcggcacct gcaggattct gggccccgac tgctgcatcg agccccacga ctggaccaag   3480
aacatcaccg acaagatcaa ccagatcatc cacgacttca tcgacaaccc tctgcccaac   3540
caggacaacg acgacaactg gtggaccggc tggcggcagt ggatacctgc cggcatcggc   3600
atcaccggca tcatcatcgc catcatcgct ctgctgtgcg tgtgcaagct gctgtgctga   3660
gaattcagat ctgctgtgcc ttctagttgc cagccatctg ttgtttgccc ctcccccgtg   3720
ccttccttga ccctggaagg tgccactccc actgtccttt cctaataaaa tgaggaaatt   3780
gcatcgcatt gtctgagtag gtgtcattct attctggggg gtggggtggg gcaggacagc   3840
aagggggagg attgggaaga caatagcagg catgctgggg atgcggtggg ctctagatat   3900
cagcgatcgc gtgagtagtg tttgggggtg ggtgggagcc tgcatgatgg gcagaatgac   3960
taaaatctgt gtttttctgt gtgttgcagc agcatgagcg gaagcgcctc ctttgaggga   4020
ggggtattca gcccttatct gacggggcgt ctcccctcct gggcgggagt gcgtcagaat   4080
gtgatgggat ccacggtgga cggccggccc gtgcagcccg cgaactcttc aaccctgacc   4140
tacgcgaccc tgagctcctc gtccgtggac gcagctgccg ccgcagctgc tgcttccgcc   4200
gccagcgccg tgcgcggaat ggccctgggc gccggctact acagctctct ggtggccaac   4260
tcgagttcca ccaataatcc cgccagcctg aacgaggaga agctgttgct gctgatggcc   4320
cagctcgagg ccctgaccca gcgcctgggc gagctgaccc agcaggtggc tcagctgcag   4380
gcggagacgc gggccgcggt tgccacggtg aaaaccaaat aaaaaatgaa tcaataaata   4440
aacggagacg gttgttgatt ttaacacaga gtcttgaatc tttatttgat tttcgcgcg    4500
cggtaggccc tggaccaccg gtctcgatca ttgagcaccc ggtggatctt ttccaggacc   4560
cggtagaggt gggcttggat gttgaggtac atgggcatga gcccgtcccg ggggtggagg   4620
tagctccatt gcagggcctc gtgctcgggg gtggtgttgt aaatcaccca gtcatagcag   4680
gggcgcaggg cgtggtgctg cacgatgtct ttgaggagga gactgatggc cacgggcagc   4740
cccttggtgt aggtgttgac gaacctattg agctgggagg gatgcatgcg gggggagatg   4800
agatgcatct tggcctggat cttgagattg gcgatgttcc cgcccagatc ccgccggggg   4860
ttcatgttgt gcaggaccac cagcacggtg tatccggtgc acttggggaa tttgtcatgc   4920
```

-continued aacttggaag ggaaggcgtg aaagaatttg gagacgccct tgtgaccgcc caggttttcc 4980
atgcactcat ccatgatgat ggcgatgggc ccgtgggcgg cggcctgggc aaagacgttt 5040
cgggggtcgg acacatcgta gttgtggtcc tgggtgagct cgtcataggc cattttaatg 5100
aatttggggc ggagggtacc cgactggggg acaaaggtgc cctcgatccc gggggcgtag 5160
ttcccctcgc agatctgcat ctcccaggcc ttgagctcgg agggggggat catgtccacc 5220
tgcggggcga tgaaaaaaac ggtttccggg gcgggggaga tgagctgcgc cgaaagcagg 5280
ttccggagca gctgggactt gccgcagccg gtggggccgt agatgacccc gatgaccggc 5340
tgcaggtggt agttgaggga gagacagctg ccgtcctcgc ggaggagggg ggccacctcg 5400
ttcatcatct cgcgcacatg catgttctcg cgcacgagtt ccgccaggag gcgctcgccc 5460
cccagcgaga ggagctcttg cagcgaggcg aagtttttca gcggcttgag cccgtcggcc 5520
atgggcattt tggagagggt ctgttgcaag agttccagac ggtcccagag ctcggtgatg 5580
tgctctaggg catctcgatc cagcagacct cctcgtttcg cgggttgggg cgactgcggg 5640
agtagggcac caggcgatgg gcgtccagcg aggccagggt ccggtccttc cagggtcgca 5700
gggtccgcgt cagcgtggtc tccgtcacgg tgaaggggtg cgcgccgggc tgggcgcttg 5760
cgagggtgcg cttcaggctc atccggctgg tcgagaaccg ctcccggtcg gcgccctgcg 5820
cgtcggccag gtagcaattg agcatgagtt cgtagttgag cgcctcggcc gcgtggccct 5880
tggcgcggag cttacctttg gaagtgtgtc cgcagacggg acagaggagg gacttgaggg 5940
cgtagagctt gggggcgagg aagacggact cgggggcgta ggcgtccgcg ccgcagctgg 6000
cgcagacggt ctcgcactcc acgagccagg tgaggtcggg gcggtcgggg tcaaaaacga 6060
ggtttcctcc gtgcttttg atgcgtttct tacctctggt ctccatgagc tcgtgtcccc 6120
gctgggtgac aaagaggctg tccgtgtccc cgtagaccga ctttatgggc cggtcctcga 6180
gcggggtgcc gcggtcctcg tcgtagagga accccgccca ctccgagacg aaggcccggg 6240
tccaggccag cacgaaggag gccacgtggg aggggtagcg gtcgttgtcc accagcgggt 6300
ccaccttctc cagggtatgc aagcacatgt cccccctcgtc cacatccagg aaggtgattg 6360
gcttgtaagt gtaggccacg tgaccggggg tcccggccgg gggggtataa aagggggcgg 6420
gcccctgctc gtcctcactg tcttccggat cgctgtccag gagcgccagc tgttggggta 6480
ggtattccct ctcgaaggcg ggcatgacct cggcactcag gttgtcagtt tctagaaacg 6540
aggaggattt gatattgacg gtgccgttgg agacgccttt catgagcccc tcgtccatct 6600
ggtcagaaaa gacgatcttt ttgttgtcga gcttggtggc gaaggagccg tagagggcgt 6660
tggagagcag cttggcgatg gagcgcatgg tctggttctt ttccttgtcg gcgcgctcct 6720
tggcggcgat gttgagctgc acgtactcgc gcgccacgca cttccattcg gggaagacgg 6780
tggtgagctc gtcgggcacg attctgaccc gccagccgcg gttgtgcagg gtgatgaggt 6840
ccacgctggt ggccacctcg ccgcgcaggg gctcgttggt ccagcagagg cgcccgccct 6900
tgcgcgagca gaaggggggc agcgggtcca gcatgagctc gtcggggggg tcggcgtcca 6960
cggtgaagat gccgggcagg agctcggggt cgaagtagct gatgcaggtg cccagatcgt 7020
ccagacttgc ttgccagtcg cgcacggcca gcgcgcgctc gtaggggctg aggggcgtgc 7080
cccagggcat ggggtgcgtg agcgcggagg cgtacatgcc gcagatgtcg tagacgtaga 7140
ggggctcctg gaggacgccg atgtaggtgg ggtagcagcg ccccccgcgg atgctggcgc 7200
gcacgtagtc gtacagctcg tgcgagggcg cgaggagccc cgtgccgaga ttggagcgct 7260
gcggcttttc ggcgcggtag acgatctggc ggaagatggc gtgggagttg gaggagatgg 7320

```
tgggcctctg gaagatgttg aagtgggcat ggggcagtcc gaccgagtcc ctgatgaagt   7380
gggcgtagga gtcctgcagc ttggcgacga gctcggcggt gacgaggacg tccagggcgc   7440
agtagtcgag ggtctcttgg atgatgtcgt acttgagctg gcccttctgc ttccacagct   7500
cgcggttgag aaggaactct tcgcggtcct tccagtactc ttcgaggggg aacccgtcct   7560
gatcggcacg gtaagagccc accatgtaga actggttgac ggccttgtag gcgcagcagc   7620
ccttctccac ggggagggcg taagcttgcg cggccttgcg cagggaggtg tgggtgaggg   7680
cgaaggtgtc gcgcaccatg actttgagga actggtgctt gaagtcgagg tcgtcgcagc   7740
cgccctgctc ccagagctgg aagtccgtgc gcttcttgta ggcggggttg ggcaaagcga   7800
aagtaacatc gttgaagagg atcttgcccg cgcggggcat gaagttgcga gtgatgcgga   7860
aaggctgggg cacctcggcc cggttgttga tgacctgggc ggcgaggacg atctcgtcga   7920
agccgttgat gttgtgcccg acgatgtaga gttccacgaa tcgcgggcgg cccttgacgt   7980
ggggcagctt cttgagctcg tcgtaggtga gctcggcggg gtcgctgagc ccgtgctgct   8040
cgagggccca gtcggcgacg tgggggttgg cgctgaggaa ggaagtccag agatccacgg   8100
ccagggcggt ctgcaagcgg tcccggtact gacggaactg ctggcccacg gccatttttt   8160
cgggggtgac gcagtagaag gtgcgggggt cgccgtgcca gcggtcccac ttgagctgga   8220
gggcgaggtc gtgggcgagc tcgacgagcg gcgggtcccc ggagagtttc atgaccagca   8280
tgaaggggac gagctgcttg ccgaaggacc ccatccaggt gtaggtttcc acatcgtagg   8340
tgaggaagag cctttcggtg cgaggatgcg agccgatggg gaagaactgg atctcctgcc   8400
accagttgga ggaatggctg ttgatgtgat ggaagtagaa atgccgacgg cgcgccgagc   8460
actcgtgctt gtgtttatac aagcgtccgc agtgctcgca acgctgcacg ggatgcacgt   8520
gctgcacgag ctgtacctgg gttcctttga cgaggaattt cagtgggcag tggagcgctg   8580
gcggctgcat ctggtgctgt actacgtcct ggccatcggc gtggccatcg tctgcctcga   8640
tggtggtcat gctgacgagc ccgcgcggga ggcaggtcca gacctcggct cggacgggtc   8700
ggagagcgag gacgagggcg cgcaggccgg agctgtccag ggtcctgaga cgctgcggag   8760
tcaggtcagt gggcagcggc ggcgcgcggt tgacttgcag gagcttttcc agggcgcgcg   8820
ggaggtccag atggtacttg atctccacgg cgccgttggt ggcgacgtcc acggcttgca   8880
gggtcccgtg cccctggggc gccaccaccg tgccccgttt cttcttgggc ggcggcggct   8940
ccatgcttag aagcggcggc gaggacgcgc gccgggcggc aggggcggct cggggcccgg   9000
aggcaggggc ggcaggggca cgtcggcgcc gcgcgcgggc aggttctggt actgcgcccg   9060
gagaagactg gcgtgagcga cgacgcgacg gttgacgtcc tggatctgac gcctctgggt   9120
gaaggccacg ggacccgtga gtttgaacct gaaagagagt tcgacagaat caatctcggt   9180
atcgttgacg gcggcctgcc gcaggatctc ttgcacgtcg cccgagttgt cctggtaggc   9240
gatctcggtc atgaactgct cgatctcctc ctcctgaagg tctccgcggc cggcgcgctc   9300
gacggtggcc gcgaggtcgt tggagatgcg gcccatgagc tgcgagaagg cgttcatgcc   9360
ggcctcgttc cagacgcggc tgtagaccac ggctccgtcg ggtcgcgcg cgcgcatgac    9420
cacctgggcg aggttgagct cgacgtggcg cgtgaagacc gcgtagttgc agaggcgctg   9480
gtagaggtag ttgagcgtgg tggcgatgtg ctcggtgacg aagaagtaca tgatccagcg   9540
gcggagcggc atctcgctga cgtcgcccag ggcttccaag cgctccatgg cctcgtagaa   9600
gtccacggcg aagttgaaaa actgggagtt gcgcgccgag acggtcaact cctcctccag   9660
```

-continued

```
aagacggatg agctcggcga tggtggcgcg cacctcgcgc tcgaaggccc cggggggctc    9720
ctcttccatt tcctcctctt cctcctccac taacatctct tctacttcct cctcaggagg    9780
cggcggcggg ggaggggccc tgcgtcgccg gcggcgcacg ggcagacggt cgatgaagcg    9840
ctcgatggtc tccccgcgcc ggcgacgcat ggtctcggtg acggcgcgcc cgtcctcgcg    9900
gggccgcagc gtgaagacgc cgccgcgcat ctccaggtgg ccgccggggg ggtctccgtt    9960
gggcagggag agggcgctga cgatgcatct tatcaattga cccgtaggga ctccgcgcaa   10020
ggacctgagc gtctcgagat ccacgggatc cgaaaaccgc tgaacgaagg cttcgagcca   10080
gtcgcagtcg caaggtaggc tgagcccggt ttcttgttct tcgggtattt ggtcgggagg   10140
cgggcgggcg atgctgctgg tgatgaagtt gaagtaggcg gtcctgagac ggcggatggt   10200
ggcgaggagc accaggtcct tgggcccggc ttgctggatg cgcagacggt cggccatgcc   10260
ccaggcgtgg tcctgacacc tggcgaggtc cttgtagtag tcctgcatga gccgctccac   10320
gggcacctcc tcctcgcccg cgcggccgtg catgcgcgtg agcccgaacc cgcgctgcgg   10380
ctggacgagc gccaggtcgg cgacgacgcg ctcggcgagg atggcctgct ggatctgggt   10440
gagggtggtc tggaagtcgt cgaagtcgac gaagcggtgg taggctccgg tgttgatggt   10500
gtaggagcag ttggccatga cggaccagtt gacggtctgg tggccggggc gcacgagctc   10560
gtggtacttg aggcgcgagt aggcgcgcgt gtcgaagatg tagtcgttgc aggtgcgcac   10620
gaggtactgg tatccgacga ggaagtgcgg cggcggctgg cggtagagcg gccatcgctc   10680
ggtggcgggg gcgccgggcg cgaggtcctc gagcatgagg cggtggtagc cgtagatgta   10740
cctggacatc caggtgatgc cggcggcggt ggtggaggcg cgcgggaact cgcggacgcg   10800
gttccagatg ttgcgcagcg gcaggaagta gttcatggtg gccgcggtct ggcccgtgag   10860
gcgcgcgcag tcgtggatgc tctagacata cgggcaaaaa cgaaagcggt cagcggctcg   10920
actccgtggc ctggaggcta agcgaacggg ttgggctgcg cgtgtacccc ggttcgaatc   10980
tcgaatcagg ctggagccgc agctaacgtg gtactggcac tcccgtctcg acccaagcct   11040
gctaacgaaa cctccaggat acggaggcgg gtcgtttttt ggccttggtc gctggtcatg   11100
aaaaactagt aagcgcggaa agcggccgcc cgcgatggct cgctgccgta gtctggagaa   11160
agaatcgcca gggttgcgtt gcggtgtgcc ccggttcgag cctcagcgct cggcgccggc   11220
cggattccgc ggctaacgtg ggcgtggctg ccccgtcgtt tccaagaccc cttagccagc   11280
cgacttctcc agttacggag cgagcccctc ttttttttctt gtgtttttgc cagatgcatc   11340
ccgtactgcg gcagatgcgc ccccaccctc caccacaacc gcccctaccg cagcagcagc   11400
aacagccggc gcttctgccc ccgccccagc agcagcagcc agccactacc gcggcggccg   11460
ccgtgagcgg agccggcgtt cagtatgacc tggccttgga agagggcgag gggctggcgc   11520
ggctgggggc gtcgtcgccg gagcggcacc cgcgcgtgca gatgaaaagg gacgctcgcg   11580
aggcctacgt gcccaagcag aacctgttca gagacaggag cggcgaggag cccgaggaga   11640
tgcgcgcctc ccgcttccac gcggggcggg agctgcggcg cggcctggac cgaaagcggg   11700
tgctgaggga cgaggatttc gaggcggacg agctgacggg gatcagcccc gcgcgcgcgc   11760
acgtggccgc ggccaacctg gtcacggcgt acgagcagac cgtgaaggag gagagcaact   11820
tccaaaaatc cttcaacaac cacgtgcgca cgctgatcgc gcgcgaggag gtgaccctgg   11880
gcctgatgca cctgtgggac ctgctggagg ccatcgtgca gaaccccacg agcaagccgc   11940
tgacggcgca gctgtttctg gtggtgcagc acagtcggga caacgagacg ttcagggagg   12000
cgctgctgaa tatcaccgag cccgagggcc gctggctcct ggacctggtg aacattctgc   12060
```

agagcatcgt ggtgcaggag cgcgggctgc cgctgtccga gaagctggcg gccatcaact 12120
tctcggtgct gagcctgggc aagtactacg ctaggaagat ctacaagacc ccgtacgtgc 12180
ccatagacaa ggaggtgaag atcgatgggt tttacatgcg catgaccctg aaagtgctga 12240
ccctgagcga cgatctgggg gtgtaccgca acgacaggat gcaccgcgcg gtgagcgcca 12300
gccgccggcg cgagctgagc gaccaggagc tgatgcacag cctgcagcgg gccctgaccg 12360
gggccgggac cgagggggag agctactttg acatgggcgc ggacctgcgc tggcagccca 12420
gccgccgggc cttggaagct gccggcggcg tgccctacgt ggaggaggtg gacgatgagg 12480
aggaggaggg cgagtacctg gaagactgat ggcgcgaccg tatttttgct agatgcagca 12540
acagccaccg ccgccgcctc ctgatcccgc gatgcgggcg gcgctgcaga gccagccgtc 12600
cggcattaac tcctcggacg attggaccca ggccatgcaa cgcatcatgg cgctgacgac 12660
ccgcaatccc gaagccttta gacagcagcc tcaggccaac cggctctcgg ccatcctgga 12720
ggccgtggtg ccctcgcgct cgaaccccac gcacgagaag gtgctggcca tcgtgaacgc 12780
gctggtggag aacaaggcca tccgcggcga cgaggccggg ctggtgtaca acgcgctgct 12840
ggagcgcgtg gcccgctaca acagcaccaa cgtgcagacg aacctggacc gcatggtgac 12900
cgacgtgcgc gaggcggtgt cgcagcgcga gcggttccac cgcgagtcga acctgggctc 12960
catggtggcg ctgaacgcct tcctgagcac gcagcccgcc aacgtgcccc ggggccagga 13020
ggactacacc aacttcatca gcgcgctgcg gctgatggtg gccgaggtgc cccagagcga 13080
ggtgtaccag tcggggccgg actacttctt ccagaccagt cgccagggct tgcagaccgt 13140
gaacctgagc caggctttca agaacttgca gggactgtgg ggcgtgcagg ccccggtcgg 13200
ggaccgcgcg acggtgtcga gcctgctgac gccgaactcg cgcctgctgc tgctgctggt 13260
ggcgcccttc acggacagcg gcagcgtgag ccgcgactcg tacctgggct acctgcttaa 13320
cctgtaccgc gaggccatcg ggcaggcgca cgtggacgag cagacctacc aggagatcac 13380
ccacgtgagc cgcgcgctgg gccaggagga cccgggcaac ctggaggcca ccctgaactt 13440
cctgctgacc aaccggtcgc agaagatccc gccccagtac gcgctgagca ccgaggagga 13500
gcgcatcctg cgctacgtgc agcagagcgt ggggctgttc ttgatgcagg agggggccac 13560
gcccagcgcc gcgctcgaca tgaccgcgcg caacatggag cccagcatgt acgcccgcaa 13620
ccgcccgttc atcaataagc tgatggacta cttgcatcgg gcggccgcca tgaactcgga 13680
ctactttacc aacgccatct tgaacccgca ctggctcccg ccgcccgggt tctacacggg 13740
cgagtacgac atgcccgacc ccaacgacgg gttcctgtgg gacgacgtgg acagcagcgt 13800
gttctcgccg cggcccacca ccaccaccgt gtggaagaaa gagggcgggg accggcggcc 13860
gtcctcggcg ctgtccggtc gcgcgggtgc tgccgcggcg gtgcccgagg ctgccagccc 13920
cttcccgagc ctgccctttt cgctgaacag cgtgcgcagc agcgagctgg gtcggctgac 13980
gcggccgcgc ctgctgggcg aggaggagta cctgaacgac tccttgttga agcccgagcg 14040
cgagaagaac ttccccaata acgggataga gagcctggtg gacaagatga gccgctggaa 14100
gacgtacgcg cacgagcaca gggacgagcc ccgagctagc agcgcaggca cccgtagacg 14160
ccagcggcac gacaggcagc ggggactggt gtgggacgat gaggattccg ccgacgacag 14220
cagcgtgttg gacttgggtg ggagtggtgg tggtaacccg ttcgctcacc tgcgcccccg 14280
tatcgggcgc ctgatgtaag aatctgaaaa aataaaagac ggtactcacc aaggccatgg 14340
cgaccagcgt gcgttcttct ctgttgtttg tagtagtatg atgaggcgcg tgtacccgga 14400

-continued

```
gggtcctcct ccctcgtacg agagcgtgat gcagcaggcg gtggcggcgg cgatgcagcc  14460
cccgctggag gcgccttacg tgccccccgcg gtacctggcg cctacggagg ggcggaacag  14520
cattcgttac tcggagctgg caccccttgta cgataccacc cggttgtacc tggtggacaa  14580
caagtcggcg gacatcgcct cgctgaacta ccagaacgac cacagcaact tcctgaccac  14640
cgtggtgcag aacaacgatt tcacccccac ggaggccagc acccagacca tcaactttga  14700
cgagcgctcg cggtggggcg gccagctgaa aaccatcatg cacaccaaca tgcccaacgt  14760
gaacgagttc atgtacagca acaagttcaa ggcgcgggtg atggtctcgc gcaagacccc  14820
caacggggtc acggtagggg atgattatga tggtagtcag gacgagctga cctacgagtg  14880
ggtggagttt gagctgcccg agggcaactt ctcggtgacc atgaccatcg atctgatgaa  14940
caacgccatc atcgacaact acttggcggt ggggcggcag aacggggtgc tggagagcga  15000
catcggcgtg aagttcgaca cgcgcaactt ccggctgggc tgggaccccg tgaccgagct  15060
ggtgatgccg ggcgtgtaca ccaacgaggc cttccacccc gacatcgtcc tgctgcccgg  15120
ctgcggcgtg gacttcaccg agagccgcct cagcaacctg ctgggcatcc gcaagcggca  15180
gcccttccag gagggcttcc agatcctgta cgaggacctg gagggggggca acatccccgc  15240
gctcttggat gtcgaagcct atgaagaaag taaggaaaaa gcagaggctg aggcaactac  15300
agccgtggct accgccgcga ctgtggcaga tgccactgtc accaggggcg atacattcgc  15360
cacccaggcg gaggaagcag ccgccctagc ggcgaccgat gatagtgaaa gtaagatagt  15420
catcaagccg gtggagaagg acagcaagaa caggagctac aacgttctac cggatggaaa  15480
gaacaccgcc taccgcagct ggtacctggc ctacaactac ggcgaccccg agaagggcgt  15540
gcgctcctgg acgctgctca ccacctcgga cgtcacctgc ggcgtggagc aagtctactg  15600
gtcgctgccc gacatgatgc aagacccggt caccttccgc tccacgcgac aagttagcaa  15660
ctacccggtg gtgggcgccg agctcctgcc cgtctactcc aagagcttct tcaacgagca  15720
ggccgtctac tcgcagcagc tgcgtgcctt cacctcgctc acgcacgtct tcaaccgctt  15780
ccccgagaac cagatcctcg tccgcccgcc cgcgcccacc attaccaccg tcagtgaaaa  15840
cgttcctgct ctcacagatc acgggaccct gccgctgcgc agcagtatcc ggggagtcca  15900
gcgcgtgacc gtcactgacg ccagacgccg cacctgcccc tacgtctaca aggccctggg  15960
cgtagtcgcg ccgcgcgtcc tctcgagccg caccttctaa aaaatgtcca ttctcatctc  16020
gcccagtaat aacaccggtt ggggcctgcg cgcgcccagc aagatgtacg gaggcgctcg  16080
ccaacgctcc acgcaacacc ccgtgcgcgt gcgcgggcac ttccgcgctc cctggggcgc  16140
cctcaagggc cgcgtgcgct cgcgcaccac cgtcgacgac gtgatcgacc aggtggtggc  16200
cgacgcgcgc aactacacgc ccgccgccgc gcccgcctcc accgtggacg ccgtcatcga  16260
cagcgtggtg gccgacgcgc gccggtacgc ccgcgccaag agccggcggc ggcgcatcgc  16320
ccggcggcac cggagcaccc ccgccatgcg cgcggcgcga gccttgctgc gcagggccag  16380
gcgcacggga cgcagggcca tgctcagggc ggccagacgc gcggcctccg gcagcagcag  16440
cgccggcagg acccgcagac gcgcggccac ggcggcggcg gcggccatcg ccagcatgtc  16500
ccgcccgcgg cgcggcaacg tgtactgggt gcgcgacgcc gccaccggtg tgcgcgtgcc  16560
cgtgcgcacc cgcccccctc gcacttgaag atgctgactt cgcgatgttg atgtgtccca  16620
gcggcgagga ggatgtccaa gcgcaaatac aaggaagaga tgctccaggt catcgcgcct  16680
gagatctacg gccccgcggc ggcggtgaag gaggaaagaa agccccgcaa actgaagcgg  16740
gtcaaaaagg acaaaaagga ggaggaagat gacggactgg tggagtttgt gcgcgagttc  16800
```

-continued gccccccggc ggcgcgtgca gtggcgcggg cggaaagtga aaccggtgct gcggcccggc 16860
accacggtgg tcttcacgcc cggcgagcgt tccggctccg cctccaagcg ctcctacgac 16920
gaggtgtacg gggacgagga catcctcgag caggcggtcg agcgtctggg cgagtttgct 16980
tacggcaagc gcagccgccc cgcgcccttg aaagaggagg cggtgtccat cccgctggac 17040
cacggcaacc ccacgccgag cctgaagccg gtgaccctgc agcaggtgct gccgagcgcg 17100
gcgccgcgcc ggggcttcaa gcgcgagggc ggcgaggatc tgtacccgac catgcagctg 17160
atggtgccca agcgccagaa gctggaggac gtgctggagc acatgaaggt ggaccccgag 17220
gtgcagcccg aggtcaaggt gcggcccatc aagcaggtgg ccccgggcct gggcgtgcag 17280
accgtggaca tcaagatccc cacggagccc atggaaacgc agaccgagcc cgtgaagccc 17340
agcaccagca ccatggaggt gcagacggat ccctggatgc cagcggcttc caccaccacc 17400
actcgccgaa gacgcaagta cggcgcggcc agcctgctga tgcccaacta cgcgctgcat 17460
ccttccatca tccccacgcc gggctaccgc ggcacgcgct tctaccgcgg ctacaccagc 17520
agccgccgcc gcaagaccac cacccgccgc cgtcgtcgca gccgccgcag cagcaccgcg 17580
acttccgcct tggtgcggag agtgtatcgc agcgggcgcg agcctctgac cctgccgcgc 17640
gcgcgctacc acccgagcat cgccatttaa ctaccgcctc ctacttgcag atatggccct 17700
cacatgccgc ctccgcgtcc ccattacggg ctaccgagga agaaagccgc gccgtagaag 17760
gctgacgggg aacgggctgc gtcgccatca ccaccggcgg cggcgcgcca tcagcaagcg 17820
gttgggggga ggcttcctgc ccgcgctgat ccccatcatc gccgcggcga tcggggcgat 17880
ccccggcata gcttccgtgg cggtgcaggc ctctcagcgc cactgagaca caaaaaagca 17940
tggatttgta ataaaaaaat ggactgacgc tcctggtcct gtgatgtgtg tttttagatg 18000
gaagacatca atttttcgtc cctggcaccg cgacacggca cgcggccgtt tatgggcacc 18060
tggagcgaca tcggcaacag ccaactgaac gggggcgcct tcaattggag cagtctctgg 18120
agcgggctta agaatttcgg gtccacgctc aaaacctatg gcaacaaggc gtggaacagc 18180
agcacagggc aggcgctgag ggaaaagctg aaagagcaga acttccagca gaaggtggtc 18240
gatggcctgg cctcgggcat caacggggtg gtggacctgg ccaaccaggc cgtgcagaaa 18300
cagatcaaca gccgcctgga cgcggtcccg cccgcggggt ccgtggagat gccccaggtg 18360
gaggaggagc tgcctcccct ggacaagcgc ggcgacaagc gaccgcgtcc cgacgcggag 18420
gagacgctgc tgacgcacac ggacgagccg cccccgtacg aggaggcggt gaaactgggt 18480
ctgcccacca cgcggcccgt ggcgcctctg gccaccgggg tgctgaaacc cagcagcagc 18540
agccagcccg cgaccctgga cttgcctccg cctgcttccc gcccctccac agtggctaag 18600
cccctgccgc cggtggccgt cgcgtcgcgc gccccccgag gccgccccca ggcgaactgg 18660
cagagcactc tgaacagcat cgtgggtctg ggagtgcaga gtgtgaagcg ccgccgctgc 18720
tattaaaaga cactgtagcg cttaacttgc ttgtctgtgt gtgtatatgt atgtccgccg 18780
accagaagga ggaagaggcg cgtcgccgag ttgcaagatg gccaccccat cgatgctgcc 18840
ccagtgggcg tacatgcaca tcgccggaca ggacgcttcg gagtacctga gtccgggtct 18900
ggtgcagttc gcccgcgcca cagacaccta cttcagtctg gggaacaagt ttaggaaccc 18960
cacggtggcg cccacgcacg atgtgaccac cgaccgcagc cagcggctga cgctgcgctt 19020
cgtgcccgtg gaccgcgagg acaacaccta ctcgtacaaa gtgcgctaca cgctggccgt 19080
gggcgacaac cgcgtgctgg acatggccag cacctacttt gacatccgcg gcgtgctgga 19140
tcggggcccc agcttcaaac cctactccgg caccgcctac aacagcctag ctcccaaggg 19200
agcgcccaac acctcacagt ggaaggattc cgacagcaaa atgcatactt ttggagttgc 19260
tgccatgccc ggtgttgttg gtaaaaaaat agaagccgat ggtctgccta ttggaataga 19320
ttcatcctct ggaactgaca ccataattta tgctgataaa actttccaac cagagccaca 19380
ggttggaagt gacagttggg tcgacaccaa tggtgcagag gaaaaatatg gaggtagagc 19440
tcttaaggac actacaaaca tgaagccctg ctacggttct tttgccaggc ctaccaacaa 19500
agaaggtgga caggctaaca taaaagattc tgaaactgcc agcactactc ctaactatga 19560
tatagatttg gcattctttg acagcaaaaa tattgcagct aactacgatc cagatattgt 19620
aatgtacaca gaaaatgttg agttgcaaac tccagatact catattgtgt ttaagccagg 19680
aacttcagat gaaagttcag aagccaattt gggccagcag gccatgccca acagacccaa 19740
ctacatcggg ttcagagaca actttatcgg gctcatgtac tacaacagca ctggcaatat 19800
gggtgtactg gctggtcagg cctcccagct aaatgctgtg gtggacttgc aggacagaaa 19860
caccgaactg tcctaccagc tcttgcttga ctctctgggt gacagaacca ggtatttcag 19920
tatgtggaat caggcggtgg acagctatga ccccgatgtg cgcattattg aaaatcacgg 19980
tgtggaggat gaactcccca attattgctt ccctttgaat ggtgtaggct ttacagatac 20040
ttaccagggt gttaaagtta agacagatac agccgctact ggtaccaatg gaacgcagtg 20100
ggacaaagat gataccacag tcagcactgc caatgagatc cactcaggca atcctttcgc 20160
catggagatc aacatccagg ccaacctgtg gcggaacttc ctctacgcga acgtggcgct 20220
gtacctgccc gactcctaca agtacacgcc ggccaacatc acgctgccga ccaacaccaa 20280
cacctacgat tacatgaacg gccgcgtggt ggcgccctcg ctggtggacg cctacatcaa 20340
catcggggcg cgctggtcgc tggaccccat ggacaacgtc aacccottca accaccaccg 20400 caacgcgggc ctgcgctacc gctccatgct cctgggcaac gggcgctacg tgcccttcca 20460
catccaggtg ccccaaaagt tttcgccat caagagcctc ctgctcctgc ccgggtccta 20520
cacctacgag tggaacttcc gcaaggacgt caacatgatc ctgcagagct ccctcggcaa 20580
cgacctgcgc acggacgggg cctccatcgc cttcaccagc atcaacctct acgccacctt 20640
cttccccatg gcgcacaaca ccgcctccac gctcgaggcc atgctgcgca acgacaccaa 20700
cgaccagtcc ttcaacgact acctctcggc ggccaacatg ctctacccca tcccggccaa 20760
cgccaccaac gtgcccatct ccatcccctc gcgcaactgg gccgccttcc gcggatggtc 20820
cttcacgcgc ctcaagaccc gcgagacgcc ctcgctcggc tccgggttcg acccctactt 20880
cgtctactcg ggctccatcc cctacctcga cggcaccttc tacctcaacc acaccttcaa 20940
gaaggtctcc atcaccttcg actcctccgt cagctggccc ggcaacgacc gcctcctgac 21000
gcccaacgag ttcgaaatca agcgcaccgt cgacggagag ggatacaacg tggcccagtg 21060
caacatgacc aaggactggt tcctggtcca gatgctggcc cactacaaca tcggctacca 21120
gggcttctac gtgcccgagg gctacaagga ccgcatgtac tccttcttcc gcaacttcca 21180
gcccatgagc cgccaggtcg tggacgaggt caactacaag gactaccagg ccgtcaccct 21240
ggcctaccag cacaacaact cgggcttcgt cggctacctc gcgcccacca tgcgccaggg 21300
ccagccctac cccgccaact acccctaccc gctcatcggc aagagcgccg tcgccagcgt 21360
cacccagaaa aagttcctct gcgaccgggt catgtggcgc atccccttct ccagcaactt 21420
catgtccatg ggcgcgctca ccgacctcgg ccagaacatg ctctacgcca actccgccca 21480
cgcgctagac atgaatttcg aagtcgaccc catggatgag tccacccttc tctatgttgt 21540

-continued

```
cttcgaagtc ttcgacgtcg tccgagtgca ccagccccac cgcggcgtca tcgaggccgt  21600
ctacctgcgc acgcccttct cggccggcaa cgccaccacc taaagccccg ctcttgcttc  21660
ttgcaagatg acggcctgtg gctccggcga gcaggagctc agggccatcc tccgcgacct  21720
gggctgcggg ccctgcttcc tgggcacctt cgacaagcgc ttcccgggat tcatggcccc  21780
gcacaagctg gcctgcgcca tcgtcaacac ggccggccgc gagaccgggg gcgagcactg  21840
gctggccttc gcctggaacc cgcgctccca cacctgctac ctcttcgacc ccttcgggtt  21900
ctcggacgag cgcctcaagc agatctacca gttcgagtac gagggcctgc tgcgccgcag  21960
cgccctggcc accgaggacc gctgcatcac cctggaaaag tccacccaga ccgtgcaggg  22020
tccgcgctcg gccgcctgcg ggctcttctg ctgcatgttc ctgcacgcct tcgtgcactg  22080
gcccgaccgc cccatggaca agaaccccac catgaacttg ctgacggggg tgcccaacgg  22140
catgctccag tcgccccagg tggaacccac cctgcgccgc aaccaggagg cgctctaccg  22200
cttcctcaac gcccactccg cctactttcg ctcccaccgc gcgcgcatcg agaaggccac  22260
cgccttcgac cgcatgaatc aagacatgta aactgtgtgt atgtgaatgc tttattcatc  22320
ataataaaca gcacatgttt atgccacctt ctctgaggct ctgactttat ttagaaatcg  22380
aaggggttct gccggctctc ggcgtgcccc gcgggcaggg atacgttgcg gaactggtac  22440
ttgggcagcc acttgaactc ggggatcagc agcttcggca cggggaggtc ggggaacgag  22500
tcgctccaca gcttgcgcgt gagttgcagg gcgcccagca ggtcgggcgc ggagatcttg  22560
aaatcgcagt tgggacccgc gttctgcgcg cgagagttgc ggtacacggg gttgcagcac  22620
tggaacacca tcagggccgg gtgcttcacg ctcgccagca ccgtcgcgtc ggtgatgccc  22680
tccacgtcca gatcctcggc gttggccatc ccgaaggggg tcatcttgca ggtctgccgc  22740
cccatgctgg gcacgcagcc gggcttgtgg ttgcaatcgc agtgcagggg gatcagcatc  22800
atctgagcct gctcggagct catgcccggg tacatggcct tcatgaaagc ctccagctgg  22860
cggaaggcct gctgcgcctt gccgccctcg gtgaagaaga ccccacagga cttgctagag  22920
aactggttgg tggcgcagcc cgcgtcgtgc acgcagcagc gcgcgtcgtt gttggccagc  22980
tgcaccacgc tgcgccccca gcggttctgg gtgatcttgg cccggtcggg gttctccttc  23040
agcgcgcgct gcccgttctc gctcgccaca tccatctcga tcgtgtgctc cttctggatc  23100
atcacggtcc cgtgcaggca ccgcagcttg ccctcggcct cggtgcaccc gtgcagccac  23160
agcgcgcagc cggtgcactc ccagttcttg tgggcgatct gggagtgcga gtgcacgaag  23220
ccctgcagga agcggcccat catcgtggtc agggtcttgt tgctggtgaa ggtcagcggg  23280
atgccgcggt gctcctcgtt cacatacagg tggcagatgc ggcggtacac ctcgccctgc  23340
tcgggcatca gctggaaggc ggacttcagg tcgctctcca cgcggtaccg ctccatcagc  23400
agcgtcatca cttccatgcc cttctcccag gccgaaacga tcggcaggct caggggggttc  23460
ttcaccgtca tcttagtcgc cgccgccgaa gtcagggggt cgttctcgtc caggtctcca  23520
aacactcgct tgccgtcctt ctcggtgatg cgcacggggg gaaagctgaa gcccacggcc  23580
gccagctcct cctcggcctg cctttcgtcc tcgctgtcct ggctgatgtc ttgcaaaggc  23640
acatgcttgg tcttgcgggg tttctttttg ggcggcagag gcggcggcgg agacgtgctg  23700
ggcgagcgcg agttctcgct caccacgact atttcttctt cttggccgtc gtccgagacc  23760
acgcggcggt aggcatgcct cttctggggc agaggcggag gcgacgggct ctcgcggttc  23820
ggcgggcggc tggcagagcc ccttccgcgt tcgggggtgc gctcctggcg gcgctgctct  23880
```

-continued

```
gactgacttc ctccgcggcc ggccattgtg ttctcctagg gagcaacaag catggagact  23940
cagccatcgt cgccaacatc gccatctgcc cccgccgccg acgagaacca gcagcagcag  24000
aatgaaagct taaccgcccc gccgcccagc cccacctccg acgccgccgc ggccccagac  24060
atgcaagaga tggaggaatc catcgagatt gacctgggct acgtgacgcc cgcggagcac  24120
gaggaggagc tggcagcgcg cttttcagcc ccggaagaga accaccaaga gcagccagag  24180
caggaagcag agagcgagca gcagcaggct gggctcgagc atggcgacta cctgagcggg  24240
gcagaggacg tgctcatcaa gcatctggcc cgccaaagca tcatcgtcaa ggacgcgctg  24300
ctcgaccgcg ccgaggtgcc cctcagcgtg gcggagctca gccgcgccta cgagcgcaac  24360
ctcttctcgc cgcgcgtgcc ccccaagcgc cagcccaacg gcacctgcga gcccaacccg  24420
cgcctcaact tctacccggt cttcgcggtg cccgaggccc tggccaccta ccacctcttt  24480
ttcaagaacc aaaggatccc cgtctcctgc cgcgccaacc gcacccgcgc cgacgccctg  24540
ctcaacctgg gtcccggcgc ccgcctacct gatatcacct ccttggaaga ggttcccaag  24600
atcttcgagg gtctgggcag cgacgagact cgggccgcga acgctctgca aggaagcgga  24660
gaggagcatg agcaccacag cgccctggtg gagttggaag gcgacaacgc gcgcctggcg  24720
gtgctcaagc gcacggtcga gctgacccac ttcgcctacc cggcgctcaa cctgcccccc  24780
aaggtcatga gcgccgtcat ggaccaggtg ctcatcaagc gcgcctcgcc cctctcagag  24840
gaggagatgc aggaccccga gagctcggac gagggcaagc ccgtggtcag cgacgagcag  24900
ctggcgcgct ggctgggagc gagcagcacc ccccagagcc tggaagagcg gcgcaagctc  24960
atgatggccg tggtcctggt gaccgtggag ctggagtgtc tgcgccgctt cttcgccgac  25020
gcggagaccc tgcgcaaggt cgaggagaac ctgcactacc tcttcaggca cgggttcgtg  25080
cgccaggcct gcaagatctc caacgtggag ctgaccaacc tggtctccta catgggcatc  25140
ctgcacgaga accgcctggg gcagaacgtg ctgcacacca ccctgcgcgg ggaggcccgc  25200
cgcgactaca tccgcgactg cgtctacctg tacctctgcc acacctggca gacgggcatg  25260
ggcgtgtggc agcagtgcct ggaggagcag aacctgaaag agctctgcaa gctcctgcag  25320
aagaacctca aggccctgtg gaccgggttc gacgagcgca ccaccgcctc ggacctggcc  25380
gacctcatct tccccgagcg cctgcggctg acgctgcgca acgggctgcc cgactttatg  25440
agccaaagca tgttgcaaaa ctttcgctct ttcatcctcg aacgctccgg gatcctgccc  25500
gccacctgct ccgcactgcc ctcggacttc gtgccgctga ccttccgcga gtgccccccg  25560
ccgctctgga gccactgcta cttgctgcgc ctggccaact acctggccta ccactcggac  25620
gtgatcgagg acgtcagcag cgagggtctg ctcgagtgcc actgccgctg caacctctgc  25680
acgccgcacc gctccttggc ctgcaacccc cagctgctga gcgagaccca gatcatcggc  25740
accttcgagt tgcaaggccc cggcgagggc aagggggggtc tcaaactcac cccggggctg  25800
tggacctcgg cctacttgcg caagttcgtg cccgaggact accatccctt cgagatcagg  25860
ttctacgagg accaatccca gccgcccaag gccgagctgt cggcctgcgt catcacccag  25920
ggggccatcc tggcccaatt gcaagccatc cagaaatccc gccaagaatt tctgctgaaa  25980
aagggccacg ggtctactt ggacccccag accggagagg agctcaaccc cagcttcccc  26040
caggatgccc cgaggaagca gcaagaagct gaaagtggag ctgccgctgc cgcccggagga  26100
tttggaggaa gactgggaga gcagtcaggc agaggagatg gaagactggg acagcactca  26160
ggcagaggag gacagcctgc aagacagtct ggaggaggaa gacgaggtgg aggaggaggc  26220
agaggaagaa gcagccgccg ccagaccgtc gtcctcggcg gaggagaaag caagcagcac  26280
```

-continued

```
ggataccatc tccgctccgg gtcggggtcg cggcggccgg gcccacagta gatgggacga  26340
gaccgggcgc ttcccgaacc ccaccaccca gaccggtaag aaggagcggc agggatacaa  26400
gtcctggcgg gggcacaaaa acgccatcgt ctcctgcttg caagcctgcg ggggcaacat  26460
ctccttcacc cggcgctacc tgctcttcca ccgcggggtg aacttccccc gcaacatctt  26520
gcattactac cgtcacctcc acagccccta ctactgtttc caagaagagg cagaaaccca  26580
gcagcagcag cagaaaacca gcggcagcag cagcagctag aaaatccaca gcggcggcag  26640
gtggactgag gatcgcggcg aacgagccgg cgcagacccg ggagctgagg aaccggatct  26700
ttcccaccct ctatgccatc ttccagcaga gtcgggggca ggagcaggaa ctgaaagtca  26760
agaaccgttc tctgcgctcg ctcacccgca gttgtctgta tcacaagagc gaagaccaac  26820
ttcagcgcac tctcgaggac gccgaggctc tcttcaacaa gtactgcgcg ctcactctta  26880
aagagtagcc cgcgcccgcc cacacacgga aaaaggcggg aattacgtca ccacctgcgc  26940
ccttcgcccg accatcatca tgagcaaaga gattcccacg ccttacatgt ggagctacca  27000
gccccagatg ggcctggccg ccggcgccgc ccaggactac tccacccgca tgaactggct  27060
cagtgccggg cccgcgatga tctcacgggt gaatgacatc cgcgcccacc gaaaccagat  27120
actcctagaa cagtcagcga tcaccgccac gccccgccat caccttaatc cgcgtaattg  27180
gcccgccgcc ctggtgtacc aggaaattcc ccagcccacg accgtactac ttccgcgaga  27240
cgcccaggcc gaagtccagc tgactaactc aggtgtccag ctggccggcg gcgccgccct  27300
gtgtcgtcac cgccccgctc agggtataaa gcggctggtg atccgaggca gaggcacaca  27360
gctcaacgac gaggtggtga gctcttcgct gggtctgcga cctgacggag tcttccaact  27420
cgccggatcg gggagatctt ccttcacgcc tcgtcaggcc gtcctgactt tggagagttc  27480
gtcctcgcag ccccgctcgg gcggcatcgg cactctccag ttcgtggagg agttcactcc  27540
ctcggtctac ttcaacccct tctccggctc ccccggccac tacccggacg agttcatccc  27600
gaacttcgac gccatcagcg agtcggtgga cggctacgat tgaatgtccc atggtggcgc  27660
ggctgaccta gctcggcttc gacacctgga ccactgttaa ttaatcgcct ctcctacgag  27720
ctcctgcagc agcgccagaa gttcacctgc ctggtcggag tcaaccccat cgtcatcacc  27780
cagcagtcgg gcgataccaa ggggtgcatc cactgctcct gcgactcccc cgactgcgtc  27840
cacactctga tcaagaccct ctgcggcctc cgcgacctcc tccccatgaa ctaatcaccc  27900
ccttatccag tgaaataaag atcatattga tgatgatttt acagaaataa agatacaatc  27960
atattgatga tttgagttta ataaaaaata aagaatcact tacttgaaat ctgataccag  28020
gtctctgtcc atgttttctg ccaacaccac ttcactcccc tcttcccagc tctggtactg  28080
caggccccgg cgggctgcaa acttcctcca cacgctgaag gggatgtcaa attcctcctg  28140
tccctcaatc ttcattttat cttctatcag atgtccaaaa agcgcgtccg ggtggatgat  28200
gacttcgacc ccgtctaccc ctacgatgca gacaacgcac cgaccgtgcc cttcatcaac  28260
ccccccttcg tctcttcaga tggattccaa gagaagcccc tgggggtgct gtccctgcga  28320
ctggccgacc ccgtcaccac caagaacggg gaaatcaccc tcaagctggg agagggggtg  28380
gacctcgact cctcgggaaa actcatctcc aacacggcca ccaaggccgc cgcccctctc  28440
agtttttcca acaacaccat ttcccttaac atggatcacc ccttttacac taaagatgga  28500
aaattatcct tacaagtttc tccaccatta aatatactga gaacaagcat tctaaacaca  28560
ctagctttag gttttggatc aggtttagga ctccgtggct ctgccttggc agtacagtta  28620
```

-continued

```
gtctctccac ttacatttga tactgatgga aacataaagc ttaccttaga cagaggtttg  28680
catgttacaa caggagatgc aattgaaagc aacataagct gggctaaagg tttaaaattt  28740
gaagatggag ccatagcaac caacattgga aatgggttag agtttggaag cagtagtaca  28800
gaaacaggtg ttgatgatgc ttacccaatc caagttaaac ttggatctgg ccttagcttt  28860
gacagtacag gagccataat ggctggtaac aaagaagacg ataaactcac tttgtggaca  28920
acacctgatc catcgccaaa ctgtcaaata ctcgcagaaa atgatgcaaa actaacactt  28980
tgcttgacta aatgtggtag tcaaatactg gccactgtgt cagtcttagt tgtaggaagt  29040
ggaaacctaa accccattac tggcaccgta agcagtgctc aggtgtttct acgttttgat  29100
gcaaacggtg ttcttttaac agaacattct acactaaaaa aatactgggg gtataggcag  29160
ggagatagca tagatggcac tccatatacc aatgctgtag gattcatgcc caatttaaaa  29220
gcttatccaa agtcacaaag ttctactact aaaaataata tagtagggca agtatacatg  29280
aatggagatg tttcaaaacc tatgcttctc actataaccc tcaatggtac tgatgacagc  29340
aacagtacat attcaatgtc attttcatac acctggacta atggaagcta tgttggagca  29400
acatttgggg ctaactctta taccttctca tacatcgccc aagaatgaac actgtatccc  29460
accctgcatg ccaacccttc ccaccccact ctgtggaaaa aactctgaaa cacaaaataa  29520
aataaagttc aagtgtttta ttgattcaac agttttacag gattcgagca gttatttttc  29580
ctccaccctc ccaggacatg gaatacacca ccctctcccc ccgcacagcc ttgaacatct  29640
gaatgccatt ggtgatggac atgcttttgg tctccacgtt ccacacagtt tcagagcgag  29700
ccagtctcgg gtcggtcagg gagatgaaac cctccgggca caattgggag aagtactcgc  29760
ctacatgggg gtagagtcat aatcgtgcat caggataggg cggtggtgct gcagcagcgc  29820
gcgaataaac tgctgccgcc gccgctccgt cctgcaggaa tacaacatgg cagtggtctc  29880
ctcagcgatg attcgcaccg cccgcagcat aaggcgcctt gtcctccggg cacagcagcg  29940
caccctgatc tcacttaaat cagcacagta actgcagcac agcaccacaa tattgttcaa  30000
aatcccacag tgcaaggcgc tgtatccaaa gctcatggcg gggaccacag aacccacgtg  30060
gccatcatac cacaagcgca ggtagattaa gtggcgaccc ctcataaaca cgctggacat  30120
aaacattacc tcttttggca tgttgtaatt caccacctcc cggtaccata taaacctctg  30180
attaaacatg gcgccatcca ccaccatcct aaaccagctg gccaaaacct gcccgccggc  30240
tatacactgc agggaaccgg gactggaaca atgacagtgg agagcccagg actcgtaacc  30300
atggatcatc atgctcgtca tgatatcaat gttggcacaa cacaggcaca cgtgcataca  30360
cttcctcagg attacaagct cctcccgcgt tagaaccata tcccagggaa caacccattc  30420
ctgaatcagc gtaaatccca cactgcaggg aagacctcgc acgtaactca cgttgtgcat  30480
tgtcaaagtg ttacattcgg gcagcagcgg atgatcctcc agtatggtag cgcgggtttc  30540
tgtctcaaaa ggaggtagac gatccctact gtacggagtg cgccgagaca accgagatcg  30600
tgttggtcgt agtgtcatgc caaatggaac gccggacgta gtcatatttc ctgaagtctt  30660
ggcgcgccaa agtctagaag cggtccatag cttaccgagc ggcagcagca gcggcacaca  30720
acaggcgcaa gagtcagaga aaagactgag ctctaacctg tccgcccgct ctctgctcaa  30780
tatatagccc agatctacac tgacgtaaag gccaaagtct aaaaataccc gccaaatagt  30840
cacacacgcc cagcacacgc ccagaaaccg gtgacacact caaaaaaata cgcgcacttc  30900
ctcaaacgcc caaactgccg tcatttccgg gttcccacgc tacgtcatca aaacacgact  30960
ttcaaattcc gtcgaccgtt aaaaacgtca cccgccccgc ccctaacggt cgcccgtctc  31020
```

-continued tcagccaatc agcgccccgc atccccaaat tcaaacacct catttgcata ttaacgcgca 31080
ccaaaagttt gaggtatatt attgatgatg 31110

<210> SEQ ID NO 6
<211> LENGTH: 31158
<212> TYPE: DNA
<213> ORGANISM: Artificial Sequence
<220> FEATURE:
<223> OTHER INFORMATION: synthetic chimpanzee adenovirus serotype ChAd63 with Marburg virus Angola codon optimized transmembrane envelope glycoprotein (GP) insert (ChAd63 GP Marburg (PB/6712))
<220> FEATURE:
<221> NAME/KEY: CDS
<222> LOCATION: (1662)...(3704)
<223> OTHER INFORMATION: Marburg virus Angola codon optimized transmembrane envelope glycoprotein (GP) insert in ChAd63 GP Marburg (PB/6712)
<220> FEATURE:
<221> NAME/KEY: CDS
<222> LOCATION: (14420)...(16048)
<223> OTHER INFORMATION: chimpanzee adenovirus serotype ChAd63 penton
<220> FEATURE:
<221> NAME/KEY: CDS
<222> LOCATION: (18815)...(21691)
<223> OTHER INFORMATION: chimpanzee adenovirus serotype ChAd63 hexon
<220> FEATURE:
<221> NAME/KEY: CDS
<222> LOCATION: (28219)...(29496)
<223> OTHER INFORMATION: chimpanzee adenovirus serotype ChAd63 fiber

<400> SEQUENCE: 6
catcatcaat aatatacctc aaacttttgg tgcgcgttaa tatgcaaatg aggtgtttga 60
atttggggat gcggggcgct gattggctga gagacgggcg accgttaggg gcggggcggg 120
tgacgttttg atgacgtggc cgtgaggcgg agccggtttg caagttctcg tgggaaaagt 180
gacgtcaaac gaggtgtggt ttgaacacgg aaatactcaa ttttcccgcg ctctctgaca 240
ggaaatgagg tgtttctggg cggatgcaag tgaaaacggg ccattttcgc gcgaaaactg 300
aatgaggaag tgaaaatctg agtaattccg cgtttatggc agggaggagt atttgccgag 360
ggccgagtag actttgaccg attacgtggg ggtttcgatt accgtatttt tcacctaaat 420
ttccgcgtac ggtgtcaaag tccggtgttt ttacggatat ctccattgca tacgttgtat 480
ccatatcata atatgtacat ttatattggc tcatgtccaa cattaccgcc atgttgacat 540
tgattattga ctagttatta atagtaatca attacggggt cattagttca tagcccatat 600
atggagttcc gcgttacata acttacggta aatggcccgc ctggctgacc gcccaacgac 660
ccccgcccat tgacgtcaat aatgacgtat gttcccatag taacgccaat agggactttc 720
cattgacgtc aatgggtgga gtatttacgg taaactgccc acttggcagt acatcaagtg 780
tatcatatgc caagtacgcc ccctattgac gtcaatgacg gtaaatggcc cgcctggcat 840
tatgcccagt acatgacctt atgggacttt cctacttggc agtacatcta cgtattagtc 900
atcgctatta ccatggtgat gcggttttgg cagtacatca atgggcgtgg atagcggttt 960
gactcacggg gatttccaag tctccacccc attgacgtca atgggagttt gttttggaac 1020
caaaatcaac gggactttcc aaaatgtcgt aacaactccg ccccattgac gcaaatgggc 1080
ggtaggcgtg tacggtggga ggtctatata agcagagctc tccctatcag tgatagagat 1140
ctccctatca gtgatagaga tcgtcgacga gctcgtttag tgaaccgtca gatcgcctgg 1200
agacgccatc cacgctgttt tgacctccat agaagacacc gggaccgatc cagcctccat 1260
cggctcgcat ctctccttca cgcgcccgcc gccctacctg aggccgccat ccacgccggt 1320

```
tgagtcgcgt tctgccgcct cccgcctgtg gtgcctcctg aactgcgtcc gccgtctagg   1380
taagtttaaa gctcaggtcg agaccgggcc tttgtccggc gctcccttgg agcctaccta   1440
gactcagccg gctctccacg ctttgcctga ccctgcttgc tcaactctag ttaacggtgg   1500
agggcagtgt agtctgagca gtactcgttg ctgccgcgcg cgccaccaga cataatagct   1560
gacagactaa cagactgttc ctttccatgg gtcttttctg cagtcaccgt cgtcgacacg   1620
tgtgatcaga tatcgcggcc gctctagaga tatcggccgc catgaagacc acctgcctgc   1680
tgatcagcct gatcctgatc cagggcgtga agaccctgcc catcctggag atcgccagca   1740
acatccagcc ccagaacgtg gacagcgtgt gcagcggcac cctgcagaag accgaggacg   1800
tgcacctgat gggcttcacc ctgagcggcc agaaggtggc cgacagccct ctggaggcca   1860
gcaagaggtg ggccttcagg gccggcgtgc cccccaagaa cgtggagtac accgagggcg   1920
aggaggccaa gacctgctac aacatcagcg tgaccgaccc cagcggcaag agcctgctgc   1980
tggaccctcc caccaacatc agggactacc ctaagtgcaa gaccatccac cacatccagg   2040
gccagaaccc tcacgcccag ggcatcgccc tgcacctgtg ggcgccttc ttcctgtacg   2100
acaggatcgc cagcaccacc atgtacagag gaaaagtgtt cacagaggga aacatcgctg   2160
ctatgatcgt gaacaagacc gtgcataaga tgatcttcag cagacaggga cagggatata   2220
gacatatgaa cctgacatcc acaaacaagt actggacaag cagcaacgga acacagacaa   2280
acgatacagg atgttttgga acactgcagg aatacaactc caccaagaac cagacatgtg   2340
cccctagcaa gaagcctctg cctctgccta cagctcatcc tgaagtgaag ctgacatcca   2400
caagcacaga tgccacaaag ctgaacacaa cagatcctaa tagcgacgac gaggatctga   2460
caacaagcgg atccggatcc ggagaacagg aaccttatac aacaagcgac gctgctacaa   2520
aacagggact gtcctccaca atgcctccta cacctagccc tcagcctagc acacctcagc   2580
agggaggcaa caacacaaac cattcccagg gagtggtgac agaacctgga aagacaaaca   2640
caacagccca gcctagcatg cctcctcata acacaacaac aatcagcaca aacaacacct   2700
ccaagcacaa tctgagcaca cctagcgtgc ctattcagaa tgccaccaac tacaacacac   2760
agtccacagc ccctgaaaac gaacagacct ccgccccttc caaaacaacc ctgctgccta   2820
cagaaaaccc tacaacagcc aagagcacaa acagcacaaa gagccctaca acaacagtgc   2880
ctaacacaac aaacaagtat agcacaagcc ctagccctac acctaattcc acagctcagc   2940
atctggtgta ttttagaaga aagagaaaca tcctgtggag agaaggagat atgttccctt   3000
ttctggatgg actgatcaac gctcctatcg attttgatcc tgtgcctaac acaaagacaa   3060
tctttgatga aagcagcagc agcggagcct ccgccgaaga agatcagcat gcctccccta   3120
acatcagcct gacactgagc tattttccta aggtgaacga aaacacagcc cattccggag   3180
aaaacgaaaa cgattgtgat gccgaactga gaatctggag cgtgcaggaa gatgatctgg   3240
ccgccggact gagctggatc ccttttttttg ggcccggaat tgaaggactg tacaccgccg   3300
gcctgatcaa gaaccagaac aacctggtgt gcaggctgag gaggctggcc aaccagaccg   3360
ccaagagcct ggagctgctg ctgagggtga ccaccgagga gaggaccttc agcctgatca   3420
acaggcacgc catcgacttc ctgctggcta ggtggggcgg cacctgcaag gtgctgggcc   3480
ccgactgctg catcggcatc gaggacctga gcaggaacat cagcgagcag atcgaccaga   3540
tcaagaagga cgagcagaag gagggcaccg gctggggcct gggcggcaag tggtggacca   3600
gcgactgggg agtgctgaca aacctgggaa tcctgctgct gctgagcatt gccgtgctca   3660
```

-continued

```
ttgctctgtc ctgtatctgt agaatcttta ccaagtacat cggatgatag atccagatct   3720
gctgtgcctt ctagttgcca gccatctgtt gtttgcccct cccccgtgcc ttccttgacc   3780
ctggaaggtg ccactcccac tgtcctttcc taataaaatg aggaaattgc atcgcattgt   3840
ctgagtaggt gtcattctat tctggggggt ggggtggggc aggacagcaa gggggaggat   3900
tgggaagaca atagcaggca tgctggggat gcggtgggct ctagatatca gcgatcgcgt   3960
gagtagtgtt tgggggtggg tgggagcctg catgatgggc agaatgacta aaatctgtgt   4020
ttttctgtgt gttgcagcag catgagcgga agcgcctcct ttgagggagg ggtattcagc   4080
ccttatctga cggggcgtct cccctcctgg gcgggagtgc gtcagaatgt gatgggatcc   4140
acggtggacg gccggcccgt gcagcccgcg aactcttcaa ccctgaccta cgcgaccctg   4200
agctcctcgt ccgtggacgc agctgccgcc gcagctgctg cttccgccgc cagcgccgtg   4260
cgcggaatgg ccctgggcgc cggctactac agctctctgg tggccaactc gagttccacc   4320
aataatcccg ccagcctgaa cgaggagaag ctgttgctgc tgatggccca gctcgaggcc   4380
ctgacccagc gcctgggcga gctgacccag caggtggctc agctgcaggc ggagacgcgg   4440
gccgcggttg ccacggtgaa aaccaaataa aaaatgaatc aataaataaa cggagacggt   4500
tgttgatttt aacacagagt cttgaatctt tatttgattt ttcgcgcgcg gtaggccctg   4560
gaccaccggt ctcgatcatt gagcacccgg tggatctttt ccaggacccg gtagaggtgg   4620
gcttggatgt tgaggtacat gggcatgagc ccgtcccggg ggtggaggta gctccattgc   4680
agggcctcgt gctcgggggt ggtgttgtaa atcacccagt catagcaggg gcgcagggcg   4740
tggtgctgca cgatgtcttt gaggaggaga ctgatggcca cgggcagccc cttggtgtag   4800
gtgttgacga acctattgag ctgggaggga tgcatgcggg gggagatgag atgcatcttg   4860
gcctggatct tgagattggc gatgttcccg cccagatccc gccgggggtt catgttgtgc   4920
aggaccacca gcacggtgta tccggtgcac ttggggaatt tgtcatgcaa cttggaaggg   4980
aaggcgtgaa agaatttgga gacgcccttg tgaccgccca ggttttccat gcactcatcc   5040
atgatgatgg cgatgggccc gtgggcggcg gcctgggcaa agacgtttcg gggtcggac    5100
acatcgtagt tgtggtcctg ggtgagctcg tcataggcca ttttaatgaa tttggggcgg   5160
agggtacccg actgggggac aaaggtgccc tcgatcccgg gggcgtagtt cccctcgcag   5220
atctgcatct cccaggcctt gagctcggag ggggggatca tgtccacctg cggggcgatg   5280
aaaaaaacgg tttccggggc gggggagatg agctgcgccg aaagcaggtt ccggagcagc   5340
tgggacttgc cgcagccggt ggggccgtag atgaccccga tgaccggctg caggtggtag   5400
ttgagggaga gacagctgcc gtcctcgcgg aggagggggg ccacctcgtt catcatctcg   5460
cgcacatgca tgttctcgcg cacgagttcc gccaggaggc gctcgccccc cagcgagagg   5520
agctcttgca gcgaggcgaa gtttttcagc ggcttgagcc cgtcggccat gggcattttg   5580
gagagggtct gttgcaagag ttccagacgg tcccagagct cggtgatgtg ctctagggca   5640
tctcgatcca gcagacctcc tcgtttcgcg ggttggggcg actgcgggag tagggcacca   5700
ggcgatgggc gtccagcgag gccagggtcc ggtccttcca gggtcgcagg gtccgcgtca   5760
gcgtggtctc cgtcacggtg aaggggtgcg cgccgggctg ggcgcttgcg agggtgcgct   5820
tcaggctcat ccggctggtc gagaaccgct cccggtcggc gccctgcgcg tcggccaggt   5880
agcaattgag catgagttcg tagttgagcg cctcggccgc gtggcccttg gcgcggagct   5940
tacctttgga agtgtgtccg cagacgggac agaggaggga cttgagggcg tagagcttgg   6000
gggcgaggaa gacggactcg gggcgtaggg cgtccgcgcc gcagctggcg cagacggtct   6060
```

cgcactccac gagccaggtg aggtcggggc ggtcggggtc aaaaacgagg tttcctccgt 6120
gctttttgat gcgtttctta cctctggtct ccatgagctc gtgtccccgc tgggtgacaa 6180
agaggctgtc cgtgtccccg tagaccgact ttatgggccg gtcctcgagc ggggtgccgc 6240
ggtcctcgtc gtagaggaac cccgcccact ccgagacgaa ggcccgggtc caggccagca 6300
cgaaggaggc cacgtgggag gggtagcggt cgttgtccac cagcgggtcc accttctcca 6360
gggtatgcaa gcacatgtcc ccctcgtcca catccaggaa ggtgattggc ttgtaagtgt 6420
aggccacgtg accgggggtc ccggccgggg gggtataaaa gggggcgggc ccctgctcgt 6480
cctcactgtc ttccggatcg ctgtccagga gcgccagctg ttggggtagg tattccctct 6540
cgaaggcggg catgacctcg gcactcaggt tgtcagtttc tagaaacgag gaggatttga 6600
tattgacggt gccgttggag acgcctttca tgagcccctc gtccatctgg tcagaaaaga 6660
cgatcttttt gttgtcgagc ttggtggcga aggagccgta gagggcgttg gagagcagct 6720
tggcgatgga gcgcatggtc tggttctttt ccttgtcggc gcgctccttg gcggcgatgt 6780
tgagctgcac gtactcgcgc gccacgcact tccattcggg gaagacggtg gtgagctcgt 6840
cgggcacgat tctgacccgc cagccgcggt tgtgcagggt gatgaggtcc acgctggtgg 6900
ccacctcgcc gcgcaggggc tcgttggtcc agcagaggcg cccgcccttg cgcgagcaga 6960
agggggcag cgggtccagc atgagctcgt cgggggggtc ggcgtccacg gtgaagatgc 7020
cgggcaggag ctcggggtcg aagtagctga tgcaggtgcc cagatcgtcc agacttgctt 7080
gccagtcgcg cacggccagc gcgcgctcgt aggggctgag gggcgtgccc cagggcatgg 7140
ggtgcgtgag cgcggaggcg tacatgccgc agatgtcgta gacgtagagg ggctcctgga 7200
ggacgccgat gtaggtgggg tagcagcgcc ccccgcggat gctggcgcgc acgtagtcgt 7260
acagctcgtg cgagggcgcg aggagccccg tgccgagatt ggagcgctgc ggcttttcgg 7320
cgcggtagac gatctggcgg aagatggcgt gggagttgga ggagatggtg ggcctctgga 7380
agatgttgaa gtgggcatgg ggcagtccga ccgagtccct gatgaagtgg gcgtaggagt 7440
cctgcagctt ggcgacgagc tcggcggtga cgaggacgtc cagggcgcag tagtcgaggg 7500
tctcttggat gatgtcgtac ttgagctggc ccttctgctt ccacagctcg cggttgagaa 7560
ggaactcttc gcggtccttc cagtactctt cgagggggaa cccgtcctga tcggcacggt 7620
aagagcccac catgtagaac tggttgacgg ccttgtaggc gcagcagccc ttctccacgg 7680
ggagggcgta agcttgcgcg gccttgcgca gggaggtgtg ggtgagggcg aaggtgtcgc 7740
gcaccatgac tttgaggaac tggtgcttga agtcgaggtc gtcgcagccg ccctgctccc 7800
agagctggaa gtccgtgcgc ttcttgtagg cggggttggg caaagcgaaa gtaacatcgt 7860
tgaagaggat cttgcccgcg cggggcatga agttgcgagt gatgcggaaa ggctggggca 7920
cctcggcccg gttgttgatg acctgggcgg cgaggacgat ctcgtcgaag ccgttgatgt 7980
tgtgcccgac gatgtagagt tccacgaatc gcgggcggcc cttgacgtgg ggcagcttct 8040
tgagctcgtc gtaggtgagc tcggcggggt cgctgagccc gtgctgctcg agggcccagt 8100
cggcgacgtg gggttggcg ctgaggaagg aagtccagag atccacggcc agggcggtct 8160
gcaagcggtc ccggtactga cggaactgct ggcccacggc catttttcg ggggtgacgc 8220
agtagaaggt gcgggggtcg ccgtgccagc ggtcccactt gagctggagg gcgaggtcgt 8280
gggcgagctc gacgagcggc gggtccccgg agagtttcat gaccagcatg aaggggacga 8340
gctgcttgcc gaaggacccc atccaggtgt aggtttccac atcgtaggtg aggaagagcc 8400

-continued

```
tttcggtgcg aggatgcgag ccgatgggga agaactggat ctcctgccac cagttggagg   8460
aatggctgtt gatgtgatgg aagtagaaat gccgacggcg cgccgagcac tcgtgcttgt   8520
gtttatacaa gcgtccgcag tgctcgcaac gctgcacggg atgcacgtgc tgcacgagct   8580
gtacctgggt tcctttgacg aggaatttca gtgggcagtg gagcgctggc ggctgcatct   8640
ggtgctgtac tacgtcctgg ccatcggcgt ggccatcgtc tgcctcgatg gtggtcatgc   8700
tgacgagccc gcgcgggagg caggtccaga cctcggctcg gacgggtcgg agagcgagga   8760
cgagggcgcg caggccggag ctgtccaggg tcctgagacg ctgcggagtc aggtcagtgg   8820
gcagcggcgg cgcgcggttg acttgcagga gcttttccag ggcgcgcggg aggtccagat   8880
ggtacttgat ctccacggcg ccgttggtgg cgacgtccac ggcttgcagg gtcccgtgcc   8940
cctggggcgc caccaccgtg ccccgtttct tcttgggcgg cggcggctcc atgcttagaa   9000
gcggcggcga ggacgcgcgc cgggcggcag gggcggctcg gggcccggag gcaggggcgg   9060
caggggcacg tcggcgccgc gcgcgggcag gttctggtac tgcgcccgga gaagactggc   9120
gtgagcgacg acgcgacggt tgacgtcctg gatctgacgc ctctgggtga aggccacggg   9180
acccgtgagt ttgaacctga aagagagttc gacagaatca atctcggtat cgttgacggc   9240
ggcctgccgc aggatctctt gcacgtcgcc cgagttgtcc tggtaggcga tctcggtcat   9300
gaactgctcg atctcctcct cctgaaggtc tccgcggccg gcgcgctcga cggtggccgc   9360
gaggtcgttg gagatgcggc ccatgagctg cgagaaggcg ttcatgccgg cctcgttcca   9420
gacgcggctg tagaccacgg ctccgtcggg gtcgcgcgcg cgcatgacca cctgggcgag   9480
gttgagctcg acgtggcgcg tgaagaccgc gtagttgcag aggcgctggt agaggtagtt   9540
gagcgtggtg gcgatgtgct cggtgacgaa gaagtacatg atccagcggc ggagcggcat   9600
ctcgctgacg tcgcccaggg cttccaagcg ctccatggcc tcgtagaagt ccacggcgaa   9660
gttgaaaaac tgggagttgc gcgccgagac ggtcaactcc tcctccagaa gacggatgag   9720
ctcggcgatg gtggcgcgca cctcgcgctc gaaggccccg gggggctcct cttccatttc   9780
ctcctcttcc tcctccacta acatctcttc tacttcctcc tcaggaggcg gcggcggggg   9840
aggggccctg cgtcgccggc ggcgcacggg cagacggtcg atgaagcgct cgatggtctc   9900
cccgcgccgg cgacgcatgg tctcggtgac ggcgcgcccg tcctcgcggg gccgcagcgt   9960
gaagacgccg ccgcgcatct ccaggtggcc gccggggggg tctccgttgg gcagggagag  10020
ggcgctgacg atgcatctta tcaattgacc cgtagggact ccgcgcaagg acctgagcgt  10080
ctcgagatcc acgggatccg aaaaccgctg aacgaaggct tcgagccagt cgcagtcgca  10140
aggtaggctg agcccggttt cttgttcttc gggtatttgg tcgggaggcg ggcgggcgat  10200
gctgctggtg atgaagttga agtaggcggt cctgagacgg cggatggtgg cgaggagcac  10260
caggtccttg ggcccggctt gctggatgcg cagacggtcg gccatgcccc aggcgtggtc  10320
ctgacacctg gcgaggtcct tgtagtagtc ctgcatgagc cgctccacgg gcacctcctc  10380
ctcgcccgcg cggccgtgca tgcgcgtgag cccgaacccg cgctgcggct ggacgagcgc  10440
caggtcggcg acgacgcgct cggcgaggat ggcctgctgg atctgggtga gggtggtctg  10500
gaagtcgtcg aagtcgacga agcggtggta ggctccggtg ttgatggtgt aggagcagtt  10560
ggccatgacg gaccagttga cggtctggtg gccggggcgc acgagctcgt ggtacttgag  10620
gcgcgagtag gcgcgcgtgt cgaagatgta gtcgttgcag gtgcgcacga ggtactggta  10680
tccgacgagg aagtgcggcg gcggctggcg gtagagcggc catcgctcgg tggcgggggc  10740
gccgggcgcg aggtcctcga gcatgaggcg gtggtagccg tagatgtacc tggacatcca  10800
```

ggtgatgccg gcggcggtgg tggaggcgcg cgggaactcg cggacgcggt tccagatgtt 10860
gcgcagcggc aggaagtagt tcatggtggc cgcggtctgg cccgtgaggc gcgcgcagtc 10920
gtggatgctc tagacatacg ggcaaaaacg aaagcggtca gcggctcgac tccgtggcct 10980
ggaggctaag cgaacgggtt gggctgcgcg tgtaccccgg ttcgaatctc gaatcaggct 11040
ggagccgcag ctaacgtggt actggcactc ccgtctcgac ccaagcctgc taacgaaacc 11100
tccaggatac ggaggcgggt cgtttttttgg ccttggtcgc tggtcatgaa aaactagtaa 11160
gcgcggaaag cggccgcccg cgatggctcg ctgccgtagt ctggagaaag aatcgccagg 11220
gttgcgttgc ggtgtgcccc ggttcgagcc tcagcgctcg gcgccggccg gattccgcgg 11280
ctaacgtggg cgtggctgcc ccgtcgtttc caagacccct tagccagccg acttctccag 11340
ttacggagcg agcccctctt tttttcttgt gtttttgcca gatgcatccc gtactgcggc 11400
agatgcgccc ccaccctcca ccacaaccgc ccctaccgca gcagcagcaa cagccggcgc 11460
ttctgccccc gccccagcag cagcagccag ccactaccgc ggcggccgcc gtgagcggag 11520
ccggcgttca gtatgacctg gccttggaag agggcgaggg gctggcgcgg ctgggggcgt 11580
cgtcgccgga gcggcacccg cgcgtgcaga tgaaaaggga cgctcgcgag gcctacgtgc 11640
ccaagcagaa cctgttcaga gacaggagcg gcgaggagcc cgaggagatg cgcgcctccc 11700
gcttccacgc ggggcgggag ctgcggcgcg gcctggaccg aaagcgggtg ctgagggacg 11760
aggatttcga ggcggacgag ctgacgggga tcagccccgc gcgcgcgcac gtggccgcgg 11820
ccaacctggt cacggcgtac gagcagaccg tgaaggagga gagcaacttc caaaaatcct 11880
tcaacaacca cgtgcgcacg ctgatcgcgc gcgaggaggt gaccctgggc ctgatgcacc 11940
tgtgggacct gctggaggcc atcgtgcaga accccacgag caagccgctg acggcgcagc 12000
tgtttctggt ggtgcagcac agtcgggaca acgagacgtt cagggaggcg ctgctgaata 12060
tcaccgagcc cgagggccgc tggctcctgg acctggtgaa cattctgcag agcatcgtgg 12120
tgcaggagcg cgggctgccg ctgtccgaga agctggcggc catcaacttc tcggtgctga 12180
gcctgggcaa gtactacgct aggaagatct acaagacccc gtacgtgccc atagacaagg 12240
aggtgaagat cgatgggttt tacatgcgca tgaccctgaa agtgctgacc ctgagcgacg 12300
atctgggggt gtaccgcaac gacaggatgc accgcgcggt gagcgccagc cgccggcgcg 12360
agctgagcga ccaggagctg atgcacagcc tgcagcgggc cctgaccggg gccgggaccg 12420
agggggagag ctactttgac atgggcgcgg acctgcgctg gcagcccagc cgccgggcct 12480
tggaagctgc cggcggcgtg ccctacgtgg aggaggtgga cgatgaggag gaggagggcg 12540
agtacctgga agactgatgg cgcgaccgta tttttgctag atgcagcaac agccaccgcc 12600
gccgcctcct gatcccgcga tgcgggcggc gctgcagagc cagccgtccg gcattaactc 12660
ctcggacgat tggacccagg ccatgcaacg catcatggcg ctgacgaccc gcaatcccga 12720
agcctttaga cagcagcctc aggccaaccg gctctcggcc atcctggagg ccgtggtgcc 12780
ctcgcgctcg aaccccacgc acgagaaggt gctggccatc gtgaacgcgc tggtggagaa 12840
caaggccatc cgcggcgacg aggccgggct ggtgtacaac gcgctgctgg agcgcgtggc 12900
ccgctacaac agcaccaacg tgcagacgaa cctggaccgc atggtgaccg acgtgcgcga 12960
ggcggtgtcg cagcgcgagc ggttccaccg cgagtcgaac ctgggctcca tggtggcgct 13020
gaacgccttc ctgagcacgc agcccgccaa cgtgccccgg ggccaggagg actacaccaa 13080
cttcatcagc gcgctgcggc tgatggtggc cgaggtgccc cagagcgagg tgtaccagtc 13140

-continued

```
ggggccggac tacttcttcc agaccagtcg ccagggcttg cagaccgtga acctgagcca  13200
ggctttcaag aacttgcagg gactgtgggg cgtgcaggcc ccggtcgggg accgcgcgac  13260
ggtgtcgagc ctgctgacgc cgaactcgcg cctgctgctg ctgctggtgg cgcccttcac  13320
ggacagcggc agcgtgagcc gcgactcgta cctgggctac ctgcttaacc tgtaccgcga  13380
ggccatcggg caggcgcacg tggacgagca gacctaccag gagatcaccc acgtgagccg  13440
cgcgctgggc caggaggacc cgggcaacct ggaggccacc ctgaacttcc tgctgaccaa  13500
ccggtcgcag aagatcccgc cccagtacgc gctgagcacc gaggaggagc gcatcctgcg  13560
ctacgtgcag cagagcgtgg ggctgttctt gatgcaggag ggggccacgc ccagcgccgc  13620
gctcgacatg accgcgcgca acatggagcc cagcatgtac gcccgcaacc gcccgttcat  13680
caataagctg atggactact tgcatcgggc ggccgccatg aactcggact actttaccaa  13740
cgccatcttg aacccgcact ggctcccgcc gcccgggttc tacacgggcg agtacgacat  13800
gcccgacccc aacgacgggt tcctgtggga cgacgtggac agcagcgtgt tctcgccgcg  13860
gcccaccacc accaccgtgt ggaagaaaga gggcggggac cggcggccgt cctcggcgct  13920
gtccggtcgc gcgggtgctg ccgcggcggt gcccgaggct gccagcccct tcccgagcct  13980
gcccttttcg ctgaacagcg tgcgcagcag cgagctgggt cggctgacgc ggccgcgcct  14040
gctgggcgag gaggagtacc tgaacgactc cttgttgaag cccgagcgcg agaagaactt  14100
ccccaataac gggatagaga gcctggtgga caagatgagc cgctggaaga cgtacgcgca  14160
cgagcacagg gacgagcccc gagctagcag cgcaggcacc cgtagacgcc agcggcacga  14220
caggcagcgg ggactggtgt gggacgatga ggattccgcc gacgacagca gcgtgttgga  14280
cttgggtggg agtggtggtg gtaacccgtt cgctcacctg cgcccccgta tcgggcgcct  14340
gatgtaagaa tctgaaaaaa taaaagacgg tactcaccaa ggccatggcg accagcgtgc  14400
gttcttctct gttgtttgta gtagtatgat gaggcgcgtg tacccggagg gtcctcctcc  14460
ctcgtacgag agcgtgatgc agcaggcggt ggcggcggcg atgcagcccc cgctggaggc  14520
gccttacgtg cccccgcggt acctggcgcc tacggagggg cggaacagca ttcgttactc  14580
ggagctggca ccccttgtacg ataccacccg gttgtacctg gtggacaaca agtcggcgga  14640
catcgcctcg ctgaactacc agaacgacca cagcaacttc ctgaccaccg tggtgcagaa  14700
caacgatttc acccccacgg aggccagcac ccagaccatc aactttgacg agcgctcgcg  14760
gtggggcggc cagctgaaaa ccatcatgca caccaacatg cccaacgtga acgagttcat  14820
gtacagcaac aagttcaagg cgcgggtgat ggtctcgcgc aagaccccca acggggtcac  14880
ggtaggggat gattatgatg gtagtcagga cgagctgacc tacgagtggg tggagtttga  14940
gctgcccgag ggcaacttct cggtgaccat gaccatcgat ctgatgaaca acgccatcat  15000
cgacaactac ttggcggtgg ggcggcagaa cggggtgctg gagagcgaca tcggcgtgaa  15060
gttcgacacg cgcaacttcc ggctgggctg ggaccccgtg accgagctgg tgatgccggg  15120
cgtgtacacc aacgaggcct tccaccccga catcgtcctg ctgcccggct gcggcgtgga  15180
cttcaccgag agccgcctca gcaacctgct gggcatccgc aagcggcagc ccttccagga  15240
gggcttccag atcctgtacg aggacctgga ggggggcaac atccccgcgc tcttggatgt  15300
cgaagcctat gaagaaagta aggaaaaagc agaggctgag gcaactacag ccgtggctac  15360
cgccgcgact gtggcagatg ccactgtcac caggggcgat acattcgcca cccaggcgga  15420
ggaagcagcc gccctagcgg cgaccgatga tagtgaaagt aagatagtca tcaagccggt  15480
ggagaaggac agcaagaaca ggagctacaa cgttctaccg gatggaaaga acaccgccta  15540
```

ccgcagctgg tacctggcct acaactacgg cgaccccgag aagggcgtgc gctcctggac 15600
gctgctcacc acctcggacg tcacctgcgg cgtggagcaa gtctactggt cgctgcccga 15660
catgatgcaa gacccggtca ccttccgctc cacgcgacaa gttagcaact acccggtggt 15720
gggcgccgag ctcctgcccg tctactccaa gagcttcttc aacgagcagg ccgtctactc 15780
gcagcagctg cgtgccttca cctcgctcac gcacgtcttc aaccgcttcc ccgagaacca 15840
gatcctcgtc cgcccgcccg cgcccaccat taccaccgtc agtgaaaacg ttcctgctct 15900
cacagatcac gggaccctgc cgctgcgcag cagtatccgg ggagtccagc gcgtgaccgt 15960
cactgacgcc agacgccgca cctgccccta cgtctacaag gccctgggcg tagtcgcgcc 16020
gcgcgtcctc tcgagccgca ccttctaaaa aatgtccatt ctcatctcgc ccagtaataa 16080
caccggttgg ggcctgcgcg cgcccagcaa gatgtacgga ggcgctcgcc aacgctccac 16140
gcaacacccc gtgcgcgtgc gcgggcactt ccgcgctccc tggggcgccc tcaagggccg 16200
cgtgcgctcg cgcaccaccg tcgacgacgt gatcgaccag gtggtggccg acgcgcgcaa 16260
ctacacgccc gccgccgcgc ccgcctccac cgtggacgcc gtcatcgaca gcgtggtggc 16320
cgacgcgcgc cggtacgccc gcgccaagag ccggcggcgg cgcatcgccc ggcggcaccg 16380
gagcaccccc gccatgcgcg cggcgcgagc cttgctgcgc agggccaggc gcacgggacg 16440
cagggccatg ctcagggcgg ccagacgcgc ggcctccggc agcagcagcg ccggcaggac 16500
ccgcagacgc gcggccacgg cggcggcggc ggccatcgcc agcatgtccc gcccgcggcg 16560
cggcaacgtg tactgggtgc gcgacgccgc caccggtgtg cgcgtgcccg tgcgcacccg 16620 ccccccctcgc acttgaagat gctgacttcg cgatgttgat gtgtcccagc ggcgaggagg 16680
atgtccaagc gcaaatacaa ggaagagatg ctccaggtca tcgcgcctga gatctacggc 16740
cccgcggcgg cggtgaagga ggaaagaaag ccccgcaaac tgaagcgggt caaaaaggac 16800
aaaaaggagg aggaagatga cggactggtg gagtttgtgc gcgagttcgc cccccggcgg 16860
cgcgtgcagt ggcgcgggcg gaaagtgaaa ccggtgctgc ggcccggcac cacggtggtc 16920
ttcacgcccg gcgagcgttc cggctccgcc tccaagcgct cctacgacga ggtgtacggg 16980
gacgaggaca tcctcgagca ggcggtcgag cgtctgggcg agtttgctta cggcaagcgc 17040
agccgccccg cgcccttgaa agaggaggcg gtgtccatcc cgctggacca cggcaacccc 17100
acgccgagcc tgaagccggt gaccctgcag caggtgctgc cgagcgcggc gccgcgccgg 17160
ggcttcaagc gcgagggcgg cgaggatctg tacccgacca tgcagctgat ggtgcccaag 17220
cgccagaagc tggaggacgt gctggagcac atgaaggtgg accccgaggt gcagcccgag 17280
gtcaaggtgc ggcccatcaa gcaggtggcc ccgggcctgg gcgtgcagac cgtggacatc 17340
aagatcccca cggagcccat ggaaacgcag accgagcccg tgaagcccag caccagcacc 17400
atggaggtgc agacggatcc ctggatgcca gcggcttcca ccaccaccac tcgccgaaga 17460
cgcaagtacg gcgcggccag cctgctgatg cccaactacg cgctgcatcc ttccatcatc 17520
cccacgccgg gctaccgcgg cacgcgcttc taccgcggct acaccagcag ccgccgccgc 17580
aagaccacca cccgccgccg tcgtcgcagc cgccgcagca gcaccgcgac ttccgccttg 17640
gtgcggagag tgtatcgcag cgggcgcgag cctctgaccc tgccgcgcgc gcgctaccac 17700
ccgagcatcg ccatttaact accgcctcct acttgcagat atggccctca catgccgcct 17760
ccgcgtcccc attacgggct accgaggaag aaagccgcgc cgtagaaggc tgacggggaa 17820
cgggctgcgt cgccatcacc accggcggcg gcgcgccatc agcaagcggt tgggggggagg 17880

-continued cttcctgccc gcgctgatcc ccatcatcgc cgcggcgatc ggggcgatcc ccggcatagc 17940
ttccgtggcg gtgcaggcct ctcagcgcca ctgagacaca aaaaagcatg gatttgtaat 18000
aaaaaaatgg actgacgctc ctggtcctgt gatgtgtgtt tttagatgga agacatcaat 18060
ttttcgtccc tggcaccgcg acacggcacg cggccgttta tgggcacctg gagcgacatc 18120
ggcaacagcc aactgaacgg gggcgccttc aattggagca gtctctggag cgggcttaag 18180
aatttcgggt ccacgctcaa aacctatggc aacaaggcgt ggaacagcag cacagggcag 18240
gcgctgaggg aaaagctgaa agagcagaac ttccagcaga aggtggtcga tggcctggcc 18300
tcgggcatca acggggtggt ggacctggcc aaccaggccg tgcagaaaca gatcaacagc 18360
cgcctggacg cggtcccgcc cgcggggtcc gtggagatgc cccaggtgga ggaggagctg 18420
cctcccctgg acaagcgcgg cgacaagcga ccgcgtcccg acgcggagga gacgctgctg 18480
acgcacacgg acgagccgcc cccgtacgag gaggcggtga aactgggtct gcccaccacg 18540
cggcccgtgg cgcctctggc caccggggtg ctgaaaccca gcagcagcag ccagcccgcg 18600
accctggact tgcctccgcc tgcttcccgc ccctccacag tggctaagcc cctgccgccg 18660
gtggccgtcg cgtcgcgcgc cccccgaggc cgcccccagg cgaactggca gagcactctg 18720
aacagcatcg tgggtctggg agtgcagagt gtgaagcgcc gccgctgcta ttaaaagaca 18780
ctgtagcgct taacttgctt gtctgtgtgt gtatatgtat gtccgccgac cagaaggagg 18840
aagaggcgcg tcgccgagtt gcaagatggc caccccatcg atgctgcccc agtgggcgta 18900
catgcacatc gccggacagg acgcttcgga gtacctgagt ccgggtctgg tgcagttcgc 18960
ccgcgccaca gacacctact tcagtctggg gaacaagttt aggaacccca cggtggcgcc 19020
cacgcacgat gtgaccaccg accgcagcca gcggctgacg ctgcgcttcg tgcccgtgga 19080
ccgcgaggac aacacctact cgtacaaagt gcgctacacg ctggccgtgg gcgacaaccg 19140
cgtgctggac atggccagca cctactttga catccgcggc gtgctggatc ggggccccag 19200
cttcaaaccc tactccggca ccgcctacaa cagcctagct cccaagggag cgcccaacac 19260
ctcacagtgg aaggattccg acagcaaaat gcatactttt ggagttgctg ccatgcccgg 19320
tgttgttggt aaaaaaatag aagccgatgg tctgcctatt ggaatagatt catcctctgg 19380
aactgacacc ataatttatg ctgataaaac tttccaacca gagccacagg ttggaagtga 19440
cagttgggtc gacaccaatg gtgcagagga aaaatatgga ggtagagctc ttaaggacac 19500
tacaaacatg aagccctgct acggttcttt tgccaggcct accaacaaag aaggtggaca 19560
ggctaacata aaagattctg aaactgccag cactactcct aactatgata tagatttggc 19620
attctttgac agcaaaaata ttgcagctaa ctacgatcca gatattgtaa tgtacacaga 19680
aaatgttgag ttgcaaactc cagatactca tattgtgttt aagccaggaa cttcagatga 19740
aagttcagaa gccaatttgg gccagcaggc catgcccaac agacccaact acatcgggtt 19800
cagagacaac tttatcgggc tcatgtacta caacagcact ggcaatatgg gtgtactggc 19860
tggtcaggcc tcccagctaa atgctgtggt ggacttgcag gacagaaaca ccgaactgtc 19920
ctaccagctc ttgcttgact ctctgggtga cagaaccagg tatttcagta tgtggaatca 19980
ggcggtggac agctatgacc ccgatgtgcg cattattgaa aatcacggtg tggaggatga 20040
actccccaat tattgcttcc ctttgaatgg tgtaggcttt acagatactt accagggtgt 20100
taaagttaag acagatacag ccgctactgg taccaatgga acgcagtggg acaaagatga 20160
taccacagtc agcactgcca atgagatcca ctcaggcaat cctttcgcca tggagatcaa 20220
catccaggcc aacctgtggc ggaacttcct ctacgcgaac gtggcgctgt acctgcccga 20280

-continued

```
ctcctacaag tacacgccgg ccaacatcac gctgccgacc aacaccaaca cctacgatta  20340
catgaacggc cgcgtggtgg cgccctcgct ggtggacgcc tacatcaaca tcggggcgcg  20400
ctggtcgctg gaccccatgg acaacgtcaa ccccttcaac caccaccgca acgcgggcct  20460
gcgctaccgc tccatgctcc tgggcaacgg gcgctacgtg cccttccaca tccaggtgcc  20520
ccaaaagttt ttcgccatca agagcctcct gctcctgccc gggtcctaca cctacgagtg  20580
gaacttccgc aaggacgtca acatgatcct gcagagctcc ctcggcaacg acctgcgcac  20640
ggacggggcc tccatcgcct tcaccagcat caacctctac gccaccttct tccccatggc  20700
gcacaacacc gcctccacgc tcgaggccat gctgcgcaac gacaccaacg accagtcctt  20760
caacgactac ctctcggcgg ccaacatgct ctaccccatc ccggccaacg ccaccaacgt  20820
gcccatctcc atcccctcgc gcaactgggc cgccttccgc ggatggtcct tcacgcgcct  20880
caagacccgc gagacgccct cgctcggctc cgggttcgac ccctacttcg tctactcggg  20940
ctccatcccc tacctcgacg gcaccttcta cctcaaccac accttcaaga aggtctccat  21000
caccttcgac tcctccgtca gctggcccgg caacgaccgc ctcctgacgc ccaacgagtt  21060
cgaaatcaag cgcaccgtcg acggagaggg atacaacgtg gcccagtgca acatgaccaa  21120
ggactggttc ctggtccaga tgctggccca ctacaacatc ggctaccagg gcttctacgt  21180
gcccgagggc tacaaggacc gcatgtactc cttcttccgc aacttccagc ccatgagccg  21240
ccaggtcgtg gacgaggtca actacaagga ctaccaggcc gtcaccctgg cctaccagca  21300
caacaactcg ggcttcgtcg gctacctcgc gcccaccatg cgccagggcc agccctaccc  21360
cgccaactac ccctacccgc tcatcggcaa gagcgccgtc gccagcgtca cccagaaaaa  21420
gttcctctgc gaccgggtca tgtggcgcat ccccttctcc agcaacttca tgtccatggg  21480
cgcgctcacc gacctcggcc agaacatgct ctacgccaac tccgcccacg cgctagacat  21540
gaatttcgaa gtcgacccca tggatgagtc cacccttctc tatgttgtct tcgaagtctt  21600
cgacgtcgtc cgagtgcacc agccccaccg cggcgtcatc gaggccgtct acctgcgcac  21660
gcccttctcg gccggcaacg ccaccaccta aagccccgct cttgcttctt gcaagatgac  21720
ggcctgtggc tccggcgagc aggagctcag ggccatcctc cgcgacctgg gctgcgggcc  21780
ctgcttcctg ggcaccttcg acaagcgctt cccgggattc atggccccgc acaagctggc  21840
ctgcgccatc gtcaacacgg ccggccgcga gaccgggggc gagcactggc tggccttcgc  21900
ctggaacccg cgctcccaca cctgctacct cttcgacccc ttcgggttct cggacgagcg  21960
cctcaagcag atctaccagt tcgagtacga gggcctgctg cgccgcagcg ccctggccac  22020
cgaggaccgc tgcatcaccc tggaaaagtc cacccagacc gtgcagggtc cgcgctcggc  22080
cgcctgcggg ctcttctgct gcatgttcct gcacgccttc gtgcactggc ccgaccgccc  22140
catggacaag aaccccacca tgaacttgct gacgggggtg cccaacggca tgctccagtc  22200
gccccaggtg gaacccaccc tgcgccgcaa ccaggaggcg ctctaccgct tcctcaacgc  22260
ccactccgcc tactttcgct cccaccgcgc gcgcatcgag aaggccaccg ccttcgaccg  22320
catgaatcaa gacatgtaaa ctgtgtgtat gtgaatgctt tattcatcat aataaacagc  22380
acatgtttat gccaccttct ctgaggctct gactttattt agaaatcgaa ggggttctgc  22440
cggctctcgg cgtgccccgc gggcagggat acgttgcgga actggtactt gggcagccac  22500
ttgaactcgg ggatcagcag cttcggcacg gggaggtcgg ggaacgagtc gctccacagc  22560
ttgcgcgtga gttgcagggc gcccagcagg tcgggcgcgg agatcttgaa atcgcagttg  22620
```

-continued ggacccgcgt tctgcgcgcg agagttgcgg tacacggggt tgcagcactg gaacaccatc 22680
agggccgggt gcttcacgct cgccagcacc gtcgcgtcgg tgatgccctc cacgtccaga 22740
tcctcggcgt tggccatccc gaagggggtc atcttgcagg tctgccgccc catgctgggc 22800
acgcagccgg gcttgtggtt gcaatcgcag tgcaggggga tcagcatcat ctgagcctgc 22860
tcggagctca tgcccgggta catggccttc atgaaagcct ccagctggcg gaaggcctgc 22920
tgcgccttgc cgccctcggt gaagaagacc ccacaggact tgctagagaa ctggttggtg 22980
gcgcagcccg cgtcgtgcac gcagcagcgc gcgtcgttgt tggccagctg caccacgctg 23040
cgcccccagc ggttctgggt gatcttggcc cggtcggggt tctccttcag cgcgcgctgc 23100
ccgttctcgc tcgccacatc catctcgatc gtgtgctcct tctggatcat cacggtcccg 23160
tgcaggcacc gcagcttgcc ctcggcctcg gtgcacccgt gcagccacag cgcgcagccg 23220
gtgcactccc agttcttgtg ggcgatctgg gagtgcgagt gcacgaagcc ctgcaggaag 23280
cggcccatca tcgtggtcag ggtcttgttg ctggtgaagg tcagcgggat gccgcggtgc 23340
tcctcgttca catacaggtg gcagatgcgg cggtacacct cgccctgctc gggcatcagc 23400
tggaaggcgg acttcaggtc gctctccacg cggtaccgct ccatcagcag cgtcatcact 23460
tccatgccct tctcccaggc cgaaacgatc ggcaggctca gggggttctt caccgtcatc 23520
ttagtcgccg ccgccgaagt caggggggtcg ttctcgtcca gggtctcaaa cactcgcttg 23580
ccgtccttct cggtgatgcg cacgggggga aagctgaagc ccacggccgc cagctcctcc 23640
tcggcctgcc tttcgtcctc gctgtcctgg ctgatgtctt gcaaaggcac atgcttggtc 23700
ttgcggggtt tctttttggg cggcagaggc ggcggcggag acgtgctggg cgagcgcgag 23760
ttctcgctca ccacgactat ttcttcttct tggccgtcgt ccgagaccac gcggcggtag 23820
gcatgcctct tctggggcag aggcggaggc gacgggctct cgcggttcgg cgggcggctg 23880
gcagagcccc ttccgcgttc gggggtgcgc tcctggcggc gctgctctga ctgacttcct 23940
ccgcggccgg ccattgtgtt ctcctaggga gcaacaagca tggagactca gccatcgtcg 24000
ccaacatcgc catctgcccc cgccgccgac gagaaccagc agcagcagaa tgaaagctta 24060
accgccccgc cgcccagccc cacctccgac gccgccgcgg ccccagacat gcaagagatg 24120
gaggaatcca tcgagattga cctgggctac gtgacgcccg cggagcacga ggaggagctg 24180
gcagcgcgct tttcagcccc ggaagagaac caccaagagc agccagagca ggaagcagag 24240
agcgagcagc agcaggctgg gctcgagcat ggcgactacc tgagcggggc agaggacgtg 24300
ctcatcaagc atctggcccg ccaaagcatc atcgtcaagg acgcgctgct cgaccgcgcc 24360
gaggtgcccc tcagcgtggc ggagctcagc cgcgcctacg agcgcaacct cttctcgccg 24420
cgcgtgcccc ccaagcgcca gcccaacggc acctgcgagc ccaacccgcg cctcaacttc 24480
tacccggtct tcgcggtgcc cgaggccctg gccacctacc acctcttttt caagaaccaa 24540
aggatccccg tctcctgccg cgccaaccgc acccgcgccg acgccctgct caacctgggt 24600
cccggcgccc gcctacctga tatcacctcc ttggaagagg ttcccaagat cttcgagggt 24660
ctgggcagcg acgagactcg ggccgcgaac gctctgcaag gaagcggaga ggagcatgag 24720
caccacagcg ccctggtgga gttggaaggc gacaacgcgc gcctggcggt gctcaagcgc 24780
acggtcgagc tgacccactt cgcctacccg gcgctcaacc tgccccccaa ggtcatgagc 24840
gccgtcatgg accaggtgct catcaagcgc gcctcgcccc tctcagagga ggagatgcag 24900
gaccccgaga gctcggacga gggcaagccc gtggtcagcg acgagcagct ggcgcgctgg 24960
ctgggagcga gcagcacccc ccagagcctg gaagagcggc gcaagctcat gatggccgtg 25020
gtcctggtga ccgtggagct ggagtgtctg cgccgcttct tcgccgacgc ggagaccctg 25080
cgcaaggtcg aggagaacct gcactacctc ttcaggcacg ggttcgtgcg ccaggcctgc 25140
aagatctcca acgtggagct gaccaacctg gtctcctaca tgggcatcct gcacgagaac 25200
cgcctggggc agaacgtgct gcacaccacc ctgcgcgggg aggcccgccg cgactacatc 25260
cgcgactgcg tctacctgta cctctgccac acctggcaga cgggcatggg cgtgtggcag 25320
cagtgcctgg aggagcagaa cctgaaagag ctctgcaagc tcctgcagaa gaacctcaag 25380
gccctgtgga ccgggttcga cgagcgcacc accgcctcgg acctggccga cctcatcttc 25440
cccgagcgcc tgcggctgac gctgcgcaac gggctgcccg actttatgag ccaaagcatg 25500
ttgcaaaact ttcgctcttt catcctcgaa cgctccggga tcctgcccgc cacctgctcc 25560
gcactgccct cggacttcgt gccgctgacc ttccgcgagt gcccccgcc gctctggagc 25620
cactgctact tgctgcgcct ggccaactac ctggcctacc actcggacgt gatcgaggac 25680
gtcagcagcg agggtctgct cgagtgccac tgccgctgca acctctgcac gccgcaccgc 25740
tccttggcct gcaaccccca gctgctgagc gagacccaga tcatcggcac cttcgagttg 25800
caaggccccg gcgagggcaa ggggggtctc aaactcaccc cggggctgtg gacctcggcc 25860
tacttgcgca agttcgtgcc cgaggactac catcccttcg agatcaggtt ctacgaggac 25920
caatcccagc cgcccaaggc cgagctgtcg gcctgcgtca tcacccaggg ggccatcctg 25980
gcccaattgc aagccatcca gaaatcccgc caagaatttc tgctgaaaaa gggccacggg 26040
gtctacttgg acccccagac cggagaggag ctcaacccca gcttccccca ggatgccccg 26100
aggaagcagc aagaagctga aagtggagct gccgctgccg ccggaggatt tggaggaaga 26160
ctgggagagc agtcaggcag aggagatgga agactgggac agcactcagg cagaggagga 26220
cagcctgcaa gacagtctgg aggaggaaga cgaggtggag gaggaggcag aggaagaagc 26280
agccgccgcc agaccgtcgt cctcggcgga ggagaaagca agcagcacgg ataccatctc 26340
cgctccgggt cggggtcgcg gcggccgggc ccacagtaga tgggacgaga ccgggcgctt 26400
cccgaacccc accacccaga ccggtaagaa ggagcggcag ggatacaagt cctggcgggg 26460
gcacaaaaac gccatcgtct cctgcttgca agcctgcggg ggcaacatct ccttcacccg 26520
gcgctacctg ctcttccacc gcggggtgaa cttcccccgc aacatcttgc attactaccg 26580
tcacctccac agcccctact actgtttcca agaagaggca gaaacccagc agcagcagca 26640
gaaaaccagc ggcagcagca gcagctagaa aatccacagc ggcggcaggt ggactgagga 26700
tcgcggcgaa cgagccggcg cagacccggg agctgaggaa ccggatcttt cccaccctct 26760
atgccatctt ccagcagagt cgggggcagg agcaggaact gaaagtcaag aaccgttctc 26820
tgcgctcgct cacccgcagt tgtctgtatc acaagagcga agaccaactt cagcgcactc 26880
tcgaggacgc cgaggctctc ttcaacaagt actgcgcgct cactcttaaa gagtagcccg 26940
cgcccgccca cacacggaaa aaggcgggaa ttacgtcacc acctgcgccc ttcgcccgac 27000
catcatcatg agcaaagaga ttcccacgcc ttacatgtgg agctaccagc cccagatggg 27060
cctggccgcc ggcgccgccc aggactactc cacccgcatg aactggctca gtgccgggcc 27120
cgcgatgatc tcacgggtga atgacatccg cgcccaccga aaccagatac tcctagaaca 27180
gtcagcgatc accgccacgc cccgccatca ccttaatccg cgtaattggc ccgccgccct 27240
ggtgtaccag gaaattcccc agcccacgac cgtactactt ccgcgagacg cccaggccga 27300
agtccagctg actaactcag gtgtccagct ggccggcggc gccgccctgt gtcgtcaccg 27360
ccccgctcag ggtataaagc ggctggtgat ccgaggcaga ggcacacagc tcaacgacga 27420
ggtggtgagc tcttcgctgg gtctgcgacc tgacggagtc ttccaactcg ccggatcggg 27480
gagatcttcc ttcacgcctc gtcaggccgt cctgactttg gagagttcgt cctcgcagcc 27540
ccgctcgggc ggcatcggca ctctccagtt cgtggaggag ttcactccct cggtctactt 27600
caaccccttc tccggctccc ccggccacta cccggacgag ttcatcccga acttcgacgc 27660
catcagcgag tcggtggacg gctacgattg aatgtcccat ggtggcgcgg ctgacctagc 27720
tcggcttcga cacctggacc actgttaatt aatcgcctct cctacgagct cctgcagcag 27780
cgccagaagt tcacctgcct ggtcggagtc aaccccatcg tcatcaccca gcagtcgggc 27840
gataccaagg ggtgcatcca ctgctcctgc gactcccccg actgcgtcca cactctgatc 27900
aagaccctct gcggcctccg cgacctcctc cccatgaact aatcaccccc ttatccagtg 27960
aaataaagat catattgatg atgattttac agaaataaag atacaatcat attgatgatt 28020
tgagtttaat aaaaaataaa gaatcactta cttgaaatct gataccaggt ctctgtccat 28080
gttttctgcc aacaccactt cactcccctc ttcccagctc tggtactgca ggccccggcg 28140
ggctgcaaac ttcctccaca cgctgaaggg gatgtcaaat tcctcctgtc cctcaatctt 28200
cattttatct tctatcagat gtccaaaaag cgcgtccggg tggatgatga cttcgacccc 28260
gtctacccct acgatgcaga caacgcaccg accgtgccct tcatcaaccc ccccttcgtc 28320
tcttcagatg gattccaaga gaagcccctg gggggtgctgt ccctgcgact ggccgacccc 28380
gtcaccacca agaacgggga aatcaccctc aagctgggag agggggtgga cctcgactcc 28440
tcgggaaaac tcatctccaa cacggccacc aaggccgccg cccctctcag tttttccaac 28500
aacaccattt cccttaacat ggatcacccc ttttacacta aagatggaaa attatcctta 28560
caagtttctc caccattaaa tatactgaga acaagcattc taaacacact agctttaggt 28620
tttggatcag gtttaggact ccgtggctct gccttggcag tacagttagt ctctccactt 28680
acatttgata ctgatggaaa cataaagctt accttagaca gaggtttgca tgttacaaca 28740
ggagatgcaa ttgaaagcaa cataagctgg gctaaaggtt taaaatttga agatggagcc 28800
atagcaacca acattggaaa tgggttagag tttggaagca gtagtacaga aacaggtgtt 28860
gatgatgctt acccaatcca agttaaactt ggatctggcc ttagctttga cagtacagga 28920
gccataatgg ctggtaacaa agaagacgat aaactcactt tgtggacaac acctgatcca 28980
tcgccaaact gtcaaatact cgcagaaaat gatgcaaaac taacactttg cttgactaaa 29040
tgtggtagtc aaatactggc cactgtgtca gtcttagttg taggaagtgg aaacctaaac 29100
cccattactg gcaccgtaag cagtgctcag gtgtttctac gttttgatgc aaacggtgtt 29160
cttttaacag aacattctac actaaaaaaa tactgggggt ataggcaggg agatagcata 29220
gatggcactc catataccaa tgctgtagga ttcatgccca atttaaaagc ttatccaaag 29280
tcacaaagtt ctactactaa aaataatata gtagggcaag tatacatgaa tggagatgtt 29340
tcaaaaccta tgcttctcac tataaccctc aatggtactg atgacagcaa cagtacatat 29400
tcaatgtcat tttcatacac ctggactaat ggaagctatg ttggagcaac atttggggct 29460
aactcttata ccttctcata catcgcccaa gaatgaacac tgtatcccac cctgcatgcc 29520
aacccttccc accccactct gtggaaaaaa ctctgaaaca caaaataaaa taaagttcaa 29580
gtgttttatt gattcaacag ttttacagga ttcgagcagt tatttttcct ccaccctccc 29640
aggacatgga atacaccacc ctctcccccc gcacagcctt gaacatctga atgccattgg 29700
tgatggacat gcttttggtc tccacgttcc acacagtttc agagcgagcc agtctcgggt 29760

```
cggtcaggga gatgaaaccc tccgggcaca attgggagaa gtactcgcct acatgggggt  29820

agagtcataa tcgtgcatca ggatagggcg gtggtgctgc agcagcgcgc gaataaactg  29880

ctgccgccgc cgctccgtcc tgcaggaata caacatggca gtggtctcct cagcgatgat  29940

tcgcaccgcc cgcagcataa ggcgccttgt cctccgggca cagcagcgca ccctgatctc  30000

acttaaatca gcacagtaac tgcagcacag caccacaata ttgttcaaaa tcccacagtg  30060

caaggcgctg tatccaaagc tcatggcggg gaccacagaa cccacgtggc catcatacca  30120

caagcgcagg tagattaagt ggcgacccct cataaacacg ctggacataa acattacctc  30180

ttttggcatg ttgtaattca ccacctcccg gtaccatata aacctctgat taaacatggc  30240

gccatccacc accatcctaa accagctggc caaaacctgc ccgccggcta tacactgcag  30300

ggaaccggga ctggaacaat gacagtggag agcccaggac tcgtaaccat ggatcatcat  30360

gctcgtcatg atatcaatgt tggcacaaca caggcacacg tgcatacact tcctcaggat  30420

tacaagctcc tcccgcgtta gaaccatatc ccagggaaca acccattcct gaatcagcgt  30480

aaatcccaca ctgcagggaa gacctcgcac gtaactcacg ttgtgcattg tcaaagtgtt  30540

acattcgggc agcagcggat gatcctccag tatggtagcg cgggtttctg tctcaaaagg  30600

aggtagacga tccctactgt acggagtgcg ccgagacaac cgagatcgtg ttggtcgtag  30660

tgtcatgcca aatggaacgc cggacgtagt catatttcct gaagtcttgg cgcgccaaag  30720

tctagaagcg gtccatagct taccgagcgg cagcagcagc ggcacacaac aggcgcaaga  30780

gtcagagaaa agactgagct ctaacctgtc cgcccgctct ctgctcaata tatagcccag  30840

atctacactg acgtaaaggc caaagtctaa aaatacccgc caaatagtca cacacgccca  30900

gcacacgccc agaaaccggt gacacactca aaaaaatacg cgcacttcct caaacgccca  30960

aactgccgtc atttccgggt tcccacgcta cgtcatcaaa acacgacttt caaattccgt  31020

cgaccgttaa aaacgtcacc cgccccgccc ctaacggtcg cccgtctctc agccaatcag  31080

cgccccgcat ccccaaattc aaacacctca tttgcatatt aacgcgcacc aaaagtttga  31140

ggtatattat tgatgatg                                                31158
```

<210> SEQ ID NO 7
<211> LENGTH: 37168
<212> TYPE: DNA
<213> ORGANISM: Artificial Sequence
<220> FEATURE:
<223> OTHER INFORMATION: synthetic chimpanzee adenovirus serotype PanAd3 with Ebola virus Zaire wild type transmembrane envelope glycoprotein (GP) insert (PanAd3 Ebola Zaire (PB/6001))
<220> FEATURE:
<221> NAME/KEY: CDS
<222> LOCATION: (2133)...(4434)
<223> OTHER INFORMATION: Ebola virus Zaire wild type transmembrane envelope glycoprotein (GP) insert in PanAd3 Ebola Zaire (PB/6001)
<220> FEATURE:
<221> NAME/KEY: CDS
<222> LOCATION: (15442)...(17196)
<223> OTHER INFORMATION: chimpanzee adenovirus serotype ChAd63 penton
<220> FEATURE:
<221> NAME/KEY: CDS
<222> LOCATION: (20287)...(23181)
<223> OTHER INFORMATION: chimpanzee adenovirus serotype ChAd63 hexon
<220> FEATURE:
<221> NAME/KEY: CDS
<222> LOCATION: (34065)...(35693)
<223> OTHER INFORMATION: chimpanzee adenovirus serotype ChAd63 fiber

<400> SEQUENCE: 7

```
catcatcaat aatatacctt attttggatt gaagccaata tgataatgag gtgggcggag     60
cggggcgggg cggggaggag cggcggcgcg gggcgggccg ggaggtgtgg cggaagttga    120
gtttgtaagt gtggcggatg tgacttgcta gcgccggatg tggtaaaagt gacgtttttt    180
ggagtgcgac aacgcccacg ggaagtgaca tttttcccgc ggtttttacc ggatgtcgta    240
gtgaatttgg gcgttaccaa gtaagatttg gccattttcg cgggaaaact gaaatgggga    300
agtgaaatct gattaatttc gcgttagtca taccgcgtaa tatttgccga gggccgaggg    360
actttgaccg attacgtgga ggaatcgccc aggtgttttt tgaggtgaat ttccgcgttc    420
cgggtcaaag tctccgtttt attattatag gtatacccat tgcatacgtt gtatccatat    480
cataatatgt acatttatat tggctcatgt ccaacattac cgccatgttg acattgatta    540
ttgactagtt attaatagta atcaattacg gggtcattag ttcatagccc atatatggag    600
ttccgcgtta cataacttac ggtaaatggc ccgcctggct gaccgcccaa cgacccccgc    660
ccattgacgt caataatgac gtatgttccc atagtaacgc caatagggac tttccattga    720
cgtcaatggg tggagtattt acggtaaact gcccacttgg cagtacatca agtgtatcat    780
atgccaagta cgccccctat tgacgtcaat gacggtaaat ggcccgcctg gcattatgcc    840
cagtacatga ccttatggga ctttcctact tggcagtaca tctacgtatt agtcatcgct    900
attaccatgg tgatgcggtt ttggcagtac atcaatgggc gtggatagcg gtttgactca    960
cggggatttc caagtctcca ccccattgac gtcaatggga gtttgttttg gaaccaaaat   1020
caacgggact ttccaaaatg tcgtaacaac tccgccccat tgacgcaaat gggcggtagg   1080
cgtgtacggt gggaggtcta tataagcaga gctctcccta tcagtgatag agatctccct   1140
atcagtgata gagatcgtcg acgagctcgt ttagtgaacc gtcagatcgc ctggagacgc   1200
catccacgct gttttgacct ccatagaaga caccgggacc gatccagcct ccgcggccgg   1260
gaacggtgca ttggaacgcg gattccccgt gccaagagtg acgtaagtac cgcctataga   1320
ctctataggc acaccccttt ggctcttatg catgctatac tgtttttggc ttggggccta   1380
tacacccccg cttccttatg ctataggtga tggtatagct tagcctatag gtgtgggtta   1440
ttgaccatta ttgaccactc ccctattggt gacgatactt tccattacta atccataaca   1500
tggctctttg ccacaactat ctctattggc tatatgccaa tactctgtcc ttcagagact   1560
gacacggact ctgtattttt acaggatggg gtcccattta ttatttacaa attcacatat   1620
acaacaacgc cgtcccccgt gcccgcagtt tttattaaac atagcgtggg atctccacgc   1680
gaatctcggg tacgtgttcc ggacatgggc tcttctccgg tagcggcgga gcttccacat   1740
ccgagccctg gtcccatgcc tccagcggct catggtcgct cggcagctcc ttgctcctaa   1800
cagtggaggc cagacttagg cacagcacaa tgcccaccac caccagtgtg ccgcacaagg   1860
ccgtggcggt agggtatgtg tctgaaaatg agcgtggaga ttgggctcgc acggctgacg   1920
cagatggaag acttaaggca gcggcagaag aagatgcagg cagctgagtt gttgtattct   1980
gataagagtc agaggtaact cccgttgcgg tgctgttaac ggtggagggc agtgtagtct   2040
gagcagtact cgttgctgcc gcgcgcgcca ccagacataa tagctgacag actaacagac   2100
tgttcctttc catgggtctt ttctgcagtc accgtcgtcg acacgtgtga tcagatatcg   2160
cggccgctct agaccaggcc ctggatcgat ccaacaacac aatgggcgtt acaggaatat   2220
tgcagttacc tcgtgatcga ttcaagagga catcattctt tctttgggta attatccttt   2280
tccaaagaac attttccatc ccacttggag tcatccacaa tagcacatta caggttagtg   2340
```

-continued

```
atgtcgacaa actagtttgt cgtgacaaac tgtcatccac aaatcaattg agatcagttg   2400
gactgaatct cgaagggaat ggagtggcaa ctgacgtgcc atctgcaact aaaagatggg   2460
gcttcaggtc cggtgtccca ccaaaggtgg tcaattatga agctggtgaa tgggctgaaa   2520
actgctacaa tcttgaaatc aaaaaacctg acgggagtga gtgtctacca gcagcgccag   2580
acgggattcg gggcttcccc cggtgccggt atgtgcacaa agtatcagga acgggaccgt   2640
gtgccggaga ctttgccttc cataaagagg gtgctttctt cctgtatgat cgacttgctt   2700
ccacagttat ctaccgagga acgactttcg ctgaaggtgt cgttgcattt ctgatactgc   2760
cccaagctaa gaaggacttc ttcagctcac accccttgag agagccggtc aatgcaacgg   2820
aggacccgtc tagtggctac tattctacca caattagata tcaggctacc ggttttggaa   2880
ccaatgagac agagtacttg ttcgaggttg acaatttgac ctacgtccaa cttgaatcaa   2940
gattcacacc acagtttctg ctccagctga atgagacaat atatacaagt gggaaaagga   3000
gcaataccac gggaaaacta atttggaagg tcaaccccga aattgataca acaatcgggg   3060
agtgggcctt ctgggaaact aaaaaaaacc tcactagaaa aattcgcagt gaagagttgt   3120
ctttcacagt tgtatcaaac ggagccaaaa acatcagtgg tcagagtccg gcgcgaactt   3180
cttccgaccc agggaccaac acaacaactg aagaccacaa aatcatggct tcagaaaatt   3240
cctctgcaat ggttcaagtg cacagtcaag gaagggaagc tgcagtgtcg catctaacaa   3300
cccttgccac aatctccacg agtccccaat ccctcacaac caaaccaggt ccggacaaca   3360
gcacccataa tacacccgtg tataaacttg acatctctga ggcaactcaa gttgaacaac   3420
atcaccgcag aacagacaac gacagcacag cctccgacac tccctctgcc acgaccgcag   3480
ccggaccccc aaaagcagag aacaccaaca cgagcaagag cactgacttc ctggaccccg   3540
ccaccacaac aagtccccaa aaccacagcg agaccgctgg caacaacaac actcatcacc   3600
aagataccgg agaagagagt gccagcagcg ggaagctagg cttaattacc aatactattg   3660
ctggagtcgc aggactgatc acaggcggga gaagaactcg aagagaagca attgtcaatg   3720
ctcaacccaa atgcaaccct aatttacatt actggactac tcaggatgaa ggtgctgcaa   3780
tcggactggc ctggatacca tatttcgggc cagcagccga gggaatttac atagaggggc   3840
taatgcacaa tcaagatggt ttaatctgtg ggttgagaca gctggccaac gagacgactc   3900
aagctcttca actgttcctg agagccacaa ctgagctacg caccttttca atcctcaacc   3960
gtaaggcaat tgatttcttg ctgcagcgat ggggcggcac atgccacatt ctgggaccgg   4020
actgctgtat cgaaccacat gattggacca agaacataac agacaaaatt gatcagatta   4080
ttcatgattt tgttgataaa acccttccgg accaggggga caatgacaat tggtggacag   4140
gatggagaca atggataccg gcaggtattg gagttacagg cgttgtaatt gcagttatcg   4200
ctttattctg tatatgcaaa tttgtctttt agtttttctt cagattgctt catggaaaag   4260
ctcagcctca aatcaatgaa accaggattt aattatatgg attacttgaa tctaagatta   4320
cttgacaaat gataatataa tacactggag ctttaaacat agccaatgtg attctaactc   4380
ctttaaactc acagttaatc ataaacaagg tttgaggtac cgagctcgaa ttgatctgct   4440
gtgccttcta gttgccagcc atctgttgtt tgcccctccc ccgtgccttc cttgaccctg   4500
gaaggtgcca ctcccactgt cctttcctaa taaaatgagg aaattgcatc gcattgtctg   4560
agtaggtgtc attctattct ggggggtggg gtggggcagg acagcaaggg ggaggattgg   4620
gaagacaata gcaggcatgc tggggatgcg gtgggctcta gatatcagcg atcgctgagg   4680
tgggtgagtg ggcgtggtct gggggtggga agcaatatat aagttggggg tcttagggtc   4740
```

tctgtgtctg ttttgcagag ggaccgccgg cgccatgagc gggagcagta gcagcaacgc 4800
cttggatggc agcatcgtga gcccttattt gacgacgcgc atgccccact gggccggggt 4860
gcgtcagaat gtgatgggct ccagcatcga cggacgaccc gtgctgcccg caaattccgc 4920
cacgctgacc tacgcgaccg tcgcggggac cccgttggac gccaccgccg ccgccgccgc 4980
caccgccgcc gcctcggccg tgcgcagcct ggccacggac tttgcattct tgggaccctt 5040
ggccaccggg gcggccgccc gtgccgccgt tcgcgatgac aagctgaccg ccctgctggc 5100
gcagttggat gcgcttaccc gggaactggg tgacctttcg cagcaggtcg tggccctgcg 5160
ccagcaggtc tccgccctgc aggctagcgg gaatgcttct cctgcaaatg ccgtttaaga 5220
taaataaaac cagactctgt tgataaataa aaccagactc tgtttggatt aaagaaaagt 5280
agcaagtgca ttgctctctt tatttcataa ttttccgcgc gcgataggcc cgagtccagc 5340
gttctcggtc gttgagggtg cggtgtatct tctccaggac gtggtagagg tggctctgga 5400
cgttgagata catgggcatg agcccgtccc gggggtggag gtagcaccac tgcagagctt 5460
catgctccgg ggtggtgttg tagatgatcc agtcgtagca ggagcgctgg gcatggtgcc 5520
taaaaatgtc cttaagcagc aggccgatgg ccaggggag gcccttggtg taagtgttta 5580
caaaacggtt gagttgggaa gggtgcatgc ggggtgagat gatgtgcatc ttagattgta 5640
tttttagatt ggcgatgttt cctcccagat cccttctggg attcatgttg tggaggacca 5700
ccagcacagt atatccggtg cacttgggaa atttgtcatg cagcttagag ggaaatgcgt 5760
ggaagaactt ggagacgccc ttgtggcctc ccagattctc catgcattcg tccatgatga 5820
tggcaatggg cccgcgggag gcggcctggg caaagatgtt tctggggtca ctgacatcgt 5880
agttgtgttc cagggtgaga tcgtcatagg ccatttttat aaagcgcggg cggagggtgc 5940
ccgactgggg gatgatggtt ccctcgggcc ccggggcgta gttgccttcg cagatctgca 6000
tttcccaggc cttaatctct gagggggaa tcatatccac ttgcggggcg atgaagaaaa 6060
cggtttccgg agccggggag attaactggg atgagagcag gtttctcagc agctgtgact 6120
ttccacagcc ggtgggtcca taaataacac ctataaccgg ctgcagctgg tagttgagcg 6180
agctgcagct gccgtcgtcc cggaggaggg ggccacctc attgagcatg tcccggacgc 6240
gcttgttctc ctcgaccagg tccgccagaa ggcgctcgcc gcccagggac agcagctctt 6300
gcaaggaagc aaagtttttc agcggtttga ggccgtccgc cgtgggcatg tttttcaggg 6360
tctggccgag cagctccagg cggtcccaga gctcggtgac gtgctctacg gcatctctat 6420
ccagcatatc tcctcgtttc gcgggttggg gcggctttcg ctgtagggca ccaggcgatg 6480
gtcgtccagc gcggccagag tcatgtcctt ccatgggcgc agggtcctcg tcagggtggt 6540
ctgggtcacg gtgaaggggt gcgccccggg ctgggcgctg gccagggtgc gcttgagact 6600
ggtcctgctg gtgctgaagc gctgccggtc ttcgccctgc gcgtcggcca ggtagcattt 6660
gaccatggtg tcgtagtcca gcccctccgc ggcgtgtccc ttggcgcgca gcttgccctt 6720
ggaggtggcg ccgcacgcgg ggcactgcag gctcttgagc gcgtagagct tgggggcgag 6780
gaagaccgat tcgggggagt aggcgtccgc gccgcaggcc ccgcacacgg tctcgcactc 6840
caccagccag gtgagctcgg ggcgctcggg gtcaaaaacc aggtttcccc catgcttttt 6900
gatgcgtttc ttacctcggg tctccatgag gcggtgtccc cgttcggtga cgaagaggct 6960
gtccgtgtct ccgtagaccg acttgagggg tctgtcctcc aggggggtcc ctcggtcctc 7020
ttcgtagaga aactcggacc actctgagac aaaggcccgc gtccaggcca ggacgaagga 7080

-continued

```
ggccaggtgg gaggggtacc ggtcgttgtc cactaggggg tccaccttct ccaaggtgtg   7140
aagacacatg tcgccctcct cggcgtccag gaaggtgatt ggcttgtagg tgtaggccac   7200
gtgacccggg gttccggacg ggggggtata aaagggggtg ggggcgcgct cgtcctcact   7260
ctcttccgca tcgctgtctg cgagggccag ctgctggggt gagtattccc tctcgaaggc   7320
gggcatgacc tcagcgctga ggctgtcagt ttctaaaaac gaggaggatt tgatgttcac   7380
ctgtcccgag ctgatgcctt tgagggtgcc cgcgtccatc tggtcagaaa acacgatctt   7440
tttattgtcc agcttggtgg cgaacgaccc gtagagggcg ttggagagca gcttggcgat   7500
ggagcgcagg gtctgattct tgtcccggtc ggcgcgctcc ttggccgcga tgttgagctg   7560
cacgtactcg cgcgcgacgc agcgccactc ggggaagacg gtggtgcgct cgtcgggcac   7620
caggcgcacg cgccagccgc ggttgtgcag ggtgacgagg tccacgctgg tggcgacctc   7680
gccgcgcagg cgctcgttgg tccagcagag gcgcccgccc ttgcgcgagc agaagggggg   7740
cagggggtcg agttgggttt cgtccggggg gtccgcgtcc accgtgaaga ccccggggcg   7800
caggcgcgcg tcgaagtagt cgatcttgca tccttgcaag tccagcgccc gctgccagtc   7860
gcgggcggcg agcgcgcgct cgtaggggtt gagcggcggg ccccagggca tggggtgggt   7920
gagcgcggag gcgtacatgc cgcagatgtc atagacgtag aggggctccc ggaggatgcc   7980
caggtaggtg gggtagcagc ggccgccgcg gatgctggcg cgcacgtagt cgtagagctc   8040
gtgcgagggg gcgaggaggt cggggcccag gttggtgcgg gcggggcgct ccgcgcggaa   8100
gacgatctgc ctgaagatgg catgcgagtt ggaagagatg gtggggcgct ggaagacgtt   8160
gaagctggcg tcctgcaggc cgacggcgtc gcgcacgaag gaggcgtagg actcgcgcag   8220
cttgtgcacc agctcggcgg tgacctgcac gtcgagcgcg cagtagtcga gggtctcgcg   8280
gatgatgtca tacttagcct gccccttctt tttccacagc tcgcggttga ggacgaactc   8340
ttcgcggtct ttccagtact cttggatcgg gaaaccgtcc ggctccgaac ggtaagagcc   8400
cagcatgtag aactggttga cggcctggta ggcgcagcag cccttctcca cgggcagggc   8460
gtaggcctgc gcggccttgc ggagcgaggt gtgggtcagg gcgaaggtgt ccctgaccat   8520
gaccttgagg tactggtgtt tgaagtcgga gtcgtcgcag ccgcccccgct cccagagcga   8580
gaagtcggtg cgctttttgg agcgggggtt gggcagcgcg aaggtgacat cgttgtagag   8640
gatcttgccc gcgcgaggca tgaagttgcg ggtgatgcgg aagggccccg gcacttccga   8700
gcggttgttg atgacctggg cggcgagcac gatctcgtcg aagccgttga tgttgtggcc   8760
cacgatgtag agttccagga agcggggccg gcccttgacg ctgggcagct tctttagctc   8820
ttcgtaggtg agctcctcgg gcgaggcgag gccgtgctcg gccagggccc agtccgccag   8880
gtgcgggttg tccgcgagga aggaccgcca gaggtcgcgg gccaggaggg tctgcaggcg   8940
gtccctgaag gtcctgaact ggcggcctac ggccatcttt tcgggggtga cgcagtagaa   9000
ggtgaggggg tcttgctgcc aggggtccca gtcgagctcc agggcgaggt cgcgcgcggc   9060
ggcgaccagg cgctcgtcgc ccccgaattt catgaccagc atgaagggca cgagctgctt   9120
tccgaaggcg cccatccaag tgtaggtctc tacatcgtag gtgacaaaga gacgttccgt   9180
gcgaggatgc gagccgatcg ggaagaactg gatctcccgc caccagttgg aggagtggct   9240
gttgatgtgg tgaaagtaga agtcccgtcg gcgggccgag cactcgtgct ggcttttgta   9300
aaagcgagcg cagtactggc agcgctgcac gggctgtacc tcttgcacga gatgcacctg   9360
ccgaccgcgg acgaggaagc tgagtgggaa tctgagcccc ccgcatggct cgcggcctgg   9420
ctggtgctct tctactttgg atgcgtggcc gtcaccgtct ggctcctcga ggggtgttac   9480
```

-continued

```
ggtggagcgg atcaccacgc cgcgcgagcc gcaggtccag atatcggcgc gcggcggtcg   9540
gagtttgatg acgacatcgc gcagctggga gctgtccatg gtctggagct cccgcggcgg   9600
cggcaggtca gccgggagtt cttgcaggtt tacctcgcag agacgggcca gggcgcgggg   9660
caggtccagg tggtacttga attcgagagg cgtgttggtg gcggcgtcga tggcttgcag   9720
tatgccgcag ccccggggcg cgacgacggt gccccgcggg gcggtgaagc tcccgccgcc   9780
gctcctgctg tcgccgccgg tggcggggct tagaagcggt gccgcggtcg ggcccccgga   9840
ggtagggggg gctccggtcc cgcgggcagg ggcggcagcg gcacgtcggc gccgcgcgcg   9900
ggcaggagct ggtgctgcgc ccggaggttg ctggcgaagg cgacgacgcg gcggttgatc   9960
tcctggatct ggcgcctctg cgtgaagacg acgggtccgg tgagcttgaa cctgaaagag  10020
agttcgacag aatcaatctc ggtgtcattg accgcgacct ggcgcaggat ctcctgcacg  10080
tcgcccgagt tgtcttggta ggcgatctcg gccatgaact gttcaatctc ttcctcctgg  10140
aggtctccgc gtccggcgcg ctccacggtg gccgccaggt cgttggagat gcgcgccatg  10200
agctgcgaga aggcgttgag tccgccctcg ttccacactc ggctgtagac cacgccgccc  10260
tggtcgtcgc gggcgcgcat gaccacctgc gcgaggttga gttccacgtg gcgcgcaaag  10320
acggcgtagt tgcgcaggcg ctggaagagg tagttgaggg tggtggcggt gtgctcggcc  10380
acaaagaagt acatgaccca gcggcgcaac gtggattcgt tgatgtcccc caaggcctcc  10440
agtcgctcca tggcctcgta gaagtccacg gcgaagttga aaaactggga gttgcgcgcc  10500
gacacggtca actcctcctc cagaagacgg atgagctcgg cgacggtgtc gcgcacctcg  10560
cgctcgaagg ctatgggaat ctcttcctcc gccagcatca ccacctcttc ctcttcttcc  10620
tcctctggca cttccatgat ggcttcctcc tcttcggggg gtggcggcgg gggagggggc  10680
gctcggcgcc ggcggcggcg caccgggagg cggtccacga agcgctcgat catctccccg  10740
cggcggcgac gcatggtctc ggtgacggcg cggccgttct ctcggggacg cagctggaag  10800
acgccgccgg tcatctggtg ctggggcggg tggccgtggg gcagcgagac cgcgctgacg  10860
atgcatctta acaattgctg cgtaggtacg ccgccgaggg acctgaggga gtccagatcc  10920
accggatccg aaaacctttc gaggaaggca tctaaccagt cgcagtcgca aggtaggctg  10980
agcaccgtgg cgggcggcgg ggggtggggg gagtgtctgg cggaggtgct gctgatgatg  11040
taattgaagt aggcggtctt gacacggcgg atggtcgaca ggagcaccat gtctttgggc  11100
ccggcctgct ggatgcggag gcggtcggcc atgccccagg cttcgttctg gcatctgcgc  11160
aggtctttgt agtagtcttg catgagcctt tccaccggca cctcttctcc ttcttcttct  11220
gacatctctg ctgcatctgc ggccctgggg cgacggcgcg cgcccctgcc ccccatgcgc  11280
gtcaccccga accccctgag cggctggagc agggccaggt cggcgacgac gcgctcggcc  11340
aggatggcct gctggacctg cgtgagggtg gtttggaagt catccaagtc cacgaagcgg  11400
tggtaggcgc ccgtgttgat ggtgtaggtg cagttggcca tgacggacca gttgacggtc  11460
tggtggcccg gttgcgtcat ctcggtgtac ctgaggcgcg agtaggcgcg cgagtcgaag  11520
atgtagtcgt tgcaagtccg caccaggtac tggtagccca ccaggaagtg cggcggcggc  11580
tggcggtaga ggggccagcg gagggtggcg ggggctccgg gggccaggtc ttccagcatg  11640
aggcggtggt attcgtagat gtacctggac atccaggtga tgcccgcggc ggtggtggag  11700
gcgcgcggga agtcgcgcac ccggttccag atgttgcgca gcggcagaaa gtgctccatg  11760
gtaggcgtgc tctggccggt caggcgcgcg cagtcgttga tactctagac cagggaaaac  11820
```

-continued

```
gaaagccggt cagcgggcac tcttccgtgg tctggtggat aaattcgcaa gggtatcatg  11880
gcggagggcc tcggttcgag ccccgggccc gggccggacg gtccgccatg atccacgcgg  11940
ttaccgcccg cgtgtcgaac ccaggtggcg acgtcagaca acggtggagt gttccttttg  12000
ggtttttttc caaatttttc tggccgggcg ccgacgccgc cgcgtaagag actagagtgc  12060
aaaagcgaaa gcagtaagtg gctcgctccc tgtagcccgg aggatccttg ctaagggttg  12120
cgttgcggcg aaccccggtt cgagtctggc tctcgctggg ccgctcgggt cggccggaac  12180
cgcggctaag gcgggattgg cctccccctc attaaagacc ccgcttgcgg attcctccgg  12240
acacagggga cgagcccctt tttacttttg cttttctcag atgcatccgg tgctgcggca  12300
gatgcgcccc ccgccccagc agcagcagca gcaacatcag caagagcggc accagcagca  12360
gcgggagtca tgcagggccc cctcgcccac gctcggcggt ccggcgacct cggcgtccgc  12420
ggccgtgtct ggagccggcg gcggtgggct ggcggacgac ccggaggagc ccccgcggcg  12480
cagggccaga cagtacctgg acctggagga gggcgagggc ctggcgcgac tgggggcgcc  12540
gtcccccgag cgccacccgc gggtgcagct gaagcgcgac tcgcgcgagg cgtacgtgcc  12600
tcggcagaac ctgttcagag accgcgcggg cgaggagccc gaggagatgc gggaccgcag  12660
gttcgccgcg gggcgggagc tgcggcaggg gctgaaccgg gagcggctgc tgcgcgagga  12720
ggactttgag cccgacgcgc ggacggggat cagccccgcg cgcgcgcacg tggcggccgc  12780
cgacctggtg acggcgtacg agcagacggt gaaccaggag atcaacttcc aaaaaagctt  12840
caacaaccac gtgcgcacgc tggtggcgcg cgaggaggtg accatcggcc tgatgcacct  12900
gtgggacttt gtgagcgcgc tggagcagaa ccccaacagc aagcctctga cggcgcagct  12960
gttcctgata gtgcagcaca gcagggacaa cgaggcgttc agggacgcgc tgctgaacat  13020
caccgagccc gagggtcggt ggctgctgga cctgattaac atcttgcaga gcatagtggt  13080
gcaggagcgc agcctgagcc tggccgacaa ggtggcggcc atcaattact cgatgctcag  13140
tctgggcaag ttttacgcgc gcaagatcta ccagacgccg tacgtgccca tagacaagga  13200
ggtgaagatc gacggcttct acatgcgcat ggcgctgaag gtgctgaccc tgagcgacga  13260
cctgggcgtg taccgcaacg agcgcatcca caaggccgtg agcgtgagcc ggcggcgcga  13320
gctgagcgac cgcgagctga tgcacagcct gcagcgggcg ctggcggggg ccggcagcgg  13380
cgacagggag gccgagtcct acttcgaggc gggggcggac ctgcgctggg tgcccagccg  13440
gagggccctg gaggccgcgg gggcccgccg cgaggactat gcagacgagg aggaggagga  13500
tgacgaggag tacgagctag aggagggcga gtacctggac taaaccgcag gtggtgtttt  13560
tggtagatgc aagacccgaa cgtggtggac ccggcgctgc gggcggctct gcagagccag  13620
ccgtccggcc ttaactctac agacgactgg cgacaggtca tggaccgcat catgtcgctg  13680
acggcgcgca atccggacgc gttccggcag cagccgcagg ccaacaggct ctccgccatc  13740
ttggaggcgg tggtgcctgc gcgcgcgaac ccccacgcacg agaaggtgct ggccatagtg  13800
aacgcgctgg ccgagaacag ggccatccgc ccggacgagg ccgggctggt gtacgacgcg  13860
ctgctgcagc gcgtggcccg ctacaacagc ggcaacgtgc agaccaacct ggaccggctg  13920
gtgggggacg tgcgcgaggc ggtggcgcag cgggagcgcg cggagcggca gggaaacctg  13980
ggctccatgg tggcgctgaa cgccttcctg agcacgcagc cggccaacgt gccgcggggg  14040
caggaggact acaccaactt tgtgagcgcg ctgcggctga tggtgaccga gacccccccag  14100
agcgaggtgt accagtcggg gccggactac tttttccaga ccagcagaca gggcctgcag  14160
acggtgaacc tgagccaggc tttcaagaac ctgcgggggc tgtggggcgt gaaggcgccc  14220
```

-continued

```
accggggacc gggcgacggt gtccagcctg ctgacgccca actcgcgcct gctgctgctg  14280
ctgatcgcgc cgttcacgga cagcggcagc gtgtcccggg agacctacct cgggcacctg  14340
ctgacgctgt accgcgaggc catcgggcag acccaggtgg acgagcacac cttccaggag  14400
atcaccagcg tgagccgcgc gctggggcag gaggacacgg gcagcctgga ggcgaccctg  14460
aactacctgc tgaccaaccg gcggcagaag atcccctcgc tgcatagttt gaccaccgag  14520
gaggagcgca tcctgcgcta cgtgcagcag agcgtgagcc tgaacctgat gcgcgacggg  14580
gtgacgccca gcgtggcgct ggacatgacc gcgcgcaaca tggaaccggg catgtacgcc  14640
gcgcatcggc cttacatcaa ccgcctgatg gactacttgc atcgcgcggc ggccgtgaac  14700
cccgagtact tcaccaacgc catcctgaac ccgcactggc tcccgccgcc cgggttctac  14760
agcgggggct tcgaggtccc cgaggccaac gacggcttcc tgtgggacga catggacgac  14820
agcgtgttct ccccgcggcc gcaggcgctg gcggaggcgt cgctgctccg cctccccaag  14880
aaagaagaga gccgccggcc cagcagcgcg gcggcctctc tgtccgagct gggggcggcg  14940
gccgcgcggc ccgggtccct gggggggcagc cccctttccca gtctggtggg gtctctgcag  15000
agcgggcgca ccacccggcc ccggctgctg ggcgaggacg agtacctgaa caactccctg  15060
atgcagccgg tgcgggagaa aaacctgccc cccgccttcc ccaacaacgg gatagagagc  15120
ctggtagaca agatgagcag atggaagacc tatgcgcagg agcacaggga ctcgcccgtg  15180
ctccgtccgc ccacgcggcg ccagcgccac gaccggcagc gggggctggt atgggatgac  15240
gaggactccg cggacgatag cagcgtgctg gacctggggg ggagcggcgg taacccgttc  15300
gcgcacctgc gcccccgcct ggggaggatg tttcaataag aaaaatcaag catgatgcaa  15360
ggtttttttaa gcggataaat aaaaaactca ccaaggccat ggcgaccgag cgttgttggt  15420
ttcttgttgt gttcccttag tatgcggcgc gcggcgatgt accacgaggg acctcctccc  15480
tcttatgaga gcgtggtggg cgcggcggcg gcctctccct ttgcgtcgca gctggagccg  15540
ccgtacgtgc ctccgcggta cctgcggcct acggggggaa gaaacagcat ccgttactcg  15600
gagctggcgc ccctgtacga caccacccgg gtgtacctgg tggacaacaa gtcggcggac  15660
gtggcctccc tgaactacca gaacgaccac agcaattttt tgaccacggt catccagaac  15720
aatgactaca ccccgagcga ggccagcacc cagaccatca atctggatga ccggtcgcac  15780
tggggcggcg acctgaaaac catcctgcac accaacatgc ccaacgtgaa cgagttcatg  15840
ttcaccaata agttcaaggc gcgggtgatg gtgtcgcgtt cgcacaccaa ggacgaccgg  15900
gtggagctga agtacgagtg ggtagagttc gagctgcccg agggcaacta ctcggagacc  15960
atgaccatag acctgatgaa caacgcgatc gtggagcact atctgaaagt gggcaggcag  16020
aacggggtcc tggagagcga catcggggtc aagttcgaca ccaggaactt ccgcctgggg  16080
ctggacccgg tcaccgggct ggtcatgccc ggggtctaca ccaacgaggc cttccacccc  16140
gacatcatcc tgctgcccgg ctgcggggtg gacttcacct acagccgcct gagcaacctg  16200
ctgggcatcc gcaagcggca gcccttccag gagggcttta ggatcaccta cgaggacctg  16260
gagggggggca acatccccgc gctcctggat gtggaggcct accaggatag cttgaaggaa  16320
gaagaggcgg gagagggcag cggcggcggc ggcggcgccg gtcaggagga gggcggggcc  16380
tcctctgagg cctctgcgga cgccgccgct gccgccgagg cggaggcggc cgaccccgcg  16440
atggtggtag aggaagagaa ggatatgaat gacgaggcgg tgcgcggcga cacctttgcc  16500
acccgggggg aggagaagaa agcggaggcc gaggccgcgg cagaggaggc ggcagcggcg  16560
```

-continued

```
gcggcggcgg cagtagaggc ggcggccgag gcggagaagc cccccaagga gcccgtgatt  16620
aaggccctga ccgaagatag caagaagcgc agttacaacg tgctcaagga cagcaccaac  16680
accgcgtacc gcagctggta cctggcctac aactacggcg acccggcgac gggggtgcgc  16740
tcctggaccc tgctgtgtac gccggacgtg acctgcggct cggagcaggt gtactggtcg  16800
ctgcccgaca tgatgcaaga ccccgtgacc ttccgctcca cgcggcaggt cagcaacttc  16860
ccggtggtgg gcgccgagct gctgcccgtg cactccaaga gcttctacaa cgaccaggcc  16920
gtctactccc agctcatccg ccagttcacc tctctgaccc acgtgttcaa tcgctttcct  16980
gagaaccaga ttctggcgcg cccgcccgcc cccaccatca ccaccgtcag tgaaaacgtt  17040
cctgctctca cagatcacgg gacgctaccg ctgcgcaaca gcatcggagg agtccagcga  17100
gtgaccgtaa ctgacgccag acgccgcacc tgtccctacg tttacaaggc cctgggcata  17160
gtctcgccgc gcgtcctttc cagccgcact ttttaagcat gtccatcctc atctcgccca  17220
gcaataacac cggctggggc ctgctgcgcg cgcccagcaa gatgtttgga ggggcgagga  17280
agcgctccga ccagcacccc gtgcgcgtgc gcgggcacta ccgcgccccc tggggcgcgc  17340
acaaacgcgg gcgcaccggc accgcggggc gcaccaccgt ggacgaagcc atcgactcgg  17400
tggtggagca ggcgcgcaac tacacgcccg cggtctccac cgtggacgcg gctatcgaga  17460
gcgtggtgcg aggcgcgcgg cggtacgcca aggcgaagag ccgccggagg cgcgtggccc  17520
gccgccaccg ccgtcgaccc ggaagcgccg ccaagcgcgc cgccgccgcc ttgcttcgtc  17580
gggccagacg cacgggccgc cgcgccgcca tgagggccgc gcgccgcctg gccgccggca  17640
tcaccaccgt ggcccccgc gccagaagac gcgcggccgc tgccgccgcc gcggccatca  17700
gcgacctggc caccaggcgc cggggcaacg tgtactgggt gcgcgactcg gtgagcggca  17760
cgcgcgtgcc cgtgcgcttc cgcccccgc ggacttgaga ggagaggaca ggaaaaaagc  17820
atcaacaaca ccaccactga gtctcctgct gttgtgtgta tcccagcggc gcgcgcgcac  17880
acggcgacat gtccaagcgc aaaatcaaag aagagatgct ccaggtcgtc gcgccggaaa  17940
tctatgggcc cccgaagaag gaagagcagg atttcaagcc ccgcaagata aagcgggtca  18000
aaaagaaaaa gaaagatgac gatgatggcg aggtggagtt tctgcgcgcc acggcgccca  18060
ggcgcccgct gcagtggaag ggtcggcgcg taaagcgcgt tctgcgcccc ggcaccgcgg  18120
tggtcttcac gcccggcgag cgctccaccc gcactttcaa gcgcgtctat gacgaggtgt  18180
acggcgacga agacctgctg gagcaggcca acgatcgctc cggagagttt gcttacggga  18240
agcggcaccg ggcgatggag aaggacgagg tgctggcgct gccgctggac cggggcaacc  18300
ccacccccag cctgaagccc gtgaccctgc agcaggtgct gccggccagc gcgccctccg  18360
agatgaagcg gggcctgaag cgcgagggcg gcgacctggc gcccaccgtg cagctgatgg  18420
tgcccaagcg gcagaggctg gaggacgtgc tggagaaaat gaaagtagac cccggcctgc  18480
agccggacat cagggtccgc cccatcaagc aggtggcgcc gggcctcggc gtgcagaccg  18540
tggacgtggt catccccacc ggcgcctcct cttccagcgc cgccgccgcc actagcaccg  18600
cggacatgga gacgcagact agctccgccc tcgccgcccc cgcggccgcc gccgccgcca  18660
cctcctcggc ggaggtacag acggacccct ggatgccgcc gccggcggcc gccccctcgc  18720
gcgcacgccg cgggcgcagg aagtacggcg ccgccagcgc gctcatgccc gagtacgcct  18780
tgcatccttc catcgcgccc acccccggct accgaggcta cagctaccgc ccgcgaagag  18840
ccaagggctc cacccgccgc agccgccgcg ccgccacctc tacccgccgc cgcagtcgcc  18900
gccgccgccg gcagcccgcg ctggctccga tctccgtgag gagagtggcg cgcaacgggg  18960
```

-continued

```
acaccttggt gctgcccagg gcgcgctacc accccagcat cgtttaaaag cctgttgtgg  19020
ttcttgcaga tatggccctc acttgccgcc tccgtttccc ggtgccggga taccgaggaa  19080
gatcgcgccg tagaaggggt atggccggac gcggcctgag cggaggcagc cgccgtgcgc  19140
accggcggcg acgcgccacc agccgacgca tgcgcggcgg ggtgctgcct ctgctgatcc  19200
ccctgatcgc cgcggcgatc ggcgccgtgc ccgggatcgc ctccgtggcc ttgcaggcgt  19260
cccagaggcg ttgacacaga cttcttgcaa gcttgcaaaa atatggaaaa aatcccccca  19320
ataaaaaagt ctagactctc acgctcgctt ggtcctgtga ctattttgta gaaaaaaaga  19380
tggaagacat caactttgcg tcgctggccc cgcgtcacgg ctcgcgcccg ttcctgggac  19440
actggaacga tatcggcacc agcaacatga gcggtggcgc cttcagttgg ggctctctgt  19500
ggagcggcat taaaaatatc ggttctgccg ttaagaatta cggctccaag gcctggaaca  19560
gcagcacggg ccagatgttg agagacaagt tgaaagagca gaacttccag cagaaggtgg  19620
tggagggcct ggcctccggc atcaacgggg tggtggacct ggccaatcag gccgtgcaaa  19680
ataagatcaa cagcagactg gacccccggc cgccggtgga agagctgccg ccggcgctgg  19740
agacggtgtc ccccgatggg cggggcgaaa agcgcccgcg gcccgacagg gaagagacca  19800
ctctggtcac gcacaccgat gagccgcccc cctacgagga agctctgaag caaggcttgc  19860
ccaccactcg gcccatcgcg cccatggcca ccggggtggt gggccgccac acccccgcca  19920
ggctggacct gcctcctcct cctgtttctt cttcggccgc cgatgcgcag cagcagaagg  19980
cggcgctgcc cggtccgccc gcggccgccc cccgtcccac cgccagtcga gcgcccctgc  20040
gtcgcgcggc cagcggcccc cgcggggtcg cgaggcacag cagcggcaac tggcagaaca  20100
cgctgaacag catcgtgggt ctgggggtgc agtccgtgaa gcgccgccga tgctactgaa  20160
tagcttagct aacggtgttg tatgtgtgta tgcgtcctat gtcaccgcca gaggagctgc  20220
tgagtcgccg ccgttcgcgc gcccaccgcc actaccaccg ccggtaccac tccagcgccc  20280
ctcaagatgg cgaccccatc gatgatgccg cagtggtcgt acatgcacat ctcgggccag  20340
gacgcctcgg agtacctgag ccccgggctg gtgcagttcg cccgcgccac cgacagctac  20400
ttcagcctga gtaacaagtt taggaacccc acggtggcgc ccacgcacga tgtgaccacc  20460
gaccggtccc agcgcctgac gctgcggttc atccccgtgg accgcgagga caccgcgtac  20520
tcttacaagg cgcggttcac cctggccgtg ggcgacaacc gcgtgctgga catggcctcc  20580
acctactttg acatccgcgg cgtgctggac aggggcccca ccttcaagcc ctactccggc  20640
accgcctaca actccctggc ccccaagggc gcccccaact cctgcgagtg ggagcaagag  20700
gagactcaga cagctgaaga ggcacaagac gaagaagaag atgaagctga agctgaggag  20760
gaaatgcctc aggaagagca agcacctgtc aaaaagactc atgtatatgc tcaggctccc  20820
ctttctggcg aaaaaattac taaagacggt ctgcagatag gaacggacgc tacagctacc  20880
gaacaaaaac ctatttatgc agatcccaca ttccagccag aaccccaaat tggtgaatct  20940
cagtggaatg aggcagatgc ttcagttgcc ggcggtagag tgctgaagaa aactactccc  21000
atgaaaccct gttatggttc ctatgccagg cccacaaatg ccaatggagg tcagggtgta  21060
ttggtggaga aagacggtgg aaagatggaa agccaagtag atatgcaatt cttttcgact  21120
tctgaaaacg cccgtaacga ggctaacaac attcagccca aattggtgct gtacagcgag  21180
gatgtgcata tggagacccc agacacacac atttcttaca agcctgcaaa aagcgatgat  21240
aattcgaaag tcatgctggg tcagcagtcc atgcccaaca ggccaaatta catcggcttc  21300
```

```
agagacaact ttatcgggct catgtattac aacagcactg gcaacatggg ggtgctggca  21360
ggtcaggcct cacagttgaa tgcggtggtg gacttgcaag acagaaacac agaactgtcc  21420
taccagctct tgcttgattc catgggagac agaaccagat acttttccat gtggaatcag  21480
gcggtggaca gttatgatcc agatgtcaga attattgaaa atcatggaac tgaagatgag  21540
ctgcccaact attgtttccc tctgggaggc ataggggtaa ctgacactta ccaggccatt  21600
aagactaatg gcaatggcaa cggcgggggc aataccactt ggaccaagga tgaaactttt  21660
gcagaccgca acgagatagg ggtgggaaac aatttcgcca tggagatcaa cctcagtgcc  21720
aacctgtgga ggaacttcct ctactccaac gtggccctgt acctgccaga caagcttaag  21780
tacaacccct ccaacgtgga aatctctgac aaccccaaca cctacgacta catgaacaag  21840
cgagtggtgg ccccggggct ggtggactgc tacatcaacc tgggcgcgcg ctggtccctg  21900
gactacatgg acaacgtcaa ccccttcaac caccaccgca acgcgggcct gcgctaccgc  21960
tccatgcttc tgggcaacgg gcgctacgtg cccttccaca tccaggtgcc ccagaagttc  22020
tttgccatca agaacctcct cctcctgccg ggctcctaca cctacgagtg gaacttcagg  22080
aaggatgtca acatggtcct ccagagctct ctgggtaacg acctcagggt cgacggggcc  22140
agcatcaagt tcgagagcat ctgcctctac gccaccttct tccccatggc ccacaacacg  22200
gcctccacgc tcgaggccat gctcaggaac gacaccaacg accagtcctt caacgactac  22260
ctctccgccg ccaacatgct ctaccccatc cccgccaacg ccaccaacgt tcccatctcc  22320
atcccctcgc gcaactgggc ggccttccgc ggctgggcct tcacccgcct caagaccaag  22380
gagacccccct ccctgggctc gggtttcgac ccctactaca cctactcggg ctccataccc  22440
tacctggacg gaaccttcta cctcaaccac actttcaaga aggtctcggt caccttcgac  22500
tcctcggtca gctggccggg caacgatcgc ctgctcaccc ccaacgagtt cgagatcaag  22560
cgctcggtcg acggggaggg ctacaacgtg gcccagtgca acatgaccaa ggactggttc  22620
ctcatccaaa tgctggccaa ctacaacatc ggctatcagg gcttctacat cccagagagc  22680
tacaaggaca ggatgtactc cttctttagg aacttccagc ccatgagccg gcaggtggtg  22740
gacgaaacca agtacaagga ctaccagcag gtgggcatca tccaccagca caacaactcg  22800
ggcttcgtgg gctacctcgc cccccaccatg cgcgagggac aggcctaccc cgccaacttc  22860
ccctacccgc tcattggcaa gaccgcggtc gacagcgtca cccagaaaaa gttcctctgc  22920
gaccgcaccc tctggcgcat ccccttctcc agcaacttca tgtccatggg tgcgctcacg  22980
gacctgggcc agaacctgct ctatgccaac tccgcccacg cgctcgacat gaccttcgag  23040
gtcgacccca tggacgagcc cacccttctc tatgttctgt tcgaagtctt tgacgtggtc  23100
cgggtccacc agccgcaccg cggcgtcatc gagaccgtgt acctgcgcac gcccttctcg  23160
gccggcaacg ccaccaccta aagaagcaag ccgccaccgc caccacctgc atgtcgtcgg  23220
gttccaccga gcaggagctc aaggccatcg tcagagacct gggatgcggg ccctattttt  23280
tgggcacctt cgacaaacgc ttcccgggct tcgtcgcccc gcacaagctg gcctgcgcca  23340
tcgtcaacac ggccggccgc gagaccgggg gcgtgcactg gctggccttc gcctggaacc  23400
cgcgctccaa aacatgctac ctctttgacc ccttcggatt ctcggaccag cggctcaagc  23460
agatctacca gttcgagtac gagggcctgc tgcgccgcag cgccatcgcc tcctcgcccg  23520
accgctgcgt caccctcgag aagtccaccc agaccgtgca ggggcccgac tcggccgcct  23580
gcggtctctt ctgctgcatg ttcctgcatg cctttgtgca ctggccccag agtcccatgg  23640
accgcaaccc caccatgaac ttgctgacgg ggatccccaa ctccatgctc cagagccccc  23700
```

aggtcgcgcc caccctgcgc cgcaaccagg agcggctcta cagcttcctg gaacgccact 23760
cgccctactt ccgccgccac agcgcgcaga tcaggggggc cacctctttc tgccgcatgc 23820
aagagatgca agggaaaatg caatgatgta cacagacact ttttcttttc tcaataaatg 23880
gcaactttat ttatacatgc tctctctcgg gtattcattt ccccaccacc caccacccgc 23940
cgccgccgta accatctgct gctggctttt tttttttttt ttaaaaatcg aaagggttct 24000
gccgggaatc gccgtgcgcc acgggcaggg acacgttgcg gaactggtag cgggtgcccc 24060
acttgaactc gggcaccacc atgcggggca agtcggggaa gttgtcggcc cacaggctgc 24120
gggtcagcac cagcgcgttc attaggtcgg gcgccgagat cttgaagtcg cagttggggc 24180
cgccgccctg cgcgcgcgag ttgcggtaca ccgggttgca acactggaac accagcagcg 24240
ccggataatt cacactggcc agcacgctcc ggtcggagat cagctcggcg tccaggtcct 24300
ccgcgttgct cagcgcgaac ggggtcagct tgggcacctg ccgccccagg aagggagcgt 24360
gccccggctt cgagttgcag tcgcagcgca gcgggatcag caggtgcccg cggccggact 24420
cggcgttggg gtacagcgcg cgcatgaagg cctccatctg gcggaaggcc atctgggcct 24480
tggcgccctc cgagaagaac atgccgcagg acttgcccga gaactggttc gcggggcagc 24540
tagcgtcgtg caggcagcag cgcgcgtcgg tgttggcgat ctgcaccacg ttgcgccccc 24600
accggttctt cacgattttg gccttggaag cctgctcctt cagcgcgcgc tgcccgttct 24660
cgctggtcac atccatctcg atcacgtgct ccttgttcac catgctgctg ccgtgcagac 24720
acttcagctc gccctccacc tcggtgcagc ggtgctgcca tagcgcgcag cccgtgggct 24780
cgaaatgctt gtaggtcacc tccgcgtagg actgcaggta ggcctgcagg aagcgcccca 24840
tcatggtcac gaaggtcttg ttgctgctga aggtcagctg cagcccgcgg tgctcctcgt 24900
tcagccaggc cttgcacacg gccgccagcg cctccacctg gtcgggcagc atcttgaagt 24960
tcagcttcag ctcattctcc acatggtact tgtccatcag cgcgcgcgca gcctccatgc 25020
ccttctccca ggccgacacc agcggcaggc tcaaggggtt caccaccgtc gcagccgccg 25080
ctgcgctttc gctttccgct ccgctgttct cttcttcctc ctcctcttct tcctcgccgc 25140
ccgcgcgcag cccccgcacc acggggtcgt cttcctgcag gcgccgcacc gagcgcttgc 25200
cgctcctgcc ctgcttgata cgcacgggcg ggttgctgaa gcctaccatc accagcgcgg 25260
cctcttcttg ctcgtcctcg ctgtccacta tgacctcggg ggagggcgac ctcagaaccg 25320
tggcgcgctg cctcttcttt ttcctggggg cgtttgccag ctccgcggcc gcggccgccg 25380
ccgaggtcga aggccgaggg ctgggcgtgc gcggcaccag cgcgtcctgc gagccgtcct 25440
cgtcctcgga ctcgaggcgg cagcgagccc gcttcttcgg gggcgcgcgg ggcggcggcg 25500
gcgggggcgg cggcgacgga gacggggacg agacatcgtc cagggtggga ggacggcggg 25560
ccgcgccgcg tccgcgctcg gggggtggttt cgcgctggtc ctcttcccga ctggccatct 25620
cccactgctc cttctcctat aggcagaaag agatcatgga gtctctcatg caagtcgaga 25680
aggaggagga cagcctaacc accaccgccc cctctgagcc ctccgccgcc gccgcggacg 25740
acgcgcccac caccaccgcc gccgccacca ccaccattac caccctaccc ggcgacgcag 25800
ccccgatcga gaaggaagtg ttgatcgagc aggacccggg ttttgtgagc gaagaggagg 25860
atgaggagga tgaaaaggag aaggataccg ccgcctcagt gccaaaagag gataaaaagc 25920
aagaccagga cgacgcagag acagatgagg cagcagtcgg gcggggggac ggaaggcatg 25980
atgatgatga cggctaccta gacgtgggag acgacgtgct gcttaagcac ctgcaccgcc 26040

-continued agtgcgtcat cgtctgcgac gcgctgcagg agcgctgcga agtgcccctg gacgtggcgg 26100
aggtcagccg cgcctacgag cggcacctct tcgcgccaca cgtgcccccc aagcgccggg 26160
agaacggcac ctgcgagccc aacccgcgcc tcaacttcta cccggtcttc gcggtacccg 26220
aggtgctggc cacctaccac atcttcttcc aaaactgcaa gatcccccctc tcctgccgcg 26280 ccaaccgcac ccgcgccgac aagacgctgg ccctgcggca gggcgcccac atacctgata 26340
tcgcctctct ggaggaggtg cccaagatct tcgagggtct cggtcgcgac gagaaacggg 26400
cggcgaacgc tctgcaagga gacagcgaaa acgagagtca ctcgggggtg ctggtggagc 26460
tcgagggcga caacgcgcgc ctggccgtgc tcaagcgcag catcgaagtc acccacttcg 26520
cctacccggc gctcaacctg ccccccaagg tcatgagtgt ggtcatgagt gagctcatca 26580
tgcgccgcgc ccagcccctg gacgcggatg caaacttgca agagccctcc gaggaaggcc 26640
tgcccgcggt cagcgacgag cagctggcgc gctggctgga gacccgcgac cccgcccagc 26700
tggaggagcg gcgcaagctc atgatggccg cggtgctcgt caccgtggag ctcgagtgtc 26760
tgcagcgctt cttcggggac cccgagatgc agcgcaagct cgaggagacc ctgcactaca 26820
ccttccgcca gggctacgtg cgccaggcct gcaagatctc caacgtggag ctctgcaacc 26880
tggtctccta cctgggcatc ctgcacgaga accgcctcgg gcagaacgtc ctgcactcca 26940
ccctcaaagg ggaggcgcgc cgcgactacg tccgcgactg cgtctacctc ttcctctgct 27000
acacgtggca gacggccatg gggtctggc agcagtgcct ggaggagcgc aacctcaagg 27060
agctggagaa gctcctccgg cgcgccctca gggacctctg gacgggcttc aacgagcgct 27120
cggtggccgc cgcgctggcg gacatcatct tccccgagcg cctgctcaaa accctgcagc 27180
agggcctgcc cgacttcacc agccagagca tgctgcagaa cttcaggacc ttcatcctgg 27240
agcgctcggg catcctgccg gccacctgct gcgcgctgcc cagcgacttc gtgcccatca 27300
ggtacaggga gtgcccgccg ccgctctggg gccactgcta cctcttccag ctggccaact 27360
acctcgccta ccactcggat ctcatggaag acgtgagcgg cgagggcctg ctcgagtgcc 27420
actgccgctg caacctgtgc acgccccacc gctctctagt ctgcaatccg cagctgctca 27480
gcgagagtca gattatcggt accttcgagc tgcagggtcc ctcgcccgac gaaaagtccg 27540
cggctccggg gttgaaactc actccggggc tgtggacttc cgcctaccta cgcaaatttg 27600
tacctgaaga ctaccacgcc cacgagatca ggttttacga agaccaatcc cgcccgccca 27660
aggcggagct caccgcctgc gtcattaccc agggccacat cctgggccaa ttgcaagcca 27720
tcaacaaagc ccgccaagag ttcttgctga aaaagggtcg gggggtgtac ctggaccccc 27780
agtccggcga ggagctaaac ccgctacccc cgccgccgcc ccagcagcgg gaccttgctt 27840
cccaggatgg cacccagaaa gaagcagccg ccgccgccgc cagcatacat gcttctggag 27900
gaagaggagg actgggacag tcaggcagag gaggtttcgg acgaggacga ggaggaggag 27960
atgatggaag actgggagga ggacagccta gacgaggaag cttcagaggc cgaagaggtg 28020
gcagacgcaa caccatcacc ctcggccgca gccccctcgc cggcgccccc gaaatcctcc 28080
gaccccagca gcagcgctat aacctccgct cctccggcgc cggcgcccac ccgcagcaga 28140
cccaaccgta gatgggacac tacaggaacc ggggtcggta agtccaagtg ccccccagcg 28200
ccgcccccgc aacaggagca acagcagcag cagcggcgac agggctaccg ctcgtggcgc 28260
ggacacaaga acgccatagt cgcctgcttg caagactgcg gggcaacat ctccttcgcc 28320 cgccgcttcc tgctcttcca ccacggggtg gcttttcccc gcaatgtcct gcattactac 28380
cgtcatctct acagccccta ctgcggcggc agcggcgacc cagagggagc ggcggcagca 28440

-continued

```
gcagcgccag ccacagcggc gaccacctag gaagacctcc gcgggcaaga cggcgggagc  28500
cgggagaccc gcggcggcgg cggtagcggc ggcggcgggc gcactgcgcc tctcgcccaa  28560
cgaacccctc tcgacccggg agctcagaca caggatcttc cccactctgt atgctatctt  28620
ccagcagagc agaggccagg aacaggagct caaaataaaa aacagatctc tgcgctccct  28680
cacccgcagc tgtctgtatc acaaaagcga agatcagctt cggcgcacgc tggaggacgc  28740
ggaggcactc ttcagcaaat actgcgcgct gactcttaag gactagccgc gcgcccttct  28800
cgaatttagg cgggagaaag actacgtcat cgccgaccgc cgcccagccc acccagccga  28860
catgagcaaa gagattccca cgccctacat gtggagctac cagccgcaga tgggactcgc  28920
ggcgggagcg gcccaagact actccacccg catgaactac atgagcgcgg ggccccacat  28980
gatctcacgg gttaatggga tccgcgccca gcgaaaccaa atactgctgg aacaggcggc  29040
cataaccgcc acaccccgtc atgacctcaa tccccgaaat tggcccgccg ccctcgtgta  29100
ccaggaaacc ccctctgcca ccaccgtggt acttccgcgt gacacccagg ccgaagtcca  29160
gatgactaac tcaggggcgc agctcgcggg cggctttcgt cacggggtgc ggccgcaccg  29220
gccgggtata ttacacctgg cgatcagagg ccgaggtatt cagctcaacg acgagtcggt  29280
gagctcttcg ctcggtctcc gtccggacgg aaccttccag atcgccggat caggtcgctc  29340
ctcattcacg cctcgccagg cgtatctgac tctgcagacc tcctcctcgg agcctcgctc  29400
cggcggcatc ggcaccctcc agttcgtgga ggagttcgtg ccctcggtct acttcaaccc  29460
cttctcggga cctcccggac gctaccccga ccagttcatc ccgaactttg acgcggtgaa  29520
ggactcggcg gacggctacg actgaatgtc aagtgctgag gcagagagcg ttcgcctgaa  29580
acacctccag cactgccgcc gcttcgcctg ctttgcccgc agctccggtg agttctgcta  29640
ctttcagctg cccgaggagc ataccgaagg gccggcgcac ggcgtccgcc taaccaccca  29700
gggcgaggtt acctgtaccc ttatccggga gtttaccctc cgtcccctgc tagtggagcg  29760
ggagcggggt tcttgtgtca taactatcgc ctgcaactgc cctaaccctg gattacatca  29820
agatctttgt tgtcacctgt gcgctgagta taataaacgc tgagatcaga ctctactggg  29880
gctcctgtcg ccatcctgtg aacgccaccg tcttcaccca ccccgagcag ccccaggcga  29940
acctcacctg cggcctgcgt cggagggcca agaagtacct cacctggtac ttcaacggca  30000
ccccctttgt ggtttacaac agcttcgacc aggacggagt tgccttgaga gacgaccttt  30060
ccggtctcag ctactccatt cacaagaaca ccaccctcca cctcttccct ccctacctgc  30120
cgggaaccta cgagtgcgtc accggccgct gcacccacct cctccgcctg atcgtaaacc  30180
agacctttcc gggaacacac ctcttcccca gaacaggagg tgagctcagg aaacccccctg  30240
gggcccaggg cggagactta ccttcgaccc ttgtggggtt aggatttttt atcgccgggt  30300
tgctggctct cctgatcaaa gcttccttca gatttgttct ctccctttac ttttatgaac  30360
agctcaactt ctaataacgc taccttttct caggaatcga gtagtaactt ctcttccgaa  30420
atcgggctgg gtgtgctgct tactctgttg attttttttcc ttatcatact tagccttctg  30480
tgcctcaggc tcgccgcctg ctgcgcacat atctacatct acagccggtt gcttaactgc  30540
tggggtcgcc atccaagatg aacggggctc aggtgctatg tctgctggcc ctggtggcct  30600
gcagtgccgc cgtcaatttt gaggaacccg cttgcaatgt gactttcaag cctgagggcg  30660
cacattgcac cactctggtt aaatgtgtga cctctcatga aaaactgctc atcgcctaca  30720
aaaacaaaac aggccagatc gcagtctata gcgagtggct acccggagac cataataact  30780
```

actcagtcac cgtcttcgag ggtgcggagt ctaagaaatt cgattacacc tttcccttcg 30840
aggagatgtg tgatgcggtc atgtacctgt ccaaacagta caagctgtgg ccccccaccc 30900
ccaaggcgtg tgtggaaaac actgggtctt tctgctgtct ctctctggca atcactgtgc 30960
ttgctctaat ctgcacgctg ctatacatga gattcaggca gaggcgaatc tttatcgatg 31020
agaaaaaaat gccttgatcg ctaacaccgg ctttctgtct gcagaatgaa agcaatcacc 31080
tccctactaa tcagcaccac cctccttgcg attgcccatg ggttgacacg aatcgaagtg 31140
ccagtggggt ccaatgtcac catggtgggc cccgccggca attcctccct gatgtgggaa 31200
aaatatgtcc gtaatcaatg ggatcattac tgctctaatc gaatctgtat caagcccaga 31260
gccacctgcg acgggcaaaa tctaactttg attgatgtgc aaatgacgga tgctgggtac 31320
tattacgggc agcggggaga aatgattaat tactggcgac cccacaagga ctacatgctg 31380
catgtagtca aggcagtccc aactactacc acccccacca ctaccactcc cactaccacc 31440
acccccacca ctaccactag cactgctact accgctgccc gcaaagctat tacccgcaaa 31500
agcaccatgc ttagcaccaa gccccattct cactcccacg ccggcgggcc caccggtgcg 31560
gcctcagaaa ccaccgagct ttgcttctgc caatgcacta acgccagcgc ccacgaactg 31620
ttcgacctgg agaatgagga cgatgaccag ctgagctccg cttgcccggt cccgctgccc 31680
gcagagccgg tcgccctgaa gcagctcggt gatccattta atgactctcc tgtttatccc 31740
tctcccgaat accctcccga ctctaccttc cacatcacgg gcaccaaaga ccccaacctc 31800
tccttctacc tgatgctgct gctctgtatc tctgtggtat cttccgcgct catgttactg 31860
ggcatgttct gctgcctcat ctgccgcaga aaaagaaagt ctcgctctca gggccaacca 31920
ctgatgccct tcccctaccc cccagatttt gcagataaca agatatgagc acgctgctga 31980
cactaaccgc tttactcgcc tgcgctctaa ccettgtcgc ttgcgaatcc agataccaca 32040
atgtcacagt tgtgacagga gaaaatgtta cattcaactc cacggccgac acccagtggt 32100
cgtggagtgg ccacggtagc tatgtataca tctgcaatag ctccacctcc cctagcatgt 32160
cctctcccaa gtaccactgc aatgacagcc tgttcaccct catcaacgcc tccacctcgg 32220
acaatggact ctatgtaggc tatgtgacac ccggtgggca gggaaagacc cacgcctaca 32280
acctgcaagt tcgccacccc tccaccaccg ccaccacctc tgccgcccct acccgcagca 32340
gcagcagcag cagcagcagc agcagcagca gcagcagcag attcctgact ttaatcctag 32400
ccagctcaac aaccaccgcc accgctgaga ccacccacag ctccgcgccc gaaaccaccc 32460
acacccacca cccagagacg accgcggcct ccagcgacca gatgtcggcc aacatcaccg 32520
cctcgggtct tgaacttgct tcaaccccca ccccaaaacc agtggatgca gccgacgtct 32580
ccgccctcgt caatgactgg gcggggctgg gaatgtggtg gttcgccata ggcatgatgg 32640
cgctctgcct gcttctgctc tggctcatct gctgcctcaa ccgcaggcgg gccagaccca 32700
tctatagacc catcattgtt ctcaaccccg ctgatgatgg gatccataga ttggatggtc 32760
tgaaaaacct actttctct tttacagtat gataaattga gacatgcctc gcattttcat 32820
gtacttgaca cttctcccac tttttctggg gtgttctacg ctggccgccg tctctcacct 32880
cgaggtagac tgcctcacac ccttcactgt ctacctgatt tacggattgg tcaccctcac 32940
tctcatctgc agcctaatca cagtagtcat cgccttcatc cagtgcattg actacatctg 33000
tgtgcgcctc gcatacctga gacaccaccc gcagtaccga gacaggaaca ttgcccaact 33060
cctaagactg ctctaatcat gcataagact gtgatctgcc tcctcatcct cctctccctg 33120
cccgctctcg tctcatgcca gcccaccaca aaacctccac gaaaaagaca tgcctcctgt 33180

-continued cgcttgagcc aactgtggaa tattcccaaa tgctacaatg aaaagagcga gctttccgaa 33240
gcctggctat atgcggtcat gtgtgtcctt gtcttctgca gcacaatctt tgccctcatg 33300
atctaccccc actttgattt gggatggaat gcggtcgatg ccatgaatta ccctaccttt 33360
cccgcgcccg atatgattcc actccgacag gttgtggtgc ccgtcgccct caatcaacgc 33420
cccccatccc ctacacccac tgaggtcagc tactttaatc taacaggcgg agatgactga 33480
cactctagat ctagaaatgg acggcatcgg caccgagcag cgtctcctac agaggcgcaa 33540
gcaggcggct gaacaagagc gcctcaatca ggagctccga gatctcatta acctgcacca 33600
gtgcaaaaaa ggcatctttt gcctggtcaa gcaggccgat gtcacctacg agaaaaccgg 33660
taacagccac cgcctcagct acaagctgcc cacccaacgc cagaagttgg tgctcatggt 33720
gggtcagaat cccatcaccg tcacccagca ctcggtggag accgaggggt gtctgcactc 33780
cccctgtcag ggtccggaag acctctgcac cctggtaaag accctgtgtg gtcttagaga 33840
tttaatcccc tttaactaat caaacactgg aatcaataaa aagaatcact tactttaaat 33900
cagtcagcag gtctctgtcc actttattca gcagcacctc cttcccctcc tcccaactct 33960
ggtactccaa acgcctcctg gcggcaaact tcctccacac cctgaaggga atgtcagatt 34020
cttgctcctg tccctccgca cccactatct tcatgttgtt gcagatgaag cgcgccaaaa 34080
cgtctgacga gaccttcaac cccgtgtacc cctatgacac ggaaaacggg cctccctccg 34140
ttcctttcct cacccctccc ttcgtgtccc ccgacggatt tcaagaaagc cccccagggg 34200
tcctgtctct gcgcctgtca gagcccctgg tcacttccca cggcatgctt gccctgaaaa 34260
tgggaaatgg cctctccctg gatgacgccg gcaacctcac ctctcaagat gtcaccaccg 34320
tcacccctcc cctcaaaaaa accaagacca acctcagcct ccagacctca gccccccctga 34380
ccgttagctc tgggtccctc accgtcgcgg ccgccgctcc actggcggtg gccggcacct 34440
ctctcaccat gcaatctcag gccccccttga cggtgcaaga tgcaaaactg ggtctggcca 34500
cccagggacc cctgaccgtg tctgaaggca aactcacctt gcagacatcg gctccactga 34560
cggccgccga cagcagcact ctcactgttg gcaccacacc gccaatcagt gtgagcagtg 34620
gaagtctagg cttagatatg gaagacccca tgtatactca cgatggaaaa ctgggaatca 34680
gaattggtgg cccactgcaa gtagtagaca gcttgcacac actcactgta gttactggaa 34740
acggaataac tgtagctaac aatgcccttc aaactaaagt tgcgggtgcc ctgggttatg 34800
actcatctgg caatctagaa ttgcgagccg caggggggtat gcgaattaac acagggggtc 34860
aactcattct tgatgtggct tatccatttg atgctcagaa caatctcagc cttagactcg 34920
gccagggacc tttatatgtg aacaccaatc acaacctaga tttaaattgc aacagaggtc 34980
tgaccacaac caccagcagt aacacaacca aacttgaaac taaaatcgat tcgggcttag 35040
actataacgc caatggggct atcattgcta aacttggcac tgggttaacc tttgacaaca 35100
caggtgccat aactgtggga aacactgggg atgacaaact cactctgtgg actaccccag 35160
atccctctcc taactgcaga attcacgcag acaaagactg caagtttact ctagtcctga 35220
ctaagtgtgg aagtcaaatt ctggcctccg tcgccgccct ggcggtgtct ggaaacctat 35280
catcaatgac aggcactgtc tccagcgtta ccatctttct cagattcgat cagaatggag 35340
ttcttatgga aaattcctcg ctagacaagg agtactggaa cttcagaaat ggtaattcca 35400
ccaatgccac cccctacacc aatgcggttg ggttcatgcc caacctcagc gcctacccca 35460
aaacccagag tcaaactgca aaaaacaaca ttgtaagtga ggtttactta catggggaca 35520

```
aatctaaacc catgatcctt accattaccc ttaatggcac aaatgaatcc agtgaaacta  35580

gtcaggtgag tcactactcc atgtcattta catggtcgag ggacagtggg aaatatgcca  35640

ccgaaacctt tgccaccaac tcttttacct tctcctacat tgctgaacaa taaagaagca  35700

taacgctgct gttcatttgt aatcaagtgt tacttttta tttttcaatt acaacagaat  35760

cattcaagtc attctccatt tagcttaata gaccccagta gtgcaaagcc ccatactagc  35820

ttatttcagc aattgggaga agtactcgcc tacatggggg tagagtcata atcgtgcatc  35880

aggatagggc ggtggtgctg cagcagcgcg cgaataaact gctgccgccg ccgctccgtc  35940

ctgcaggaat acaacatggc agtggtctcc tcagcgatga ttcgcaccgc ccgcagcata  36000

aggcgccttg tcctccgggc acagcagcgc accctgatct cacttaaatc agcacagtaa  36060

ctgcagcaca gcaccacaat attgttcaaa atcccacagt gcaaggcgct gtatccaaag  36120

ctcatggcgg ggaccacaga acccacgtgg ccatcatacc acaagcgcag gtagattaag  36180

tggcgacccc tcataaacac gctggacata aacattacct cttttggcat gttgtaattc  36240

accacctccc ggtaccatat aaacctctga ttaaacatgg cgccatccac caccatccta  36300

aaccagctgg ccaaaacctg cccgccggct atacactgca gggaaccggg actggaacaa  36360

tgacagtgga gagcccagga ctcgtaacca tggatcatca tgctcgtcat gatatcaatg  36420

ttggcacaac acaggcacac gtgcatacac ttcctcagga ttacaagctc ctcccgcgtt  36480

agaaccatat cccagggaac aacccattcc tgaatcagcg taaatcccac actgcaggga  36540

agacctcgca cgtaactcac gttgtgcatt gtcaaagtgt tacattcggg cagcagcgga  36600

tgatcctcca gtatggtagc gcgggtttct gtctcaaaag gaggtagacg atccctactg  36660

tacggagtgc gccgagacaa ccgagatcgt gttggtcgta gtgtcatgcc aaatggaacg  36720

ccggacgtag tcatatttcc tgaagtcttg gcgcgccaga cccgagtctt accaggaaaa  36780

ttttaaaaaa gattcctcaa cgcagcacca gcaccaacac ctgtcagtgt aaaatgccaa  36840

gcgccgagcg agtatatata ggaataaaaa gtgacgtaaa cggttaaagt ccagaaaacg  36900

cccagaaaaa ccgcacgcga acctacgccc cgaaacgaaa gccaaaaaac agtgaacacg  36960

ccctttcggc gtcaacttcc gctttcccac ggtacgtcac ttccgcatat agtaaaacta  37020

cgctacccaa catgcaagaa gccacgcccc aaaacacgtc acacctcccg gcccgccccg  37080

cgccgccgct cctccccgcc ccgccccgct ccgcccacct cattatcata ttggcttcaa  37140

tccaaaataa ggtatattat tgatgatg                                     37168


<210> SEQ ID NO 8
<211> LENGTH: 36397
<212> TYPE: DNA
<213> ORGANISM: Artificial Sequence
<220> FEATURE:
<223> OTHER INFORMATION: synthetic chimpanzee adenovirus serotype PanAd3
      with Ebola virus Sudan/Gulu codon optimized
      transmembrane envelope glycoprotein (GP) insert
      (PanAd3 GP Ebola S/G (PB/6611))
<220> FEATURE:
<221> NAME/KEY: CDS
<222> LOCATION: (1624)...(3654)
<223> OTHER INFORMATION: Ebola virus Sudan/Gulu codon optimized
      transmembrane envelope glycoprotein (GP) insert in PanAd3 GP Ebola
      S/G (PB/6611)
<220> FEATURE:
<221> NAME/KEY: CDS
<222> LOCATION: (14671)...(16425)
<223> OTHER INFORMATION: chimpanzee adenovirus serotype ChAd63 penton
<220> FEATURE:
<221> NAME/KEY: CDS
<222> LOCATION: (19516)...(22410)
```

-continued

<223> OTHER INFORMATION: chimpanzee adenovirus serotype ChAd63 hexon
<220> FEATURE:
<221> NAME/KEY: CDS
<222> LOCATION: (33294)...(34922)
<223> OTHER INFORMATION: chimpanzee adenovirus serotype ChAd63 fiber

<400> SEQUENCE: 8

```
catcatcaat aatatacctt attttggatt gaagccaata tgataatgag gtgggcggag     60
cggggcgggg cggggaggag cggcggcgcg gggcgggccg ggaggtgtgg cggaagttga    120
gtttgtaagt gtggcggatg tgacttgcta gcgccggatg tggtaaaagt gacgtttttt    180
ggagtgcgac aacgcccacg ggaagtgaca tttttcccgc ggtttttacc ggatgtcgta    240
gtgaatttgg gcgttaccaa gtaagatttg gccattttcg cgggaaaact gaaatgggga    300
agtgaaatct gattaatttc gcgttagtca taccgcgtaa tatttgccga gggccgaggg    360
actttgaccg attacgtgga ggaatcgccc aggtgttttt tgaggtgaat ttccgcgttc    420
cgggtcaaag tctccgtttt attattatag gtatacccat tgcatacgtt gtatccatat    480
cataatatgt acatttatat tggctcatgt ccaacattac cgccatgttg acattgatta    540
ttgactagtt attaatagta atcaattacg gggtcattag ttcatagccc atatatggag    600
ttccgcgtta cataacttac ggtaaatggc ccgcctggct gaccgcccaa cgacccccgc    660
ccattgacgt caataatgac gtatgttccc atagtaacgc caatagggac tttccattga    720
cgtcaatggg tggagtattt acggtaaact gcccacttgg cagtacatca agtgtatcat    780
atgccaagta cgccccctat tgacgtcaat gacggtaaat ggcccgcctg gcattatgcc    840
cagtacatga ccttatggga ctttcctact tggcagtaca tctacgtatt agtcatcgct    900
attaccatgg tgatgcggtt ttggcagtac atcaatgggc gtggatagcg gtttgactca    960
cggggatttc caagtctcca ccccattgac gtcaatggga gtttgttttg gaaccaaaat   1020
caacgggact ttccaaaatg tcgtaacaac tccgccccat tgacgcaaat gggcggtagg   1080
cgtgtacggt gggaggtcta tataagcaga gctctcccta tcagtgatag agatctccct   1140
atcagtgata gagatcgtcg acgagctcgt ttagtgaacc gtcagatcgc ctggagacgc   1200
catccacgct gttttgacct ccatagaaga caccgggacc gatccagcct ccatcggctc   1260
gcatctctcc ttcacgcgcc cgccgcccta cctgaggccg ccatccacgc cggttgagtc   1320
gcgttctgcc gcctcccgcc tgtggtgcct cctgaactgc gtccgccgtc taggtaagtt   1380
taaagctcag gtcgagaccg ggcctttgtc cggcgctccc ttggagccta cctagactca   1440
gccggctctc cacgctttgc ctgaccctgc ttgctcaact ctagttaacg gtggagggca   1500
gtgtagtctg agcagtactc gttgctgccg cgcgcgccac cagacataat agctgacaga   1560
ctaacagact gttcctttcc atgggtcttt tctgcagtca ccgtcgtcga cgatatcgcc   1620
gccatggagg gcctgagcct gctgcagctg cccagggaca agttcaggaa gagcagcttc   1680
ttcgtgtggg tgatcatcct gttccagaag gccttcagca tgcccctggg cgtggtgacc   1740
aacagcaccc tggaggtgac cgagatcgac cagctggtgt gcaaggacca cctggccagc   1800
accgaccagc tgaagagcgt gggcctgaac ctggagggca gcggcgtgag caccgacatc   1860
cccagcgcca ccaagaggtg gggcttcagg agcggcgtgc ctcccaaggt ggtgagctac   1920
gaggccggcg agtgggccga gaactgctac aacctggaga tcaagaagcc cgacggcagc   1980
gagtgcctgc ctcctcctcc tgacggcgtg aggggcttcc ccaggtgcag gtacgtgcac   2040
aaggcccagg gcaccggccc ctgccccggc gactacgcct tccacaagga cggcgccttc   2100
ttcctgtacg acaggctggc cagcaccgtg atctacaggg gcgtgaactt cgccgagggc   2160
```

-continued

```
gtgatcgcct tcctgatcct ggccaagccc aaggagacct tcctgcagag ccctcccatc   2220
agggaggccg tgaactacac cgagaacacc agcagctact acgccaccag ctatctagag   2280
tacgagatcg agaacttcgg cgcccagcac agcaccaccc tgttcaagat cgacaacaac   2340
accttcgtga ggctggacag gccccacacc cctcagttcc tgttccagct gaacgacacc   2400
atccacctgc accagcagct gagcaacacc accggcaggc tgatctggac cctggacgcc   2460
aacatcaacg ccgacatcgg cgagtgggcc ttctgggaga acaagaagaa cctgagcgag   2520
cagctgaggg gcgaggagct gagcttcgag gccctgagcc tgaacgagac cgaggacgac   2580
gacgccgcca gcagcaggat caccaagggc aggatcagcg acagggccac caggaagtac   2640
agcgacctgg tgcccaagaa cagccccggc atggtgcccc tgcacatccc cgagggcgag   2700
accaccctgc ccagccagaa cagcaccgag ggcaggaggg tgggcgtgaa cacccaggag   2760
accatcaccg agaccgccgc caccatcatc ggcaccaacg gcaaccacat gcagatcagc   2820
accatcggca tcaggcccag cagcagccag atccccagca gcagccccac caccgcccct   2880
agccccgagg cccagacccc caccacccac accagcggac ccagcgtgat ggccaccgag   2940
gagcccacca cccctcccgg cagcagcccc ggacccacca ccgaggcccc taccctgacc   3000
accccctgaga acatcaccac cgccgtgaag accgtgctgc cccaggagag caccagcaac   3060
ggcctgatca ccagcaccgt gaccggcatc ctgggcagcc tgggcctgag gaagaggagc   3120
aggaggcaga ccaacaccaa ggccaccggc aagtgcaacc ccaacctgca ctactggacc   3180
gcccaggagc agcacaacgc cgccggcatc gcctggattc cctacttcgg ccccggcgcc   3240
gagggcatct acaccgaggg cctgatgcac aaccagaacg ccctggtgtg cggcctgagg   3300
cagctggcca acgagaccac ccaggccctg cagctgttcc tgagggccac caccgagctg   3360
aggacctaca ccatcctgaa caggaaggcc atcgacttcc tgctgaggag gtggggcggc   3420
acctgcagga ttctgggccc cgactgctgc atcgagcccc acgactggac caagaacatc   3480
accgacaaga tcaaccagat catccacgac ttcatcgaca accctctgcc caaccaggac   3540
aacgacgaca actggtggac cggctggcgg cagtggatac ctgccggcat cggcatcacc   3600
ggcatcatca tcgccatcat cgctctgctg tgcgtgtgca agctgctgtg ctgagaattc   3660
agatctgctg tgccttctag ttgccagcca tctgttgttt gcccctcccc cgtgccttcc   3720
ttgaccctgg aaggtgccac tcccactgtc ctttcctaat aaaatgagga aattgcatcg   3780
cattgtctga gtaggtgtca ttctattctg gggggtgggg tggggcagga cagcaagggg   3840
gaggattggg aagacaatag caggcatgct ggggatgcgg tgggctctag atatcagcga   3900
tcgctgaggt gggtgagtgg gcgtggtctg gggtgggaa gcaatatata agttgggggt   3960
cttagggtct ctgtgtctgt tttgcagagg gaccgccggc gccatgagcg ggagcagtag   4020
cagcaacgcc ttggatggca gcatcgtgag cccttatttg acgacgcgca tgccccactg   4080
ggccggggtg cgtcagaatg tgatgggctc cagcatcgac ggacgacccg tgctgcccgc   4140
aaattccgcc acgctgacct acgcgaccgt cgcggggacc ccgttggacg ccaccgccgc   4200
cgccgccgcc accgccgccg cctcggccgt gcgcagcctg gccacggact ttgcattctt   4260
gggaccccttg gccaccgggg cggccgcccg tgccgccgtt cgcgatgaca agctgaccgc   4320
cctgctggcg cagttggatg cgcttacccg ggaactgggt gacctttcgc agcaggtcgt   4380
ggccctgcgc cagcaggtct ccgccctgca ggctagcggg aatgcttctc ctgcaaatgc   4440
cgtttaagat aaataaaacc agactctgtt gataaataaa accagactct gtttggatta   4500
```

-continued

```
aagaaaagta gcaagtgcat tgctctcttt atttcataat tttccgcgcg cgataggccc   4560
gagtccagcg ttctcggtcg ttgagggtgc ggtgtatctt ctccaggacg tggtagaggt   4620
ggctctggac gttgagatac atgggcatga gcccgtcccg ggggtggagg tagcaccact   4680
gcagagcttc atgctccggg gtggtgttgt agatgatcca gtcgtagcag gagcgctggg   4740
catggtgcct aaaaatgtcc ttaagcagca ggccgatggc caggggggagg cccttggtgt   4800
aagtgtttac aaaacggttg agttgggaag ggtgcatgcg gggtgagatg atgtgcatct   4860
tagattgtat ttttagattg gcgatgtttc ctcccagatc ccttctggga ttcatgttgt   4920
ggaggaccac cagcacagta tatccggtgc acttgggaaa tttgtcatgc agcttagagg   4980
gaaatgcgtg gaagaacttg gagacgccct tgtggcctcc cagattctcc atgcattcgt   5040
ccatgatgat ggcaatgggc ccgcgggagg cggcctgggc aaagatgttt ctggggtcac   5100
tgacatcgta gttgtgttcc agggtgagat cgtcataggc catttttata aagcgcgggc   5160
ggagggtgcc cgactggggg atgatggttc cctcgggccc cggggcgtag ttgccttcgc   5220
agatctgcat ttcccaggcc ttaatctctg aggggggaat catatccact tgcggggcga   5280
tgaagaaaac ggtttccgga gccgggggaga ttaactggga tgagagcagg tttctcagca   5340
gctgtgactt tccacagccg gtgggtccat aaataacacc tataaccggc tgcagctggt   5400
agttgagcga gctgcagctg ccgtcgtccc ggaggagggg ggccacctca ttgagcatgt   5460
cccggacgcg cttgttctcc tcgaccaggt ccgccagaag gcgctcgccg cccagggaca   5520
gcagctcttg caaggaagca aagtttttca gcggtttgag gccgtccgcc gtgggcatgt   5580
tttcagggt ctggccgagc agctccaggc ggtcccagag ctcggtgacg tgctctacgg   5640
catctctatc cagcatatct cctcgtttcg cgggttgggg cggctttcgc tgtagggcac   5700
caggcgatgg tcgtccagcg cggccagagt catgtccttc catgggcgca gggtcctcgt   5760
cagggtggtc tgggtcacgg tgaaggggtg cgcccccgggc tgggcgctgg ccagggtgcg   5820
cttgagactg gtcctgctgg tgctgaagcg ctgccggtct tcgccctgcg cgtcggccag   5880
gtagcatttg accatggtgt cgtagtccag cccctccgcg gcgtgtccct tggcgcgcag   5940
cttgcccttg gaggtggcgc cgcacgcggg gcactgcagg ctcttgagcg cgtagagctt   6000
gggggcgagg aagaccgatt cgggggagta ggcgtccgcg ccgcaggccc cgcacacggt   6060
ctcgcactcc accagccagg tgagctcggg gcgctcgggg tcaaaaacca ggtttccccc   6120
atgcttttg atgcgtttct tacctcgggt ctccatgagg cggtgtcccc gttcggtgac   6180
gaagaggctg tccgtgtctc cgtagaccga cttgaggggt ctgtcctcca ggggggtccc   6240
tcggtcctct tcgtagagaa actcggacca ctctgagaca aaggcccgcg tccaggccag   6300
gacgaaggag gccaggtggg aggggtaccg gtcgttgtcc actagggggt ccaccttctc   6360
caaggtgtga agacacatgt cgccctcctc ggcgtccagg aaggtgattg gcttgtaggt   6420
gtaggccacg tgacccgggg ttccggacgg gggggtataa aagggggtgg gggcgcgctc   6480
gtcctcactc tcttccgcat cgctgtctgc gagggccagc tgctggggtg agtattccct   6540
ctcgaaggcg ggcatgacct cagcgctgag gctgtcagtt tctaaaaacg aggaggattt   6600
gatgttcacc tgtcccgagc tgatgccttt gagggtgccc gcgtccatct ggtcagaaaa   6660
cacgatcttt ttattgtcca gcttggtggc gaacgacccg tagagggcgt tggagagcag   6720
cttggcgatg gagcgcaggg tctgattctt gtcccggtcg gcgcgctcct tggccgcgat   6780
gttgagctgc acgtactcgc gcgcgacgca gcgccactcg ggaagacgg tggtgcgctc   6840
gtcgggcacc aggcgcacgc gccagccgcg gttgtgcagg gtgacgaggt ccacgctggt   6900
```

-continued

```
ggcgacctcg ccgcgcaggc gctcgttggt ccagcagagg cgcccgccct tgcgcgagca   6960
gaagggggc agggggtcga gttgggtttc gtccgggggg tccgcgtcca ccgtgaagac   7020
cccggggcgc aggcgcgcgt cgaagtagtc gatcttgcat ccttgcaagt ccagcgcccg   7080
ctgccagtcg cgggcggcga gcgcgcgctc gtaggggttg agcggcgggc cccagggcat   7140
ggggtgggtg agcgcggagg cgtacatgcc gcagatgtca tagacgtaga ggggctcccg   7200
gaggatgccc aggtaggtgg ggtagcagcg gccgccgcgg atgctggcgc gcacgtagtc   7260
gtagagctcg tgcgaggggg cgaggaggtc ggggcccagg ttggtgcggg cggggcgctc   7320
cgcgcggaag acgatctgcc tgaagatggc atgcgagttg gaagagatgg tggggcgctg   7380
gaagacgttg aagctggcgt cctgcaggcc gacggcgtcg cgcacgaagg aggcgtagga   7440
ctcgcgcagc ttgtgcacca gctcggcggt gacctgcacg tcgagcgcgc agtagtcgag   7500
ggtctcgcgg atgatgtcat acttagcctg cccccttcttt ttccacagct cgcggttgag   7560
gacgaactct tcgcggtctt tccagtactc ttggatcggg aaaccgtccg gctccgaacg   7620
gtaagagccc agcatgtaga actggttgac ggcctggtag gcgcagcagc ccttctccac   7680
gggcagggcg taggcctgcg cggccttgcg gagcgaggtg tgggtcaggg cgaaggtgtc   7740
cctgaccatg accttgaggt actggtgttt gaagtcggag tcgtcgcagc cgccccgctc   7800
ccagagcgag aagtcggtgc gctttttgga gcgggggttg ggcagcgcga aggtgacatc   7860
gttgtagagg atcttgcccg cgcgaggcat gaagttgcgg gtgatgcgga agggccccgg   7920
cacttccgag cggttgttga tgacctgggc ggcgagcacg atctcgtcga agccgttgat   7980
gttgtggccc acgatgtaga gttccaggaa gcggggccgg cccttgacgc tgggcagctt   8040
ctttagctct tcgtaggtga gctcctcggg cgaggcgagg ccgtgctcgg ccagggccca   8100
gtccgccagg tgcgggttgt ccgcgaggaa ggaccgccag aggtcgcggg ccaggagggt   8160
ctgcaggcgg tccctgaagg tcctgaactg gcggcctacg gccatctttt cgggggtgac   8220
gcagtagaag gtgagggggt cttgctgcca ggggtcccag tcgagctcca gggcgaggtc   8280
gcgcgcggcg gcgaccaggc gctcgtcgcc cccgaatttc atgaccagca tgaagggcac   8340
gagctgcttt ccgaaggcgc ccatccaagt gtaggtctct acatcgtagg tgacaaagag   8400
acgttccgtg cgaggatgcg agccgatcgg gaagaactgg atctcccgcc accagttgga   8460
ggagtggctg ttgatgtggt gaaagtagaa gtcccgtcgg cgggccgagc actcgtgctg   8520
gcttttgtaa aagcgagcgc agtactggca gcgctgcacg ggctgtacct cttgcacgag   8580
atgcacctgc cgaccgcgga cgaggaagct gagtgggaat ctgagccccc cgcatggctc   8640
gcggcctggc tggtgctctt ctactttgga tgcgtggccg tcaccgtctg gctcctcgag   8700
gggtgttacg gtggagcgga tcaccacgcc gcgcgagccg caggtccaga tatcggcgcg   8760
cggcggtcgg agtttgatga cgacatcgcg cagctgggag ctgtccatgg tctggagctc   8820
ccgcggcggc ggcaggtcag ccgggagttc ttgcaggttt acctcgcaga gacgggccag   8880
ggcgcggggc aggtccaggt ggtacttgaa ttcgagaggc gtgttggtgg cggcgtcgat   8940
ggcttgcagt atgccgcagc cccggggcgc gacgacggtg ccccgcgggg cggtgaagct   9000
cccgccgccg ctcctgctgt cgccgccggt ggcggggctt agaagcggtg ccgcggtcgg   9060
gcccccggag gtaggggggg ctccggtccc gcgggcaggg gcggcagcgg cacgtcggcg   9120
ccgcgcgcgg gcaggagctg gtgctgcgcc cggaggttgc tggcgaaggc gacgacgcgg   9180
cggttgatct cctggatctg gcgcctctgc gtgaagacga cgggtccggt gagcttgaac   9240
```

-continued

```
ctgaaagaga gttcgacaga atcaatctcg gtgtcattga ccgcgacctg gcgcaggatc   9300
tcctgcacgt cgcccgagtt gtcttggtag gcgatctcgg ccatgaactg ttcaatctct   9360
tcctcctgga ggtctccgcg tccggcgcgc tccacggtgg ccgccaggtc gttggagatg   9420
cgcgccatga gctgcgagaa ggcgttgagt ccgccctcgt tccacactcg gctgtagacc   9480
acgccgccct ggtcgtcgcg ggcgcgcatg accacctgcg cgaggttgag ttccacgtgg   9540
cgcgcaaaga cggcgtagtt gcgcaggcgc tggaagaggt agttgagggt ggtggcggtg   9600
tgctcggcca caaagaagta catgacccag cggcgcaacg tggattcgtt gatgtccccc   9660
aaggcctcca gtcgctccat ggcctcgtag aagtccacgg cgaagttgaa aaactgggag   9720
ttgcgcgccg acacggtcaa ctcctcctcc agaagacgga tgagctcggc gacggtgtcg   9780
cgcacctcgc gctcgaaggc tatgggaatc tcttcctccg ccagcatcac cacctcttcc   9840
tcttcttcct cctctggcac ttccatgatg gcttcctcct cttcgggggg tggcggcggg   9900
ggagggggcg ctcggcgccg gcggcggcgc accgggaggc ggtccacgaa gcgctcgatc   9960
atctccccgc ggcggcgacg catggtctcg gtgacggcgc ggccgttctc tcggggacgc  10020
agctggaaga cgccgccggt catctggtgc tggggcgggt ggccgtgggg cagcgagacc  10080
gcgctgacga tgcatcttaa caattgctgc gtaggtacgc cgccgaggga cctgagggag  10140
tccagatcca ccggatccga aaacctttcg aggaaggcat ctaaccagtc gcagtcgcaa  10200
ggtaggctga gcaccgtggc gggcggcggg gggtgggggg agtgtctggc ggaggtgctg  10260
ctgatgatgt aattgaagta ggcggtcttg acacggcgga tggtcgacag gagcaccatg  10320
tctttgggcc cggcctgctg gatgcggagg cggtcggcca tgccccaggc ttcgttctgg  10380
catctgcgca ggtctttgta gtagtcttgc atgagccttt ccaccggcac ctcttctcct  10440
tcttcttctg acatctctgc tgcatctgcg gccctggggc gacggcgcgc gcccctgccc  10500
cccatgcgcg tcaccccgaa ccccctgagc ggctggagca gggccaggtc ggcgacgacg  10560
cgctcggcca ggatggcctg ctggacctgc gtgagggtgg tttggaagtc atccaagtcc  10620
acgaagcggt ggtaggcgcc cgtgttgatg gtgtaggtgc agttggccat gacggaccag  10680
ttgacggtct ggtggcccgg ttgcgtcatc tcggtgtacc tgaggcgcga gtaggcgcgc  10740
gagtcgaaga tgtagtcgtt gcaagtccgc accaggtact ggtagcccac caggaagtgc  10800
ggcggcggct ggcggtagag gggccagcgg agggtggcgg gggctccggg ggccaggtct  10860
tccagcatga ggcggtggta ttcgtagatg tacctggaca tccaggtgat gcccgcggcg  10920
gtggtggagg cgcgcgggaa gtcgcgcacc cggttccaga tgttgcgcag cggcagaaag  10980
tgctccatgg taggcgtgct ctggccggtc aggcgcgcgc agtcgttgat actctagacc  11040
agggaaaacg aaagccggtc agcgggcact cttccgtggt ctggtggata aattcgcaag  11100
ggtatcatgg cggagggcct cggttcgagc cccgggcccg ggccggacgg tccgccatga  11160
tccacgcggt taccgcccgc gtgtcgaacc caggtggcga cgtcagacaa cggtggagtg  11220
ttccttttgg gtttttttcc aaatttttct ggccgggcgc cgacgccgcc gcgtaagaga  11280
ctagagtgca aaagcgaaag cagtaagtgg ctcgctccct gtagcccgga ggatccttgc  11340
taagggttgc gttgcggcga accccggttc gagtctggct ctcgctgggc cgctcgggtc  11400
ggccggaacc gcggctaagg cgggattggc ctccccctca ttaaagaccc cgcttgcgga  11460
ttcctccgga cacaggggac gagccccttt ttacttttgc ttttctcaga tgcatccggt  11520
gctgcggcag atgcgccccc cgccccagca gcagcagcag caacatcagc aagagcggca  11580
ccagcagcag cgggagtcat gcagggcccc ctcgcccacg ctcggcggtc cggcgacctc  11640
```

```
ggcgtccgcg gccgtgtctg gagccggcgg cggtgggctg gcggacgacc cggaggagcc  11700
cccgcggcgc agggccagac agtacctgga cctggaggag ggcgagggcc tggcgcgact  11760
gggggcgccg tcccccgagc gccacccgcg ggtgcagctg aagcgcgact cgcgcgaggc  11820
gtacgtgcct cggcagaacc tgttcagaga ccgcgcgggc gaggagcccg aggagatgcg  11880
ggaccgcagg ttcgccgcgg ggcgggagct gcggcagggg ctgaaccggg agcggctgct  11940
gcgcgaggag gactttgagc ccgacgcgcg gacggggatc agccccgcgc gcgcgcacgt  12000
ggcggccgcc gacctggtga cggcgtacga gcagacggtg aaccaggaga tcaacttcca  12060
aaaaagcttc aacaaccacg tgcgcacgct ggtggcgcgc gaggaggtga ccatcggcct  12120
gatgcacctg tgggactttg tgagcgcgct ggagcagaac cccaacagca agcctctgac  12180
ggcgcagctg ttcctgatag tgcagcacag cagggacaac gaggcgttca gggacgcgct  12240
gctgaacatc accgagcccg agggtcggtg gctgctggac ctgattaaca tcttgcagag  12300
catagtggtg caggagcgca gcctgagcct ggccgacaag gtggcggcca tcaattactc  12360
gatgctcagt ctgggcaagt tttacgcgcg caagatctac cagacgccgt acgtgcccat  12420
agacaaggag gtgaagatcg acggcttcta catgcgcatg gcgctgaagg tgctgaccct  12480
gagcgacgac ctgggcgtgt accgcaacga gcgcatccac aaggccgtga gcgtgagccg  12540
gcggcgcgag ctgagcgacc gcgagctgat gcacagcctg cagcgggcgc tggcgggggc  12600
cggcagcggc gacagggagg ccgagtccta cttcgaggcg ggggcggacc tgcgctgggt  12660
gcccagccgg agggccctgg aggccgcggg ggcccgccgc gaggactatg cagacgagga  12720
ggaggaggat gacgaggagt acgagctaga ggagggcgag tacctggact aaaccgcagg  12780
tggtgttttt ggtagatgca agacccgaac gtggtggacc cggcgctgcg ggcggctctg  12840
cagagccagc cgtccggcct taactctaca gacgactggc gacaggtcat ggaccgcatc  12900
atgtcgctga cggcgcgcaa tccggacgcg ttccggcagc agccgcaggc caacaggctc  12960
tccgccatct tggaggcggt ggtgcctgcg cgcgcgaacc ccacgcacga gaaggtgctg  13020
gccatagtga acgcgctggc cgagaacagg gccatccgcc cggacgaggc cgggctggtg  13080
tacgacgcgc tgctgcagcg cgtggcccgc tacaacagcg gcaacgtgca gaccaacctg  13140
gaccggctgg tgggggacgt gcgcgaggcg gtggcgcagc gggagcgcgc ggagcggcag  13200
ggaaacctgg gctccatggt ggcgctgaac gccttcctga gcacgcagcc ggccaacgtg  13260
ccgcgggggc aggaggacta caccaacttt gtgagcgcgc tgcggctgat ggtgaccgag  13320
accccccaga gcgaggtgta ccagtcgggg ccggactact tttccagac cagcagacag  13380
ggcctgcaga cggtgaacct gagccaggct ttcaagaacc tgcgggggct gtggggcgtg  13440
aaggcgccca ccggggaccg ggcgacggtg tccagcctgc tgacgcccaa ctcgcgcctg  13500
ctgctgctgc tgatcgcgcc gttcacggac agcggcagcg tgtcccggga gacctacctc  13560
gggcacctgc tgacgctgta ccgcgaggcc atcgggcaga cccaggtgga cgagcacacc  13620
ttccaggaga tcaccagcgt gagccgcgcg ctggggcagg aggacacggg cagcctggag  13680
gcgaccctga actacctgct gaccaaccgg cggcagaaga tcccctcgct gcatagtttg  13740
accaccgagg aggagcgcat cctgcgctac gtgcagcaga gcgtgagcct gaacctgatg  13800
cgcgacgggg tgacgcccag cgtggcgctg gacatgaccg cgcgcaacat ggaaccgggc  13860
atgtacgccg cgcatcggcc ttacatcaac cgcctgatgg actacttgca tcgcgcggcg  13920
gccgtgaacc ccgagtactt caccaacgcc atcctgaacc cgcactggct cccgccgccc  13980
```

-continued

```
gggttctaca gcgggggctt cgaggtcccc gaggccaacg acggcttcct gtgggacgac  14040
atggacgaca gcgtgttctc cccgcggccg caggcgctgg cggaggcgtc gctgctccgc  14100
ctccccaaga aagaagagag ccgccggccc agcagcgcgg cggcctctct gtccgagctg  14160
ggggcggcgg ccgcgcggcc cgggtccctg gggggcagcc cctttcccag tctggtgggg  14220
tctctgcaga gcgggcgcac cacccggccc cggctgctgg gcgaggacga gtacctgaac  14280
aactccctga tgcagccggt gcgggagaaa aacctgcccc ccgccttccc caacaacggg  14340
atagagagcc tggtagacaa gatgagcaga tggaagacct atgcgcagga gcacagggac  14400
tcgcccgtgc tccgtccgcc cacgcggcgc cagcgccacg accggcagcg ggggctggta  14460
tgggatgacg aggactccgc ggacgatagc agcgtgctgg acctgggggg gagcggcggt  14520
aacccgttcg cgcacctgcg cccccgcctg ggaggatgt ttcaataaga aaaatcaagc  14580
atgatgcaag gtttttaag cggataaata aaaaactcac caaggccatg gcgaccgagc  14640
gttgttggtt tcttgttgtg ttcccttagt atgcggcgcg cggcgatgta ccacgaggga  14700
cctcctccct cttatgagag cgtggtgggc gcggcggcgg cctctccctt tgcgtcgcag  14760
ctggagccgc cgtacgtgcc tccgcggtac ctgcggccta cgggggggaag aaacagcatc  14820
cgttactcgg agctggcgcc cctgtacgac accacccggg tgtacctggt ggacaacaag  14880
tcggcggacg tggcctccct gaactaccag aacgaccaca gcaattttt gaccacggtc  14940
atccagaaca atgactacac cccgagcgag gccagcaccc agaccatcaa tctggatgac  15000
cggtcgcact ggggcggcga cctgaaaacc atcctgcaca ccaacatgcc caacgtgaac  15060
gagttcatgt tcaccaataa gttcaaggcg cgggtgatgg tgtcgcgttc gcacaccaag  15120
gacgaccggg tggagctgaa gtacgagtgg gtagagttcg agctgcccga gggcaactac  15180
tcggagacca tgaccataga cctgatgaac aacgcgatcg tggagcacta tctgaaagtg  15240
ggcaggcaga acggggtcct ggagagcgac atcggggtca agttcgacac caggaacttc  15300
cgcctggggc tggacccggt caccgggctg gtcatgcccg gggtctacac caacgaggcc  15360
ttccaccccg acatcatcct gctgcccggc tgcggggtgg acttcaccta cagccgcctg  15420
agcaacctgc tgggcatccg caagcggcag cccttccagg agggctttag gatcacctac  15480
gaggacctgg agggggcaa catccccgcg ctcctggatg tggaggccta ccaggatagc  15540
ttgaaggaag aagaggcggg agagggcagc ggcggcggcg gcggcgccgg tcaggaggag  15600
ggcggggcct cctctgaggc ctctgcggac gccgccgctg ccgccgaggc ggaggcggcc  15660
gaccccgcga tggtggtaga ggaagagaag gatatgaatg acgaggcggt gcgcggcgac  15720
acctttgcca cccgggggga ggagaagaaa gcggaggccg aggccgcggc agaggaggcg  15780
gcagcggcgg cggcggcggc agtagaggcg gcggccgagg cggagaagcc ccccaaggag  15840
cccgtgatta aggccctgac cgaagatagc aagaagcgca gttacaacgt gctcaaggac  15900
agcaccaaca ccgcgtaccg cagctggtac ctggcctaca actacggcga cccggcgacg  15960
ggggtgcgct cctggaccct gctgtgtacg ccggacgtga cctgcggctc ggagcaggtg  16020
tactggtcgc tgcccgacat gatgcaagac cccgtgacct tccgctccac gcggcaggtc  16080
agcaacttcc cggtggtggg cgccgagctg ctgcccgtgc actccaagag cttctacaac  16140
gaccaggccg tctactccca gctcatccgc cagttcacct ctctgaccca cgtgttcaat  16200
cgctttcctg agaaccagat tctggcgcgc ccgcccgccc ccaccatcac caccgtcagt  16260
gaaaacgttc ctgctctcac agatcacggg acgctaccgc tgcgcaacag catcggagga  16320
gtccagcgag tgaccgtaac tgacgccaga cgccgcacct gtccctacgt ttacaaggcc  16380
```

-continued ctgggcatag tctcgccgcg cgtcctttcc agccgcactt tttaagcatg tccatcctca 16440
tctcgcccag caataacacc ggctggggcc tgctgcgcgc gcccagcaag atgtttggag 16500
gggcgaggaa gcgctccgac cagcaccccg tgcgcgtgcg cgggcactac cgcgcccccct 16560
ggggcgcgca caaacgcggg cgcaccggca ccgcggggcg caccaccgtg gacgaagcca 16620
tcgactcggt ggtggagcag gcgcgcaact acacgcccgc ggtctccacc gtggacgcgg 16680
ctatcgagag cgtggtgcga ggcgcgcggc ggtacgccaa ggcgaagagc cgccggaggc 16740
gcgtggcccg ccgccaccgc cgtcgacccg gaagcgccgc caagcgcgcc gccgccgcct 16800
tgcttcgtcg ggccagacgc acgggccgcc gcgccgccat gagggccgcg cgccgcctgg 16860
ccgccggcat caccaccgtg gcccccgcg ccagaagacg cgcggccgct gccgccgccg 16920
cggccatcag cgacctggcc accaggcgcc ggggcaacgt gtactgggtg cgcgactcgg 16980
tgagcggcac gcgcgtgccc gtgcgcttcc gccccccgcg gacttgagag gagaggacag 17040
gaaaaaagca tcaacaacac caccactgag tctcctgctg ttgtgtgtat cccagcggcg 17100
cgcgcgcaca cggcgacatg tccaagcgca aaatcaaaga agagatgctc caggtcgtcg 17160
cgccggaaat ctatgggccc ccgaagaagg aagagcagga tttcaagccc cgcaagataa 17220
agcgggtcaa aaagaaaaag aaagatgacg atgatggcga ggtggagttt ctgcgcgcca 17280
cggcgcccag gcgcccgctg cagtggaagg gtcggcgcgt aaagcgcgtt ctgcgccccg 17340
gcaccgcggt ggtcttcacg cccggcgagc gctccacccg cactttcaag cgcgtctatg 17400
acgaggtgta cggcgacgaa gacctgctgg agcaggccaa cgatcgctcc ggagagtttg 17460
cttacgggaa gcggcaccgg gcgatggaga aggacgaggt gctggcgctg ccgctggacc 17520
ggggcaaccc cacccccagc ctgaagcccg tgaccctgca gcaggtgctg ccggccagcg 17580
cgccctccga gatgaagcgg ggcctgaagc gcgagggcgg cgacctggcg cccaccgtgc 17640
agctgatggt gcccaagcgg cagaggctgg aggacgtgct ggagaaaatg aaagtagacc 17700
ccggcctgca gccggacatc agggtccgcc ccatcaagca ggtggcgccg ggcctcggcg 17760
tgcagaccgt ggacgtggtc atccccaccg gcgcctcctc ttccagcgcc gccgccgcca 17820
ctagcaccgc ggacatggag acgcagacta gctccgccct cgccgccccc gcggccgccg 17880
ccgccgccac ctcctcggcg gaggtacaga cggacccctg gatgccgccg ccggcggccg 17940
ccccctcgcg cgcacgccgc gggcgcagga agtacggcgc cgccagcgcg ctcatgcccg 18000
agtacgcctt gcatccttcc atcgcgccca cccccggcta ccgaggctac agctaccgcc 18060
cgcgaagagc caagggctcc acccgccgca gccgccgcgc cgccacctct acccgccgcc 18120
gcagtcgccg ccgccgccgg cagcccgcgc tggctccgat ctccgtgagg agagtggcgc 18180
gcaacgggga caccttggtg ctgcccaggg cgcgctacca ccccagcatc gtttaaaagc 18240
ctgttgtggt tcttgcagat atggccctca cttgccgcct ccgtttcccg gtgccgggat 18300
accgaggaag atcgcgccgt agaaggggta tggccggacg cggcctgagc ggaggcagcc 18360
gccgtgcgca ccggcggcga cgcgccacca gccgacgcat gcgcggcggg gtgctgcctc 18420
tgctgatccc cctgatcgcc gcggcgatcg gcgccgtgcc cgggatcgcc tccgtggcct 18480
tgcaggcgtc ccagaggcgt tgacacagac ttcttgcaag cttgcaaaaa tatggaaaaa 18540
atccccccaa taaaaaagtc tagactctca cgctcgcttg gtcctgtgac tattttgtag 18600
aaaaaaagat ggaagacatc aactttgcgt cgctggcccc gcgtcacggc tcgcgcccgt 18660
tcctgggaca ctggaacgat atcggcacca gcaacatgag cggtggcgcc ttcagttggg 18720

-continued

```
gctctctgtg gagcggcatt aaaaatatcg gttctgccgt taagaattac ggctccaagg  18780
cctggaacag cagcacgggc cagatgttga gagacaagtt gaaagagcag aacttccagc  18840
agaaggtggt ggagggcctg gcctccggca tcaacggggt ggtggacctg gccaatcagg  18900
ccgtgcaaaa taagatcaac agcagactgg acccccggcc gccggtggaa gagctgccgc  18960
cggcgctgga gacggtgtcc cccgatgggc ggggcgaaaa gcgcccgcgg cccgacaggg  19020
aagagaccac tctggtcacg cacaccgatg agccgccccc ctacgaggaa gctctgaagc  19080
aaggcttgcc caccactcgg cccatcgcgc ccatggccac cggggtggtg ggccgccaca  19140
cccccgccag gctggacctg cctcctcctc ctgtttcttc ttcggccgcc gatgcgcagc  19200
agcagaaggc ggcgctgccc ggtccgcccg cggccgcccc ccgtcccacc gccagtcgag  19260
cgcccctgcg tcgcgcggcc agcggccccc gcggggtcgc gaggcacagc agcggcaact  19320
ggcagaacac gctgaacagc atcgtgggtc tgggggtgca gtccgtgaag cgccgccgat  19380
gctactgaat agcttagcta acggtgttgt atgtgtgtat gcgtcctatg tcaccgccag  19440
aggagctgct gagtcgccgc cgttcgcgcg cccaccgcca ctaccaccgc cggtaccact  19500
ccagcgcccc tcaagatggc gaccccatcg atgatgccgc agtggtcgta catgcacatc  19560
tcgggccagg acgcctcgga gtacctgagc cccgggctgg tgcagttcgc ccgcgccacc  19620
gacagctact tcagcctgag taacaagttt aggaacccca cggtggcgcc cacgcacgat  19680
gtgaccaccg accggtccca gcgcctgacg ctgcggttca tccccgtgga ccgcgaggac  19740
accgcgtact cttacaaggc gcggttcacc ctggccgtgg gcgacaaccg cgtgctggac  19800
atggcctcca cctactttga catccgcggc gtgctggaca ggggccccac cttcaagccc  19860
tactccggca ccgcctacaa ctccctggcc cccaagggcg cccccaactc ctgcgagtgg  19920
gagcaagagg agactcagac agctgaagag gcacaagacg aagaagaaga tgaagctgaa  19980
gctgaggagg aaatgcctca ggaagagcaa gcacctgtca aaaagactca tgtatatgct  20040
caggctcccc tttctggcga aaaaattact aaagacggtc tgcagatagg aacggacgct  20100
acagctaccg aacaaaaacc tatttatgca gatcccacat tccagccaga accccaaatt  20160
ggtgaatctc agtggaatga ggcagatgct tcagttgccg gcggtagagt gctgaagaaa  20220
actactccca tgaaaccctg ttatggttcc tatgccaggc ccacaaatgc caatggaggt  20280
cagggtgtat tggtggagaa agacggtgga aagatggaaa gccaagtaga tatgcaattc  20340
ttttcgactt ctgaaaacgc ccgtaacgag gctaacaaca ttcagcccaa attggtgctg  20400
tacagcgagg atgtgcatat ggagacccca gacacacaca tttcttacaa gcctgcaaaa  20460
agcgatgata attcgaaagt catgctgggt cagcagtcca tgcccaacag gccaaattac  20520
atcggcttca gagacaactt tatcgggctc atgtattaca acagcactgg caacatgggg  20580
gtgctggcag gtcaggcctc acagttgaat gcggtggtgg acttgcaaga cagaaacaca  20640
gaactgtcct accagctctt gcttgattcc atgggagaca gaaccagata cttttccatg  20700
tggaatcagg cggtggacag ttatgatcca gatgtcagaa ttattgaaaa tcatggaact  20760
gaagatgagc tgcccaacta ttgtttccct ctgggaggca taggggtaac tgacacttac  20820
caggccatta agactaatgg caatggcaac ggcgggggca ataccacttg gaccaaggat  20880
gaaacttttg cagaccgcaa cgagataggg gtgggaaaca atttcgccat ggagatcaac  20940
ctcagtgcca acctgtggag gaacttcctc tactccaacg tggccctgta cctgccagac  21000
aagcttaagt acaacccctc caacgtggaa atctctgaca accccaacac ctacgactac  21060
atgaacaagc gagtggtggc cccggggctg gtggactgct acatcaacct gggcgcgcgc  21120
```

```
tggtccctgg actacatgga caacgtcaac cccttcaacc accaccgcaa cgcgggcctg  21180
cgctaccgct ccatgcttct gggcaacggg cgctacgtgc ccttccacat ccaggtgccc  21240
cagaagttct ttgccatcaa gaacctcctc ctcctgccgg gctcctacac ctacgagtgg  21300
aacttcagga aggatgtcaa catggtcctc cagagctctc tgggtaacga cctcagggtc  21360
gacggggcca gcatcaagtt cgagagcatc tgcctctacg ccaccttctt ccccatggcc  21420
cacaacacgg cctccacgct cgaggccatg ctcaggaacg acaccaacga ccagtccttc  21480
aacgactacc tctccgccgc caacatgctc taccccatcc ccgccaacgc caccaacgtt  21540
cccatctcca tcccctcgcg caactgggcg gccttccgcg gctgggcctt cacccgcctc  21600
aagaccaagg agacccccctc cctgggctcg ggtttcgacc cctactacac ctactcgggc  21660
tccataccct acctggacgg aaccttctac ctcaaccaca ctttcaagaa ggtctcggtc  21720
accttcgact cctcggtcag ctggccgggc aacgatcgcc tgctcacccc caacgagttc  21780
gagatcaagc gctcggtcga cggggagggc tacaacgtgg cccagtgcaa catgaccaag  21840
gactggttcc tcatccaaat gctggccaac tacaacatcg gctatcaggg cttctacatc  21900
ccagagagct acaaggacag gatgtactcc ttctttagga acttccagcc catgagccgg  21960
caggtggtgg acgaaaccaa gtacaaggac taccagcagg tgggcatcat ccaccagcac  22020
aacaactcgg gcttcgtggg ctacctcgcc cccaccatgc gcgagggaca ggcctacccc  22080
gccaacttcc cctacccgct cattggcaag accgcggtcg acagcgtcac ccagaaaaag  22140
ttcctctgcg accgcaccct ctggcgcatc cccttctcca gcaacttcat gtccatgggt  22200
gcgctcacgg acctgggcca gaacctgctc tatgccaact ccgcccacgc gctcgacatg  22260
accttcgagg tcgaccccat ggacgagccc acccttctct atgttctgtt cgaagtcttt  22320
gacgtggtcc gggtccacca gccgcaccgc ggcgtcatcg agaccgtgta cctgcgcacg  22380
cccttctcgg ccggcaacgc caccacctaa agaagcaagc cgccaccgcc accacctgca  22440
tgtcgtcggg ttccaccgag caggagctca aggccatcgt cagagacctg ggatgcgggc  22500
cctatttttt gggcaccttc gacaaacgct tcccgggctt cgtcgccccg cacaagctgg  22560
cctgcgccat cgtcaacacg gccggccgcg agaccggggg cgtgcactgg ctggccttcg  22620
cctggaaccc gcgctccaaa acatgctacc tctttgaccc cttcggattc tcggaccagc  22680
ggctcaagca gatctaccag ttcgagtacg agggcctgct gcgccgcagc gccatcgcct  22740
cctcgcccga ccgctgcgtc accctcgaga agtccaccca gaccgtgcag gggcccgact  22800
cggccgcctg cggtctcttc tgctgcatgt tcctgcatgc ctttgtgcac tggccccaga  22860
gtcccatgga ccgcaacccc accatgaact tgctgacggg gatccccaac tccatgctcc  22920
agagccccca ggtcgcgccc accctgcgcc gcaaccagga gcggctctac agcttcctgg  22980
aacgccactc gccctacttc cgccgccaca gcgcgcagat caggggggcc acctctttct  23040
gccgcatgca agagatgcaa gggaaaatgc aatgatgtac acagacactt tttcttttct  23100
caataaatgg caactttatt tatacatgct ctctctcggg tattcatttc cccaccaccc  23160
accacccgcc gccgccgtaa ccatctgctg ctggcttttt tttttttttt taaaaatcga  23220
aagggttctg ccgggaatcg ccgtgcgcca cgggcaggga cacgttgcgg aactggtagc  23280
gggtgcccca cttgaactcg ggcaccacca tgcggggcaa gtcggggaag ttgtcggccc  23340
acaggctgcg ggtcagcacc agcgcgttca ttaggtcggg cgccgagatc ttgaagtcgc  23400
agttggggcc gccgccctgc gcgcgcgagt tgcggtacac cgggttgcaa cactggaaca  23460
```

```
ccagcagcgc cggataattc acactggcca gcacgctccg gtcggagatc agctcggcgt  23520
ccaggtcctc cgcgttgctc agcgcgaacg gggtcagctt gggcacctgc cgccccagga  23580
agggagcgtg ccccggcttc gagttgcagt cgcagcgcag cgggatcagc aggtgcccgc  23640
ggccggactc ggcgttgggg tacagcgcgc gcatgaaggc ctccatctgg cggaaggcca  23700
tctgggcctt ggcgccctcc gagaagaaca tgccgcagga cttgcccgag aactggttcg  23760
cggggcagct agcgtcgtgc aggcagcagc gcgcgtcggt gttggcgatc tgcaccacgt  23820
tgcgcccccca ccggttcttc acgattttgg ccttggaagc ctgctccttc agcgcgcgct  23880
gcccgttctc gctggtcaca tccatctcga tcacgtgctc cttgttcacc atgctgctgc  23940
cgtgcagaca cttcagctcg ccctccacct cggtgcagcg gtgctgccat agcgcgcagc  24000
ccgtgggctc gaaatgcttg taggtcacct ccgcgtagga ctgcaggtag gcctgcagga  24060
agcgccccat catggtcacg aaggtcttgt tgctgctgaa ggtcagctgc agcccgcggt  24120
gctcctcgtt cagccaggcc ttgcacacgg ccgccagcgc ctccacctgg tcgggcagca  24180
tcttgaagtt cagcttcagc tcattctcca catggtactt gtccatcagc gcgcgcgcag  24240
cctccatgcc cttctcccag gccgacacca gcggcaggct caaggggttc accaccgtcg  24300
cagccgccgc tgcgctttcg ctttccgctc cgctgttctc ttcttcctcc tcctcttctt  24360
cctcgccgcc cgcgcgcagc ccccgcacca cggggtcgtc ttcctgcagg cgccgcaccg  24420
agcgcttgcc gctcctgccc tgcttgatac gcacgggcgg gttgctgaag cctaccatca  24480
ccagcgcggc ctcttcttgc tcgtcctcgc tgtccactat gacctcgggg gagggcgacc  24540
tcagaaccgt ggcgcgctgc ctcttctttt tcctgggggc gtttgccagc tccgcggccg  24600
cggccgccgc cgaggtcgaa ggccgagggc tgggcgtgcg cggcaccagc gcgtcctgcg  24660
agccgtcctc gtcctcggac tcgaggcggc agcgagcccg cttcttcggg ggcgcgcggg  24720
gcggcggcgg cgggggcggc ggcgacggag acggggacga gacatcgtcc agggtgggag  24780
gacggcgggc cgcgccgcgt ccgcgctcgg gggtggtttc gcgctggtcc tcttcccgac  24840
tggccatctc ccactgctcc ttctcctata ggcagaaaga gatcatggag tctctcatgc  24900
aagtcgagaa ggaggaggac agcctaacca ccaccgcccc ctctgagccc tccgccgccg  24960
ccgcggacga cgcgcccacc accaccgccg ccgccaccac caccattacc accctacccg  25020
gcgacgcagc cccgatcgag aaggaagtgt tgatcgagca ggacccgggt tttgtgagcg  25080
aagaggagga tgaggaggat gaaaaggaga aggataccgc cgcctcagtg ccaaaaagag  25140
ataaaaagca agaccaggac gacgcagaga cagatgaggc agcagtcggg cgggggggacg  25200
gaaggcatga tgatgatgac ggctacctag acgtgggaga cgacgtgctg cttaagcacc  25260
tgcaccgcca gtgcgtcatc gtctgcgacg cgctgcagga gcgctgcgaa gtgcccctgg  25320
acgtggcgga ggtcagccgc gcctacgagc ggcacctctt cgcgccacac gtgcccccca  25380
agcgccggga gaacggcacc tgcgagccca acccgcgcct caacttctac ccggtcttcg  25440
cggtacccga ggtgctggcc acctaccaca tcttcttcca aaactgcaag atccccctct  25500
cctgccgcgc caaccgcacc cgcgccgaca agacgctggc cctgcggcag ggcgcccaca  25560
tacctgatat cgcctctctg gaggaggtgc ccaagatctt cgagggtctc ggtcgcgacg  25620
agaaacgggc ggcgaacgct ctgcaaggag acagcgaaaa cgagagtcac tcgggggtgc  25680
tggtggagct cgagggcgac aacgcgcgcc tggccgtgct caagcgcagc atcgaagtca  25740
cccacttcgc ctacccggcg ctcaacctgc cccccaaggt catgagtgtg gtcatgagtg  25800
agctcatcat gcgccgcgcc cagcccctgg acgcggatgc aaacttgcaa gagccctccg  25860
```

-continued

```
aggaaggcct gcccgcggtc agcgacgagc agctggcgcg ctggctggag acccgcgacc  25920
ccgcccagct ggaggagcgg cgcaagctca tgatggccgc ggtgctcgtc accgtggagc  25980
tcgagtgtct gcagcgcttc ttcggggacc ccgagatgca gcgcaagctc gaggagaccc  26040
tgcactacac cttccgccag ggctacgtgc gccaggcctg caagatctcc aacgtggagc  26100
tctgcaacct ggtctcctac ctgggcatcc tgcacgagaa ccgcctcggg cagaacgtcc  26160
tgcactccac cctcaaaggg gaggcgcgcc gcgactacgt ccgcgactgc gtctacctct  26220
tcctctgcta cacgtggcag acggccatgg gggtctggca gcagtgcctg gaggagcgca  26280
acctcaagga gctggagaag ctcctccggc gcgccctcag ggacctctgg acgggcttca  26340
acgagcgctc ggtggccgcc gcgctggcgg acatcatctt ccccgagcgc ctgctcaaaa  26400
ccctgcagca gggcctgccc gacttcacca gccagagcat gctgcagaac ttcaggacct  26460
tcatcctgga gcgctcgggc atcctgccgg ccacctgctg cgcgctgccc agcgacttcg  26520
tgcccatcag gtacagggag tgcccgccgc cgctctgggg ccactgctac ctcttccagc  26580
tggccaacta cctcgcctac cactcggatc tcatggaaga cgtgagcggc gagggcctgc  26640
tcgagtgcca ctgccgctgc aacctgtgca cgcccccaccg ctctctagtc tgcaatccgc  26700
agctgctcag cgagagtcag attatcggta ccttcgagct gcagggtccc tcgcccgacg  26760
aaaagtccgc ggctccgggg ttgaaactca ctccggggct gtggacttcc gcctacctac  26820
gcaaatttgt acctgaagac taccacgccc acgagatcag gttttacgaa gaccaatccc  26880
gcccgcccaa ggcggagctc accgcctgcg tcattaccca gggccacatc ctgggccaat  26940
tgcaagccat caacaaagcc cgccaagagt tcttgctgaa aaagggtcgg ggggtgtacc  27000
tggaccccca gtccggcgag gagctaaacc cgctaccccc gccgccgccc cagcagcggg  27060
accttgcttc ccaggatggc acccagaaag aagcagccgc cgccgccgcc agcatacatg  27120
cttctggagg aagaggagga ctgggacagt caggcagagg aggtttcgga cgaggacgag  27180
gaggaggaga tgatggaaga ctgggaggag gacagcctag acgaggaagc ttcagaggcc  27240
gaagaggtgg cagacgcaac accatcaccc tcggccgcag cccccctcgcc ggcgcccccg  27300
aaatcctccg accccagcag cagcgctata acctccgctc ctccggcgcc ggcgcccacc  27360
cgcagcagac ccaaccgtag atgggacact acaggaaccg gggtcggtaa gtccaagtgc  27420
cccccagcgc cgcccccgca acaggagcaa cagcagcagc agcggcgaca gggctaccgc  27480
tcgtggcgcg gacacaagaa cgccatagtc gcctgcttgc aagactgcgg gggcaacatc  27540
tccttcgccc gccgcttcct gctcttccac cacggggtgg cttttccccg caatgtcctg  27600
cattactacc gtcatctcta cagcccctac tgcggcggca gcggcgaccc agagggagcg  27660
gcggcagcag cagcgccagc cacagcggcg accacctagg aagacctccg cgggcaagac  27720
ggcgggagcc gggagacccg cggcggcggc ggtagcggcg gcggcgggcg cactgcgcct  27780
ctcgcccaac gaacccctct cgacccggga gctcagacac aggatcttcc ccactctgta  27840
tgctatcttc cagcagagca gaggccagga acaggagctc aaaataaaaa acagatctct  27900
gcgctccctc acccgcagct gtctgtatca caaaagcgaa gatcagcttc ggcgcacgct  27960
ggaggacgcg gaggcactct tcagcaaata ctgcgcgctg actcttaagg actagccgcg  28020
cgcccttctc gaatttaggc gggagaaaga ctacgtcatc gccgaccgcc gcccagccca  28080
cccagccgac atgagcaaag agattcccac gccctacatg tggagctacc agccgcagat  28140
gggactcgcg gcgggagcgg cccaagacta ctccacccgc atgaactaca tgagcgcggg  28200
```

gccccacatg atctcacggg ttaatgggat ccgcgcccag cgaaaccaaa tactgctgga 28260
acaggcggcc ataaccgcca caccccgtca tgacctcaat ccccgaaatt ggcccgccgc 28320
cctcgtgtac caggaaaccc cctctgccac caccgtggta cttccgcgtg acacccaggc 28380
cgaagtccag atgactaact caggggcgca gctcgcgggc ggctttcgtc acggggtgcg 28440
gccgcaccgg ccgggtatat tacacctggc gatcagaggc cgaggtattc agctcaacga 28500
cgagtcggtg agctcttcgc tcggtctccg tccggacgga accttccaga tcgccggatc 28560
aggtcgctcc tcattcacgc ctcgccaggc gtatctgact ctgcagacct cctcctcgga 28620
gcctcgctcc ggcggcatcg gcaccctcca gttcgtggag gagttcgtgc cctcggtcta 28680
cttcaacccc ttctcgggac ctcccggacg ctaccccgac cagttcatcc cgaactttga 28740
cgcggtgaag gactcggcgg acggctacga ctgaatgtca agtgctgagg cagagagcgt 28800
tcgcctgaaa cacctccagc actgccgccg cttcgcctgc tttgcccgca gctccggtga 28860
gttctgctac tttcagctgc ccgaggagca taccgaaggg ccggcgcacg gcgtccgcct 28920
aaccacccag ggcgaggtta cctgtaccct tatccgggag tttaccctcc gtcccctgct 28980
agtggagcgg gagcggggtt cttgtgtcat aactatcgcc tgcaactgcc ctaaccctgg 29040
attacatcaa gatctttgtt gtcacctgtg cgctgagtat aataaacgct gagatcagac 29100
tctactgggg ctcctgtcgc catcctgtga acgccaccgt cttcacccac cccgagcagc 29160
cccaggcgaa cctcacctgc ggcctgcgtc ggagggccaa gaagtacctc acctggtact 29220
tcaacggcac cccctttgtg gtttacaaca gcttcgacca ggacggagtt gccttgagag 29280
acgacctttc cggtctcagc tactccattc acaagaacac caccctccac ctcttccctc 29340
cctacctgcc gggaacctac gagtgcgtca ccggccgctg cacccacctc ctccgcctga 29400
tcgtaaacca gacctttccg ggaacacacc tcttccccag aacaggaggt gagctcagga 29460
aacccccctgg ggcccagggc ggagacttac cttcgaccct tgtggggtta ggattttta 29520
tcgccgggtt gctggctctc ctgatcaaag cttccttcag atttgttctc tccctttact 29580
tttatgaaca gctcaacttc taataacgct accttttctc aggaatcgag tagtaacttc 29640
tcttccgaaa tcgggctggg tgtgctgctt actctgttga tttttttcct tatcatactt 29700
agccttctgt gcctcaggct cgccgcctgc tgcgcacata tctacatcta cagccggttg 29760
cttaactgct ggggtcgcca tccaagatga acggggctca ggtgctatgt ctgctggccc 29820
tggtggcctg cagtgccgcc gtcaattttg aggaacccgc ttgcaatgtg actttcaagc 29880
ctgagggcgc acattgcacc actctggtta aatgtgtgac ctctcatgaa aaactgctca 29940
tcgcctacaa aaacaaaaca ggccagatcg cagtctatag cgagtggcta cccggagacc 30000
ataataacta ctcagtcacc gtcttcgagg gtgcggagtc taagaaattc gattacacct 30060
ttcccttcga ggagatgtgt gatgcggtca tgtacctgtc caaacagtac aagctgtggc 30120
cccccacccc caaggcgtgt gtggaaaaca ctgggtcttt ctgctgtctc tctctggcaa 30180
tcactgtgct tgctctaatc tgcacgctgc tatacatgag attcaggcag aggcgaatct 30240
ttatcgatga gaaaaaaatg ccttgatcgc taacaccggc tttctgtctg cagaatgaaa 30300
gcaatcacct ccctactaat cagcaccacc ctccttgcga ttgcccatgg gttgacacga 30360
atcgaagtgc cagtggggtc caatgtcacc atggtgggcc ccgccggcaa ttcctccctg 30420
atgtgggaaa aatatgtccg taatcaatgg gatcattact gctctaatcg aatctgtatc 30480
aagcccagag ccacctgcga cgggcaaaat ctaactttga ttgatgtgca aatgacggat 30540
gctgggtact attacgggca gcggggagaa atgattaatt actggcgacc ccacaaggac 30600
tacatgctgc atgtagtcaa ggcagtccca actactacca cccccaccac taccactccc 30660
actaccacca cccccaccac taccactagc actgctacta ccgctgcccg caaagctatt 30720
acccgcaaaa gcaccatgct tagcaccaag ccccattctc actcccacgc cggcgggccc 30780
accggtgcgg cctcagaaac caccgagctt tgcttctgcc aatgcactaa cgccagcgcc 30840
cacgaactgt tcgacctgga gaatgaggac gatgaccagc tgagctccgc ttgcccggtc 30900
ccgctgcccg cagagccggt cgccctgaag cagctcggtg atccatttaa tgactctcct 30960
gtttatccct ctcccgaata ccctcccgac tctaccttcc acatcacggg caccaaagac 31020
cccaacctct ccttctacct gatgctgctg ctctgtatct ctgtggtatc ttccgcgctc 31080
atgttactgg gcatgttctg ctgcctcatc tgccgcagaa aaagaaagtc tcgctctcag 31140
ggccaaccac tgatgccctt cccctacccc ccagattttg cagataacaa gatatgagca 31200
cgctgctgac actaaccgct ttactcgcct gcgctctaac ccttgtcgct tgcgaatcca 31260
gataccacaa tgtcacagtt gtgacaggag aaaatgttac attcaactcc acggccgaca 31320
cccagtggtc gtggagtggc cacggtagct atgtatacat ctgcaatagc tccacctccc 31380
ctagcatgtc ctctcccaag taccactgca atgacagcct gttcaccctc atcaacgcct 31440
ccacctcgga caatggactc tatgtaggct atgtgacacc cggtgggcag ggaaagaccc 31500
acgcctacaa cctgcaagtt cgccacccct ccaccaccgc caccacctct gccgccccta 31560
cccgcagcag cagcagcagc agcagcagca gcagcagcag cagcagcaga ttcctgactt 31620
taatcctagc cagctcaaca accaccgcca ccgctgagac cacccacagc tccgcgcccg 31680
aaaccaccca cacccaccac ccagagacga ccgcggcctc cagcgaccag atgtcggcca 31740
acatcaccgc ctcgggtctt gaacttgctt caacccccac cccaaaacca gtggatgcag 31800
ccgacgtctc cgccctcgtc aatgactggg cggggctggg aatgtggtgg ttcgccatag 31860
gcatgatggc gctctgcctg cttctgctct ggctcatctg ctgcctcaac cgcaggcggg 31920
ccagacccat ctatagaccc atcattgttc tcaaccccgc tgatgatggg atccatagat 31980
tggatggtct gaaaaaccta cttttctctt ttacagtatg ataaattgag acatgcctcg 32040
cattttcatg tacttgacac ttctcccact tttctgggg tgttctacgc tggccgccgt 32100
ctctcacctc gaggtagact gcctcacacc cttcactgtc tacctgattt acggattggt 32160
caccctcact ctcatctgca gcctaatcac agtagtcatc gccttcatcc agtgcattga 32220
ctacatctgt gtgcgcctcg catacctgag acaccacccg cagtaccgag acaggaacat 32280
tgcccaactc ctaagactgc tctaatcatg cataagactg tgatctgcct cctcatcctc 32340
ctctccctgc ccgctctcgt ctcatgccag cccaccacaa aacctccacg aaaaagacat 32400
gcctcctgtc gcttgagcca actgtggaat attcccaaat gctacaatga aaagagcgag 32460
ctttccgaag cctggctata tgcggtcatg tgtgtccttg tcttctgcag cacaatcttt 32520
gccctcatga tctaccccca ctttgatttg ggatggaatg cggtcgatgc catgaattac 32580
cctacctttc ccgcgcccga tatgattcca ctccgacagg ttgtggtgcc cgtcgccctc 32640
aatcaacgcc ccccatcccc tacacccact gaggtcagct actttaatct aacaggcgga 32700
gatgactgac actctagatc tagaaatgga cggcatcggc accgagcagc gtctcctaca 32760
gaggcgcaag caggcggctg aacaagagcg cctcaatcag gagctccgag atctcattaa 32820
cctgcaccag tgcaaaaaag gcatcttttg cctggtcaag caggccgatg tcacctacga 32880
gaaaaccggt aacagccacc gcctcagcta caagctgccc acccaacgcc agaagttggt 32940
gctcatggtg ggtcagaatc ccatcaccgt cacccagcac tcggtggaga ccgaggggtg 33000
tctgcactcc ccctgtcagg gtccggaaga cctctgcacc ctggtaaaga ccctgtgtgg 33060
tcttagagat ttaatcccct ttaactaatc aaacactgga atcaataaaa agaatcactt 33120
actttaaatc agtcagcagg tctctgtcca ctttattcag cagcacctcc ttcccctcct 33180
cccaactctg gtactccaaa cgcctcctgg cggcaaactt cctccacacc ctgaagggaa 33240
tgtcagattc ttgctcctgt ccctccgcac ccactatctt catgttgttg cagatgaagc 33300
gcgccaaaac gtctgacgag accttcaacc ccgtgtaccc ctatgacacg gaaaacgggc 33360
ctccctccgt tcctttcctc acccctccct tcgtgtcccc cgacggattt caagaaagcc 33420
ccccaggggt cctgtctctg cgcctgtcag agcccctggt cacttcccac ggcatgcttg 33480
ccctgaaaat gggaaatggc ctctccctgg atgacgccgg caacctcacc tctcaagatg 33540
tcaccaccgt cacccctccc ctcaaaaaaa ccaagaccaa cctcagcctc cagacctcag 33600
cccccctgac cgttagctct gggtccctca ccgtcgcggc cgccgctcca ctggcggtgg 33660
ccggcacctc tctcaccatg caatctcagg cccccttgac ggtgcaagat gcaaaactgg 33720
gtctggccac ccagggaccc ctgaccgtgt ctgaaggcaa actcaccttg cagacatcgg 33780
ctccactgac ggccgccgac agcagcactc tcactgttgg caccacaccg ccaatcagtg 33840
tgagcagtgg aagtctaggc ttagatatgg aagaccccat gtatactcac gatggaaaac 33900
tgggaatcag aattggtggc ccactgcaag tagtagacag cttgcacaca ctcactgtag 33960
ttactggaaa cggaataact gtagctaaca atgcccttca aactaaagtt gcgggtgccc 34020
tgggttatga ctcatctggc aatctagaat tgcgagccgc aggggggtatg cgaattaaca 34080 caggggggtca actcattctt gatgtggctt atccatttga tgctcagaac aatctcagcc 34140
ttagactcgg ccagggacct ttatatgtga acaccaatca caacctagat ttaaattgca 34200
acagaggtct gaccacaacc accagcagta acacaaccaa acttgaaact aaaatcgatt 34260
cgggcttaga ctataacgcc aatggggcta tcattgctaa acttggcact gggttaacct 34320
ttgacaacac aggtgccata actgtgggaa acactgggga tgacaaactc actctgtgga 34380
ctaccccaga tccctctcct aactgcagaa ttcacgcaga caaagactgc aagtttactc 34440
tagtcctgac taagtgtgga agtcaaattc tggcctccgt cgccgccctg gcggtgtctg 34500
gaaacctatc atcaatgaca ggcactgtct ccagcgttac catctttctc agattcgatc 34560
agaatggagt tcttatggaa aattcctcgc tagacaagga gtactggaac ttcagaaatg 34620
gtaattccac caatgccacc ccctacacca atgcggttgg gttcatgccc aacctcagcg 34680
cctaccccaa aacccagagt caaactgcaa aaaacaacat tgtaagtgag gtttacttac 34740
atggggacaa atctaaaccc atgatcctta ccattaccct taatggcaca aatgaatcca 34800
gtgaaactag tcaggtgagt cactactcca tgtcatttac atggtcgagg gacagtggga 34860
aatatgccac cgaaaccttt gccaccaact cttttacctt ctcctacatt gctgaacaat 34920
aaagaagcat aacgctgctg ttcatttgta atcaagtgtt actttttttat ttttcaatta 34980 caacagaatc attcaagtca ttctccattt agcttaatag accccagtag tgcaaagccc 35040
catactagct tatttcagca attgggagaa gtactcgcct acatgggggt agagtcataa 35100
tcgtgcatca ggatagggcg gtggtgctgc agcagcgcgc gaataaactg ctgccgccgc 35160
cgctccgtcc tgcaggaata caacatggca gtggtctcct cagcgatgat tcgcaccgcc 35220
cgcagcataa ggcgccttgt cctccgggca cagcagcgca ccctgatctc acttaaatca 35280
gcacagtaac tgcagcacag caccacaata ttgttcaaaa tcccacagtg caaggcgctg 35340
tatccaaagc tcatggcggg gaccacagaa cccacgtggc catcatacca caagcgcagg 35400
tagattaagt ggcgacccct cataaacacg ctggacataa acattacctc ttttggcatg 35460
ttgtaattca ccacctcccg gtaccatata aacctctgat taaacatggc gccatccacc 35520
accatcctaa accagctggc caaaacctgc ccgccggcta tacactgcag ggaaccggga 35580
ctggaacaat gacagtggag agcccaggac tcgtaaccat ggatcatcat gctcgtcatg 35640
atatcaatgt tggcacaaca caggcacacg tgcatacact tcctcaggat tacaagctcc 35700
tcccgcgtta gaaccatatc ccagggaaca acccattcct gaatcagcgt aaatcccaca 35760
ctgcagggaa gacctcgcac gtaactcacg ttgtgcattg tcaaagtgtt acattcgggc 35820
agcagcggat gatcctccag tatggtagcg cgggtttctg tctcaaaagg aggtagacga 35880
tccctactgt acggagtgcg ccgagacaac cgagatcgtg ttggtcgtag tgtcatgcca 35940
aatggaacgc cggacgtagt catatttcct gaagtcttgg cgcgccagac ccgagtctta 36000
ccaggaaaat tttaaaaaag attcctcaac gcagcaccag caccaacacc tgtcagtgta 36060
aaatgccaag cgccgagcga gtatatatag gaataaaaag tgacgtaaac ggttaaagtc 36120
cagaaaacgc ccagaaaaac cgcacgcgaa cctacgcccc gaaacgaaag ccaaaaaaca 36180
gtgaacacgc cctttcggcg tcaacttccg ctttcccacg gtacgtcact tccgcatata 36240
gtaaaactac gctacccaac atgcaagaag ccacgcccca aaacacgtca cacctcccgg 36300
cccgccccgc gccgccgctc ctccccgccc cgccccgctc cgcccacctc attatcatat 36360
tggcttcaat ccaaaataag gtatattatt gatgatg 36397

<210> SEQ ID NO 9
<211> LENGTH: 36445
<212> TYPE: DNA
<213> ORGANISM: Artificial Sequence
<220> FEATURE:
<223> OTHER INFORMATION: synthetic chimpanzee adenovirus serotype PanAd3
with Marburg virus Angola codon optimized
transmembrane envelope glycoprotein (GP) insert
(PanAd3 GP Marburg (PB/6712))
<220> FEATURE:
<221> NAME/KEY: CDS
<222> LOCATION: (1656)...(3698)
<223> OTHER INFORMATION: Marburg virus Angola codon optimized
transmembrane envelope glycoprotein (GP) insert in PanAd3 GP
Marburg (PB/6712)
<220> FEATURE:
<221> NAME/KEY: CDS
<222> LOCATION: (14719)...(16473)
<223> OTHER INFORMATION: chimpanzee adenovirus serotype ChAd63 penton
<220> FEATURE:
<221> NAME/KEY: CDS
<222> LOCATION: (19564)...(22458)
<223> OTHER INFORMATION: chimpanzee adenovirus serotype ChAd63 hexon
<220> FEATURE:
<221> NAME/KEY: CDS
<222> LOCATION: (33342)...(34970)
<223> OTHER INFORMATION: chimpanzee adenovirus serotype ChAd63 fiber

<400> SEQUENCE: 9
catcatcaat aatatacctt attttggatt gaagccaata tgataatgag gtgggcggag 60
cggggcgggg cggggaggag cggcggcgcg gggcgggccg ggaggtgtgg cggaagttga 120
gtttgtaagt gtggcggatg tgacttgcta gcgccggatg tggtaaaagt gacgtttttt 180
ggagtgcgac aacgcccacg ggaagtgaca tttttcccgc ggtttttacc ggatgtcgta 240
gtgaatttgg gcgttaccaa gtaagatttg gccattttcg cgggaaaact gaaatgggga 300
agtgaaatct gattaatttc gcgttagtca taccgcgtaa tatttgccga gggccgaggg 360

-continued

```
actttgaccg attacgtgga ggaatcgccc aggtgttttt tgaggtgaat ttccgcgttc    420
cgggtcaaag tctccgtttt attattatag gtatacccat tgcatacgtt gtatccatat    480
cataatatgt acatttatat tggctcatgt ccaacattac cgccatgttg acattgatta    540
ttgactagtt attaatagta atcaattacg gggtcattag ttcatagccc atatatggag    600
ttccgcgtta cataacttac ggtaaatggc ccgcctggct gaccgcccaa cgacccccgc    660
ccattgacgt caataatgac gtatgttccc atagtaacgc caatagggac tttccattga    720
cgtcaatggg tggagtattt acggtaaact gcccacttgg cagtacatca agtgtatcat    780
atgccaagta cgccccctat tgacgtcaat gacggtaaat ggcccgcctg gcattatgcc    840
cagtacatga ccttatggga ctttcctact tggcagtaca tctacgtatt agtcatcgct    900
attaccatgg tgatgcggtt ttggcagtac atcaatgggc gtggatagcg gtttgactca    960
cggggatttc caagtctcca ccccattgac gtcaatggga gtttgttttg gaaccaaaat   1020
caacgggact ttccaaaatg tcgtaacaac tccgccccat tgacgcaaat gggcggtagg   1080
cgtgtacggt gggaggtcta tataagcaga gctctcccta tcagtgatag agatctccct   1140
atcagtgata gagatcgtcg acgagctcgt ttagtgaacc gtcagatcgc ctggagacgc   1200
catccacgct gttttgacct ccatagaaga caccgggacc gatccagcct ccatcggctc   1260
gcatctctcc ttcacgcgcc cgccgcccta cctgaggccg ccatccacgc cggttgagtc   1320
gcgttctgcc gcctcccgcc tgtggtgcct cctgaactgc gtccgccgtc taggtaagtt   1380
taaagctcag gtcgagaccg ggcctttgtc cggcgctccc ttggagccta cctagactca   1440
gccggctctc cacgctttgc ctgaccctgc ttgctcaact ctagttaacg gtggagggca   1500
gtgtagtctg agcagtactc gttgctgccg cgcgcgccac cagacataat agctgacaga   1560
ctaacagact gttcctttcc atgggtcttt tctgcagtca ccgtcgtcga cacgtgtgat   1620
cagatatcgc ggccgctcta gagatatcgg ccgccatgaa gaccacctgc ctgctgatca   1680
gcctgatcct gatccagggc gtgaagaccc tgcccatcct ggagatcgcc agcaacatcc   1740
agccccagaa cgtggacagc gtgtgcagcg gcaccctgca gaagaccgag gacgtgcacc   1800
tgatgggctt caccctgagc ggccagaagg tggccgacag ccctctggag gccagcaaga   1860
ggtgggcctt cagggccggc gtgcccccca agaacgtgga gtacaccgag ggcgaggagg   1920
ccaagacctg ctacaacatc agcgtgaccg accccagcgg caagagcctg ctgctggacc   1980
ctcccaccaa catcagggac taccctaagt gcaagaccat ccaccacatc cagggccaga   2040
accctcacgc ccagggcatc gccctgcacc tgtggggcgc cttcttcctg tacgacagga   2100
tcgccagcac caccatgtac agaggaaaag tgttcacaga gggaaacatc gctgctatga   2160
tcgtgaacaa gaccgtgcat aagatgatct tcagcagaca gggacaggga tatagacata   2220
tgaacctgac atccacaaac aagtactgga caagcagcaa cggaacacag acaaacgata   2280
caggatgttt tggaacactg caggaataca actccaccaa gaaccagaca tgtgccccta   2340
gcaagaagcc tctgcctctg cctacagctc atcctgaagt gaagctgaca tccacaagca   2400
cagatgccac aaagctgaac acaacagatc ctaatagcga cgacgaggat ctgacaacaa   2460
gcggatccgg atccggagaa caggaacctt atacaacaag cgacgctgct acaaaacagg   2520
gactgtcctc cacaatgcct cctacaccta gccctcagcc tagcacacct cagcagggag   2580
gcaacaacac aaaccattcc cagggagtgg tgacagaacc tggaaagaca aacacaacag   2640
cccagcctag catgcctcct cataacacaa caacaatcag cacaaacaac acctccaagc   2700
```

-continued

```
acaatctgag cacacctagc gtgcctattc agaatgccac caactacaac acacagtcca   2760
cagcccctga aaacgaacag acctccgccc cttccaaaac aaccctgctg cctacagaaa   2820
accctacaac agccaagagc acaaacagca caaagagccc tacaacaaca gtgcctaaca   2880
caacaaacaa gtatagcaca agccctagcc ctacacctaa ttccacagct cagcatctgg   2940
tgtattttag aagaaagaga aacatcctgt ggagagaagg agatatgttc ccttttctgg   3000
atggactgat caacgctcct atcgattttg atcctgtgcc taacacaaag acaatctttg   3060
atgaaagcag cagcagcgga gcctccgccg aagaagatca gcatgcctcc cctaacatca   3120
gcctgacact gagctatttt cctaaggtga acgaaaacac agcccattcc ggagaaaacg   3180
aaaacgattg tgatgccgaa ctgagaatct ggagcgtgca ggaagatgat ctggccgccg   3240
gactgagctg gatccctttt tttgggcccg gaattgaagg actgtacacc gccggcctga   3300
tcaagaacca gaacaacctg gtgtgcaggc tgaggaggct ggccaaccag accgccaaga   3360
gcctggagct gctgctgagg gtgaccaccg aggagaggac cttcagcctg atcaacaggc   3420
acgccatcga cttcctgctg gctaggtggg gcggcacctg caaggtgctg ggccccgact   3480
gctgcatcgg catcgaggac ctgagcagga acatcagcga gcagatcgac cagatcaaga   3540
aggacgagca gaaggagggc accggctggg gcctgggcgg caagtggtgg accagcgact   3600
ggggagtgct gacaaacctg ggaatcctgc tgctgctgag cattgccgtg ctcattgctc   3660
tgtcctgtat ctgtagaatc tttaccaagt acatcggatg atagatccag atctgctgtg   3720
ccttctagtt gccagccatc tgttgtttgc ccctcccccg tgccttcctt gaccctggaa   3780
ggtgccactc ccactgtcct ttcctaataa aatgaggaaa ttgcatcgca ttgtctgagt   3840
aggtgtcatt ctattctggg gggtggggtg gggcaggaca gcaaggggga ggattgggaa   3900
gacaatagca ggcatgctgg ggatgcggtg ggctctagat atcagcgatc gctgaggtgg   3960
gtgagtgggc gtggtctggg ggtgggaagc aatatataag ttgggggtct tagggtctct   4020
gtgtctgttt tgcagaggga ccgccggcgc catgagcggg agcagtagca gcaacgcctt   4080
ggatggcagc atcgtgagcc cttatttgac gacgcgcatg ccccactggg ccggggtgcg   4140
tcagaatgtg atgggctcca gcatcgacgg acgacccgtg ctgcccgcaa attccgccac   4200
gctgacctac gcgaccgtcg cggggacccc gttggacgcc accgccgccg ccgccgccac   4260
cgccgccgcc tcggccgtgc gcagcctggc cacggacttt gcattcttgg gacccttggc   4320
caccggggcg gccgcccgtg ccgccgttcg cgatgacaag ctgaccgccc tgctggcgca   4380
gttggatgcg cttacccggg aactgggtga cctttcgcag caggtcgtgg ccctgcgcca   4440
gcaggtctcc gccctgcagg ctagcgggaa tgcttctcct gcaaatgccg tttaagataa   4500
ataaaaccag actctgttga taaataaaac cagactctgt ttggattaaa gaaaagtagc   4560
aagtgcattg ctctctttat ttcataattt tccgcgcgcg ataggcccga gtccagcgtt   4620
ctcggtcgtt gagggtgcgg tgtatcttct ccaggacgtg gtagaggtgg ctctggacgt   4680
tgagatacat gggcatgagc ccgtcccggg ggtggaggta gcaccactgc agagcttcat   4740
gctccggggt ggtgttgtag atgatccagt cgtagcagga gcgctgggca tggtgcctaa   4800
aaatgtcctt aagcagcagg ccgatggcca gggggaggcc cttggtgtaa gtgtttacaa   4860
aacggttgag ttgggaaggg tgcatgcggg gtgagatgat gtgcatctta gattgtattt   4920
ttagattggc gatgtttcct cccagatccc ttctgggatt catgttgtgg aggaccacca   4980
gcacagtata tccggtgcac ttgggaaatt tgtcatgcag cttagaggga aatgcgtgga   5040
agaacttgga gacgcccttg tggcctccca gattctccat gcattcgtcc atgatgatgg   5100
```

caatgggccc gcgggaggcg gcctgggcaa agatgtttct ggggtcactg acatcgtagt 5160
tgtgttccag ggtgagatcg tcataggcca tttttataaa gcgcgggcgg agggtgcccg 5220
actgggggat gatggttccc tcgggccccg gggcgtagtt gccttcgcag atctgcattt 5280
cccaggcctt aatctctgag gggggaatca tatccacttg cggggcgatg aagaaaacgg 5340
tttccggagc cggggagatt aactgggatg agagcaggtt tctcagcagc tgtgactttc 5400
cacagccggt gggtccataa ataacaccta taaccggctg cagctggtag ttgagcgagc 5460
tgcagctgcc gtcgtcccgg aggagggggg ccacctcatt gagcatgtcc cggacgcgct 5520
tgttctcctc gaccaggtcc gccagaaggc gctcgccgcc cagggacagc agctcttgca 5580
aggaagcaaa gtttttcagc ggtttgaggc cgtccgccgt gggcatgttt ttcagggtct 5640
ggccgagcag ctccaggcgg tcccagagct cggtgacgtg ctctacggca tctctatcca 5700
gcatatctcc tcgtttcgcg ggttggggcg gctttcgctg tagggcacca ggcgatggtc 5760
gtccagcgcg gccagagtca tgtccttcca tgggcgcagg gtcctcgtca gggtggtctg 5820
ggtcacggtg aaggggtgcg ccccgggctg ggcgctggcc agggtgcgct tgagactggt 5880
cctgctggtg ctgaagcgct gccggtcttc gccctgcgcg tcggccaggt agcatttgac 5940
catggtgtcg tagtccagcc cctccgcggc gtgtcccttg gcgcgcagct tgcccttgga 6000
ggtggcgccg cacgcggggc actgcaggct cttgagcgcg tagagcttgg gggcgaggaa 6060
gaccgattcg gggagtaggg cgtccgcgcc gcaggccccg cacacggtct cgcactccac 6120
cagccaggtg agctcggggc gctcggggtc aaaaaccagg tttcccccat gctttttgat 6180
gcgtttctta cctcgggtct ccatgaggcg gtgtccccgt tcggtgacga agaggctgtc 6240
cgtgtctccg tagaccgact tgaggggtct gtcctccagg ggggtccctc ggtcctcttc 6300
gtagagaaac tcggaccact ctgagacaaa ggcccgcgtc caggccagga cgaaggaggc 6360
caggtgggag gggtaccggt cgttgtccac tagggggtcc accttctcca aggtgtgaag 6420
acacatgtcg ccctcctcgg cgtccaggaa ggtgattggc ttgtaggtgt aggccacgtg 6480
acccggggtt ccggacgggg gggtataaaa gggggtgggg gcgcgctcgt cctcactctc 6540
ttccgcatcg ctgtctgcga gggccagctg ctggggtgag tattccctct cgaaggcggg 6600
catgacctca gcgctgaggc tgtcagtttc taaaaacgag gaggatttga tgttcacctg 6660
tcccgagctg atgcctttga gggtgcccgc gtccatctgg tcagaaaaca cgatcttttt 6720
attgtccagc ttggtggcga acgacccgta gagggcgttg gagagcagct tggcgatgga 6780
gcgcagggtc tgattcttgt cccggtcggc gcgctccttg gccgcgatgt tgagctgcac 6840
gtactcgcgc gcgacgcagc gccactcggg gaagacggtg gtgcgctcgt cgggcaccag 6900
gcgcacgcgc cagccgcggt tgtgcagggt gacgaggtcc acgctggtgg cgacctcgcc 6960
gcgcaggcgc tcgttggtcc agcagaggcg cccgcccttg cgcgagcaga aggggggcag 7020
ggggtcgagt tgggtttcgt ccgggggggtc cgcgtccacc gtgaagaccc cggggcgcag 7080
gcgcgcgtcg aagtagtcga tcttgcatcc ttgcaagtcc agcgcccgct gccagtcgcg 7140
ggcggcgagc gcgcgctcgt aggggttgag cggcgggccc cagggcatgg ggtgggtgag 7200
cgcggaggcg tacatgccgc agatgtcata gacgtagagg ggctcccgga ggatgcccag 7260
gtaggtgggg tagcagcggc cgccgcggat gctggcgcgc acgtagtcgt agagctcgtg 7320
cgagggggcg aggaggtcgg ggcccaggtt ggtgcgggcg gggcgctccg cgcggaagac 7380
gatctgcctg aagatggcat gcgagttgga agagatggtg gggcgctgga agacgttgaa 7440

-continued

```
gctggcgtcc tgcaggccga cggcgtcgcg cacgaaggag gcgtaggact cgcgcagctt   7500
gtgcaccagc tcggcggtga cctgcacgtc gagcgcgcag tagtcgaggg tctcgcggat   7560
gatgtcatac ttagcctgcc ccttcttttt ccacagctcg cggttgagga cgaactcttc   7620
gcggtctttc cagtactctt ggatcgggaa accgtccggc tccgaacggt aagagcccag   7680
catgtagaac tggttgacgg cctggtaggc gcagcagccc ttctccacgg gcagggcgta   7740
ggcctgcgcg gccttgcgga gcgaggtgtg ggtcagggcg aaggtgtccc tgaccatgac   7800
cttgaggtac tggtgtttga agtcggagtc gtcgcagccg ccccgctccc agagcgagaa   7860
gtcggtgcgc tttttggagc gggggttggg cagcgcgaag gtgacatcgt tgtagaggat   7920
cttgcccgcg cgaggcatga agttgcgggt gatgcggaag ggccccggca cttccgagcg   7980
gttgttgatg acctgggcgg cgagcacgat ctcgtcgaag ccgttgatgt tgtggcccac   8040
gatgtagagt tccaggaagc ggggccggcc cttgacgctg ggcagcttct ttagctcttc   8100
gtaggtgagc tcctcgggcg aggcgaggcc gtgctcggcc agggcccagt ccgccaggtg   8160
cgggttgtcc gcgaggaagg accgccagag gtcgcgggcc aggagggtct gcaggcggtc   8220
cctgaaggtc ctgaactggc ggcctacggc catcttttcg ggggtgacgc agtagaaggt   8280
gagggggtct tgctgccagg ggtcccagtc gagctccagg gcgaggtcgc gcgcggcggc   8340
gaccaggcgc tcgtcgcccc cgaatttcat gaccagcatg aagggcacga gctgctttcc   8400
gaaggcgccc atccaagtgt aggtctctac atcgtaggtg acaaagagac gttccgtgcg   8460
aggatgcgag ccgatcggga agaactggat ctcccgccac cagttggagg agtggctgtt   8520
gatgtggtga aagtagaagt cccgtcggcg ggccgagcac tcgtgctggc ttttgtaaaa   8580
gcgagcgcag tactggcagc gctgcacggg ctgtacctct tgcacgagat gcacctgccg   8640
accgcggacg aggaagctga gtgggaatct gagccccccg catggctcgc ggcctggctg   8700
gtgctcttct actttggatg cgtggccgtc accgtctggc tcctcgaggg gtgttacggt   8760
ggagcggatc accacgccgc gcgagccgca ggtccagata tcggcgcgcg gcggtcggag   8820
tttgatgacg acatcgcgca gctgggagct gtccatggtc tggagctccc gcggcggcgg   8880
caggtcagcc gggagttctt gcaggtttac ctcgcagaga cgggccaggg cgcggggcag   8940
gtccaggtgg tacttgaatt cgagaggcgt gttggtggcg gcgtcgatgg cttgcagtat   9000
gccgcagccc cggggcgcga cgacggtgcc ccgcggggcg gtgaagctcc cgccgccgct   9060
cctgctgtcg ccgccggtgg cggggcttag aagcggtgcc gcggtcgggc ccccggaggt   9120
aggggggct ccggtcccgc gggcaggggc ggcagcggca cgtcggcgcc gcgcgcgggc   9180
aggagctggt gctgcgcccg gaggttgctg gcgaaggcga cgacgcggcg gttgatctcc   9240
tggatctggc gcctctgcgt gaagacgacg ggtccggtga gcttgaacct gaaagagagt   9300
tcgacagaat caatctcggt gtcattgacc gcgacctggc gcaggatctc ctgcacgtcg   9360
cccgagttgt cttggtaggc gatctcggcc atgaactgtt caatctcttc ctcctggagg   9420
tctccgcgtc cggcgcgctc cacggtggcc gccaggtcgt tggagatgcg cgccatgagc   9480
tgcgagaagg cgttgagtcc gccctcgttc cacactcggc tgtagaccac gccgccctgg   9540
tcgtcgcggg cgcgcatgac cacctgcgcg aggttgagtt ccacgtggcg cgcaaagacg   9600
gcgtagttgc gcaggcgctg gaagaggtag ttgagggtgg tggcggtgtg ctcggccaca   9660
aagaagtaca tgacccagcg gcgcaacgtg gattcgttga tgtcccccaa ggcctccagt   9720
cgctccatgg cctcgtagaa gtccacggcg aagttgaaaa actgggagtt gcgcgccgac   9780
acggtcaact cctcctccag aagacggatg agctcggcga cggtgtcgcg cacctcgcgc   9840
```

tcgaaggcta tgggaatctc ttcctccgcc agcatcacca cctcttcctc ttcttcctcc 9900
tctggcactt ccatgatggc ttcctcctct tcggggggtg gcggcggggg agggggcgct 9960
cggcgccggc ggcggcgcac cgggaggcgg tccacgaagc gctcgatcat ctccccgcgg 10020
cggcgacgca tggtctcggt gacggcgcgg ccgttctctc ggggacgcag ctggaagacg 10080
ccgccggtca tctggtgctg gggcgggtgg ccgtggggca gcgagaccgc gctgacgatg 10140
catcttaaca attgctgcgt aggtacgccg ccgagggacc tgagggagtc cagatccacc 10200
ggatccgaaa acctttcgag gaaggcatct aaccagtcgc agtcgcaagg taggctgagc 10260
accgtggcgg gcggcggggg gtggggggag tgtctggcgg aggtgctgct gatgatgtaa 10320
ttgaagtagg cggtcttgac acggcggatg gtcgacagga gcaccatgtc tttgggcccg 10380
gcctgctgga tgcggaggcg gtcggccatg ccccaggctt cgttctggca tctgcgcagg 10440
tctttgtagt agtcttgcat gagcctttcc accggcacct cttctccttc ttcttctgac 10500
atctctgctg catctgcggc cctggggcga cggcgcgcgc ccctgccccc catgcgcgtc 10560
accccgaacc ccctgagcgg ctggagcagg gccaggtcgg cgacgacgcg ctcggccagg 10620
atggcctgct ggacctgcgt gagggtggtt tggaagtcat ccaagtccac gaagcggtgg 10680
taggcgcccg tgttgatggt gtaggtgcag ttggccatga cggaccagtt gacggtctgg 10740
tggcccggtt gcgtcatctc ggtgtacctg aggcgcgagt aggcgcgcga gtcgaagatg 10800
tagtcgttgc aagtccgcac caggtactgg tagcccacca ggaagtgcgg cggcggctgg 10860
cggtagaggg gccagcggag ggtggcgggg gctccggggg ccaggtcttc cagcatgagg 10920
cggtggtatt cgtagatgta cctggacatc caggtgatgc ccgcggcggt ggtggaggcg 10980
cgcgggaagt cgcgcacccg gttccagatg ttgcgcagcg gcagaaagtg ctccatggta 11040
ggcgtgctct ggccggtcag gcgcgcgcag tcgttgatac tctagaccag ggaaaacgaa 11100
agccggtcag cgggcactct tccgtggtct ggtggataaa ttcgcaaggg tatcatggcg 11160
gagggcctcg gttcgagccc cgggcccggg ccggacggtc cgccatgatc cacgcggtta 11220
ccgcccgcgt gtcgaaccca ggtggcgacg tcagacaacg gtggagtgtt ccttttgggt 11280
ttttttccaa atttttctgg ccgggcgccg acgccgccgc gtaagagact agagtgcaaa 11340
agcgaaagca gtaagtggct cgctccctgt agcccggagg atccttgcta agggttgcgt 11400
tgcggcgaac cccggttcga gtctggctct cgctgggccg ctcgggtcgg ccggaaccgc 11460
ggctaaggcg ggattggcct ccccctcatt aaagaccccg cttgcggatt cctccggaca 11520
caggggacga gcccctttt acttttgctt ttctcagatg catccggtgc tgcggcagat 11580
gcgcccccg ccccagcagc agcagcagca acatcagcaa gagcggcacc agcagcagcg 11640
ggagtcatgc agggccccct cgcccacgct cggcggtccg gcgacctcgg cgtccgcggc 11700
cgtgtctgga gccggcggcg gtgggctggc ggacgacccg gaggagcccc cgcggcgcag 11760
ggccagacag tacctggacc tggaggaggg cgagggcctg gcgcgactgg gggcgccgtc 11820
ccccgagcgc cacccgcggg tgcagctgaa gcgcgactcg cgcgaggcgt acgtgcctcg 11880
gcagaacctg ttcagagacc gcgcgggcga ggagcccgag gagatgcggg accgcaggtt 11940
cgccgcgggg cgggagctgc ggcaggggct gaaccgggag cggctgctgc gcgaggagga 12000
ctttgagccc gacgcgcgga cggggatcag ccccgcgcgc gcgcacgtgg cggccgccga 12060
cctggtgacg gcgtacgagc agacggtgaa ccaggagatc aacttccaaa aaagcttcaa 12120
caaccacgtg cgcacgctgg tggcgcgcga ggaggtgacc atcggcctga tgcacctgtg 12180

```
ggactttgtg agcgcgctgg agcagaaccc caacagcaag cctctgacgg cgcagctgtt  12240
cctgatagtg cagcacagca gggacaacga ggcgttcagg gacgcgctgc tgaacatcac  12300
cgagcccgag ggtcggtggc tgctggacct gattaacatc ttgcagagca tagtggtgca  12360
ggagcgcagc ctgagcctgg ccgacaaggt ggcggccatc aattactcga tgctcagtct  12420
gggcaagttt tacgcgcgca agatctacca gacgccgtac gtgcccatag acaaggaggt  12480
gaagatcgac ggcttctaca tgcgcatggc gctgaaggtg ctgaccctga gcgacgacct  12540
gggcgtgtac cgcaacgagc gcatccacaa ggccgtgagc gtgagccggc ggcgcgagct  12600
gagcgaccgc gagctgatgc acagcctgca gcgggcgctg gcgggggccg gcagcggcga  12660
cagggaggcc gagtcctact tcgaggcggg ggcggacctg cgctgggtgc ccagccggag  12720
ggccctggag gccgcggggg cccgccgcga ggactatgca gacgaggagg aggaggatga  12780
cgaggagtac gagctagagg agggcgagta cctggactaa accgcaggtg gtgtttttgg  12840
tagatgcaag acccgaacgt ggtggacccg gcgctgcggg cggctctgca gagccagccg  12900
tccggcctta actctacaga cgactggcga caggtcatgg accgcatcat gtcgctgacg  12960
gcgcgcaatc cggacgcgtt ccggcagcag ccgcaggcca acaggctctc cgccatcttg  13020
gaggcggtgg tgcctgcgcg cgcgaacccc acgcacgaga aggtgctggc catagtgaac  13080
gcgctggccg agaacagggc catccgcccg gacgaggccg ggctggtgta cgacgcgctg  13140
ctgcagcgcg tggcccgcta caacagcggc aacgtgcaga ccaacctgga ccggctggtg  13200
ggggacgtgc gcgaggcggt ggcgcagcgg gagcgcgcgg agcggcaggg aaacctgggc  13260
tccatggtgg cgctgaacgc cttcctgagc acgcagccgg ccaacgtgcc gcgggggcag  13320
gaggactaca ccaactttgt gagcgcgctg cggctgatgg tgaccgagac cccccagagc  13380
gaggtgtacc agtcggggcc ggactacttt ttccagacca gcagacaggg cctgcagacg  13440
gtgaacctga gccaggcttt caagaacctg cgggggctgt ggggcgtgaa ggcgcccacc  13500
ggggaccggg cgacggtgtc cagcctgctg acgcccaact cgcgcctgct gctgctgctg  13560
atcgcgccgt tcacggacag cggcagcgtg tcccgggaga cctacctcgg gcacctgctg  13620
acgctgtacc gcgaggccat cgggcagacc caggtggacg agcacacctt ccaggagatc  13680
accagcgtga gccgcgcgct ggggcaggag gacacgggca gcctggaggc gaccctgaac  13740
tacctgctga ccaaccggcg gcagaagatc ccctcgctgc atagtttgac caccgaggag  13800
gagcgcatcc tgcgctacgt gcagcagagc gtgagcctga acctgatgcg cgacggggtg  13860
acgcccagcg tggcgctgga catgaccgcg cgcaacatgg aaccgggcat gtacgccgcg  13920
catcggcctt acatcaaccg cctgatggac tacttgcatc gcgcggcggc cgtgaacccc  13980
gagtacttca ccaacgccat cctgaacccg cactggctcc cgccgcccgg gttctacagc  14040
gggggcttcg aggtccccga ggccaacgac ggcttcctgt gggacgacat ggacgacagc  14100
gtgttctccc cgcggccgca ggcgctggcg gaggcgtcgc tgctccgcct ccccaagaaa  14160
gaagagagcc gccggcccag cagcgcggcg gcctctctgt ccgagctggg ggcggcggcc  14220
gcgcggcccg ggtccctggg gggcagcccc tttcccagtc tggtggggtc tctgcagagc  14280
gggcgcacca cccggccccg gctgctgggc gaggacgagt acctgaacaa ctccctgatg  14340
cagccggtgc gggagaaaaa cctgcccccc gccttcccca acaacgggat agagagcctg  14400
gtagacaaga tgagcagatg gaagacctat gcgcaggagc acagggactc gcccgtgctc  14460
cgtccgccca cgcggcgcca gcgccacgac cggcagcggg ggctggtatg ggatgacgag  14520
gactccgcgg acgatagcag cgtgctggac ctgggggga gcggcggtaa cccgttcgcg  14580
```

-continued cacctgcgcc cccgcctggg gaggatgttt caataagaaa aatcaagcat gatgcaaggt 14640
tttttaagcg gataaataaa aaactcacca aggccatggc gaccgagcgt tgttggtttc 14700
ttgttgtgtt cccttagtat gcggcgcgcg gcgatgtacc acgagggacc tcctccctct 14760
tatgagagcg tggtgggcgc ggcggcggcc tctccctttg cgtcgcagct ggagccgccg 14820
tacgtgcctc cgcggtacct gcggcctacg gggggaagaa acagcatccg ttactcggag 14880
ctggcgcccc tgtacgacac cacccgggtg tacctggtgg acaacaagtc ggcggacgtg 14940
gcctccctga actaccagaa cgaccacagc aattttttga ccacggtcat ccagaacaat 15000
gactacaccc cgagcgaggc cagcacccag accatcaatc tggatgaccg gtcgcactgg 15060
ggcggcgacc tgaaaaccat cctgcacacc aacatgccca acgtgaacga gttcatgttc 15120
accaataagt tcaaggcgcg ggtgatggtg tcgcgttcgc acaccaagga cgaccgggtg 15180
gagctgaagt acgagtgggt agagttcgag ctgcccgagg gcaactactc ggagaccatg 15240
accatagacc tgatgaacaa cgcgatcgtg gagcactatc tgaaagtggg caggcagaac 15300
ggggtcctgg agagcgacat cggggtcaag ttcgacacca ggaacttccg cctggggctg 15360
gacccggtca ccgggctggt catgcccggg gtctacacca acgaggcctt ccacccccgac 15420 atcatcctgc tgcccggctg cggggtggac ttcacctaca gccgcctgag caacctgctg 15480
ggcatccgca agcggcagcc cttccaggag ggctttagga tcacctacga ggacctggag 15540
gggggcaaca tccccgcgct cctggatgtg gaggcctacc aggatagctt gaaggaagaa 15600
gaggcgggag agggcagcgg cggcggcggc ggcgccggtc aggaggaggg cggggcctcc 15660
tctgaggcct ctgcggacgc cgccgctgcc gccgaggcgg aggcggccga ccccgcgatg 15720
gtggtagagg aagagaagga tatgaatgac gaggcggtgc gcggcgacac ctttgccacc 15780
cggggggagg agaagaaagc ggaggccgag gccgcggcag aggaggcggc agcggcggcg 15840
gcggcggcag tagaggcggc ggccgaggcg gagaagcccc ccaaggagcc cgtgattaag 15900
gccctgaccg aagatagcaa gaagcgcagt tacaacgtgc tcaaggacag caccaacacc 15960
gcgtaccgca gctggtacct ggcctacaac tacggcgacc cggcgacggg ggtgcgctcc 16020
tggaccctgc tgtgtacgcc ggacgtgacc tgcggctcgg agcaggtgta ctggtcgctg 16080
cccgacatga tgcaagaccc cgtgaccttc cgctccacgc ggcaggtcag caacttcccg 16140
gtggtgggcg ccgagctgct gcccgtgcac tccaagagct tctacaacga ccaggccgtc 16200
tactcccagc tcatccgcca gttcacctct ctgacccacg tgttcaatcg ctttcctgag 16260
aaccagattc tggcgcgccc gcccgccccc accatcacca ccgtcagtga aaacgttcct 16320
gctctcacag atcacgggac gctaccgctg cgcaacagca tcggaggagt ccagcgagtg 16380
accgtaactg acgccagacg ccgcacctgt ccctacgttt acaaggccct gggcatagtc 16440
tcgccgcgcg tcctttccag ccgcactttt taagcatgtc catcctcatc tcgcccagca 16500
ataacaccgg ctggggcctg ctgcgcgcgc ccagcaagat gtttggaggg gcgaggaagc 16560
gctccgacca gcaccccgtg cgcgtgcgcg ggcactaccg cgccccctgg ggcgcgcaca 16620
aacgcgggcg caccggcacc gcggggcgca ccaccgtgga cgaagccatc gactcggtgg 16680
tggagcaggc gcgcaactac acgcccgcgg tctccaccgt ggacgcggct atcgagagcg 16740
tggtgcgagg cgcgcggcgg tacgccaagg cgaagagccg ccggaggcgc gtggcccgcc 16800
gccaccgccg tcgacccgga agcgccgcca agcgcgccgc cgccgccttg cttcgtcggg 16860
ccagacgcac gggccgccgc gccgccatga gggccgcgcg ccgcctggcc gccggcatca 16920

-continued

```
ccaccgtggc cccccgcgcc agaagacgcg cggccgctgc cgccgccgcg gccatcagcg  16980
acctggccac caggcgccgg ggcaacgtgt actgggtgcg cgactcggtg agcggcacgc  17040
gcgtgcccgt gcgcttccgc cccccgcgga cttgagagga gaggacagga aaaaagcatc  17100
aacaacacca ccactgagtc tcctgctgtt gtgtgtatcc cagcggcgcg cgcgcacacg  17160
gcgacatgtc caagcgcaaa atcaaagaag agatgctcca ggtcgtcgcg ccggaaatct  17220
atgggccccc gaagaaggaa gagcaggatt tcaagccccg caagataaag cgggtcaaaa  17280
agaaaaagaa agatgacgat gatggcgagg tggagtttct gcgcgccacg gcgcccaggc  17340
gcccgctgca gtggaagggt cggcgcgtaa agcgcgttct gcgccccggc accgcggtgg  17400
tcttcacgcc cggcgagcgc tccacccgca ctttcaagcg cgtctatgac gaggtgtacg  17460
gcgacgaaga cctgctggag caggccaacg atcgctccgg agagtttgct tacgggaagc  17520
ggcaccgggc gatggagaag gacgaggtgc tggcgctgcc gctggaccgg ggcaacccca  17580
cccccagcct gaagcccgtg accctgcagc aggtgctgcc ggccagcgcg ccctccgaga  17640
tgaagcgggg cctgaagcgc gagggcggcg acctggcgcc caccgtgcag ctgatggtgc  17700
ccaagcggca gaggctggag gacgtgctgg agaaaatgaa agtagacccc ggcctgcagc  17760
cggacatcag ggtccgcccc atcaagcagg tggcgccggg cctcggcgtg cagaccgtgg  17820
acgtggtcat ccccaccggc gcctcctctt ccagcgccgc cgccgccact agcaccgcgg  17880
acatggagac gcagactagc tccgccctcg ccgcccccgc ggccgccgcc gccgccacct  17940
cctcggcgga ggtacagacg gacccctgga tgccgccgcc ggcggccgcc ccctcgcgcg  18000
cacgccgcgg gcgcaggaag tacggcgccg ccagcgcgct catgcccgag tacgccttgc  18060
atccttccat cgcgcccacc cccggctacc gaggctacag ctaccgcccg cgaagagcca  18120
agggctccac ccgccgcagc cgccgcgccg ccacctctac ccgccgccgc agtcgccgcc  18180
gccgccggca gcccgcgctg gctccgatct ccgtgaggag agtggcgcgc aacggggaca  18240
ccttggtgct gcccagggcg cgctaccacc ccagcatcgt ttaaaagcct gttgtggttc  18300
ttgcagatat ggccctcact tgccgcctcc gtttcccggt gccgggatac cgaggaagat  18360
cgcgccgtag aaggggtatg gccggacgcg gcctgagcgg aggcagccgc cgtgcgcacc  18420
ggcggcgacg cgccaccagc cgacgcatgc gcggcggggt gctgcctctg ctgatccccc  18480
tgatcgccgc ggcgatcggc gccgtgcccg ggatcgcctc cgtggccttg caggcgtccc  18540
agaggcgttg acacagactt cttgcaagct tgcaaaaata tggaaaaaat ccccccaata  18600
aaaaagtcta gactctcacg ctcgcttggt cctgtgacta ttttgtagaa aaaaagatgg  18660
aagacatcaa ctttgcgtcg ctggccccgc gtcacggctc gcgcccgttc ctgggacact  18720
ggaacgatat cggcaccagc aacatgagcg gtggcgcctt cagttggggc tctctgtgga  18780
gcggcattaa aaatatcggt tctgccgtta agaattacgg ctccaaggcc tggaacagca  18840
gcacgggcca gatgttgaga gacaagttga aagagcagaa cttccagcag aaggtggtgg  18900
agggcctggc ctccggcatc aacggggtgg tggacctggc caatcaggcc gtgcaaaata  18960
agatcaacag cagactggac ccccggccgc cggtggaaga gctgccgccg gcgctggaga  19020
cggtgtcccc cgatgggcgg ggcgaaaagc gcccgcggcc cgacagggaa gagaccactc  19080
tggtcacgca caccgatgag ccgccccccct acgaggaagc tctgaagcaa ggcttgccca  19140
ccactcggcc catcgcgccc atggccaccg gggtggtggg ccgccacacc cccgccaggc  19200
tggacctgcc tcctcctcct gtttcttctt cggccgccga tgcgcagcag cagaaggcgg  19260
cgctgcccgg tccgcccgcg gccgcccccc gtcccaccgc cagtcgagcg cccctgcgtc  19320
```

gcgcggccag cggcccccgc ggggtcgcga ggcacagcag cggcaactgg cagaacacgc 19380
tgaacagcat cgtgggtctg ggggtgcagt ccgtgaagcg ccgccgatgc tactgaatag 19440
cttagctaac ggtgttgtat gtgtgtatgc gtcctatgtc accgccagag gagctgctga 19500
gtcgccgccg ttcgcgcgcc caccgccact accaccgccg gtaccactcc agcgcccctc 19560
aagatggcga ccccatcgat gatgccgcag tggtcgtaca tgcacatctc gggccaggac 19620
gcctcggagt acctgagccc cgggctggtg cagttcgccc gcgccaccga cagctacttc 19680
agcctgagta acaagtttag gaaccccacg gtggcgccca cgcacgatgt gaccaccgac 19740
cggtcccagc gcctgacgct gcggttcatc cccgtggacc gcgaggacac cgcgtactct 19800
tacaaggcgc ggttcaccct ggccgtgggc gacaaccgcg tgctggacat ggcctccacc 19860
tactttgaca tccgcggcgt gctggacagg ggccccacct tcaagcccta ctccggcacc 19920
gcctacaact ccctggcccc caagggcgcc cccaactcct gcgagtggga gcaagaggag 19980
actcagacag ctgaagaggc acaagacgaa gaagaagatg aagctgaagc tgaggaggaa 20040
atgcctcagg aagagcaagc acctgtcaaa aagactcatg tatatgctca ggctcccctt 20100
tctggcgaaa aaattactaa agacggtctg cagataggaa cggacgctac agctaccgaa 20160
caaaaaccta tttatgcaga tcccacattc cagccagaac cccaaattgg tgaatctcag 20220
tggaatgagg cagatgcttc agttgccggc ggtagagtgc tgaagaaaac tactcccatg 20280
aaaccctgtt atggttccta tgccaggccc acaaatgcca atggaggtca gggtgtattg 20340
gtggagaaag acggtggaaa gatggaaagc caagtagata tgcaattctt ttcgacttct 20400
gaaaacgccc gtaacgaggc taacaacatt cagcccaaat tggtgctgta cagcgaggat 20460
gtgcatatgg agaccccaga cacacacatt tcttacaagc ctgcaaaaag cgatgataat 20520
tcgaaagtca tgctgggtca gcagtccatg cccaacaggc caaattacat cggcttcaga 20580
gacaacttta tcgggctcat gtattacaac agcactggca acatgggggt gctggcaggt 20640
caggcctcac agttgaatgc ggtggtggac ttgcaagaca gaaacacaga actgtcctac 20700
cagctcttgc ttgattccat gggagacaga accagatact tttccatgtg gaatcaggcg 20760
gtggacagtt atgatccaga tgtcagaatt attgaaaatc atggaactga agatgagctg 20820
cccaactatt gtttccctct gggaggcata ggggtaactg acacttacca ggccattaag 20880
actaatggca atggcaacgg cgggggcaat accacttgga ccaaggatga aacttttgca 20940
gaccgcaacg agataggggt gggaaacaat ttcgccatgg agatcaacct cagtgccaac 21000
ctgtggagga acttcctcta ctccaacgtg gccctgtacc tgccagacaa gcttaagtac 21060
aacccctcca acgtggaaat ctctgacaac cccaacacct acgactacat gaacaagcga 21120
gtggtggccc cggggctggt ggactgctac atcaacctgg gcgcgcgctg gtccctggac 21180
tacatggaca acgtcaaccc cttcaaccac caccgcaacg cgggcctgcg ctaccgctcc 21240
atgcttctgg gcaacgggcg ctacgtgccc ttccacatcc aggtgcccca gaagttcttt 21300
gccatcaaga acctcctcct cctgccgggc tcctacacct acgagtggaa cttcaggaag 21360
gatgtcaaca tggtcctcca gagctctctg ggtaacgacc tcagggtcga cggggccagc 21420
atcaagttcg agagcatctg cctctacgcc accttcttcc ccatggccca caacacggcc 21480
tccacgctcg aggccatgct caggaacgac accaacgacc agtccttcaa cgactacctc 21540
tccgccgcca acatgctcta ccccatcccc gccaacgcca ccaacgttcc catctccatc 21600
ccctcgcgca actgggcggc cttccgcggc tgggccttca cccgcctcaa gaccaaggag 21660 acccccctccc tgggctcggg tttcgacccc tactacacct actcgggctc catacccctac 21720 ctggacggaa ccttctacct caaccacact ttcaagaagg tctcggtcac cttcgactcc 21780
tcggtcagct ggccgggcaa cgatcgcctg ctcaccccca acgagttcga gatcaagcgc 21840
tcggtcgacg gggagggcta caacgtggcc cagtgcaaca tgaccaagga ctggttcctc 21900
atccaaatgc tggccaacta caacatcggc tatcagggct tctacatccc agagagctac 21960
aaggacagga tgtactcctt ctttaggaac ttccagccca tgagccggca ggtggtggac 22020
gaaaccaagt acaaggacta ccagcaggtg ggcatcatcc accagcacaa caactcgggc 22080
ttcgtgggct acctcgcccc caccatgcgc gagggacagg cctaccccgc caacttcccc 22140
tacccgctca ttggcaagac cgcggtcgac agcgtcaccc agaaaaagtt cctctgcgac 22200
cgcaccctct ggcgcatccc cttctccagc aacttcatgt ccatgggtgc gctcacggac 22260
ctgggccaga acctgctcta tgccaactcc gcccacgcgc tcgacatgac cttcgaggtc 22320
gaccccatgg acgagcccac ccttctctat gttctgttcg aagtctttga cgtggtccgg 22380
gtccaccagc cgcaccgcgg cgtcatcgag accgtgtacc tgcgcacgcc cttctcggcc 22440
ggcaacgcca ccacctaaag aagcaagccg ccaccgccac cacctgcatg tcgtcgggtt 22500
ccaccgagca ggagctcaag gccatcgtca gagacctggg atgcgggccc tatttttgg 22560 gcaccttcga caaacgcttc ccgggcttcg tcgccccgca caagctggcc tgcgccatcg 22620
tcaacacggc cggccgcgag accgggggcg tgcactggct ggccttcgcc tggaacccgc 22680
gctccaaaac atgctacctc tttgacccct tcggattctc ggaccagcgg ctcaagcaga 22740
tctaccagtt cgagtacgag ggcctgctgc gccgcagcgc catcgcctcc tcgcccgacc 22800
gctgcgtcac cctcgagaag tccacccaga ccgtgcaggg gcccgactcg gccgcctgcg 22860
gtctcttctg ctgcatgttc ctgcatgcct ttgtgcactg gccccagagt cccatggacc 22920
gcaaccccac catgaacttg ctgacgggga tccccaactc catgctccag agcccccagg 22980
tcgcgcccac cctgcgccgc aaccaggagc ggctctacag cttcctggaa cgccactcgc 23040
cctacttccg ccgccacagc gcgcagatca gggggggccac ctctttctgc cgcatgcaag 23100
agatgcaagg gaaaatgcaa tgatgtacac agacactttt tcttttctca ataaatggca 23160
actttattta tacatgctct ctctcgggta ttcatttccc caccacccac cacccgccgc 23220
cgccgtaacc atctgctgct ggcttttttt ttttttttta aaaatcgaaa gggttctgcc 23280
gggaatcgcc gtgcgccacg ggcagggaca cgttgcggaa ctggtagcgg gtgcccccact 23340 tgaactcggg caccaccatg cggggcaagt cggggaagtt gtcggcccac aggctgcggg 23400
tcagcaccag cgcgttcatt aggtcgggcg ccgagatctt gaagtcgcag ttggggccgc 23460
cgccctgcgc gcgcgagttg cggtacaccg ggttgcaaca ctggaacacc agcagcgccg 23520
gataattcac actggccagc acgctccggt cggagatcag ctcggcgtcc aggtcctccg 23580
cgttgctcag cgcgaacggg gtcagcttgg gcacctgccg ccccaggaag ggagcgtgcc 23640
ccggcttcga gttgcagtcg cagcgcagcg ggatcagcag gtgcccgcgg ccggactcgg 23700
cgttggggta cagcgcgcgc atgaaggcct ccatctggcg gaaggccatc tgggccttgg 23760
cgccctccga gaagaacatg ccgcaggact tgcccgagaa ctggttcgcg gggcagctag 23820
cgtcgtgcag gcagcagcgc gcgtcggtgt tggcgatctg caccacgttg cgcccccacc 23880
ggttcttcac gattttggcc ttggaagcct gctccttcag cgcgcgctgc ccgttctcgc 23940
tggtcacatc catctcgatc acgtgctcct tgttcaccat gctgctgccg tgcagacact 24000
tcagctcgcc ctccacctcg gtgcagcggt gctgccatag cgcgcagccc gtgggctcga 24060

-continued

```
aatgcttgta ggtcacctcc gcgtaggact gcaggtaggc ctgcaggaag cgccccatca  24120
tggtcacgaa ggtcttgttg ctgctgaagg tcagctgcag cccgcggtgc tcctcgttca  24180
gccaggcctt gcacacggcc gccagcgcct ccacctggtc gggcagcatc ttgaagttca  24240
gcttcagctc attctccaca tggtacttgt ccatcagcgc gcgcgcagcc tccatgccct  24300
tctcccaggc cgacaccagc ggcaggctca aggggttcac caccgtcgca gccgccgctg  24360
cgctttcgct ttccgctccg ctgttctctt cttcctcctc ctcttcttcc tcgccgcccg  24420
cgcgcagccc ccgcaccacg gggtcgtctt cctgcaggcg ccgcaccgag cgcttgccgc  24480
tcctgccctg cttgatacgc acgggcgggt tgctgaagcc taccatcacc agcgcggcct  24540
cttcttgctc gtcctcgctg tccactatga cctcgggga gggcgacctc agaaccgtgg  24600
cgcgctgcct cttctttttc ctgggggcgt ttgccagctc cgcggccgcg gccgccgccg  24660
aggtcgaagg ccgagggctg ggcgtgcgcg gcaccagcgc gtcctgcgag ccgtcctcgt  24720
cctcggactc gaggcggcag cgagcccgct tcttcggggg cgcgcggggc ggcggcggcg  24780
ggggcggcgg cgacggagac ggggacgaga catcgtccag ggtgggagga cggcgggccg  24840
cgccgcgtcc gcgctcgggg gtggtttcgc gctggtcctc ttcccgactg gccatctccc  24900
actgctcctt ctccctatagg cagaaagaga tcatggagtc tctcatgcaa gtcgagaagg  24960
aggaggacag cctaaccacc accgcccccct ctgagccctc cgccgccgcc gcggacgacg  25020
cgcccaccac caccgccgcc gccaccacca ccattaccac cctacccggc gacgcagccc  25080
cgatcgagaa ggaagtgttg atcgagcagg acccgggttt tgtgagcgaa gaggaggatg  25140
aggaggatga aaaggagaag gataccgccg cctcagtgcc aaaagaggat aaaaagcaag  25200
accaggacga cgcagagaca gatgaggcag cagtcgggcg gggggacgga aggcatgatg  25260
atgatgacgg ctacctagac gtgggagacg acgtgctgct taagcacctg caccgccagt  25320
gcgtcatcgt ctgcgacgcg ctgcaggagc gctgcgaagt gcccctggac gtggcggagg  25380
tcagccgcgc ctacgagcgg cacctcttcg cgccacacgt gcccccccaag cgccgggaga  25440
acggcacctg cgagcccaac ccgcgcctca acttctaccc ggtcttcgcg gtacccgagg  25500
tgctggccac ctaccacatc ttcttccaaa actgcaagat cccccctctcc tgccgcgcca  25560
accgcacccg cgccgacaag acgctggccc tgcggcaggg cgcccacata cctgatatcg  25620
cctctctgga ggaggtgccc aagatcttcg agggtctcgg tcgcgacgag aaacgggcgg  25680
cgaacgctct gcaaggagac agcgaaaacg agagtcactc gggggtgctg gtggagctcg  25740
agggcgacaa cgcgcgcctg gccgtgctca agcgcagcat cgaagtcacc cacttcgcct  25800
acccggcgct caacctgccc cccaaggtca tgagtgtggt catgagtgag ctcatcatgc  25860
gccgcgccca gcccctggac gcggatgcaa acttgcaaga gccctccgag gaaggcctgc  25920
ccgcggtcag cgacgagcag ctggcgcgct ggctggagac ccgcgacccc gcccagctgg  25980
aggagcggcg caagctcatg atggccgcgg tgctcgtcac cgtggagctc gagtgtctgc  26040
agcgcttctt cggggacccc gagatgcagc gcaagctcga ggagaccctg cactacacct  26100
tccgccaggg ctacgtgcgc caggcctgca agatctccaa cgtggagctc tgcaacctgg  26160
tctcctacct gggcatcctg cacgagaacc gcctcgggca gaacgtcctg cactccaccc  26220
tcaaagggga ggcgcgccgc gactacgtcc gcgactgcgt ctacctcttc ctctgctaca  26280
cgtggcagac ggccatgggg gtctggcagc agtgcctgga ggagcgcaac ctcaaggagc  26340
tggagaagct cctccggcgc gccctcaggg acctctggac gggcttcaac gagcgctcgg  26400
```

-continued

```
tggccgccgc gctggcggac atcatcttcc ccgagcgcct gctcaaaacc ctgcagcagg  26460
gcctgcccga cttcaccagc cagagcatgc tgcagaactt caggaccttc atcctggagc  26520
gctcgggcat cctgccggcc acctgctgcg cgctgcccag cgacttcgtg cccatcaggt  26580
acagggagtg cccgccgccg ctctggggcc actgctacct cttccagctg gccaactacc  26640
tcgcctacca ctcggatctc atggaagacg tgagcggcga gggcctgctc gagtgccact  26700
gccgctgcaa cctgtgcacg ccccaccgct ctctagtctg caatccgcag ctgctcagcg  26760
agagtcagat tatcggtacc ttcgagctgc agggtccctc gcccgacgaa aagtccgcgg  26820
ctccggggtt gaaactcact ccggggctgt ggacttccgc ctacctacgc aaatttgtac  26880
ctgaagacta ccacgcccac gagatcaggt tttacgaaga ccaatcccgc ccgcccaagg  26940
cggagctcac cgcctgcgtc attacccagg gccacatcct gggccaattg caagccatca  27000
acaaagcccg ccaagagttc ttgctgaaaa agggtcgggg ggtgtacctg gacccccagt  27060
ccggcgagga gctaaacccg ctacccccgc cgccgcccca gcagcgggac cttgcttccc  27120
aggatggcac ccagaaagaa gcagccgccg ccgccgccag catacatgct tctggaggaa  27180
gaggaggact gggacagtca ggcagaggag gtttcggacg aggacgagga ggaggagatg  27240
atggaagact gggaggagga cagcctagac gaggaagctt cagaggccga agaggtggca  27300
gacgcaacac catcaccctc ggccgcagcc ccctcgccgg cgcccccgaa atcctccgac  27360
cccagcagca gcgctataac ctccgctcct ccggcgccgg cgcccacccg cagcagaccc  27420
aaccgtagat gggacactac aggaaccggg gtcggtaagt ccaagtgccc cccagcgccg  27480
cccccgcaac aggagcaaca gcagcagcag cggcgacagg gctaccgctc gtggcgcgga  27540
cacaagaacg ccatagtcgc ctgcttgcaa gactgcgggg gcaacatctc cttcgcccgc  27600
cgcttcctgc tcttccacca cggggtggct tttccccgca atgtcctgca ttactaccgt  27660
catctctaca gcccctactg cggcggcagc ggcgacccag agggagcggc ggcagcagca  27720
gcgccagcca cagcggcgac cacctaggaa gacctccgcg ggcaagacgg cgggagccgg  27780
gagacccgcg gcggcggcgg tagcggcggc ggcgggcgca ctgcgcctct cgcccaacga  27840
acccctctcg acccgggagc tcagacacag gatcttcccc actctgtatg ctatcttcca  27900
gcagagcaga ggccaggaac aggagctcaa aataaaaaac agatctctgc gctccctcac  27960
ccgcagctgt ctgtatcaca aaagcgaaga tcagcttcgg cgcacgctgg aggacgcgga  28020
ggcactcttc agcaaatact gcgcgctgac tcttaaggac tagccgcgcg cccttctcga  28080
atttaggcgg gagaaagact acgtcatcgc cgaccgccgc ccagcccacc cagccgacat  28140
gagcaaagag attcccacgc cctacatgtg gagctaccag ccgcagatgg gactcgcggc  28200
gggagcggcc caagactact ccacccgcat gaactacatg agcgcggggc cccacatgat  28260
ctcacgggtt aatgggatcc gcgcccagcg aaaccaaata ctgctggaac aggcggccat  28320
aaccgccaca ccccgtcatg acctcaatcc ccgaaattgg cccgccgccc tcgtgtacca  28380
ggaaaccccc tctgccacca ccgtggtact tccgcgtgac acccaggccg aagtccagat  28440
gactaactca ggggcgcagc tcgcgggcgg ctttcgtcac ggggtgcggc cgcaccggcc  28500
gggtatatta cacctggcga tcagaggccg aggtattcag ctcaacgacg agtcggtgag  28560
ctcttcgctc ggtctccgtc cggacggaac cttccagatc gccggatcag gtcgctcctc  28620
attcacgcct cgccaggcgt atctgactct gcagacctcc tcctcggagc ctcgctccgg  28680
cggcatcggc accctccagt tcgtggagga gttcgtgccc tcggtctact tcaacccctt  28740
ctcgggacct cccggacgct accccgacca gttcatcccg aactttgacg cggtgaagga  28800
```

ctcggcggac ggctacgact gaatgtcaag tgctgaggca gagagcgttc gcctgaaaca 28860
cctccagcac tgccgccgct tcgcctgctt tgcccgcagc tccggtgagt tctgctactt 28920
tcagctgccc gaggagcata ccgaagggcc ggcgcacggc gtccgcctaa ccacccaggg 28980
cgaggttacc tgtaccctta tccgggagtt taccctccgt cccctgctag tggagcggga 29040
gcggggttct tgtgtcataa ctatcgcctg caactgccct aaccctggat tacatcaaga 29100
tctttgttgt cacctgtgcg ctgagtataa taaacgctga gatcagactc tactggggct 29160
cctgtcgcca tcctgtgaac gccaccgtct tcacccaccc cgagcagccc caggcgaacc 29220
tcacctgcgg cctgcgtcgg agggccaaga agtacctcac ctggtacttc aacggcaccc 29280
cctttgtggt ttacaacagc ttcgaccagg acggagttgc cttgagagac gacctttccg 29340
gtctcagcta ctccattcac aagaacacca ccctccacct cttccctccc tacctgccgg 29400
gaacctacga gtgcgtcacc ggccgctgca cccacctcct ccgcctgatc gtaaaccaga 29460
cctttccggg aacacacctc ttccccagaa caggaggtga gctcaggaaa ccccctgggg 29520
cccagggcgg agacttacct tcgacccttg tggggttagg attttttatc gccgggttgc 29580
tggctctcct gatcaaagct tccttcagat ttgttctctc cctttacttt tatgaacagc 29640
tcaacttcta ataacgctac cttttctcag gaatcgagta gtaacttctc ttccgaaatc 29700
gggctgggtg tgctgcttac tctgttgatt tttttcctta tcatacttag ccttctgtgc 29760
ctcaggctcg ccgcctgctg cgcacatatc tacatctaca gccggttgct taactgctgg 29820
ggtcgccatc caagatgaac ggggctcagg tgctatgtct gctggccctg gtggcctgca 29880
gtgccgccgt caattttgag gaacccgctt gcaatgtgac tttcaagcct gagggcgcac 29940
attgcaccac tctggttaaa tgtgtgacct ctcatgaaaa actgctcatc gcctacaaaa 30000
acaaaacagg ccagatcgca gtctatagcg agtggctacc cggagaccat aataactact 30060
cagtcaccgt cttcgagggt gcggagtcta agaaattcga ttacaccttt cccttcgagg 30120
agatgtgtga tgcggtcatg tacctgtcca aacagtacaa gctgtggccc cccacccccca 30180
aggcgtgtgt ggaaaacact gggtctttct gctgtctctc tctggcaatc actgtgcttg 30240
ctctaatctg cacgctgcta tacatgagat tcaggcagag gcgaatcttt atcgatgaga 30300
aaaaaatgcc ttgatcgcta acaccggctt tctgtctgca gaatgaaagc aatcacctcc 30360
ctactaatca gcaccaccct ccttgcgatt gcccatgggt tgacacgaat cgaagtgcca 30420
gtggggtcca atgtcaccat ggtgggcccc gccggcaatt cctccctgat gtgggaaaaa 30480
tatgtccgta atcaatggga tcattactgc tctaatcgaa tctgtatcaa gcccagagcc 30540
acctgcgacg ggcaaaatct aactttgatt gatgtgcaaa tgacggatgc tgggtactat 30600
tacgggcagc ggggagaaat gattaattac tggcgacccc acaaggacta catgctgcat 30660
gtagtcaagg cagtcccaac tactaccacc cccaccacta ccactcccac taccaccacc 30720
cccaccacta ccactagcac tgctactacc gctgcccgca aagctattac ccgcaaaagc 30780
accatgctta gcaccaagcc ccattctcac tcccacgccg gcgggcccac cggtgcggcc 30840
tcagaaacca ccgagctttg cttctgccaa tgcactaacg ccagcgccca cgaactgttc 30900
gacctggaga atgaggacga tgaccagctg agctccgctt gcccggtccc gctgcccgca 30960
gagccggtcg ccctgaagca gctcggtgat ccatttaatg actctcctgt ttatccctct 31020
cccgaatacc ctcccgactc taccttccac atcacgggca ccaaagaccc caacctctcc 31080
ttctacctga tgctgctgct ctgtatctct gtggtatctt ccgcgctcat gttactgggc 31140
atgttctgct gcctcatctg ccgcagaaaa agaaagtctc gctctcaggg ccaaccactg 31200
atgcccttcc cctacccccc agattttgca gataacaaga tatgagcacg ctgctgacac 31260
taaccgcttt actcgcctgc gctctaaccc ttgtcgcttg cgaatccaga taccacaatg 31320
tcacagttgt gacaggagaa aatgttacat tcaactccac ggccgacacc cagtggtcgt 31380
ggagtggcca cggtagctat gtatacatct gcaatagctc cacctcccct agcatgtcct 31440
ctcccaagta ccactgcaat gacagcctgt tcaccctcat caacgcctcc acctcggaca 31500
atggactcta tgtaggctat gtgacacccg gtgggcaggg aaagacccac gcctacaacc 31560
tgcaagttcg ccacccctcc accaccgcca ccacctctgc cgcccctacc cgcagcagca 31620
gcagcagcag cagcagcagc agcagcagca gcagcagatt cctgacttta atcctagcca 31680
gctcaacaac caccgccacc gctgagacca cccacagctc cgcgcccgaa accacccaca 31740
cccaccaccc agagacgacc gcggcctcca gcgaccagat gtcggccaac atcaccgcct 31800
cgggtcttga acttgcttca acccccaccc caaaaccagt ggatgcagcc gacgtctccg 31860
ccctcgtcaa tgactgggcg gggctgggaa tgtggtggtt cgccataggc atgatggcgc 31920
tctgcctgct tctgctctgg ctcatctgct gcctcaaccg caggcgggcc agacccatct 31980
atagacccat cattgttctc aaccccgctg atgatgggat ccatagattg gatggtctga 32040
aaaacctact tttctctttt acagtatgat aaattgagac atgcctcgca ttttcatgta 32100
cttgacactt ctcccacttt ttctggggtg ttctacgctg gccgccgtct ctcacctcga 32160
ggtagactgc ctcacaccct tcactgtcta cctgatttac ggattggtca ccctcactct 32220
catctgcagc ctaatcacag tagtcatcgc cttcatccag tgcattgact acatctgtgt 32280
gcgcctcgca tacctgagac accacccgca gtaccgagac aggaacattg cccaactcct 32340
aagactgctc taatcatgca taagactgtg atctgcctcc tcatcctcct ctccctgccc 32400
gctctcgtct catgccagcc caccacaaaa cctccacgaa aaagacatgc ctcctgtcgc 32460
ttgagccaac tgtggaatat tcccaaatgc tacaatgaaa agagcgagct ttccgaagcc 32520
tggctatatg cggtcatgtg tgtccttgtc ttctgcagca caatctttgc cctcatgatc 32580
tacccccact ttgatttggg atggaatgcg gtcgatgcca tgaattaccc tacctttccc 32640
gcgcccgata tgattccact ccgacaggtt gtggtgcccg tcgccctcaa tcaacgcccc 32700
ccatccccta cacccactga ggtcagctac tttaatctaa caggcggaga tgactgacac 32760
tctagatcta gaaatggacg gcatcggcac cgagcagcgt ctcctacaga ggcgcaagca 32820
ggcggctgaa caagagcgcc tcaatcagga gctccgagat ctcattaacc tgcaccagtg 32880
caaaaaaggc atcttttgcc tggtcaagca ggccgatgtc acctacgaga aaaccggtaa 32940
cagccaccgc ctcagctaca agctgcccac ccaacgccag aagttggtgc tcatggtggg 33000
tcagaatccc atcaccgtca cccagcactc ggtggagacc gaggggtgtc tgcactcccc 33060
ctgtcagggt ccggaagacc tctgcaccct ggtaaagacc ctgtgtggtc ttagagattt 33120
aatcccctt aactaatcaa acactggaat caataaaaag aatcacttac tttaaatcag 33180
tcagcaggtc tctgtccact ttattcagca gcacctcctt cccctcctcc caactctggt 33240
actccaaacg cctcctggcg gcaaacttcc tccacaccct gaagggaatg tcagattctt 33300
gctcctgtcc ctccgcaccc actatcttca tgttgttgca gatgaagcgc gccaaaacgt 33360
ctgacgagac cttcaacccc gtgtacccct atgacacgga aaacgggcct ccctccgttc 33420
ctttcctcac ccctcccttc gtgtccccccg acggatttca agaaagcccc ccaggggtcc 33480
tgtctctgcg cctgtcagag cccctggtca cttcccacgg catgcttgcc ctgaaaatgg 33540
gaaatggcct ctccctggat gacgccggca acctcacctc tcaagatgtc accaccgtca 33600
cccctcccct caaaaaaacc aagaccaacc tcagcctcca gacctcagcc cccctgaccg 33660
ttagctctgg gtccctcacc gtcgcggccg ccgctccact ggcggtggcc ggcacctctc 33720
tcaccatgca atctcaggcc cccttgacgg tgcaagatgc aaaactgggt ctggccaccc 33780
agggacccct gaccgtgtct gaaggcaaac tcaccttgca gacatcggct ccactgacgg 33840
ccgccgacag cagcactctc actgttggca ccacaccgcc aatcagtgtg agcagtggaa 33900
gtctaggctt agatatggaa gaccccatgt atactcacga tggaaaactg ggaatcagaa 33960
ttggtggccc actgcaagta gtagacagct tgcacacact cactgtagtt actggaaacg 34020
gaataactgt agctaacaat gcccttcaaa ctaaagttgc gggtgccctg ggttatgact 34080
catctggcaa tctagaattg cgagccgcag gggtatgcg aattaacaca gggggtcaac 34140
tcattcttga tgtggcttat ccatttgatg ctcagaacaa tctcagcctt agactcggcc 34200
agggaccttt atatgtgaac accaatcaca acctagattt aaattgcaac agaggtctga 34260
ccacaaccac cagcagtaac acaaccaaac ttgaaactaa aatcgattcg ggcttagact 34320
ataacgccaa tggggctatc attgctaaac ttggcactgg gttaaccttt gacaacacag 34380
gtgccataac tgtgggaaac actggggatg acaaactcac tctgtggact accccagatc 34440
cctctcctaa ctgcagaatt cacgcagaca aagactgcaa gtttactcta gtcctgacta 34500
agtgtggaag tcaaattctg gcctccgtcg ccgccctggc ggtgtctgga aacctatcat 34560
caatgacagg cactgtctcc agcgttacca tctttctcag attcgatcag aatggagttc 34620
ttatggaaaa ttcctcgcta gacaaggagt actggaactt cagaaatggt aattccacca 34680
atgccacccc ctacaccaat gcggttgggt tcatgcccaa cctcagcgcc taccccaaaa 34740
cccagagtca aactgcaaaa aacaacattg taagtgaggt ttacttacat ggggacaaat 34800
ctaaacccat gatccttacc attaccctta atggcacaaa tgaatccagt gaaactagtc 34860
aggtgagtca ctactccatg tcatttacat ggtcgaggga cagtgggaaa tatgccaccg 34920
aaacctttgc caccaactct tttaccttct cctacattgc tgaacaataa agaagcataa 34980
cgctgctgtt catttgtaat caagtgttac tttttattt ttcaattaca acagaatcat 35040
tcaagtcatt ctccatttag cttaatagac cccagtagtg caaagcccca tactagctta 35100
tttcagcaat tgggagaagt actcgcctac atgggggtag agtcataatc gtgcatcagg 35160
atagggcggt ggtgctgcag cagcgcgcga ataaactgct gccgccgccg ctccgtcctg 35220
caggaataca acatggcagt ggtctcctca gcgatgattc gcaccgcccg cagcataagg 35280
cgccttgtcc tccgggcaca gcagcgcacc ctgatctcac ttaaatcagc acagtaactg 35340
cagcacagca ccacaatatt gttcaaaatc ccacagtgca aggcgctgta tccaaagctc 35400
atggcgggga ccacagaacc cacgtggcca tcataccaca agcgcaggta gattaagtgg 35460
cgacccctca taaacacgct ggacataaac attacctctt ttggcatgtt gtaattcacc 35520
acctcccggt accatataaa cctctgatta aacatggcgc catccaccac catcctaaac 35580
cagctggcca aaacctgccc gccggctata cactgcaggg aaccgggact ggaacaatga 35640
cagtggagag cccaggactc gtaaccatgg atcatcatgc tcgtcatgat atcaatgttg 35700
gcacaacaca ggcacacgtg catacacttc ctcaggatta caagctcctc ccgcgttaga 35760
accatatccc agggaacaac ccattcctga atcagcgtaa atcccacact gcagggaaga 35820
cctcgcacgt aactcacgtt gtgcattgtc aaagtgttac attcgggcag cagcggatga 35880

```
tcctccagta tggtagcgcg ggtttctgtc tcaaaaggag gtagacgatc cctactgtac  35940

ggagtgcgcc gagacaaccg agatcgtgtt ggtcgtagtg tcatgccaaa tggaacgccg  36000

gacgtagtca tatttcctga agtcttggcg cgccagaccc gagtcttacc aggaaaattt  36060

taaaaaagat tcctcaacgc agcaccagca ccaacacctg tcagtgtaaa atgccaagcg  36120

ccgagcgagt atatatagga ataaaaagtg acgtaaacgg ttaaagtcca gaaaacgccc  36180

agaaaaaccg cacgcgaacc tacgccccga aacgaaagcc aaaaaacagt gaacacgccc  36240

tttcggcgtc aacttccgct ttcccacggt acgtcacttc cgcatatagt aaaactacgc  36300

tacccaacat gcaagaagcc acgccccaaa acacgtcaca cctcccggcc cgccccgcgc  36360

cgccgctcct ccccgccccg ccccgctccg cccacctcat tatcatattg gcttcaatcc  36420

aaaataaggt atattattga tgatg                                        36445


<210> SEQ ID NO 10
<211> LENGTH: 2302
<212> TYPE: DNA
<213> ORGANISM: Ebola virus
<220> FEATURE:
<223> OTHER INFORMATION: Ebola virus Zaire wild type transmembrane
      envelope glycoprotein (GP) (EBOV GP Zaire wild type)

<400> SEQUENCE: 10

cgtcgtcgac acgtgtgatc agatatcgcg gccgctctag accaggccct ggatcgatcc     60

aacaacacaa tgggcgttac aggaatattg cagttacctc gtgatcgatt caagaggaca    120

tcattctttc tttgggtaat tatccttttc caaagaacat tttccatccc acttggagtc    180

atccacaata gcacattaca ggttagtgat gtcgacaaac tagtttgtcg tgacaaactg    240

tcatccacaa atcaattgag atcagttgga ctgaatctcg aagggaatgg agtggcaact    300

gacgtgccat ctgcaactaa aagatggggc ttcaggtccg gtgtcccacc aaaggtggtc    360

aattatgaag ctggtgaatg ggctgaaaac tgctacaatc ttgaaatcaa aaaacctgac    420

gggagtgagt gtctaccagc agcgccagac gggattcggg gcttcccccg gtgccggtat    480

gtgcacaaag tatcaggaac gggaccgtgt gccggagact ttgccttcca taaagagggt    540

gctttcttcc tgtatgatcg acttgcttcc acagttatct accgaggaac gactttcgct    600

gaaggtgtcg ttgcatttct gatactgccc caagctaaga aggacttctt cagctcacac    660

cccttgagag agccggtcaa tgcaacggag gacccgtcta gtggctacta ttctaccaca    720

attagatatc aggctaccgg ttttggaacc aatgagacag agtacttgtt cgaggttgac    780

aatttgacct acgtccaact tgaatcaaga ttcacaccac agtttctgct ccagctgaat    840

gagacaatat atacaagtgg gaaaaggagc aataccacgg gaaaactaat ttggaaggtc    900

aaccccgaaa ttgatacaac aatcggggag tgggccttct gggaaactaa aaaaaacctc    960

actagaaaaa ttcgcagtga agagttgtct ttcacagttg tatcaaacgg agccaaaaac   1020

atcagtggtc agagtccggc gcgaacttct tccgacccag ggaccaacac aacaactgaa   1080

gaccacaaaa tcatggcttc agaaaattcc tctgcaatgg ttcaagtgca cagtcaagga   1140

agggaagctg cagtgtcgca tctaacaacc cttgccacaa tctccacgag tccccaatcc   1200

ctcacaacca aaccaggtcc ggacaacagc acccataata cacccgtgta taaacttgac   1260

atctctgagg caactcaagt tgaacaacat caccgcagaa cagacaacga cagcacagcc   1320

tccgacactc cctctgccac gaccgcagcc ggacccccaa aagcagagaa caccaacacg   1380

agcaagagca ctgacttcct ggaccccgcc accacaacaa gtccccaaaa ccacagcgag   1440
```

-continued accgctggca acaacaacac tcatcaccaa gataccggag aagagagtgc cagcagcggg 1500
aagctaggct taattaccaa tactattgct ggagtcgcag gactgatcac aggcgggaga 1560
agaactcgaa gagaagcaat tgtcaatgct caacccaaat gcaaccctaa tttacattac 1620
tggactactc aggatgaagg tgctgcaatc ggactggcct ggataccata tttcgggcca 1680
gcagccgagg gaatttacat agaggggcta atgcacaatc aagatggttt aatctgtggg 1740
ttgagacagc tggccaacga gacgactcaa gctcttcaac tgttcctgag agccacaact 1800
gagctacgca ccttttcaat cctcaaccgt aaggcaattg atttcttgct gcagcgatgg 1860
ggcggcacat gccacattct gggaccggac tgctgtatcg aaccacatga ttggaccaag 1920
aacataacag acaaaattga tcagattatt catgattttg ttgataaaac ccttccggac 1980 caggggggaca atgacaattg gtggacagga tggagacaat ggataccggc aggtattgga 2040
gttacaggcg ttgtaattgc agttatcgct ttattctgta tatgcaaatt tgtcttttag 2100
tttttcttca gattgcttca tggaaaagct cagcctcaaa tcaatgaaac caggatttaa 2160
ttatatggat tacttgaatc taagattact tgacaaatga taatataata cactggagct 2220
ttaaacatag ccaatgtgat tctaactcct ttaaactcac agttaatcat aaacaaggtt 2280
tgaggtaccg agctcgaatt ga 2302

<210> SEQ ID NO 11
<211> LENGTH: 2031
<212> TYPE: DNA
<213> ORGANISM: Artificial Sequence
<220> FEATURE:
<223> OTHER INFORMATION: synthetic Ebola virus Sudan/Gulu codon optimized transmembrane envelope glycoprotein (GP) (EBOV GP Sudan/Gulu codon optimized)

<400> SEQUENCE: 11
atggagggcc tgagcctgct gcagctgccc agggacaagt tcaggaagag cagcttcttc 60
gtgtgggtga tcatcctgtt ccagaaggcc ttcagcatgc ccctgggcgt ggtgaccaac 120
agcaccctgg aggtgaccga gatcgaccag ctggtgtgca aggaccacct ggccagcacc 180
gaccagctga agagcgtggg cctgaacctg gagggcagcg gcgtgagcac cgacatcccc 240
agcgccacca agaggtgggg cttcaggagc ggcgtgcctc ccaaggtggt gagctacgag 300
gccggcgagt gggccgagaa ctgctacaac ctggagatca agaagcccga cggcagcgag 360
tgcctgcctc ctcctcctga cggcgtgagg ggcttcccca ggtgcaggta cgtgcacaag 420
gcccagggca ccggcccctg ccccggcgac tacgccttcc acaaggacgg cgccttcttc 480
ctgtacgaca ggctggccag caccgtgatc tacaggggcg tgaacttcgc cgagggcgtg 540
atcgccttcc tgatcctggc caagcccaag gagaccttcc tgcagagccc tcccatcagg 600
gaggccgtga actacaccga gaacaccagc agctactacg ccaccagcta tctagagtac 660
gagatcgaga acttcggcgc ccagcacagc accaccctgt tcaagatcga caacaacacc 720
ttcgtgaggc tggacaggcc ccacacccct cagttcctgt tccagctgaa cgacaccatc 780
cacctgcacc agcagctgag caacaccacc ggcaggctga tctggaccct ggacgccaac 840
atcaacgccg acatcggcga gtgggccttc tgggagaaca agaagaacct gagcgagcag 900
ctgaggggcg aggagctgag cttcgaggcc ctgagcctga acgagaccga ggacgacgac 960
gccgccagca gcaggatcac caagggcagg atcagcgaca gggccaccag gaagtacagc 1020
gacctggtgc ccaagaacag ccccggcatg gtgcccctgc acatccccga gggcgagacc 1080
accctgccca gccagaacag caccgagggc aggagggtgg gcgtgaacac ccaggagacc 1140
atcaccgaga ccgccgccac catcatcggc accaacggca accacatgca gatcagcacc 1200
atcggcatca ggcccagcag cagccagatc cccagcagca gccccaccac cgcccctagc 1260
cccgaggccc agacccccac cacccacacc agcggaccca gcgtgatggc caccgaggag 1320
cccaccaccc ctcccggcag cagccccgga cccaccaccg aggcccctac cctgaccacc 1380
cctgagaaca tcaccaccgc cgtgaagacc gtgctgcccc aggagagcac cagcaacggc 1440
ctgatcacca gcaccgtgac cggcatcctg ggcagcctgg gcctgaggaa gaggagcagg 1500
aggcagacca acaccaaggc caccggcaag tgcaacccca acctgcacta ctggaccgcc 1560
caggagcagc acaacgccgc cggcatcgcc tggattccct acttcggccc cggcgccgag 1620
ggcatctaca ccgagggcct gatgcacaac cagaacgccc tggtgtgcgg cctgaggcag 1680
ctggccaacg agaccaccca ggccctgcag ctgttcctga gggccaccac cgagctgagg 1740
acctacacca tcctgaacag gaaggccatc gacttcctgc tgaggaggtg gggcggcacc 1800
tgcaggattc tgggccccga ctgctgcatc gagccccacg actggaccaa gaacatcacc 1860
gacaagatca accagatcat ccacgacttc atcgacaacc ctctgcccaa ccaggacaac 1920
gacgacaact ggtggaccgg ctggcggcag tggatacctg ccggcatcgg catcaccggc 1980
atcatcatcg ccatcatcgc tctgctgtgc gtgtgcaagc tgctgtgctg a 2031

<210> SEQ ID NO 12
<211> LENGTH: 2043
<212> TYPE: DNA
<213> ORGANISM: Artificial Sequence
<220> FEATURE:
<223> OTHER INFORMATION: synthetic Marburg virus Angola codon optimized
transmembrane envelope glycoprotein (GP) (Marburg
virus Angola codon optimized)

<400> SEQUENCE: 12
atgaagacca cctgcctgct gatcagcctg atcctgatcc agggcgtgaa gaccctgccc 60
atcctggaga tcgccagcaa catccagccc cagaacgtgg acagcgtgtg cagcggcacc 120
ctgcagaaga ccgaggacgt gcacctgatg ggcttcaccc tgagcggcca gaaggtggcc 180
gacagccctc tggaggccag caagaggtgg gccttcaggg ccggcgtgcc ccccaagaac 240
gtggagtaca ccgagggcga ggaggccaag acctgctaca acatcagcgt gaccgacccc 300
agcggcaaga gcctgctgct ggaccctccc accaacatca gggactaccc taagtgcaag 360
accatccacc acatccaggg ccagaaccct cacgcccagg gcatcgccct gcacctgtgg 420
ggcgccttct tcctgtacga caggatcgcc agcaccacca tgtacagagg aaaagtgttc 480
acagagggaa acatcgctgc tatgatcgtg aacaagaccg tgcataagat gatcttcagc 540
agacagggac agggatatag acatatgaac ctgacatcca caaacaagta ctggacaagc 600
agcaacggaa cacagacaaa cgatacagga tgttttggaa cactgcagga atacaactcc 660
accaagaacc agacatgtgc ccctagcaag aagcctctgc ctctgcctac agctcatcct 720
gaagtgaagc tgacatccac aagcacagat gccacaaagc tgaacacaac agatcctaat 780
agcgacgacg aggatctgac aacaagcgga tccggatccg gagaacagga accttataca 840
acaagcgacg ctgctacaaa acagggactg tcctccacaa tgcctcctac acctagccct 900
cagcctagca cacctcagca gggaggcaac aacacaaacc attcccaggg agtggtgaca 960
gaacctggaa agacaaacac aacagcccag cctagcatgc ctcctcataa cacaacaaca 1020
atcagcacaa acaacacctc caagcacaat ctgagcacac ctagcgtgcc tattcagaat 1080

```
gccaccaact acaacacaca gtccacagcc cctgaaaacg aacagacctc cgccccttcc   1140

aaaacaaccc tgctgcctac agaaaaccct acaacagcca agagcacaaa cagcacaaag   1200

agccctacaa caacagtgcc taacacaaca aacaagtata gcacaagccc tagccctaca   1260

cctaattcca cagctcagca tctggtgtat tttagaagaa agagaaacat cctgtggaga   1320

gaaggagata tgttcccttt tctggatgga ctgatcaacg ctcctatcga ttttgatcct   1380

gtgcctaaca caaagacaat ctttgatgaa agcagcagca gcggagcctc cgccgaagaa   1440

gatcagcatg cctcccctaa catcagcctg acactgagct attttcctaa ggtgaacgaa   1500

aacacagccc attccggaga aaacgaaaac gattgtgatg ccgaactgag aatctggagc   1560

gtgcaggaag atgatctggc cgccggactg agctggatcc ctttttttgg gcccggaatt   1620

gaaggactgt acaccgccgg cctgatcaag aaccagaaca acctggtgtg caggctgagg   1680

aggctggcca accagaccgc caagagcctg gagctgctgc tgagggtgac caccgaggag   1740

aggaccttca gcctgatcaa caggcacgcc atcgacttcc tgctggctag gtggggcggc   1800

acctgcaagg tgctgggccc cgactgctgc atcggcatcg aggacctgag caggaacatc   1860

agcgagcaga tcgaccagat caagaaggac gagcagaagg agggcaccgg ctggggcctg   1920

ggcggcaagt ggtggaccag cgactgggga gtgctgacaa acctgggaat cctgctgctg   1980

ctgagcattg ccgtgctcat tgctctgtcc tgtatctgta gaatctttac caagtacatc   2040

gga                                                                  2043
```

<210> SEQ ID NO 13
<211> LENGTH: 2028
<212> TYPE: DNA
<213> ORGANISM: Ebola virus
<220> FEATURE:
<223> OTHER INFORMATION: Ebola virus Sudan/Gulu wild type transmembrane envelope glycoprotein (GP) (EBOV GP Sudan/Gulu wild type)

<400> SEQUENCE: 13

```
atgggggggtc ttagcctact ccaattgccc agggacaaat ttcggaaaag ctctttcttt     60
```

```
gtttgggtca tcatcttatt ccaaaaggcc ttttccatgc ctttgggtgt tgtgactaac    120

agcactttag aagtaacaga gattgaccag ctagtctgca aggatcatct tgcatctact    180

gaccagctga aatcagttgg tctcaacctc gaggggagcg gagtatctac tgatatccca    240

tctgcaacaa agcgttgggg cttcagatct ggtgttcctc ccaaggtggt cagctatgaa    300

gcgggagaat gggctgaaaa ttgctacaat cttgaaataa agaagccgga cgggagcgaa    360

tgcttacccc caccgccaga tggtgtcaga ggctttccaa ggtgccgcta tgttcacaaa    420

gcccaaggaa ccgggccctg cccaggtgac tacgcctttc acaaggatgg agctttcttc    480

ctctatgaca ggctggcttc aactgtaatt tacagaggag tcaattttgc tgagggggta    540

attgcattct tgatattggc taaaccaaaa gaaacgttcc ttcagtcacc ccccattcga    600

gaggcagtaa actacactga aaatacatca agttattatg ccacatccta cttggagtat    660

gaaatcgaaa attttggtgc tcaacactcc acgacccttt tcaaaattga caataatact    720

tttgttcgtc tggacaggcc ccacacgcct cagttccttt tccagctgaa tgataccatt    780

caccttcacc aacagttgag taatacaact gggagactaa tttggacact agatgctaat    840

atcaatgctg atattggtga atgggctttt tgggaaaata aaaaaaatct ctccgaacaa    900

ctacgtggag aagagctgtc tttcgaagct ttatcgctca acgagacaga agacgatgat    960

gcggcatcgt cgagaattac aaagggaaga atctccgacc gggccaccag gaagtattcg   1020
```

gacctggttc caaagaattc ccctgggatg gttccattgc acataccaga aggggaaaca 1080
acattgccgt ctcagaattc gacagaaggt cgaagagtag gtgtgaacac tcaggagacc 1140
attacagaga cagctgcaac aattataggc actaacggca accatatgca gatctccacc 1200
atcgggataa gaccgagctc cagccaaatc ccgagttcct caccgaccac ggcaccaagc 1260
cctgaggctc agacccccac aacccacaca tcaggtccat cagtgatggc caccgaggaa 1320
ccaacaacac caccgggaag ctcccccggc ccaacaacag aagcacccac tctcaccacc 1380
ccagaaaata taacaacagc ggttaaaact gtcctgccac aggagtccac aagcaacggt 1440
ctaataactt caacagtaac agggattctt gggagtcttg ggcttcgaaa acgcagcaga 1500
agacaaacta acaccaaagc cacgggtaag tgcaatccca acttacacta ctggactgca 1560
caagaacaac ataatgctgc tgggattgcc tggatcccgt actttggacc gggtgcggaa 1620
ggcatataca ctgaaggcct gatgcataac caaaatgcct tagtctgtgg acttaggcaa 1680
cttgcaaatg aaacaactca agctctgcag cttttcttaa gagccacaac ggagctgcgg 1740
acatatacca tactcaatag gaaggccata gatttccttc tgcgacgatg ggcgggacaa 1800
tgcaggatcc tgggaccaga ttgttgcatt gagccacatg attggacaaa aaacatcact 1860
gataaaatca accaaatcat ccatgatttc atcgacaacc ccttacctaa tcaggataat 1920
gatgataatt ggtggacggg ctggagacag tggatccctg caggaatagg cattactgga 1980
attattattg caattattgc tcttctttgc gtttgcaagc tgctttgc 2028

<210> SEQ ID NO 14
<211> LENGTH: 2031
<212> TYPE: DNA
<213> ORGANISM: Artificial Sequence
<220> FEATURE:
<223> OTHER INFORMATION: synthetic Ebola virus Zaire codon optimized transmembrane envelope glycoprotein (GP) (EBOV GP Zaire codon optimized)

<400> SEQUENCE: 14
atgggcgtga ccggcatcct gcagctgccc agggacaggt tcaagaggac cagcttcttc 60
ctgtgggtga tcatcctgtt ccagaggacc ttcagcatcc ccctgggcgt gatccacaac 120
agcaccctgc aggtgagcga cgtggacaag ctggtgtgca gggacaagct gagcagcacc 180
aaccagctga ggagcgtggg cctgaacctg gagggcaacg gcgtggccac cgacgtgccc 240
agcgccacca agaggtgggg cttcaggagc ggcgtgcctc ccaaggtggt gaactacgag 300
gccggcgagt gggccgagaa ctgctacaac ctggagatca agaagcccga cggcagcgag 360
tgcctgcccg ccgcccctga cggcatcagg ggcttcccca ggtgcaggta cgtgcacaag 420
gtgagcggca ccggcccctg cgccggcgac ttcgccttcc acaaggaggg cgccttcttc 480
ctgtacgaca ggctggccag caccgtgatc tacaggggca ccaccttcgc cgagggcgtg 540
gtggccttcc tgatcctgcc ccaggccaag aaggacttct tcagcagcca ccctctgagg 600
gagcccgtga acgccaccga ggaccccagc agcggctact acagcaccac catcaggtac 660
caggccaccg gcttcggcac caacgagacc gagtacctgt tcgaggtgga caacctgacc 720
tacgtgcagc tggagtctag attcacccct cagttcctgc tgcagctgaa cgagaccatc 780
tacaccagcg gcaagaggag caacaccacc ggcaagctga tctggaaggt gaaccccgag 840
atcgacacca ccatcggcga gtgggccttc tgggagacca agaagaacct gaccaggaag 900
atcaggagcg aggagctgag cttcaccgtc gtgagcaacg gggccaagaa catcagcggc 960

-continued

| | |
|---|---|
| cagagccccg ccaggaccag cagcgacccc ggcaccaaca ccaccaccga ggaccacaag | 1020 |
| atcatggcca gcgagaacag cagcgccatg gtgcaggtgc acagccaggg cagggaggcc | 1080 |
| gccgtgagcc acctgaccac cctggccacc atcagcacca gccctcagtc tttaaccacc | 1140 |
| aagcccggcc ccgacaacag cacccacaac accccctgtgt acaagctgga catcagcgag | 1200 |
| gccacccagg tggagcagca ccacaggagg accgacaacg acagcaccgc cagcgacacc | 1260 |
| ccttccgcca ccaccgccgc cggccctccg aaggccgaga acaccaacac cagcaagagc | 1320 |
| accgactttc tggatcccgc caccaccacc agccctcaga accacagcga gaccgccggc | 1380 |
| aacaacaaca cccaccacca ggacaccggc gaggagagcg ccagcagcgg caagctgggc | 1440 |
| ctgatcacca acaccatcgc cggcgtggcc ggcctgatca ccggcggcag gaggaccagg | 1500 |
| agggaggcca tcgtgaacgc ccagcccaag tgcaacccca acctgcacta ctggaccacc | 1560 |
| caggacgagg gcgccgccat cggcctggcc tggattccct acttcggccc cgccgccgag | 1620 |
| ggcatctaca tcgagggcct gatgcacaac caggacggcc tgatctgcgg cctgaggcag | 1680 |
| ctggccaacg agaccaccca ggccctgcag ctgttcctga gggccaccac cgagctgagg | 1740 |
| accttcagca tcctgaacag gaaggccatc gacttcctgc tgcagaggtg gggcggcacc | 1800 |
| tgccacatcc tgggccccga ctgctgcatc gagccccacg actggaccaa gaacatcacc | 1860 |
| gacaagatcg accagatcat ccacgacttc gtggacaaga ccctgccaga ccagggcgac | 1920 |
| aacgacaact ggtggaccgg ctggcggcag tggatacctg ccggcatcgg cgtgaccggc | 1980 |
| gtggtgatcg ccgtgatcgc tctgttctgc atctgcaagt tcgtgttctg a | 2031 |